US006716963B1

(12) United States Patent
Henkin et al.

(10) Patent No.: US 6,716,963 B1
(45) Date of Patent: Apr. 6, 2004

(54) PEPTIDE ANTIANGIOGENIC DRUGS

(75) Inventors: Jack Henkin, Highland Park, IL (US); Fortuna Haviv, Deerfield, IL (US); Michael F. Bradley, Chicago, IL (US); Douglas M. Kalvin, Buffalo Grove, IL (US); Andrew J. Schneider, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/447,226

(22) Filed: Nov. 22, 1999

Related U.S. Application Data

(63) Continuation-in-part of application No. 09/316,888, filed on May 21, 1999.
(60) Provisional application No. 60/126,546, filed on Mar. 26, 1999, and provisional application No. 60/086,536, filed on May 22, 1998.

(51) Int. Cl.$^7$ .................................................. C07K 7/00
(52) U.S. Cl. ......................................... 530/328; 514/15
(58) Field of Search ............................. 530/328; 514/15

(56) References Cited

U.S. PATENT DOCUMENTS

| | | | |
|---|---|---|---|
| 5,155,038 A | 10/1992 | Eyal et al. ............... 435/240.2 |
| 5,190,918 A | 3/1993 | Deutch et al. ................ 514/12 |
| 5,190,920 A | 3/1993 | Eyal et al. .................... 514/17 |
| 5,192,744 A | 3/1993 | Bouck et al. .................. 514/8 |
| 5,200,397 A | 4/1993 | Deutch et al. ................ 514/15 |
| 5,367,059 A | 11/1994 | Tuszynski et al. .......... 530/395 |
| 5,426,100 A | 6/1995 | Deutch et al. ................ 514/15 |
| 5,491,130 A | 2/1996 | Roberts et al. ............... 514/13 |
| 5,506,208 A | 4/1996 | Eyal et al. .................... 514/17 |
| 5,648,461 A | 7/1997 | Eyal et al. ................... 530/329 |
| 5,654,277 A | 8/1997 | Eyal et al. .................... 514/18 |
| 5,770,563 A | 6/1998 | Roberts et al. ................. 514/8 |
| 5,840,692 A | 11/1998 | Deutch et al. ................ 514/12 |
| 5,849,701 A | 12/1998 | Roberts et al. ............... 514/17 |
| 6,051,549 A | 4/2000 | Roberts et al. ................. 514/2 |
| 6,239,110 B1 | 5/2001 | Eyal et al. .................... 514/17 |
| 6,339,062 B1 | 1/2002 | Williams et al. ............. 514/15 |
| 6,380,161 B1 | 4/2002 | Williams et al. ............. 514/12 |

FOREIGN PATENT DOCUMENTS

| | | |
|---|---|---|
| EP | 0443404 | 8/1991 |
| WO | 9316716 | 9/1993 |
| WO | 96/11214 | 4/1996 |
| WO | 9741824 | 11/1997 |
| WO | 9841542 | 9/1998 |

OTHER PUBLICATIONS

Gasparini, et al., *Journal of Clinical Oncology*, vol. 13, No. 3, pp. 765–782.
Santoro and Frazier, *Methods of Enzymology*, 144: 438–446 (1987).
Majack and Bornstein, *Cell Membranes Methods–Reviews*, 3:55–77 (1987).
Haverstick, et al., *Biochemistry*, 23:5597–5603 (1984).
Lawler and Hynes, *J. Cell Biology*, 103:1635–1648 (1986).
Hennesy, et al., *J. Cell Biology*, 108:729–736 (1989).
Donoviel, *J. Biological Chemistry*, 263:18590–18593 (1988).

Primary Examiner—Christopher S. F. Low
Assistant Examiner—David Lukton
(74) *Attorney, Agent, or Firm*—Gregory W. Steele; B. Gregory Donner; Portia Chen

(57) ABSTRACT

Peptides having the formula:

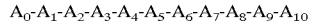

$$A_0\text{-}A_1\text{-}A_2\text{-}A_3\text{-}A_4\text{-}A_5\text{-}A_6\text{-}A_7\text{-}A_8\text{-}A_9\text{-}A_{10}$$

wherein $A_0$ is selected from hydrogen or an acyl group; $A_{10}$ is a hydroxyl group or an amino acid amide; and $A_1, A_2, A_3, A_4, A_5, A_6, A_7, A_8$, and $A_9$ are amino acyl residues as defined herein.

42 Claims, No Drawings

PEPTIDE ANTIANGIOGENIC DRUGS

This application is a continuation-in-part of U.S. patent application Ser. No. 09/316,888, filed May 21, 1999, pending, and claims the benefit of U.S. Provisional Patent Applications 60/126,546, filed Mar. 26, 1999 and 60/086,536 filed May 21, 1998, both of which are hereby incorporated by reference.

TECHNICAL FIELD

The invention relates to novel compounds having activity useful for treating conditions which arise or are exacerbated by angiogenesis, pharmaceutical compositions comprising these compounds, a method of treating using said compounds, and a method of inhibiting angiogensis.

BACKGROUND OF THE INVENTION

Angiogenesis is the fundamental process by which new blood vessels are formed and is essential to a variety of normal body activities (such as reproduction, development and wound repair). Although the process is not completely understood, it is believed to involve a complex interplay of molecules which both stimulate and inhibit the growth of endothelial cells, the primary cells of the capillary blood vessels. Under normal conditions, these molecules appear to maintain the microvasculature in a quiescent state (i.e. one of no capillary growth) for prolonged periods which may last for as long as weeks or in some cases, decades. When necessary however (such as during wound repair), these same cells can undergo rapid proliferation and turnover within a five day period. (Folkman, J. and Shing, Y., *The Journal of Biological Chemistry*, 267(16): 10931–10934, and Folkman J. and Klagsbrun, M., *Science*, 235: 442–447 (1987)).

Although angiogenesis is a highly regulated process under normal conditions, many diseases (characterized as "angiogenic diseases") are driven by persistent unregulated angiogenesis. Otherwise stated, unregulated angiogenesis may either cause a particular disease directly or exaserbate an existing pathological condition. For example, ocular neovacularization has been implicated as the most common cause of blindness. In certain existing conditions such as arthritis, newly formed capillary blood vessels invade the joints and destroy cartilage. In diabetes, new capillaries formed in the retina invade the vitreous, bleed, and cause blindness. Growth and metastasis of solid tumors are also angiogenesis-dependent (Folkman, J., *Cancer Research*, 46: 467–473 (1986), Folkman, J., *Journal of the National Cancer Institute*, 82: 4–6 (1989)). It has been shown for example that tumors which enlarge to greater than 2 mm, must obtain their own blood supply and do so by inducing the growth of new capillary blood vessels. Once these new blood vessels become embedded in the tumor, they provide a means for tumor cells to enter the circulation and metastasize to distant sites, such as liver, lung or bone (Weidner, N., et al., *The New England Journal of Medicine*, 324(1): 1–8 (1991)).

Although several angiogenesis inhibitors are currently under development for use in treating angiogenic diseases (Gasparini, G. and Harris, A. L., *J Clin Oncol* 13(3): 765–782, (1995)), there are disadvantages associated with several of these compounds. For example, suramin is a potent angiogenesis inhibitor, but causes (at doses required to reach antitumor activity) severe systemic toxicity in humans. Other compounds, such as retinoids, interferons and antiestrogens are safe for human use but have only a weak anti-angiogenic effect.

SUMMARY OF THE INVENTION

In one aspect, the present invention provides a compound of formula:

$$A_0\text{-}A_1\text{-}A_2\text{-}A_3\text{-}A_4\text{-}A_5\text{-}A_6\text{-}A_7\text{-}A_8\text{-}A_9\text{-}A_{10} \qquad (I)$$

or a pharmaceutically acceptable salt, ester, solvate or prodrug thereof, wherein:

$A_0$ is an acyl group selected from:
(1) R—(CH$_2$)$_n$—C(O)—; wherein n is an integer from 0 to 8 and R is selected from hydroxyl; methyl; N-acetylamino; methoxyl; carboxyl; cyclohexyl optionally containing one or two double bonds and optionally substituted with one to three hydroxyl groups; and a 5- or 6-membered aromatic or non-aromatic ring optionally containing one or two heteroatoms selected from nitrogen, oxygen, and sulfur, wherein the ring is optionally substituted with a moiety selected from alkyl, alkoxy, and halogen; and
(2) R$^1$—CH$_2$CH$_2$—(OCH$_2$CH$_2$O)$_p$—CH$_2$—C(O)—; wherein R$^1$ is selected from hydrogen, alkyl and N-acetylamino, and p is an integer from 1 to 8;

$A_1$ is an amino acyl residue selected from:
(1) alanyl,
(2) asparaginyl,
(3) citrullyl,
(4) glutaminyl,
(5) glutamyl,
(6) N-ethylglycyl,
(7) methionyl,
(8) N-methylalanyl,
(9) prolyl,
(10) pyro-glutamyl,
(11) sarcosyl,
(12) seryl,
(13) threonyl,
(14) —HN—(CH$_2$)$_q$—C(O)—, wherein q is 1 to 8, and
(15) —HN—CH$_2$CH$_2$—(OCH$_2$CH$_2$O)$_r$—CH$_2$—C(O)—, wherein r is 1 to 8;

$A_2$ is an amino acyl residue selected from:
(1) alanyl,
(2) asparaginyl,
(3) aspartyl,
(4) glutaminyl,
(5) glutamyl,
(6) leucyl,
(7) methionyl,
(8) phenylalanyl,
(9) prolyl,
(10) seryl,
(11) —HN—(CH$_2$)$_q$—C(O)—, wherein q is 1 to 8, and
(12) —HN—CH$_2$CH$_2$—(OCH$_2$CH$_2$O)$_r$—CH$_2$—C(O)—, wherein r is 1 to 8;

$A_3$ is an amino acyl residue selected from:
(1) alanyl,
(2) asparaginyl,
(3) citrullyl,
(4) cyclohexylalanyl,
(5) cyclohexylglycyl,
(6) glutaminyl,
(7) glutanyl,
(8) glycyl,
(9) isoleucyl,
(10) leucyl,
(11) methionyl,

(12) norvalyl,
(13) phenylalanyl,
(14) seryl,
(15) t-butylglycyl,
(16) threonyl,
(17) valyl,
(18) penicillaminyl, and
(19) cystyl;

$A_4$ is an amino acyl residue of L or D configuration selected from:
(1) allo-isoleucyl,
(2) glycyl,
(3) isoleucyl,
(4) prolyl,
(5) dehydroleucyl,
(6) D-alanyl,
(7) D-3-(naphth-1-yl)alanyl,
(8) D-3-(naphth-2-yl)alanyl,
(9) D-3-pyridyl)alanyl,
(10) D-2-aminobutyryl,
(11) D-allo-isoleucyl,
(12) D-allo-threonyl;
(13) D-allylglycyl,
(14) D-asparaginyl,
(15) D-aspartyl,
(16) D-benzothienyl,
(17) D-3-(4,4'-biphenyl)alanyl,
(18) D-chlorophenylalanyl,
(19) D-3-(3-trifluoromethylphenyl)alanyl,
(20) D-3-(3-cyanophenyl)alanyl,
(21) D-3-(3,4-difluorophenyl)alanyl,
(22) D-citrullyl,
(23) D-cyclohexylalanyl,
(24) D-cyclohexylglycyl,
(25) D-cystyl,
(26) D-cystyl(S-t-butyl),
(27) D-glutaminyl,
(28) D-glutamyl,
(29) D-histidyl,
(30) D-homoisoleucyl,
(31) D-homophenylalanyl,
(32) D-homoseryl,
(33) D-isoleucyl,
(34) D-leucyl,
(35) D-lysyl(N-epsilon-nicotinyl),
(36) D-lysyl,
(37) D-methionyl,
(38) D-neopentylglycyl,
(39) D-norleucyl,
(40) D-norvalyl,
(41) D-ornithyl,
(42) D-penicillaminyl,
(43) D-penicillaminyl(acetnidomethyl),
(44) D-penicillaminyl(S-benzyl),
(45) D-phenylalanyl,
(46) D-3-(4-aminophenyl)alanyl,
(47) D-3-(4-methylphenyl)alanyl,
(48) D-3-(4-nitrophenyl)alanyl,
(49) D-3-(3,4-dimethoxyphenyl)alanyl,
(50) D-3-(3,4,5-trifluorophenyl)alanyl,
(51) D-prolyl,
(52) D-seryl,
(53) D-seryl(O-benzyl),
(54) D-t-butylglycyl,
(55) D-thienylalanyl,
(56) D-threonyl,
(57) D-threonyl(O-benzyl),
(58) D-tryptyl,
(59) D-tyrosyl(O-benzyl),
(60) D-tyrosyl(O-ethyl),
(61) D-tyrosyl, and
(62) D-valyl;

$A_5$ is an amino acyl residue of L or D configuration selected from:
(1) alanyl,
(2) (3-pyridyl)alanyl,
(3) 3-(naphth-1-yl)alanyl,
(4) 3naphth-2-yl)alanyl,
(5) allo-threonyl,
(6) allylglycyl,
(7) glutaminyl,
(8) glycyl,
(9) histidyl,
(10) homoseryl,
(11) isoleucyl,
(12) lysyl(N-epsilon-acetyl),
(13) methionyl,
(14) norvalyl,
(15) octylglycyl,
(16) ornithyl,
(17) 3-(4-hydromethylphenyl)alanyl,
(18) prolyl,
(19) seryl,
(20) threonyl,
(21) tryptyl,
(22) tyrosyl,
(23) D-allo-threonyl,
(24) D-homoseryl,
(25) D-seryl,
(26) D-threonyl,
(27) penicillaminyl, and
(28) cystyl;

$A_6$ is an amino acyl residue of L or D configuration selected from:
(1) alanyl,
(2) 3-(naphth-1-yl)alanyl,
(3) 3-(naphth-2-yl)alanyl,
(4) (3-pyridyl)alanyl,
(5) 2-aminobutyryl,
(6) allylglycyl,
(7) arginyl,
(8) asparaginyl,
(9) aspartyl,
(10) citrullyl,
(11) cyclohexylalanyl,
(12) glutaminyl,
(13) glutamyl,
(14) glycyl,
(15) histidyl,
(16) homoalanyl,
(17) homoleucyl,
(18) homoseryl,
(19) isoleucyl,
(20) leucyl,
(21) lysyl(N-epsilon-acetyl),
(22) lysyl(N-epsilon-isopropyl),
(23) methionyl(sulfone),
(24) methionyl(sulfoxide),
(25) methionyl,
(26) norleucyl,
(27) norvalyl,
(28) octylglycyl,
(29) phenylalanyl,
(30) 3-(4-carboxyamidephenyl)alanyl,

(31) propargylglycyl,
(32) seryl,
(33) threonyl,
(34) tryptyl,
(35) tyrosyl,
(36) valyl,
(37) D-3-(naphth-1-yl)alanyl,
(38) D-3-(naphth-2-yl)alanyl,
(39) D-glutaminyl,
(40) D-homoseryl,
(41) D-leucyl,
(42) D-norvalyl,
(43) D-seryl,
(44) penicillaminyl, and
(45) cystyl;

$A_7$ is an amino acyl residue of L or D configuration selected from:
(1) alanyl,
(2) allylglycyl,
(3) aspartyl,
(4) citrullyl,
(5) cyclohexylglycyl,
(6) glutamyl,
(7) glycyl,
(8) homoseryl,
(9) isoleucyl,
(10) allo-isoleucyl,
(11) leucyl,
(12) lysyl(N-epsilon-acetyl),
(13) methionyl,
(14) 3-(naphth-1-yl)alanyl,
(15) 3-(naphth-2-yl)alanyl,
(16) norvalyl,
(17) phenylalanyl,
(18) prolyl,
(19) seryl,
(20) t-butylglycyl,
(21) tryptyl,
(22) tyrosyl,
(23) valyl,
(24) D-allo-isoleucyl,
(25) D-isoleucyl,
(26) penicillaminyl, and
(27) cystyl;

$A_8$ is an amino acyl residue selected from:
(1) 2-amino4-[(2-amino)-pyrimidinyl]butanoyl,
(2) alanyl(3-guanidino),
(3) alanyl[3-pyrrolidinyl(2-N-amidino)],
(4) alanyl[4-piperidinyl(N-amidino)],
(5) arginyl,
(6) arginyl($N^G N^{G'}$ diethyl),
(7) citrullyl,
(8) 3-(cyclohexyl)alanyl(4N'-isopropyl),
(9) glycyl[4-piperidinyl(N-amidino)],
(10) histidyl,
(11) homoarginyl,
(12) lysyl,
(13) lysyl(N-epsilon-isopropyl),
(14) lysyl(N-epsilon-nicotinyl),
(15) norarginyl,
(16) ornithyl(N-delta-isopropyl),
(17) ornithyl(N-delta-nicotinyl),
(18) ornithyl[N-delta-(2-imidazolinyl)],
(19) [4-amino(N-isopropyl)methyl)phenyl]alanyl,
(20) 3-(4-guanidinophenyl)alanyl, and
(21) 3-(4-amino-N-isopropylphenyl)alanyl;

$A_9$ is an amino acyl residue of L or D configuration selected from:
(1) 2-amino-butyryl,
(2) 2-amino-isobutyryl,
(3) homoprolyl,
(4) hydroxyprolyl,
(5) isoleucyl,
(6) leucyl,
(7) phenylalanyl,
(8) prolyl,
(9) seryl,
(10) t-butylglycyl,
(11) 1,2,3,4-tetrahydroisoquinoline-3carbonyl,
(12) threonyl,
(13) valyl,
(14) D-alanyl, and
(15) D-prolyl; and $A_{10}$ is a hydroxyl group or an amino acid amide is selected from:
(1) azaglycylamide,
(2) D-alanylamide,
(3) D-alanylethylamide,
(4) glycylamide,
(5) glycylethylamide,
(6) sarcosylamide,
(7) serylamide,
(8) D-serylamide,
(9) a group represented by the formula

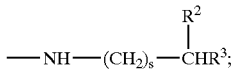

and
(9) a group represented by the formula —NH—$R^4$;
wherein:
s is an integer selected from 0 to 8,
$R^2$ is selected from hydrogen, alkyl, and a 5- to 6-membered cycloalkyl ring;
$R^3$ is selected from hydrogen, hydroxy, alkyl, phenyl, alkoxy, and a 5- to 6-membered ring optionally containing from one to two heteroatoms selected from oxygen, nitrogen, and sulfur, provided that s is not zero when $R^3$ is hydroxy or alkoxy; and
$R^4$ is selected from hydrogen, hydroxy, and a 5- to 6-membered cycloalkyl ring.

In another aspect, the present invention provides a composition for treating a patient in need of anti-angiogenesis therapy comprising a peptide defined above in pill combination with a pharmaceutically acceptable carrier.

Yet another aspect of the present invention provides a method for treating a patient in need of anti-angiogenesis therapy comprising administering to the patient a therapeutically effective amount of a peptide as defined above.

Still yet another aspect of the present invention provides a composition for the treatment of a disease selected from cancer, arthritis, psoriasis, angiogenesis of the eye associated with infection or surgical intervention, macular degeneration and diabetic retinopathy comprising a peptide as defined above in combination with a pharmaceutically acceptable carrier.

In yet another aspect, the present invention provides a method of isolating a receptor from an endothelial cell comprising binding a peptide as defined above to the receptor to form a peptide receptor complex, isolating the peptide receptor complex, and purifying the receptor.

DETAILED DESCRIPTION OF THE INVENTION

Definition of Terms

The term "alkyl" as used herein refers to a monovalent group derived from a straight or branched chain saturated hydrocarbon by the removal of a hydrogen atom. Examples of alkyl include, but are not limited to, methyl, ethyl, propyl, isopropyl, butyl, sec-butyl, iso-butyl, tert-butyl, pentyl, hexyl, and the like. Preferred alkyl groups for the invention are $C_1$–$C_6$ alkyl groups having from one to six carbon atoms. Alkyl groups of one to three carbon atoms ($C_1$–$C_3$ alkyl) are more preferred for the invention.

The term "nicotinyl" as used herein refers to the acyl group derived from nicotinic acid, i.e. pyridine-3-carboxylic acid. The term "2-Me-nicotinyl" or "2-methylnicotinyl" refers to a nicotinyl moiety substituted with a methyl group at the carbon adjacent to the nitrogen atom.

The term "shikimyl" as used herein refers to the acyl residue derived from shikimic acid or [3R-(3α,4α,5β)-3,4,5-trihydroxy]-1-cyclohexene-1-carboxylic acid. A "dihydroshikimyl" group denotes the fully saturated analog of shikimic acid.

The term "succinyl" as used herein refers to the acyl residue derived from succinic acid or (1,4-dioxobutyl)-1-carboxylic acid.

The term "N-acetylamino" as used herein refers to an amino moiety (—$NH_2$) substituted on the nitrogen atom with an acetyl ($CH_3C(O)$—) group.

The term "carbonyl" as used herein refers to the group —C(O)—.

The term "carboxy" or "carboxyl" as used herein refers to the group —C(O)OH.

The term "alkoxy" as used herein refers to an alkyl group as defined above attached to a parent molecular moiety via an ether linkage. Exemplary alkoxy groups include, but are not limited to, methoxy, ethoxy, isopropoxy, and the like.

The term "aromatic ring" as used herein refers to an unsaturated cyclic hydrocarbon associated with a system of π-electron bonds. One to two carbon atoms of the hydrocarbon ring can be substituted with a heteroatom selected from nitrogen, oxygen, or sulfur. Exemplary 5- or 6-membered aromatic rings include, but are not limited to, benzyl, pyridyl, furyl, tetrahydrofuryl, thienyl, and pyrrolyl. An aromatic ring, including rings substituted with a heteroatom, can be optionally substituted on one or more carbon atoms with substituents selected from alkyl, alkoxy, carboxy, and halogen, for example, tolyl, bromobenzyl, t-butylbenzyl, nicotinyl, 2-methylnicotinyl, 2-furoic acid, and the like.

The term "nonaromatic ring" as used herein refers to a saturated or unsaturated cyclic hydrocarbon ring, which can be optionally substituted with one or two heteroatoms selected from nitrogen, oxygen, or sulfur. Exemplary non-aromatic rings are cyclohexyl, tetrahydropyranyl, pyrrolidinyl, and piperidinyl.

The term "N-protecting group" as used herein refers to an easily removable group which is known in the art to protect an amino group against undesirable reaction during synthetic procedures and to be selectively removable. The use of N-protecting groups is well known in the art for protecting groups against undesirable reactions during a synthetic procedure and many such protecting groups are known, cf, for example, T. H. Greene and P. G. M. Wuts, Protective Groups in Organic Synthesis, 2nd edition, John Wiley & Sons, New York (1991). Examples of N-protecting groups include, but are not limited to, acyl groups including acetyl, trifluoroacetyl, acylisothiocyanate, aminocaproyl, benzoyl and the like, and acyloxy groups, including t-butyloxycarbonyl (Boc) and carbobenzyloxy (Cbz), 9-fluorenylmethoxycarbonyl (Fmoc), and the like.

As used herein the terms "Leu," "Sar," "Gln," "Gly," "Val," "Ile," "Thr," "Nva," "Arg," "Asn," "pyroGlu," "Ser," "Ala," "Homoala," "Cha," "Pro", "Phe," "Trp," "1-Nal," "2-Nal," "Azagly" and "Nle" refer to leucine, sarcosine (N-methylglycine), glutamine, glycine, valine, isoleucine, threonine, norvaline, arginine, aspargine, pyroglutamic acid, serine, alanine, homoalanine, cyclohexylalanine, proline, phenylalanine, tryptophan, 1-naphthylalanine, 2-naphthylalanine, azaglycine, and norleucine, respectively, in their L-, D- or DL forms. Unless indicated otherwise by a "D" prefix, e.g. D-Ala or D-Ile (also D-Ile), the stereochemistry of the α-carbon of the amino acids and aminoacyl residues in peptides described in this specification and the appended claims is the natural or "L" configuration. The Cahn-Ingold-Prelog "R" and "S" designations are used to specify the stereochemistry of chiral centers in certain of the acyl substituents at the N-terminus of the peptides of this invention. The designation "R,S" is meant to indicate a racemic mixture of the two enantiomeric forms. This nomenclature follows that described in R. S. Cahn, et al., Angew. Chem. Int. Ed. Engl., 5, 385–415 (1966).

For the most part, the names on naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader. Some abbreviations useful in describing the invention are defined below in the following Table 1.

TABLE 1

| Abbreviation | Definition |
|---|---|
| Abu | 2-aminobutyric acid |
| 6-Ac-Aca | 6-NAc-caproyl, 6-N-Ac-$(CH_2)_5C(O)$—, or 6-N-acetyl-aminocaproic acid |
| Aib | 2-aminoisobutyric acid |
| Ala(3-guanidino) | alanine(3-guanidino) |
| Ala(3-pyrrolidinylamidino) | alanine[3-pyrrolidinyl(2-N-amidino)] |
| Ala[4-Pip(N-amidino)] | alanine[4-piperidinyl(N-amidino)] |
| Allylgly | 2-(allyl)glycine |
| AM | aminomethyl |
| Aminopyrimidinobutanoyl | 2-amino-4-[(2-amino)pyrimidinyl]butanoic acid |
| Azagly | azaglycine |
| 3-Ac-Bala | 3-N-acetyl-beta-alanine |
| Bala | beta-alanine |
| Cha | 3-(cyclohexyl)alanine |
| Cha(4-NIsp) | 3-(cyclohexyl)alanine(4-N'-isopropyl) |
| Cit | citrulline |
| 2ClTrt | 2-chloro-trityl |
| Cys(tBu) | cysteine(S-t-butyl) |
| D-2-Thienylala | D-3-(2-thienyl)alanine |
| D-3,3-Diphenylala | D-3,3-(diphenyl)alanine |
| D-3,4-diClPhe | D-3-(3,4-dichlorophenyl)alanine |
| D-3,4-diFPhe | D-3-(3,4-difluorophenyl)alanine |
| D-3-Benzothienylala | D-3-(3-benzothienyl)alanine |
| D-3-$CF_3$Phe | D-3-(3-trifluoromethylphenyl)alanine |
| D-3-ClPhe | D-3-(3-chlorophenyl)alanine |
| D-3-CNPhe | D-3-(3-cyanophenyl)alanine |

TABLE 1-continued

| Abbreviation | Definition |
| --- | --- |
| D-3-Pal | D-(3-pyridyl)alanine |
| D-4,4'-Biphenylala | D-3-(4,4'-biphenyl)alanine |
| D-4-ClPhe | D-3-(4-chloro-phenyl)alanine |
| D-Cha | D-3-(cyclohexyl)alanine |
| D-Chg | D-cyclohexylglycine |
| Dehydroleu | dehydroleucine |
| D-Hphe | D-homophenylalanine |
| D-Ile | D-isoleucine |
| D-alloIle | D-allo-isoleucine |
| D-Lys(Nic) | D-lysine(N-epsilon-nicotinyl) |
| D-Leu | D-leucine |
| D-pentaFPhe | D-3-(pentafluorophenyl)alanine |
| D-Val | D-valine |
| 4-Ac-Gaba | 4-N-acetyl-gamma-aminobutyric acid or 4-N-acetyl-4-aminobutyric acid |
| Gaba | gamma-aminobutyric acid or 4-aminobutyric acid |
| Gly[4-Pip(N-amidino)] | glycine[4-piperidinyl(N-amidino)] |
| Harg | homoarginine |
| Hle | homoleucine |
| Hser | homoserine |
| Hyp | 4-hydroxyproline |
| Isp | isopropyl |
| Lys(Ac) | lysine(N-epsilon-acetyl) |
| Lys(Isp) | lysine(N-epsilon-isopropyl) |
| Lys(Nic) | lysine(N-epsilon-nicotinyl) |
| Met(O) | methionine sulfoxide |
| Met(O$_2$) | methionine sulfone |
| MeOAc or (MeO)acetyl | methoxyacetyl |
| 1Nal | 3-(naphth-1-yl)alanine |
| 2Nal | 3-(naphth-2-yl)alanine |
| N-Ac-Sar | N-acetylsarcosine |
| Neopentylgly | neopentylglycine |
| NEtGly | N-ethylglycine |
| Norarg | norarginine |
| Octylgly | 2-(octyl)glycine |
| Orn(Ac) | ornithine(N-delta-acetyl) |
| Orn(2-imidazo) | ornithine[N-delta-(2-imidazolinyl)] |
| Orn(Isp) | ornithine(N-delta-isopropyl) |
| Orn(Nic) | ornithine(N-delta-nicotinyl) |
| O-TBDMS | O-t-butyldimethylsilyl |
| Pen | penicillamine or β,β-dimethylcysteine |
| Pen(Acm) | penicillamine(acetamidomethyl) |
| D-Phe(3,4,5-triF) | D-3-(3,4,5-trifluorophenyl)alanine |
| D-Phe(3,4-diMeO) | D-3-(3,4-dimethoxyphenyl)alanine |
| Phe(4-CH$_2$OH) | 3-(4-hydroxymethylphenyl)alanine |
| Phe(4-CONH$_2$) | 3-(4-carboxyamidephenyl)alanine |
| Phe(4-guanidino) | 3-(4-guanidinophenyl)alanine |
| D-Phe(4-Me) | D-3-(4-methylphenyl)alanine |
| D-Phe(4-NH$_2$) | D-3-(4-aminophenyl)alanine |
| Phe(4-NIsp) | 3-(4-amino-N-isopropylphenyl)alanine |
| Phe(4-CH$_2$NHIsp) | [(4-amino(N-isopropyl)methyl)phenyl]alanine |
| D-Phe(4-NO$_2$) | D-3-(4-nitrophenyl)alanine |
| Propargylgly | propargylglycine |
| Pip | pipecolic acid or homoproline |
| pyBrop | bromo-tris-pyrrolidinophosphoniumhexafluorophosphate |
| Ser(Bzl) | serine(O-benzyl) |
| tButylgly | t-butylglyine |
| Thr(Bzl) | threonine(O-benzyl) |
| Tic | 1,2,3,4-tetrahydroisoquinoline-3-carboxylic acid |
| Trt | trityl |
| Tyr(Bzl) | tyrosine(O-benzyl) |
| Tyr(Et) | tyrosine(O-ethyl) |
| THF | tetrahydrofuryl or tetrahydrofuran |
| 2-THFcarbonyl | (tetrahydro-2-furyl)carbonyl |

When not found in the table above, nomenclature and abbreviations may be further clarified by reference to the Calbiochem-Novabiochem Corp. 1999 *Catalog and Peptide Synthesis Handbook* or the Chem-Impex International, Inc. *Tools for Peptide & Solid Phase Synthesis 1998–1999 Catalogue.*

The term "pharmaceutically acceptable salt" as used herein refers to salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences,* 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable solvate" represents an aggregate that comprises one or more molecules of the solute, such as a formula (I) compound, with one or more molecules of solvent.

The term "pharmaceutically acceptable prodrugs" as used herein refers to those prodrugs of the compounds of the present invention which are, within the scope of sound medical judgement, suitable for use in contact with with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "receptor" as used herein refers to a chemical group or molecule on the cell surface or in the cell interior that has an affinity for a specific chemical group, molecule, or virus. Isolation of receptors relevant to the antiangiogenic activity of the peptide of the invention can provide useful diagnostic tools.

In one embodiment, the present invention relates to compounds of the structure

$$A_0\text{-}A_1\text{-}A_2\text{-}A_3\text{-}A_4\text{-}A_5\text{-}A_6\text{-}A_7\text{-}A_8\text{-}A_9\text{-}A_{10} \quad (I)$$

wherein $A_0$, $A_1$, $A_2$, $A_3$, $A_7$, $A_8$, $A_9$, and $A_{10}$ are as defined above. The N-terminus of a nonapeptide represented by $A_1$-$A_9$ can be modified by an amino acyl group represented by $A_0$. $A_{10}$ represents a group suitable for modifying the C-terminus of the compound.

In the present embodiment, As is an amino acyl residue having a D configuration selected from D-allo-isoleucyl, D-allylglycyl, D-3-(3-cyanophenyl)alanyl, D-cystyl, D-isoleucyl, D-leucyl, D-penicillaminyl, D-phenylalanyl, D-3-(3,4,5-trifluorophenyl)alanyl, and D-3-(4-aminophenyl)alanyl; $A_5$ is an amino acyl residue selected from octylglycyl, glycyl, penicillaminyl, seryl, threonyl, and tyrosyl; and $A_6$ is an amino acyl residue selected from glutaminyl, leucyl, norvalyl, and seryl.

In another embodiment of the invention, the compounds have the structure (I) as defined above wherein $A_1$ is sarcosyl, $A_2$ is glycyl, $A_3$ is valyl, $A_7$ is isoleucyl, $A_8$ is arginyl, and $A_9$ is prolyl. Compounds of the present embodiment can be represented by the structure

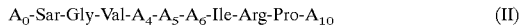

$$A_0\text{-Sar-Gly-Val-}A_4\text{-}A_5\text{-}A_6\text{-Ile-Arg-Pro-}A_{10} \quad (II)$$

wherein $A_0$ is hydrogen or an acyl group modifying the N-terminus. Suitable groups for $A_0$ can represented by the formula $R\text{---}(CH_2)_n\text{---}C(O)\text{---}$; wherein n is an integer from 0 to 8 and R is selected from hydroxyl; methyl; N-acetylamino; methoxyl; carboxyl; cyclohexyl optionally containing a one or two double bonds and optionally substituted with one to three hydroxyl groups; and a 5- or 6-membered ring aromatic or nonaromatic ring optionally containing one or two heteroatoms selected from nitrogen, oxygen, and sulfur, wherein the ring is optionally substituted with a moiety selected from alkyl, alkoxy, and halogen; or $R^1\text{---}CH_2CH_2\text{---}(OCH_2CH_2O)_p\text{---}CH_2\text{---}C(O)\text{---}$; wherein $R^1$ is selected from hydrogen, alkyl, and N-acetylamino, and p is an integer from 1 to 8.

$A_4$ is an amino acyl residue of L or D configuration selected from allo-isoleucyl, dehydroleucyl, glycyl, isoleucyl, prolyl, D-alanyl, D-3-(naphth-1-yl)alanyl, D-3-(naphth-2-yl)alanyl, D-(3-pyridyl)-alanyl, D-2-aminobutyryl, D-allo-isoleucyl, D-allo-threonyl, D-allylglycyl, D-asparaginyl, D-aspartyl, D-benzothienyl, D-3-(4,4'-biphenyl)alanyl, D-chlorophenylalanyl, D-3-(3-trifluoromethylphenyl)alanyl, D-3-(3cyanophenyl)alanyl, D-3-(3,4difluorophenyl)alanyl, D-citrullyl, D-cyclohexylalanyl, D-cyclohexylglycyl, D-cystyl, D-cystyl(S-t-butyl), D-glutaminyl, D-glutamyl, D-histidyl, D-homoisoleucyl, D-homophenylalanyl, D-homoseryl, D-isoleucyl, D-leucyl, D-lysyl(N-epsilon-nicotinyl), D-lysyl, D-methionyl, D-neopentylglycyl, D-norleucyl, D-norvalyl, D-ornithyl, D-penicillaminyl, D-penicillaminyl (acetamidomethyl), D-penicillaminyl(S-benzyl), D-phenylalanyl, D-3-(4-aminophenyl)alanyl, D-3-(4-methylphenyl)alanyl, D-3-(4-nitro-phenyl)alanyl, D-3-(3,4-dimethoxyphenyl)alanyl, D-3-(3,4,5-trifluorophenyl)alanyl, D-prolyl, D-seryl, D-seryl(O-benzyl), D-t-butylglycyl, D-thienylalanyl, D-threonyl, D-threonyl(O-benzyl), D-tryptyl, D-tyrosyl(O-benzyl), D-tyrosyl(O-ethyl), D-tyrosyl, and D-valyl.

$A_5$ is an amino acyl residue, of L or D configuration selected from alanyl, (3-pyridyl)-alanyl, 3-(naphth-1-yl) alanyl, 3naphth-2-yl)alanyl, allo-threonyl, allylglycyl, glutaminyl, glycyl, histidyl, homoseryl, isoleucyl, lysyl(N-epsilon-acetyl), methionyl, norvalyl, octylglycyl, ornithyl, 3-(4-hydroxymethylphenyl)alanyl, prolyl, seryl, threonyl, tryptyl, tyrosyl, D-allo-threonyl, D-homoseryl, D-seryl, D-threonyl, penicillaminyl, and cystyl.

$A_6$ is an amino acyl residue of L or D configuration selected from alanyl, 3-(naphth-1-yl)alanyl, 3-(naphth-2-yl) alanyl, (3-pyridyl)alanyl, 2-aminobutyryl, allylglycyl, arginyl, asparaginyl, aspartyl, citrullyl, cyclohexylalanyl, glutaminyl, glutamyl, glycyl, histidyl, homoalanyl, homoleucyl, homoseryl, isoleucyl, leucyl, lysyl(N-epsilon-acetyl), lysyl(N-epsilon-isopropyl), methionyl(sulfone), methionyl(sulfoxide), methionyl, norleucyl, norvalyl, octylglycyl, phenylalanyl, 3-(carboxyamidephenyl)alanyl, propargylglycyl, seryl, threonyl, tryptyl, tyrosyl, valyl, D-3-(naphth-1-yl)alanyl, D-3-(naphth-2-yl)alanyl, D-glutaminyl, D-homoseryl, D-leucyl, D-norvalyl, D-seryl, penicillaminyl, and cystyl.

$A_{10}$ is a hydroxyl group or an amino acid amide selected from azaglycylamide, D-alanylamide, D-alanylethylamide, glycylamide, glycylethylamide, sarcosylamide, serylamide, D-serylamide, or $A_{10}$ is a group represented by the formula

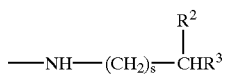

$$\text{---NH---}(CH_2)_s\text{---}\underset{\underset{R^2}{|}}{C}HR^3$$

or a group represented by the formula $\text{---NH---}R^4$, wherein s is an integer selected from 0 to 8; $R^2$ is selected from hydrogen, alkyl, and a 5- to 6-membered cycloalkyl ring; $R^3$ is selected from hydrogen, hydroxy, alkyl, phenyl, alkoxy, and a 5- to 6-membered ring optionally containing from one to two heteroatoms selected from oxygen, nitrogen, and sulfur, provided that s is not zero when $R^3$ is hydroxy or alkoxy; and $R^4$ is selected from hydrogen, hydroxy, and a 5- to 6-membered cycloalkyl ring.

Preferred compounds of the invention have the structure (II) as defined above, wherein $A_4$ is an amino acyl residue having a D configuration selected from D-alanyl, D-3-(naphth-1-yl)alanyl, D-3 naphth-2-yl)alanyl, D-(3-pyridyl)-alanyl, D-2-aminobutyryl, D-allo-isoleucyl, D-allo-threonyl, D-allylglycyl, D-asparaginyl, D-aspartyl, D-chloro-phenylalanyl, D-3-(3-trifluoromethylphenyl) alanyl, D-3-(3-cyanophenyl)alanyl, D-3-(3,4-difluorophenyl)alanyl, D-cyclohexylalanyl, D-cyclohexylglycyl, D-cystyl, D-glutaminyl, D-glutamyl, D-histidyl, D-homoisoleucyl, D-homophenylalanyl, D-homoseryl, D-isoleucyl, D-leucyl, D-lysyl(N-epsilon-nicotinyl), D-methionyl, D-neopentylglycyl, D-norleucyl, D-norvalyl, D-penicillaminyl, D-penicillaminyl (acetamidomethyl), D-penicillaminyl(S-benzyl), D-phenylalanyl, 3(4-aminophenyl)alanyl, D-3-(4-methylphenyl)alanyl, D-3(4-nitrophenyl)alanyl, D-3(3,4-dimethoxyphenyl)alanyl, D-3-(3,4,5-trifluorophenyl)alanyl, D-prolyl, D-seryl, D-seryl(O-benzyl), D-t-butylglycyl, D-thienylalanyl, D-threonyl, D-threonyl(O-benzyl), D-tyrosyl(O-ethyl), D-tyrosyl, D-valyl, and D-cystyl.

Other preferred compounds of the present invention have the structure of formula (II), wherein $A_5$ is selected from glycyl, octylglycyl, penicillaminyl, seryl, threonyl, and tyrosyl.

Additional preferred compounds of the present invention have the structure represented by formula (II), wherein $A_6$ is selected from glutaminyl, leucyl, norvalyl, and seryl.

The more preferred amino acid residues for substituting the position represented by $A_4$ are D configuration amino acids selected from D-allo-isoleucyl, D-allylglycyl, D-3-(3-cyanophenyl)alanyl, D-cystyl, D-isoleucyl, D-leucyl, D-penicillaminyl, D-phenylalanyl, D-3-(3,4,5-trifluorophenyl)alanyl, and D-3-(4aminophenyl)alanyl.

Preferred $A_0$ groups for modifying the N-terminus of the compounds in the scope of the invention are selected from acetyl, butyryl, caproyl, (4N-acetylamino)butyryl, N-acetyl-beta-alanyl, (6-N-acetylamino)caproyl, chloronicotinyl, cyclohexylacetyl, furoyl, gamma-aminobutyryl, 2-methoxyacetyl, methylnicotinyl, nicotinyl, (8-N-acetylamino)-3,6-dioxo-octanoyl, phenylacetyl, propionyl, shikimyl, succinyl, and tetrahydrofuroyl.

The preferred $A_{10}$ groups for modifying the C-terminus of the invention are selected from D-alanylamide, azaglycylamide, serylamide, ethylamide; hydroxylamide, isopropylamide, propylamide, 2-(cyclohexyl)ethylamide, 2-(1-pyrrolidine)ethylamide, 1-(cyclohexyl)ethylamide, 2-(methoxy)ethylamide, 2-hydroxy)ethylamide, 2-(2-pyridine)ethylamide, (2-pyridine)methylamide, 2-(3-pyridine)ethylamide, 2-(2-(1-methyl)pyrrolidine)ethylamide, 2-(N-morpholine)ethylamide, and cyclopropylmethylamide.

Compounds contemplated as failing within the scope of the present invention include, but are not limited to:

N-Ac-Sar-Gly-Val-D-Ile-Thr-Nva-Ile-Arg-ProNHCH$_2$CH$_3$,
pyroGlu-Gly-Val-D-Ile-Thr-Nva-Ile-Arg-ProNHCH$_2$CH$_3$,
N-Ac-Sar-Gly-Val-D-Ile-Thr-Nva-Ile-Arg-ProNHCH$_3$,
N-Ac-Sar-Gly-Val-D-Ile-Thr-Nva-Ile-Arg-ProNHCH$_2$(CH$_3$)$_2$,
N-Ac-Sar-Gly-Val-D-Ile-Thr-Nva-Ile-Arg-ProNHCH$_2$CH$_2$-(1-pyrrolidine),
N-Ac-Sar-Gly-Val-D-Ile-Thr-Nva-Ile-Arg-ProNHethylpiperidine,
N-Ac-Sar-Gly-Val-D-Ile-Thr-Nva-Ile-Arg-ProNHmethylcyclopropyl,
N-Ac-Sar-Gly-Val-D-Ile-Thr-Nva-Ile-Arg-ProNH(ethyl-1-(R)-cyclohexyl),
N-Ac-Sar-Gly-Val-D-Ile-Thr-Nva-Ile-Arg-ProNH$_2$,
N-Ac-Sar-Gly-Val-D-Ile-Thr-Nva-Ile-Arg-ProNHCH$_2$CH$_2$OCH$_3$,
N-Ac-Sar-Gly-Val-D-Ile-Thr-Nva-Ile-Arg-ProNHCH$_2$CH$_2$cyclohexyl,
N-Ac-Sar-Gly-Val-D-Ile-Thr-Nva-Ile-Arg-ProNHCH$_2$(CH$_3$)$_2$,
N-Ac-Sar-Gly-Val-D-alloIle-Thr-Nva-Ile-Arg-ProNHCH$_2$CH$_3$,
N-Ac-Sar-Gly-Val-D-Leu-Thr-Nva-Ile-Arg-ProNHCH$_2$CH$_3$,
N-Ac-Sar-Gly-Val-Ile-Thr-Nva-Ile-Arg-ProNHCH$_2$CH$_3$,
N-Ac-Sar-Gly-Val-Gly-Thr-Nva-Ile-Arg-ProNHCH$_2$CH$_3$,
N-Ac-Sar-Gly-Val-D-Val-Thr-Nva-Ile-Arg-ProNHCH$_2$CH$_3$,
N-Ac-Sar-Gly-Val-D-Ala-Thr-Nva-Ile-Arg-ProNHCH$_2$CH$_3$,
N-Ac-Sar-Gly-Val-D-Met-Thr-Nva-Ile-Arg-ProNHCH$_2$CH$_3$,
N-Ac-Sar-Gly-Val-D-Nle-Thr-Nva-Ile-Arg-ProNHCH$_2$CH$_3$,
N-Ac-Sar-Gly-Val-D-Phe-Thr-Nva-Ile-Arg-ProNHCH$_2$CH$_3$,
N-Ac-Sar-Gly-Val-D-Tyr-Thr-Nva-Ile-Arg-ProNHCH$_2$CH$_3$,
N-Ac-Sar-Gly-Val-D-4,4'-Biphenylala-Thr-Nva-Ile-Arg-ProNHCH$_2$CH$_3$,
N-Ac-Sar-Gly-Val-D-Cha-Thr-Nva-Ile-Arg-ProNHCH$_2$CH$_3$,
N-Ac-Sar-Gly-Val-D-Chg-Thr-Nva-Ile-Arg-ProNHCH$_2$CH$_3$,
N-Ac-Sar-Gly-Val-D-4-ClPhe-Thr-Nva-Ile-Arg-ProNHCH$_2$CH$_3$,
N-Ac-Sar-Gly-Val-D-Hphe-Thr-Nva-Ile-Arg-ProNHCH$_2$CH$_3$,
N-Ac-Sar-Gly-Val-Dehydroleu-Thr-Nva-Ile-Arg-ProNHCH$_2$CH$_3$,
N-Ac-Sar-Gly-Val-D-3-CF$_3$Phe-Thr-Nva-Ile-Arg-ProNHCH$_2$CH$_3$,
N-Ac-Sar-Gly-Val-D-pentaFPhe-Thr-Nva-Ile-Arg-ProNHCH$_2$CH$_3$,
N-Ac-Sar-Gly-Val-D-3,4-diClPhe-Thr-Nva-Ile-Arg-ProNHCH$_2$CH$_3$,
N-Ac-Sar-Gly-Val-D-3-ClPhe-Thr-Nva-Ile-Arg-ProNHCH$_2$CH$_3$,
N-Ac-Sar-Gly-Val-D-2-Thienylala-Thr-Nva-Ile-Arg-ProNHCH$_2$CH$_3$,
N-Ac-Sar-Gly-Val-D-3-CNPhe-Thr-Nva-Ile-Arg-ProNHCH$_2$CH$_3$,
N-Ac-Sar-Gly-Val-D-Ile-Thr-DNva-Ile-Arg-ProNHCH$_2$CH$_3$,
N-Ac-Sar-Gly-Val-D-Ile-Thr-Gln-Ile-Arg-ProNHCH$_2$CH$_3$,
N-Ac-Sar-Gly-Val-D-Ile-Thr-Cha-Ile-Arg-ProNHCH$_2$CH$_3$,
N-Ac-Sar-Gly-Val-D-Ile-Thr-Gly-Ile-Arg-ProNHCH$_2$CH$_3$,
N-Ac-Sar-Gly-Val-D-Ile-Thr-Ala-Ile-Arg-ProNHCH$_2$CH$_3$,
N-Ac-Sar-Gly-Val-D-Ile-Thr-Val-Ile-Arg-ProNHCH$_2$CH$_3$,
N-Ac-Sar-Gly-Val-D-Ile-Thr-Abu-Ile-Arg-ProNHCH$_2$CH$_3$
N-Ac-Sar-Gly-Val-D-Ile-Thr-Allylgly-Ile-Arg-ProNHCH$_2$CH$_3$,
N-Ac-Sar-Gly-Val-D-Ile-Thr-Octylgly-Ile-Arg-ProNHCH$_2$CH$_3$,
N-Ac-Sar-Gly-Val-D-Ile-Thr-Met-Ile-Arg-ProNHCH$_2$CH$_3$,
N-Cyclohexylacetyl-Sar-Gly-Val-D-Ile-Thr-Nva-Ile-Arg-ProNHCH$_2$CH$_3$,
N-(2-Me-Nicotinyl)-Sar-Gly-Val-D-Ile-Thr-Nva-Ile-Arg-ProNHCH$_2$CH$_3$,
N-Succinyl-Sar-Gly-Val-D-Ile-Thr-Nva-Ile-Arg-ProNHCH$_2$CH$_3$,
N-Nicotinyl-Sar-Gly-Val-D-Ile-Thr-Nva-Ile-Arg-ProNHCH$_2$CH$_3$,
N-Propionyl-Sar-Gly-Val-D-Ile-Thr-Nva-Ile-Arg-ProNHCH$_2$CH$_3$,
N-(MeO)acetyl-Sar-Gly-Val-D-Ile-Thr-Nva-Ile-Arg-ProNHCH$_2$CH$_3$,
N-(Shikimyl)-Sar-Gly-Val-D-Ile-Thr-Nva-Ile-Arg-ProNHCH$_2$CH$_3$,
N-(2-Furoyl)-Sar-Gly-Val-D-Ile-Thr-Nva-Ile-Arg-ProNHCH$_2$CH$_3$,
N-Butyryl-Sar-Gly-Val-D-Ile-Thr-Nva-Ile-Arg-ProNHCH$_2$CH$_3$,
N(2-THFcarbonyl)-Sar-Gly-Val-D-Ile-Thr-Nva-Ile-Arg-ProNHCH$_2$CH$_3$,
N—[CH$_3$CONH—(CH$_2$)$_2$—O—(CH$_2$)$_2$—O—CH$_2$—C(O)]-Sar-Gly-Val-D-Ile-Thr-Nva-Ile-Arg-ProNHCH$_2$CH$_3$
N[6-N-acetyl-(CH$_2$)5C(O)]-Sar-Gly-Val-D-Ile-Thr-Nva-Ile-Arg-ProNHCH$_2$CH$_3$,
N-Hexanoyl-Sar-Gly-Val-D-Ile-Thr-Nva-Ile-Arg-ProNHCH$_2$CH$_3$,
N-[4-N-Acetylaminobutyryl]-Sar-Gly-Val-D-Ile-Thr-Nva-Ile-Arg-ProNHCH$_2$CH$_3$,
H-Sar-Gly-Val-D-Ile-Thr-Nva-Ile-Arg-ProNHCH$_2$CH$_3$,
N-Ac-Sar-Gly-Asn-D-Ile-Thr-Nva-Ile-Arg-ProNHCH$_2$CH$_3$, N—[CH₃C(O)NH—(CH₂)₂—O—(CH₂)₂—O—CH₂—C(O)]-Gly-Val-D-Ile-Thr-Nva-Ile-Arg-ProNHCH₂CH₃,
N-Ac-Pro-Gly-Val-D-Ile-Thr-Nva-Ile-Arg-ProNHCH₂CH₃,
N-Ac-Gly-Gly-Val-D-Ile-Thr-Nva-Ile-Arg-ProNHCH₂CH₃,
N-Ac-Ala-Gly-Val-D-Ile-Thr-Nva-Ile-Arg-ProNHCH₂CH₃,
N-Ac-NEtGly-Gly-Val-D-Ile-Thr-Nva-Ile-Arg-ProNHCH₂CH₃,
N-Ac-Sar-Gly-Val-D-Il-Thr-Leu-Il-Arg-ProNHCH₂CH₃,
N-Ac-Sar-Gly-Val-D-Ile-Thr-Ser-Ile-Arg-ProNHCH₂CH₃,
N-Ac-Sar-Gly-Val-D-Ile-Thr-Nva-Ile-Arg-Pro-D-AlaNH₂
N-Ac-Sar-Gly-Val-D-Ile-Thr-Nva-Ile-Arg-D-ProNHCH₂CH₃,
N-Ac-Sar-Gly-Val-D-Ile-Thr-Nva-Ile-Arg-AbuNHCH₂CH₃,
N-Ac-Sar-Gly-Val-D-Ile-Thr-Nva-Ile-Arg-Phe-NHCH₂CH₃,
N-Ac-Sar-Gly-Val-D-Ile-Thr-Nva-Ile-Arg-Tic-NHCH₂CH₃,
N-Ac-Sar-Gly-Val-D-Ile-Thr-Nva-Ile-Arg-Hyp-NHCH₂CH₃,
N-Ac-Sar-Gly-Val-D-Ile-Thr-Nva-Ile-Arg-Aib-NHCH₂CH₃,
N-Ac-Sar-Gly-Val-D-Ile-Thr-Nva-Ile-Arg-D-Ala-NHCH₂CH₃,
N-Ac-Sar-Gly-Val-D-Ile-Thr-Nva-Ile-Arg-Pip-NHCH₂CH₃,
N-Ac-Sar-Gly-Val-D-Tyr(Et)-Thr-Nva-Ile-Arg-ProNHCH₂CH₃,
N-Ac-Sar-Gly-Val-D-Cys(tBu)-Thr-Nva-Ile-Arg-ProNHCH₂CH₃,
N-Ac-Sar-Gly-Val-D-Cys-Thr-Nva-Ile-Arg-ProNHCH₂CH₃,
N-Ac-Sar-Gly-Val-D-Tyr(Bzl)-Thr-Nva-Ile-Arg-ProNHCH₂CH₃,
N-Ac-Sar-Gly-Val-D-Ser(Bzl)-Thr-Nva-Ile-Arg-ProNHCH₂CH₃,
N-Ac-Sar-Gly-Val-D-1Nal-Thr-Nva-Ile-Arg-ProNHCH₂CH₃,
N-Ac-Sar-Gly-Val-D-tButylgly-Thr-Nva-Ile-Arg-ProNHCH₂CH₃,
N-Ac-Sar-Gly-Val-D-Orn-Thr-Nva-Ile-Arg-ProNHCH₂CH₃,
N-Ac-Sar-Gly-Val-D-Thr(Bzl)-Thr-Nva-Ile-Arg-ProNHCH₂CH₃,
N-Ac-Sar-Gly-Val-D-2Nal-Thr-Nva-Ile-Arg-ProNHCH₂CH₃,
N-Ac-Sar-Gly-Val-D-Phe(4-Me)-Thr-Nva-Ile-Arg-ProNHCH₂CH₃,
N-Ac-Sar-Gly-Val-D-Phe(3,4-diMeO)-Thr-Nva-Ile-Arg-ProNHCH₂CH₃,
N-Ac-Sar-Gly-Val-D-Phe(3,4,5-triF)-Thr-Nva-Ile-Arg-ProNHCH₂CH₃,
N-Ac-Sar-Gly-Val-D-(4-NO₂)Phe-Thr-Nva-Ile-Arg-ProNHCH₂CH₃,
N-Ac-Sar-Gly-Val-D-Pen-Thr-Nva-Ile-Arg-ProNHCH₂CH₃,
N-Ac-Sar-Gly-Val-D-Pen(Acm)-Thr-Nva-Ile-Arg-ProNHCH₂CH₃,
N-Ac-Sar-Gly-Val-D-Abu-Thr-Nva-Ile-Arg-ProNHCH₂CH₃,
N-Ac-Sar-Gly-Val-D-Phe(4-NH₂)-Thr-N-Nva-Ile-Arg-ProNHCH₂CH₃,
N-Ac-Sar-Gly-Val-D-Leu-Thr-Nva-Ala-Arg-ProNHCH₂CH₃,
N-Ac-Sar-Gly-Val-D-Leu-Thr-Nva-Met-Arg-ProNHCH₂CH₃,
N-Ac-Sar-Gly-Val-D-Leu-Thr-Nva-Phe-Arg-ProNHCH₂CH₃,
N-Ac-Sar-Gly-Val-D-Leu-Thr-Nva-Tyr-Arg-ProNHCH₂CH₃,
N-Ac-Sar-Gly-Val-D-Leu-Thr-Nva-Nva-Arg-ProNHCH₂CH₃,
N-Ac-Sar-Gly-Val-D-Leu-Thr-Nva-Asp-Arg-ProNHCH₂CH₃,
N-Ac-Sar-Gly-Val-D-Leu-Thr-Nva-Gly-Arg-ProNHCH₂CH₃,
N-Ac-Sar-Gly-Val-D-Leu-Thr-Nva-Lys(Ac)-Arg-ProNHCH₂CH₃,
N-Ac-Sar-Gly-Val-D-Leu-Thr-Nva-Leu-Arg-ProNHCH₂CH₃,
N-Ac-Sar-Gly-Val-D-Leu-Thr-Nva-2Nal-Arg-ProNHCH₂CH₃,
N-Ac-Sar-Gly-Val-D-Leu-Thr-Nva-1Nal-Arg-ProNHCH₂CH₃,
N-Ac-Sar-Gly-Val-D-Leu-Thr-Nva-Allylgly-Arg-ProNHCH₂CH₃,
N-Ac-Sar-Gly-Val-D-Leu-Thr-Nva-Cit-Arg-ProNHCH₂CH₃,
N-Ac-Sar-Gly-Val-D-Leu-Ala-Nva-Ile-Arg-ProNHCH₂CH₃,
N-Ac-Sar-Gly-Val-D-Leu-Pro-Nva-Ile-Arg-ProNHCH₂CH₃,
N-Ac-Sar-Gly-Val-D-Leu-Trp-Nva-Ile-Arg-ProNHCH₂CH₃,
N-Ac-Sar-Gly-Val-D-Leu-Tyr-Nva-Ile-Arg-ProNHCH₂CH₃,
N-Ac-Sar-Gly-Val-D-Leu-Nva-Nva-Ile-Arg-ProNHCH₂CH₃,
N-Ac-Sar-Gly-Val-D-Leu-Gly-Nva-Ile-Arg-ProNHCH₂CH₃,
N-Ac-Sar-Gly-Val-D-Leu-Lys(Ac)-Nva-Ile-Arg-ProNHCH₂CH₃,
N-Ac-Sar-Gly-Val-D-Leu-2Nal-Nva-Ile-Arg-ProNHCH₂CH₃,
N-Ac-Sar-Gly-Val-D-Leu-1Nal-Nva-Ile-Arg-ProNHCH₂CH₃,
N-Ac-Sar-Gly-Val-D-Leu-Octylgly-Nva-Ile-Arg-ProNHCH₂CH₃,
N-Ac-Sar-Gly-Val-D-Leu-Gln-Nva-Ile-Arg-ProNHCH₂CH₃,
N-Ac-Sar-Gly-Val-D-Leu-Met-Nva-Ile-Arg-ProNHCH₂CH₃,
N-Ac-Sar-Gly-Val-D-Leu-Ser-Nva-Ile-Arg-ProNHCH₂CH₃,
N-Ac-Sar-Gly-Val-D-Leu-Allylgly-Nva-Ile-Arg-ProNHCH₂CH₃,
N-Ac-Sar-Gly-Val-D-Leu-Ile-Nva-Ile-Arg-ProNHCH₂CH₃,
N-Ac-Sar-Gly-Val-D-Leu-D-Thr-Nva-Ile-Arg-ProNHCH₂CH₃,
N-Ac-Sar-Gly-Val-D-Ile-Thr-Ile-Ile-Arg-ProNHCH₂CH₃,
N-Ac-Sar-Gly-Val-D-Ile-Thr-Nle-Ile-Arg-ProNHCH₂CH₃,
N-Ac-Sar-Gly-Val-D-Ile-Thr-Cit-Ile-Arg-ProNHCH₂CH₃,
N-Ac-Sar-Gly-Val-D-Ile-Thr-Met(O₂)-Ile-Arg-ProNHCH₂CH₃,
N-Ac-Sar-Gly-Val-D-Ile-Thr-Arg-Ile-Arg-ProNHCH₂CH₃,
N-Ac-Sar-Gly-Val-D-Ile-Thr-Tyr-Ile-Arg-ProNHCH₂CH₃,
N-Ac-Sar-Gly-Val-D-Ile-Thr-Glu-Ile-Arg-ProNHCH₂CH₃,
N-Ac-Sar-Gly-Val-D-Ile-Thr-Lys(Ac)-Ile-Arg-ProNHCH₂CH₃,
N-Ac-Sar-Gly-Val-D-Ile-Thr-Propargylgly-Ile-Arg-ProNHCH₂CH₃,
N-Ac-Sar-Gly-Val-alloIle-Thr-Gln-Ile-Arg-ProNHCH₂CH₃,
N-Ac-Sar-Gly-Val-D-Leu-Thr-Gln-Ile-Arg-ProNHCH₂CH₃, N-Ac-Bala-Sar-Gly-Val-D-Ile-Thr-Nva-Ile-Arg-ProNHCH₂CH₃,
N-Phenylacetyl-Sar-Gly-Val-D-Ile-Thr-Nva-Ile-Arg-ProNHCH₂CH₃,
N-Ac-Sar-Gly-Val-D-Ile-Thr-Nva-Ile-Arg-Pro-Azagly-NH₂,
N-Ac-Sar-Gly-Val-D-Ile-Thr-Nva-Ile-Arg-Sar-NHCH₂CH₃,
N-Ac-Sar-Gly-Val-D-Ile-Thr-Nva-Ile-Arg-Pro-SerNH₂,
N-Succinyl-Sar-Gly-Val-D-Leu-Thr-Nva-Ile-Arg-ProNHCH₂CH₃,
N-Ac-Sar-Ala-Val-D-Ile-Thr-Nva-Ile-Arg-ProNHCH₂CH₃,
N-Ac-Sar-Leu-Val-D-Ile-Thr-Nva-Ile-Arg-ProNHCH₂CH₃,
N-Ac-Sar-Phe-Val-D-Ile-Thr-Nva-Ile-Arg-ProNHCH₂CH₃,
N-Ac-Sar-Glu-Val-D-Ile-Thr-Nva-Ile-Arg-ProNHCH₂CH₃,
N-Ac-Sar-Pro-Val-D-Leu-Thr-Nva-Ile-Arg-ProNHCH₂CH₃,
N-Ac-Sar-Asn-Val-D-Leu-Thr-Nva-Ile-Arg-ProNHCH₂CH₃,
N-Ac-Sar-Asn-Val-D-Leu-Thr-Nva-Ile-Arg-ProNHCH₂CH₃,
N-Ac-Asn-Gly-Val-D-Leu-Thr-Nva-Ile-Arg-ProNHCH₂CH₃,
N-Ac-Gln-Gly-Val-D-Leu-Thr-Nva-Ile-Arg-ProNHCH₂CH₃,
N-Ac-Ser-Gly-Val-D-Leu-Thr-Nva-Ile-Arg-ProNHCH₂CH₃,
N-Ac-Cit-Gly-Val-D-Leu-Thr-Nva-Ile-Arg-ProNHCH₂CH₃,
N-Ac-Glu-Gly-Val-D-Ile-Thr-Nva-Ile-Arg-ProNHCH₂CH₃,
N-Ac-Gaba-Gly-Val-D-Ile-Thr-Nva-Ile-Arg-ProNHCH₂CH₃,
N-Ac-Bala-Gly-Val-D-Ile-Thr-Nva-Ile-Arg-ProNHCH₂CH₃,
N-Ac-Gln-Gly-Val-D-Ile-Thr-Nva-Ile-Arg-ProNHCH₂CH₃,
N-Ac-Sar-Gly-Gly-D-Ile-Thr-Nva-Ile-Arg-ProNHCH₂CH₃,
N-Ac-Sar-Gly-Glu-D-Ile-Thr-Nva-Ile-Arg-ProNHCH₂CH₃,
N-Ac-Sar-Gly-Val-D-Ile-Thr-Gln-Ile-Arg-ProNHCH₂(CH₃)₂,
N-Succinyl-Sar-Gly-Val-D-Ile-Thr-Gln-Ile-Arg-ProNHCH₂CH₃,
N-Succinyl-Sar-Gly-Val-D-Leu-Thr-Gln-Ile-Arg-ProNHCH₂CH₃,
N-Succinyl-Sar-Gly-Val-D-Leu-Thr-Gln-Ile-Arg-ProNHCH₂(CH₃)₂,
N-Ac-Sar-Gly-Val-D-Leu-Thr-Asp-Ile-Arg-ProNHCH₂CH₃,
N-Ac-Sar-Gly-Val-D-Ile-Thr-Asp-Ile-Arg-ProNHCH₂CH₃,
N-Ac-Sar-Gly-Val-D-Ile-Thr-Asn-Ile-Arg-ProNHCH₂CH₃,
N-Ac-Sar-Gly-Val-D-Ile-Thr-Met(O)-Ile-Arg-ProNHCH₂CH₃,
N-Ac-Sar-Gly-Val-D-Leu-Thr-Asn-Ile-Arg-ProNHCH₂CH₃,
N-Ac-Sar-Gly-Val-D-Thr-Thr-Nva-Ile-Arg-ProNHCH₂CH₃,
N-Ac-Sar-Gly-Val-D-Ser-Thr-Nva-Ile-Arg-ProNHCH₂CH₃,
N-Ac-Sar-Gly-Val-D-Hser-Thr-Nva-Ile-Arg-ProNHCH₂CH₃,
N-Ac-Sar-Gly-Val-D-Gln-Thr-Nva-Ile-Arg-ProNHCH₂CH₃,
N-Ac-Sar-Gly-Val-D-Asn-Thr-Nva-Ile-Arg-ProNHCH₂CH₃,
N-Ac-Sar-Gly-Val-D-Cit-Thr-Nva-Ile-Arg-ProNHCH₂CH₃,
N-Ac-Sar-Gly-Val-D-Hcit-Thr-Nva-Ile-Arg-ProNHCH₂CH₃,
N-Ac-Sar-Gly-Val-D-Hle-Thr-Nva-Ile-Arg-ProNHCH₂CH₃,
N-Ac-Sar-Gly-Val-D-Neopentylgly-Thr-Nva-Ile-Arg-ProNHCH₂CH₃,
N-Ac-Sar-Gly-Val-D-Ile-Thr-Phe(4-CONH₂)-Ile-Arg-ProNHCH₂CH₃,
N-Ac-Sar-Gly-Val-D-Ile-Thr-Nva-Ile-His-ProNHCH₂CH₃,
N-Ac-Sar-Gly-Val-D-Ile-Thr-Nva-Ile-Lys(Isp)-ProNHCH₂CH₃,
N-Ac-Sar-Gly-Val-D-Ile-Thr-Nva-Ile-Lys(Nic)-ProNHCH₂CH₃,
N-Ac-Sar-Gly-Val-D-Ile-Thr-Nva-Ile-Orn(Nic)-ProNHCH₂CH₃,
N-Ac-Sar-Gly-Val-D-Ile-Ile-Thr-Nva-Ile-Orn(Isp)-ProNHCH₂CH₃,
N-Ac-Sar-Gly-Val-D-Ile-Thr-Nva-Ile-Phe(4-NIsp)-ProNHCH₂CH₃,
N-Ac-Sar-Gly-Val-D-Ile-Thr-Nva-Ile-Cha(4-NIsp)ProNHCH₂CH₃,
N-Ac-Sar-Gly-Val-D-Ile-Thr-Nva-Ile-Harg-ProNHCH₂CH₃,
N-Ac-Sar-Gly-Val-D-Ile-Thr-Nva-Ile-Norarg-ProNHCH₂CH₃,
N-Ac-Sar-Gly-Val-D-Ile-Thr-Nva-Ile-Cit-ProNHCH₂CH₃,
N-Ac-Sar-Gly-Val-D-Ile-Thr-Nva-Ile-Lys-ProNHCH₂CH₃,
N-Ac-Sar-Gly-Val-D-Ile-Phe(4-CH₂OH)-Nva-Ile-Arg-ProNHCH₂CH₃,
N-Ac-Sar-Gly-Val-D-Ile-Thr-Nva-Ile-Phe(4-guanidino)-ProNHCH₂CH₃,
N-Ac-Sar-Gly-Val-D-Ile-Thr-Nva-Ile-Aminopyrimidinylbutanoyl-ProNHCH₂CH₃,
N-Ac-Sar-Gly-Val-D-Ile-Thr-Nva-Ile-Phe(4-CH₂NHIsp)-ProNHCH₂CH₃,
N-Ac-Sar-Gly-Val-D-Ile-Thr-Nva-Ile-Gly[4-Pip(N-amidino)]-ProNHCH₂CH₃,
N-Ac-Sar-Gly-Val-D-Ile-Thr-Nva-Ile-Ala[4Pip(N-amidino)]-ProNHCH₂CH₃,
N-Ac-Sar-Gly-Val-D-Ile-Thr-Nva-Ile-Ala-(3-guanidino)-ProNHCH₂CH₃,
N-Ac-Sar-Gly-Val-D-Ile-Thr-Nva-Ile-Ala(3-pyrrolidinylamidino)-ProNHCH₂CH₃,
N-Ac-Sar-Gly-Val-D-Ile-Thr-Nva-Ile-Orn(2-imidazo)-ProNHCH₂CH₃,
N-Succinyl-Sar-Gly-Val-D-alloIle-Thr-Nva-Ile-Arg-ProNHCH₂CH₃,
N-Succinyl-Sar-Gly-Val-D-Ile-Thr-Gln-Ile-Arg-ProNHCH₂CH₃,
N-Succinyl-Sar-Gly-Val-D-Ile-Thr-Gln-Ile-Arg-Pro-D-AlaNH₂,
N-Succinyl-Sar-Gly-Val-D-alloIle-Thr-Gln-Ile-Arg-ProNHCH₂CH₃,
N-Succinyl-Sar-Gly-Val-D-alloIle-Thr-Gln-Ile-Arg-Pro-D-AlaNH₂,
N-Succinyl-Sar-Gly-Val-D-alloIle-Thr-Gln-Ile-Arg-ProNHCH₂(CH₃)₂,
N-Succinyl-Sar-Gly-Val-D-Ile-Thr-Gln-Ile-Arg-ProNHCH₂(CH₃)₂,
N-Ac-Sar-Gly-Val-D-alloIle-Thr-Nva-Ile-Arg-Pro-D-AlaNH₂,
N-Ac-Sar-Gly-Val-D-alloIle-Thr-Nva-Ile-Arg-ProNHCH₂(CH₃)₂,
N-Ac-Sar-Gly-Val-D-Ile-Thr-Gln-Ile-Arg-Pro-D-AlaNH₂,
N-Ac-Sar-Gly-Val-D-Ile-Thr-Gln-Ile-Arg-ProNHCH₂(CH₃)₂,
N-Ac-Sar-Gly-Val-D-alloIle-Thr-Gln-Ile-Arg-Pro-D-AlaNH₂,
N-Ac-Sar-Gly-Val-D-alloIle-Thr-Gln-Ile-Arg-ProNHCH₂(CH₃)₂,
N-Ac-Sar-Gly-Val-D-Ile-Thr-Nva-Ile-Arg-Pro-SarNH₂, N-Ac-Sar-Gly-Val-D-alloIle-Thr-Nva-Ile-Arg-Pro-SarNH$_2$,
N-Ac-Sar-Gly-Val-Ile-Thr-Gln-Ile-Arg-Pro-SarNH$_2$,
N-Ac-Sar-Gly-Val-D-alloIle-Thr-Gln-Ile-Arg-Pro-SarNH$_2$,
N-Ac-Sar-Gly-Val-D-alloIle-Thr-Ser-Ile-Arg-Pro-D-AlaNH$_2$,
N-Ac-Sar-Gly-Val-D-alloIle-Thr-Ser-Ile-Arg-ProNHCH$_2$(CH$_3$),
N-Ac-Sar-Gly-Val-D-alloIle-Thr-Ser-Ile-Arg-ProNHCH$_2$CH$_3$,
N-Ac-Sar-Gly-Val-D-Ile-Thr-Orn(Ac)-Ile-Arg-ProNHCH$_2$CH$_3$,
N-Ac-Sar-Gly-Val-D-Ile-Thr-Gln-Ile-Arg-Pro-AzaglyNH$_2$,
N-Ac-Sar-Gly-Val-D-alloIle-Thr-Nva-Ile-Arg-Pro-AzaglyNH$_2$,
N-Ac-Sar-Gly-Val-D-alloIle-Thr-Gln-Ile-Arg-Pro-AzaglyNH$_2$,
N-(2-THFcarbonyl)-Sar-Gly-Val-D-alloIle-Thr-Nva-Ile-Arg-ProNHCH$_2$CH$_3$,
N-(2-THFcarbonyl)-Sar-Gly-Val-D-Ile-Thr-Gln-Ile-Arg-ProNHCH$_2$CH$_3$,
N-(2-THFcarbonyl)-Sar-Gly-Val-D-alloIle-Thr-Gln-Ile-Arg-ProNHCH$_2$CH$_3$,
N-(2-THFcarbonyl)-Sar-Gly-Val-D-Ile-Thr-Gln-Ile-Arg-Pro-D-AlaNH$_2$,
N-(2-THFcarbonyl)-Sar-Gly-Val-D-alloIle-Thr-Gln-Ile-Arg-Pro-D-AlaNH$_2$,
N-(2-THFcarbonyl)-Sar-Gly-Val-D-alloIle-Thr-Gln-Ile-Arg-ProNHCH$_2$(CH$_3$),
N-(6-Ac-Aca)-Sar-Gly-Val-D-alloIle-Thr-Nva-Ile-Arg-ProNHCH$_2$CH$_3$,
N-(6-Ac-Aca)-Sar-Gly-Val-D-Ile-Thr-Gln-Ile-Arg-ProNHCH$_2$CH$_3$,
N-(6-Ac-Aca)-Sar-Gly-Val-D-alloIle-Thr-Gln-Ile-Arg-ProNHCH$_2$CH$_3$,
N-(6-Ac-Aca)-Sar-Gly-Val-D-Ile-Thr-Gln-Ile-Arg-Pro-D-AlaNH2,
N-(6-Ac-Aca)-Sar-Gly-Val-D-alloIle-Thr-Gln-Ile-Arg-Pro-D-AlaNH$_2$,
N-(6-Ac-Aca)-Sar-Gly-Val-D-alloIle-Thr-Gln-Ile-Arg-ProNHCH$_2$(CH$_{32}$,
N-(4-Ac-Gaba)-Sar-Gly-Val-D-alloIle-Thr-Nva-Ile-Arg-ProNHCH$_2$CH$_3$,
N-(4-Ac-Gaba)-Sar-Gly-Val-D-Ile-Thr-Gln-Ile-Arg-ProNHCH$_2$CH$_3$,
N-(4-Ac-Gaba)-Sar-Gly-Val-D-alloIle-Thr-Gln-Ile-Arg-ProNHCH$_2$CH$_3$,
N-(4-Ac-Gaba)-Sar-Gly-Val-D-Ile-Thr-Gln-Ile-Arg-Pro-D-AlaNH$_2$,
N-(4-Ac-Gaba)-Sar-Gly-Val-D-alloIle-Thr-Gln-Ile-Arg-Pro-D-AlaNH$_2$,
N-(4-Ac-Gaba)-Sar-Gly-Val-D-alloIle-Thr-Gln-Ile-Arg-ProNHCH$_2$(CH$_3$)$_2$,
N-(2-Furoyl)-Sar-Gly-Val-D-alloIle-Thr-Nva-Ile-Arg-ProNHCH$_2$CH$_3$,
N-(2-Furoyl)-Sar-Gly-Val-D-Ile-Thr-Gln-Ile-Arg-ProNHCH$_2$CH$_3$,
N-(2-Furoyl)-Sar-Gly-Val-D-alloIle-Thr-Gln-Ile-Arg-ProNHCH$_2$CH$_3$,
N-(2-Furoyl)-Sar-Gly-Val-D-Ile-Thr-Gln-Ile-Arg-Pro-D-AlaNH$_2$,
N-(2-Furoyl)-Sar-Gly-Val-D-alloIle-Thr-Gln-Ile-Arg-Pro-D-AlaNH$_2$,
N-(2-Furoyl)-Sar-Gly-Val-D-alloIle-Thr-Gln-Ile-Arg-ProNHCH$_2$(CH$_3$)$_2$,
N-(Shikimyl)-Sar-Gly-Val-alloIle-Thr-Nva-Ile-Arg-ProNHCH$_2$CH$_3$,
N-(Shikimyl)-Sar-Gly-Val-D-Ile-Thr-Gln-Ile-Arg-ProNHCH$_2$CH$_3$,
N-(Shikimyl)-Sar-Gly-Val-D-alloIle-Ile-Thr-Gln-Ile-Arg-ProNHCH$_2$CH$_3$,
N-(Shikimyl)-Sar-Gly-Val-D-Ile-Thr-Gln-Ile-Arg-Pro-D-AlaNH$_2$,
N-(Shikimyl)-Sar-Gly-Val-D-alloIle-Thr-Gln-Ile-Arg-Pro-D-AlaNH$_2$,
N-(Shikimyl)-Sar-Gly-Val-D-alloIle-Thr-Gln-Ile-Arg-ProNHCH$_2$(CH$_3$)$_2$,
N-(2-Me-Nicotinyl)-Sar-Gly-Val-D-alloIle-Thr-Nva-Ile-Arg-ProNHCH$_2$CH$_3$,
N-(2-Me-Nicotinyl)-Sar-Gly-Val-D-Ile-Thr-Gln-Ile-Arg-ProNHCH$_2$CH$_3$,
N-(2-Me-Nicotinyl)-Sar-Gly-Val-D-alloIle-Thr-Gln-Ile-Arg-ProNHCH$_2$CH$_3$,
N-(2-Me-Nicotinyl)-Sar-Gly-Val-D-Ile-Thr-Gln-Ile-Arg-Pro-D-AlaNH$_2$,
N-(2-Me-Nicotinyl)-Sar-Gly-Val-D-alloIle-Thr-Gln-Ile-Arg-Pro-D-AlaNH$_2$,
N-(2-Me-Nicotinyl)-Sar-Gly-Val-D-alloIle-Thr-Gln-Ile-Arg-ProNHCH$_2$(CH$_3$)$_2$,
N-Ac-Sar-Gly-Val-D-alloIle-Thr-Leu-Ile-Arg-Pro-D-AlaNH$_2$,
N-Ac-Sar-Gly-Val-D-Ile-Thr-Leu-Ile-Arg-ProNHCH$_2$(CH$_3$)$_2$,
N-Ac-Sar-Gly-Val-D-alloIle-Thr-Leu-Ile-Arg-ProNHCH$_2$CH$_3$,
N-Ac-Sar-Gly-Val-D-Ile-Thr-Leu-Ile-Arg-Pro-D-AlaNH$_2$,
N-Succinyl-Sar-Gly-Val-D-Ile-Thr-Leu-Ile-Arg-Pro-D-AlaNH$_2$,
N-Succinyl-Sar-Gly-Val-D-Ile-Thr-Leu-Ile-Arg-ProNHCH$_2$(CH$_3$)$_2$,
N-Succinyl-Sar-Gly-Val-D-Ile-Thr-Leu-Ile-Arg-ProNHCH$_2$CH$_3$,
N-Succinyl-Sar-Gly-Val-D-alloIle-Thr-Leu-Ile-Arg-ProNHCH$_2$CH$_3$,
N-Succinyl-Sar-Gly-Val-D-alloIle-Thr-Leu-Ile-Arg-Pro-D-AlaNH$_2$,
N-Succinyl-Sar-Gly-Val-D-Ile-Thr-Leu-Ile-Arg-Pro-AzaglyNH$_2$,
N-Ac-Sar-Gly-Val-D-alloIle-Thr-Nva-Ile-Arg-ProNHethyl-(1-pyrrolidine),
N-Ac-Sar-Gly-Val-D-alloIle-Thr-Nva-Ile-Arg-ProNH(ethyl-1-cyclohexyl),
N-Ac-Sar-Gly-Val-D-Ile-Thr-Gln-Ile-Arg-ProNHethyl-(1-pyrrolidine),
N-Ac-Sar-Gly-Val-D-Ile-Thr-Gln-Ile-Arg-ProNH(ethyl-1-cyclohexyl),
N-Succinyl-Sar-Gly-Val-D-Ile-Thr-Gln-Ile-Arg-ProNH(ethyl-1-cyclohexyl),
N-Ac-Sar-Gly-Val-D-alloIle-Thr-Nva-Ile-Arg-ProNHCH$_2$CH$_2$OCH$_3$,
N-Ac-Sar-Gly-Val-D-Ile-Thr-Gln-Ile-Arg-ProNHCH$_2$CH$_2$OCH$_3$,
N-Ac-Sar-Gly-Val-D-Ile-Thr-Gln-Ile-Arg-ProNHCH$_2$CH$_2$OCH$_3$,
N-Ac-Sar-Gly-Val-D-Ile-Thr-Ser-Ile-Arg-ProNHCH$_2$CH$_2$OCH$_3$,
N-Succinyl-Sar-Gly-Val-D-Ile-Thr-Nva-Ile-Arg-ProNHCH$_2$CH$_2$OCH$_3$,
N-Succinyl-Sar-Gly-Val-D-Ile-Thr-Gln-Ile-Arg-ProNHCH$_2$CH$_2$OCH$_3$,
N-Succinyl-Sar-Gly-Val-D-Ile-Thr-Gln-Ile-Arg-ProNHCH$_2$CH$_2$OCH$_3$,
N-Ac-Sar-Gly-Val-D-Ile-Ser-Nva-Ile-Arg-ProNHCH$_2$CH$_2$OCH$_3$,
N-Ac-Sar-Gly-Val-D-Leu-Ser-Nva-Ile-Arg-ProNHCH$_2$CH$_2$OCH$_3$, N-Ac-Sar-Gly-Val-D-alloIle-Thr-Allygly-Ile-Arg-ProNHCH₂CH₃,
N-Ac-Sar-Gly-Val-D-Ile-Thr-Allygly-Ile-Arg-ProNHCH₂(CH₃),
N-Ac-Sar-Gly-Val-D-Ile-Thr-Allygly-Ile-Arg-Pro-D-AlaNH₂,
N-Ac-Sar-Gly-Val-D-alloIle-Thr-Allygly-Ile-Arg-Pro-D-AlaNH₂,
N-Succinyl-Sar-Gly-Val-D-Ile-Thr-Allygly-Ile-Arg-Pro-D-AlaNH₂,
N-Ac-Sar-Gly-Val-D-Ile-Ser-Allygly-Ile-Arg-Pro-ProNHCH₂CH₃,
N-Ac-Sar-Gly-Val-D-Leu-Ser-Allygly-Ile-Arg-Pro-ProNHCH₂CH₃,
N-Ac-Sar-Gly-Val-D-Ile-Thr-Nva-Ile-Arg-Pro-SarNH₂,
N-Ac-Sar-Gly-Val-D-Ile-Thr-Nva-Ile-Arg-ProNHOH,
N-Ac-Sar-Gly-Val-D-Ile-Ser-Nva-Ile-Arg-ProNHCH₂CH₃,
N-Ac-Sar-Gly-Val-D-alloIle-Ser-Nva-Ile-Arg-ProNHCH₂CH₃,
N-Ac-Sar-Gly-Val-D-Leu-Hser-Nva-Ile-Arg-ProNHCH₂CH₃,
N-Ac-Sar-Gly-Gln-D-Ile-Thr-Nva-Ile-Arg-ProNHCH₂CH₃,
N-Ac-Sar-Gly-Nva-D-Ile-Thr-Nva-Ile-Arg-ProNHCH₂CH₃,
N-Ac-Sar-Gly-Ile-D-Ile-Thr-Nva-Ile-Arg-ProNHCH₂CH₃,
N-Ac-Sar-Gly-Phe-D-Ile-Thr-Nva-Ile-Arg-ProNHCH₂CH₃,
N-Ac-Sar-Gly-Leu-D-Ile-Thr-Nva-Ile-Arg-ProNHCH₂CH₃,
N-Ac-Sar-Gly-Ser-D-Ile-Thr-Nva-Ile-Arg-ProNHCH₂CH₃,
N-Ac-Thr-Gly-Val-D-Leu-Thr-Nva-Ile-Arg-ProNHCH₂CH₃,
N-Ac-Sar-Gly-Val-D-alloIle-Thr-Ala-Ile-Arg-ProNHCH₂CH₃,
N-Ac-Sar-Gly-Val-D-Ile-Thr-Ala-Ile-Arg-ProNHCH₂(CH₃)₂,
N-Ac-Sar-Gly-Val-D-Ile-Thr-Ala-Ile-Arg-Pro-D-AlaNH₂,
N-Ac-Sar-Gly-Val-D-alloIle-Thr-Ala-Ile-Arg-Pro-D-AlaNH₂,
N-Succinyl-Sar-Gly-Val-D-Ile-Thr-Ala-Ile-Arg-Pro-D-AlaNH₂,
N-Ac-Sar-Gly-Val-D-Ile-Ser-Ala-Ile-Arg-ProNHCH₂CH₃,
N-Ac-Sar-Gly-Val-D-Leu-Ser-Ala-Ile-Arg-ProNHCH₂CH₃,
N-Ac-Sar-Gly-Val-D-alloIle-Thr-Val-Ile-Arg-ProNHCH₂CH₃,
N-Ac-Sar-Gly-Val-D-Ile-Thr-Val-Ile-Arg-ProNHCH₂(CH₃)₂,
N-Ac-Sar-Gly-Val-D-Ile-Thr-Val-Ile-Arg-Pro-D-AlaNH₂,
N-Ac-Sar-Gly-Val-D-alloIle-Thr-Val-Ile-Arg-Pro-D-AlaNH₂,
N-Succinyl-Sar-Gly-Val-D-Ile-Thr-Val-Ile-Arg-Pro-D-AlaNH₂,
N-Ac-Sar-Gly-Val-D-Ile-Ser-Val-Ile-Arg-ProNHCH₂CH₃,
N-Ac-Sar-Gly-Val-D-Leu-Ser-Val-Ile-Arg-ProNHCH₂CH₃,
N-Ac-Sar-Gly-Val-D-alloIle-Thr-D-Nva-Ile-Arg-ProNHCH₂CH₃,
N-Ac-Sar-Gly-Val-D-Ile-Thr-D-Nva-Ile-Arg-ProNHCH₂(CH₃)₂,
N-Ac-Sar-Gly-Val-D-Ile-Thr-D-Nva-Ile-Arg-Pro-D-AlaNH₂,
N-Ac-Sar-Gly-Val-D-alloIle-Thr-D-Nva-Ile-Arg-Pro-D-AlaNH₂,
N-Succinyl-Sar-Gly-Val-D-Ile-Thr-D-Nva-Ile-Arg-Pro-D-AlaNH₂,
N-Ac-Sar-Gly-Val-D-Ile-Ser-D-Nva-Ile-Arg-ProNHCH₂CH₃,
N-Ac-Sar-Gly-Val-D-Leu-Ser-D-Nva-Ile-Arg-ProNHCH₂CH₃,
N-Ac-Sar-Gly-Val-D-Ile-Ser-Gln-Ile-Arg-ProNHCH₂CH₃,
N-Ac-Sar-Gly-Val-D-Leu-Ser-Gln-Ile-Arg-ProNHCH₂CH₃,
N-Ac-Sar-Gly-Val-D-Leu-Ser-Nva-Ile-Arg-Pro-D-AlaNH₂,
N-Ac-Sar-Gly-Val-D-Ile-Ser-Nva-Ile-Arg-Pro-D-AlaNH₂,
N-Succinyl-Sar-Gly-Val-D-Leu-Ser-Nva-Ile-Arg-ProNHCH₂CH₃,
N-Succinyl-Sar-Gly-Val-D-Ile-Ser-Nva-Ile-Arg-ProNHCH₂CH₃,
N-Succinyl-Sar-Gly-Val-D-Leu-Ser-Gln-Ile-Arg-ProNHCH₂CH₃,
N-Succinyl-Sar-Gly-Val-D-Ile-Ser-Gln-Ile-Arg-ProNHCH₂CH₃,
N-Ac-Sar-Gly-Val-D-Ile-Ser-Ser-Ile-Arg-ProNHCH₂CH₃,
N-Ac-Sar-Gly-Val-Leu-Ser-Ser-Ile-Arg-ProNHCH₂CH₃,
N-Ac-Sar-Gly-Val-D-Leu-Ser-Nva-Ile-Arg-ProNHCH₂(CH₃)₂,
N-Ac-Sar-Gly-Val-D-Ile-Ser-Nva-Ile-Arg-ProNHCH₂(CH₃)₂,
N-Ac-Sar-Gly-Val-D-Leu-Ser-Leu-Ile-Arg-ProNHCH₂CH₃,
N-Ac-Sar-Gly-Val-D-Ile-Ser-Leu-Ile-Arg-ProNHCH₂CH₃,
N-Ac-Sar-Gly-Val-D-alloIle-Ser-Nva-Ile-Arg-ProNHCH₂CH₃,
N-Ac-Sar-Gly-Val-D-alloIle-Ser-Gln-Ile-Arg-ProNHCH₂CH₃,
N-Succinyl-Sar-Gly-Val-D-alloIle-Ser-Nva-Ile-Arg-ProNHCH₂CH₃,
N-Ac-Sar-Gly-Val-D-alloIle-Ser-Nva-Ile-Arg-ProNHCH₂(CH₃),
N-Ac-Sar-Gly-Val-D-alloIle-Ser-Nva-Ile-Arg-Pro-D-AlaNH₂,
N-Ac-Sar-Gly-Val-D-alloIle-Ser-Leu-Ile-Arg-ProNHCH₂CH₃,
N-Ac-Sar-Gly-Val-D-alloIle-Ser-Ser-Ile-Arg-ProNHCH₂CH₃,
N-Ac-Sar-Gly-Val-D-Ile-Gly-Nva-Ile-Arg-ProNHCH₂CH₃,
N-Ac-Sar-Gly-Val-D-alloIle-Gly-Nva-Ile-Arg-ProNHCH₂CH₃,
N-Ac-Sar-Gly-Val-D-Leu-Gly-Gln-Ile-Arg-ProNHCH₂CH₃,
N-Ac-Sar-Gly-Val-D-Ile-Gly-Gln-Ile-Arg-ProNHCH₂CH₃,
N-Ac-Sar-Gly-Val-D-alloIle-Gly-Gln-Ile-Arg-ProNHCH₂CH₃,
N-Ac-Sar-Gly-Val-D-Ile-Tyr-Nva-Ile-Arg-ProNHCH₂CH₃,
N-Ac-Sar-Gly-Val-D-alloIle-Tyr-Nva-Ile-Arg-ProNHCH₂CH₃,
N-Ac-Sar-Gly-Val-D-Leu-Tyr-Gln-Ile-Arg-ProNHCH₂CH₃,
N-Ac-Sar-Gly-Val-D-Ile-Tyr-Gln-Ile-Arg-ProNHCH₂CH₃,
N-Ac-Sar-Gly-Val-D-alloIle-Tyr-Gln-Ile-Arg-ProNHCH₂CH₃,
N-Ac-Sar-Gly-Val-D-Ser-Thr-Nva-Ile-Arg-ProNHCH₂CH₃,
N-Ac-Sar-Gly-Val-D-Thr-Thr-Nva-Ile-Arg-ProNHCH₂CH₃,
N-Ac-Sar-Gly-Val-D-Gln-Thr-Nva-Ile-Arg-ProNHCH₂CH₃,
N-Ac-Sar-Gly-Val-D-Asn-Thr-Nva-Ile-Arg-ProNHCH₂CH₃,
N-Ac-Sar-Gly-Val-D-Arg-Thr-Nva-Ile-Arg-ProNHCH₂CH₃,
N-Ac-Sar-Gly-Val-D-3-Pal-Thr-Nva-Ile-Arg-ProNHCH₂CH₃,
N-Ac-Sar-Gly-Val-D-Glu-Thr-Nva-Ile-Arg-ProNHCH₂CH₃,
N-Ac-Sar-Gly-Val-D-Asp-Thr-Nva-Ile-Arg-ProNHCH₂CH₃, N-Ac-Sar-Gly-Val-D-His-Thr-Nva-Ile-Arg-ProNHCH$_2$CH$_3$,
N-Ac-Sar-Gly-Val-D-Hser-Thr-Nva-Ile-Arg-ProNHCH$_2$CH$_3$,
N-Ac-Sar-Gly-Val-D-alloThr-Thr-Nva-Ile-Arg-ProNHCH$_2$CH$_3$,
N-Ac-Sar-Gly-Val-D-Ile-Thr-Nva-D-Ile-Arg-ProNHCH$_2$CH$_3$,
N-Ac-Sar-Gly-Val-D-Ser-Thr-Gln-Ile-Arg-ProNHCH$_2$CH$_3$,
N-Ac-Sar-Gly-Val-D-Thr-Thr-Gln-Ile-Arg-ProNHCH$_2$CH$_3$,
N-Ac-Sar-Gly-Val-D-alloThr-Thr-Gln-Ile-Arg-ProNHCH$_2$CH$_3$,
N-Ac-Sar-Gly-Val-D-Ser-Ser-Nva-Ile-Arg-ProNHCH$_2$CH$_3$,
N-Ac-Sar-Gly-Val-D-Thr-Ser-Nva-Ile-Arg-ProNHCH$_2$CH$_3$,
N-Ac-Sar-Gly-Val-D-alloThr-Ser-Nva-Ile-Arg-ProNHCH$_2$CH$_3$,
N-Ac-Sar-Gly-Val-D-alloThr-Ser-Gln-Ile-Arg-ProNHCH$_2$CH$_3$,
N-Ac-Sar-Gly-Val-D-Thr-Ser-Gln-Ile-Arg-ProNHCH$_2$CH$_3$,
N-(6-Ac-Aca)-Sar-Gly-Val-D-Leu-Ser-Gln-Ile-Arg-ProNHCH$_2$(CH$_3$)$_2$,
N-(6-Ac-Aca)-Sar-Gly-Val-D-Leu-Ser-Nva-Ile-Arg-ProNHCH$_2$(CH$_3$)$_2$,
N-(4-Ac-Gaba)-Sar-Gly-Val-D-Leu-Ser-Gln-Ile-Arg-ProNHCH$_2$(CH$_3$)$_2$,
N-(4-Ac-Gaba)-Sar-Gly-Val-D-Leu-Ser-Nva-Ile-Arg-ProNHCH$_2$(CH$_3$)$_2$,
N-(2-Furoyl)-Sar-Gly-Val-D-Leu-Ser-Gln-Ile-Arg-ProNHCH$_2$(CH$_3$)$_2$,
N-(2-Furoyl)-Sar-Gly-Val-D-Leu-Ser-Nva-Ile-Arg-ProNHCH$_2$(CH$_3$)$_2$,
N-(Shikimyl)-Sar-Gly-Val-D-Leu-Ser-Gln-Ile-Arg-ProNHCH$_2$(CH$_3$)$_2$,
N-(Shikimyl)-Sar-Gly-Val-D-Leu-Ser-Nva-Ile-Arg-ProNHCH$_2$(CH$_3$)$_2$,
N-(Shikimyl)-Sar-Gly-Val-D-Leu-Ser-Gln-Ile-Arg-ProNHCH$_2$(CH$_3$)$_2$,
N-(Shikimyl)-Sar-Gly-Val-D-Leu-Ser-Nva-Ile-Arg-ProNHCH$_2$(CH$_3$)$_2$,
N-(2-Me-nicotinyl)-Sar-Gly-Val-D-Leu-Ser-Gln-Ile-Arg-ProNHCH$_2$(CH$_3$)$_2$,
N-(2-Me-nicotinyl)-Sar-Gly-Val-D-Leu-Ser-Nva-Ile-Arg-ProNHCH$_2$(CH$_3$)$_2$,
N-Ac-Sar-Gly-Val-D-Leu-Ser-Nva-Ile-Arg-ProNHethyl-1-(R)-cyclohexyl,
N-Ac-Sar-Gly-Val-D-Leu-Ser-Gln-Ile-Arg-ProNHethyl-1-(R)-cyclohexyl,
N-Ac-Sar-Gly-Val-D-Ile-Thr-Ser-Ile-Arg-ProNHethyl-1-(R)-cyclohexyl,
N-Ac-Sar-Gly-Val-D-Leu-Thr-Nva-Ile-Arg-ProNHethyl-1-(R)-cyclohexyl,
N-Ac-Sar-Gly-Val-D-Leu-Ser-Ser-Ile-Arg-ProNHethyl-1-(R)-cyclohexyl,
N-Ac-Sar-Gly-Val-D-Ile-Thr-Nva-Ile-Arg-ProNHethyl-1-(S)-cyclohexyl),
N-Ac-Sar-Gly-Val-D-Pen-Ser-Nva-Ile-Arg-ProNHCH$_2$CH$_3$,
N-Ac-Sar-Gly-Val-D-Pen-Gly-Nva-Ile-Arg-ProNHCH$_2$CH$_3$,
N-Ac-Sar-Gly-Val-D-Pen-Thr-Gln-Ile-Arg-ProNHCH$_2$CH$_3$,
N-Ac-Sar-Gly-Val-D-Pen-Ser-Nva-Ile-Arg-ProNHCH$_2$(CH$_3$)$_2$,
N-Succinyl-Sar-Gly-Val-D-Pen-Ser-Nva-Ile-Arg-ProNHCH$_2$CH$_3$,
N-Ac-Sar-Gly-Val-D-Pen-Ser-Nva-Ile-Arg-Pro-D-AlaNH$_2$,
N-Ac-Sar-Gly-Val-D-Pen-Ser-Gln-Ile-Arg-ProNHCH$_2$CH$_3$,
N-Ac-Sar-Gly-Val-D-Pen-Gly-Gln-Ile-Arg-ProNHCH$_2$CH$_3$,
N-Ac-Sar-Gly-Val-D-Pen-Ser-Ser-Ile-Arg-ProNHCH$_2$CH$_3$,
N-Ac-Sar-Gly-Val-D-Pen-Thr-Ser-Ile-Arg-ProNHCH$_2$CH$_3$,
N-Ac-Sar-Gly-Val-D-Pen-Thr-Leu-Ile-Arg-ProNHCH$_2$CH$_3$,
N-Ac-Sar-Gly-Val-D-Pen-Ser-Leu-Ile-Arg-ProNHCH$_2$CH$_3$,
N-Succinyl-Sar-Gly-Val-D-Pen-Ser-Ser-Ile-Arg-ProNHCH$_2$CH$_3$,
N-Succinyl-Sar-Gly-Val-D-Pen-Ser-Leu-Ile-Arg-ProNHCH$_2$CH$_3$,
N-Succinyl-Sar-Gly-Val-D-Pen-Thr-Gln-Ile-Arg-ProNHCH$_2$(CH$_3$)$_2$,
N-Ac-Sar-Gly-Val-D-Cys-Thr-Nva-Ile-Arg-ProNHCH$_2$CH$_3$,
N-Ac-Sar-Gly-Val-D-Cys-Ser-Nva-Ile-Arg-ProNHCH$_2$CH$_3$,
N-Ac-Sar-Gly-Val-D-Cys-Gly-Nva-Ile-Arg-ProNHCH$_2$CH$_3$,
N-Ac-Sar-Gly-Val-D-Cys-Thr-Gln-Ile-Arg-ProNHCH$_2$CH$_3$,
N-Ac-Sar-Gly-Val-D-Cys-Ser-Nva-Ile-Arg-ProNHCH$_2$(CH$_3$)$_2$,
N-Succinyl-Sar-Gly-Val-D-Cys-Ser-Nva-Ile-Arg-ProNHCH$_2$CH$_3$,
N-Ac-Sar-Gly-Val-D-Cys-Ser-Nva-Ile-Arg-Pro-D-AlaNH$_2$,
N-Ac-Sar-Gly-Val-D-Cys-Ser-Gln-Ile-Arg-ProNHCH$_2$CH$_3$,
N-Ac-Sar-Gly-Val-D-Cys-Gly-Gln-Ile-Arg-ProNHCH$_2$CH$_3$,
N-Ac-Sar-Gly-Val-D-Cys-Ser-Ser-Ile-Arg-ProNHCH$_2$CH$_3$,
N-Ac-Sar-Gly-Val-D-Cys-Thr-Ser-Ile-Arg-ProNHCH$_2$CH$_3$,
N-Ac-Sar-Gly-Val-D-Cys-Thr-Leu-Ile-Arg-ProNHCH$_2$CH$_3$,
N-Ac-Sar-Gly-Val-D-Cys-Ser-Leu-Ile-Arg-ProNHCH$_2$CH$_3$,
N-Succinyl-Sar-Gly-Val-D-Cys-Ser-Ser-Ile-Arg-ProNHCH$_2$CH$_3$,
N-Succinyl-Sar-Gly-Val-D-Cys-Ser-Leu-Ile-Arg-ProNHCH$_2$CH$_3$,
N-Ac-Sar-Gly-Pen-D-Ile-Thr-Nva-Ile-Arg-ProNHCH$_2$CH$_3$,
N-Ac-Sar-Gly-Cys-D-Ile-Thr-Nva-Ile-Arg-ProNHCH$_2$CH$_3$,
N-Ac-Sar-Gly-Pen-D-alloIle-Thr-Nva-Ile-Arg-ProNHCH$_2$CH$_3$,
N-Ac-Sar-Gly-Pen-D-Leu-Thr-Nva-Ile-Arg-ProNHCH$_2$CH$_3$,
N-Ac-Sar-Gly-Pen-D-Ile-Thr-Gln-Ile-Arg-ProNHCH$_2$CH$_3$,
N-Ac-Sar-Gly-Pen-D-Ile-Ser-Nva-Ile-Arg-ProNHCH$_2$CH$_3$,
N-Ac-Sar-Gly-Pen-D-Ile-Thr-Nva-Ile-Arg-ProNHCH$_2$(CH$_3$)$_2$,
N-Ac-Sar-Gly-Pen-D-Ile-Thr-Nva-Re-Arg-Pro-D-AlaNH$_2$,
N-Succinyl-Gly-Pen-D-Ile-Thr-Nva-Ile-Arg-ProNHCH$_2$CH$_3$,
N-Succinyl-Sar-Gly-Pen-D-Ile-Thr-Gln-Ile-Arg-ProNHCH$_2$CH$_3$,
N-Succinyl-Sar-Gly-Pen-D-Il-Thr-Gln-Ile-Arg-ProNHCH$_2$(CH$_3$),
N-Ac-Sar-Gly-Val-D-Leu-Pen-Nva-Ile-Arg-ProNHCH$_2$CH$_3$,
N-Ac-Sar-Gly-Val-D-Ile-Pen-Nva-Ile-Arg-ProNHCH$_2$CH$_3$,
N-Ac-Sar-Gly-Val-D-alloIle-Pen-Nva-Ile-Arg-ProNHCH$_2$CH$_3$,
N-Ac-Sar-Gly-Val-D-Ile-Pen-Gln-Ile-Arg-ProNHCH$_2$CH$_3$,
N-Ac-Sar-Gly-Val-D-Ile-Pen-Ser-Ile-Arg-ProNHCH$_2$CH$_3$, N-Ac-Sar-Gly-Val-D-Ile-Pen-Leu-Ile-Arg-ProNHCH$_2$CH$_3$,
N-Ac-Sar-Gly-Val-D-Ile-Pen-Nva-Ile-Arg-ProNHCH$_2$(CH$_3$)$_2$,
N-Ac-Sar-Gly-Val-D-Ile-Pen-Nva-Ile-Arg-Pro-D-AlaNH$_2$,
N-Succinyl-Sar-Gly-Val-D-Ile-Pen-Nva-Ile-Arg-ProNHCH$_2$CH$_3$,
N-Succinyl-Sar-Gly-Val-D-Ile-Pen-Gln-Ile-Arg-ProNHCH$_2$CH$_3$,
N-Succinyl-Sar-Gly-Val-D-Ile-Pen-Gln-Ile-Arg-ProNHCH$_2$(CH$_3$)$_2$,
N-Ac-Sar-Gly-Val-D-Ile-Thr-Pen-Ile-Arg-ProNHCH$_2$CH$_3$,
N-Ac-Sar-Gly-Val-D-alloIle-Thr-Pen-Ile-Arg-ProNHCH$_2$CH$_3$,
N-Ac-Sar-Gly-Val-D-Leu-Thr-Pen-Ile-Arg-ProNHCH$_2$CH$_3$,
N-Ac-Sar-Gly-Val-D-Ile-Thr-Pen-Ile-Arg-Pro-D-AlaNH$_2$.
N-Succinyl-Sar-Gly-Val-D-Ile-Thr-Pen-Ile-Arg-ProNHCH$_2$CH$_3$,
N-Ac-Sar-Gly-Val-D-Ile-Thr-Pen-Ile-Arg-ProNHCH$_2$(CH$_3$)$_2$,
N-Ac-Sar-Gly-Val-D-Leu-Ser-Pen-Ile-Arg-ProNHCH$_2$CH$_3$,
N-Ac-Sar-Gly-Val-D-Leu-Gly-Pen-Ile-Arg-ProNHCH$_2$CH$_3$,
N-Succinyl-Sar-Gly-Val-D-Leu-Ser-Pen-Ile-Arg-ProNHCH$_2$CH$_3$,
N-Ac-Sar-Gly-Val-D-Phe(3,4,5-triF)-Thr-Gln-Ile-Arg-ProNHCH$_2$CH$_3$,
N-Ac-Sar-Gly-Val-D-Phe(3,4,5-triF)-Ser-Nva-Ile-Arg-ProNHCH$_2$CH$_3$,
N-Ac-Sar-Gly-Val-D-Phe(3,4,5-triF)-Gly-Nva-Ile-Arg-ProNHCH$_2$CH$_3$,
N-Ac-Sar-Gly-Val-D-Phe(3,4,5-triF)-Ser-Leu-Ile-Arg-ProNHCH$_2$CH$_3$,
N-Ac-Sar-Gly-Val-D-Phe(3,4,5-triF)-Ser-Nva-Ile-Arg-Pro-D-AlaNH$_2$,
N-Succinyl-Sar-Gly-Val-D-Phe(3,4,5-triF)-Thr-Gln-Ile-Arg-ProNHCH$_2$CH$_3$,
N-Succinyl-Sar-Gly-Val-D-Phe(3,4,5-triF)-Ser-Gln-Ile-Arg-ProNHCH$_2$CH$_3$,
N-Succinyl-Sar-Gly-Val-D-Phe(3,4,5-triF)-Thr-Gln-Ile-Arg-ProNHCH$_2$(CH$_3$)$_2$,
N-Ac-Sar-Gly-Val-D-Phe(3,4,5-triF)-Ser-Gln-Ile-Arg-ProNHCH$_2$CH$_3$,
N-Ac-Sar-Gly-Val-D-Phe(3,4,5-triF)-Ser-Ser-Ile-Arg-ProNHCH$_2$CH$_3$,
N-Ac-Say-Ala-Val-D-alloIle-Thr-Nva-Ile-Arg-ProNHCH$_2$CH$_3$,
N-Ac-Sar-Ala-Val-D-Leu-Thr-Nva-Ile-Arg-ProNHCH$_2$CH$_3$,
N-Ac-Sar-Ala-Val-D-Ile-Thr-Gln-Ile-Arg-ProNHCH$_2$CH$_3$,
N-Ac-Sar-Ala-Val-D-Leu-Ser-Nva-Ile-Arg-ProNHCH$_2$CH$_3$,
N-Ac-Sar-Ala-Val-D-Leu-Ser-Gln-Ile-Arg-ProNHCH$_2$CH$_3$,
N-Succinyl-Sar-Ala-Val-D-Ile-Thr-Nva-Ile-Arg-ProNHCH$_2$CH$_3$,
N-Succinyl-Sar-Ala-Val-D-Ile-Thr-Gln-Nva-Ile-Arg-ProNHCH$_2$CH$_3$,
N-Succinyl-Sar-Ala-Val-D-Ile-Thr-Gln-Nva-Ile-Arg-ProNHCH$_2$(CH$_{3)2}$,
N-Succinyl-Sar-Ala-Val-D-Ile-Thr-Gln-Nva-Ile-Arg-Pro-D-AlaNH$_2$,
N-(3-Ac-Bala)-Sar-Gly-Val-D-alloIle-Thr-Nva-Ile-Arg-ProNHCH$_2$CH$_3$,
N-(3-Ac-Bala)-Sar-Gly-Val-D-Ile-Thr-Gln-Ile-Arg-ProNHCH$_2$CH$_3$,
N-(3-Ac-Bala)-Sar-Gly-Val-D-alloIle-Thr-Gln-Ile-Arg-ProNHCH$_2$CH$_3$,
N-(3-Ac-Bala)-Sar-Gly-Val-D-Ile-Thr-Gln-Ile-Arg-Pro-D-AlaNH$_2$,
N-(3-Ac-Bala)-Sar-Gly-Val-D-alloIle-Thr-Gln-Ile-Arg-Pro-D-AlaNH2,
N-(3-Ac-Bala)-Sar-Gly-Val-D-alloIle-Thr-Gln-Ile-Arg-ProNHCH$_2$(CH$_3$)$_2$,
N-(3-Ac-Bala)-Sar-Gly-Val-D-Leu-Ser-Nva-Ile-Arg-ProNHCH$_2$CH$_3$,
N-(3-Ac-Bala)-Sar-Gly-Val-D-Leu-Thr-Nva-Ile-Arg-ProNHCH$_2$CH$_3$,
N-(3-Ac-Bala)-Sar-Gly-Val-D-Pen-Thr-Nva-Ile-Arg-ProNHCH$_2$CH$_3$,
N-(3-Ac-Bala)-Sar-Gly-Val-D-Ile-Ser-Nva-Ile-Arg-ProNHCH$_2$CH$_3$,
N-(3-Ac-Bala)-Sar-Ala-Val-D-alloIle-Ser-Nva-Ile-Arg-ProNHCH$_2$CH$_3$,
N-(3-Ac-Bala)-Sar-Ala-Val-D-Ile-Ser-Nva-Ile-Arg-ProNHCH$_2$CH$_3$,
N-(3-Ac-Bala)-Sar-Ala-Val-D-Leu-Ser-Nva-Ile-Arg-ProNHCH$_2$CH$_3$,
N-(3-Ac-Bala)-Sar-Ala-Val-D-Leu-Ser-Gln-Ile-Arg-ProNHCH$_2$CH$_3$,
N-Ac-Sar-Gly-Val-D-Ile-Thr-Nva-Ile-Arg-Pro-OH,
N-Ac-Sar-Gly-Val-D-alloIle-Thr-Nva-Ile-Arg-Pro-OH,
N-Ac-Sar-Gly-Val-D-Leu-Thr-Nva-Ile-Arg-Pro-OH,
N-Ac-Sar-Gly-Val-D-Pen-Thr-Nva-Ile-Arg-Pro-OH,
N-Ac-Sar-Gly-Val-D-Phe(3,4,5-triF)-Thr-Nva-Ile-Arg-Pro-OH,
N-Ac-Sar-Gly-Val-D-Ile-Thr-Gln-Ile-Arg-Pro-OH,
N-Ac-Sar-Gly-Val-D-Leu-Ser-Nva-Ile-Arg-Pro-OH,
N-Ac-Sar-Ala-Val-D-Ile-Thr-Nva-Ile-Arg-Pro-OH,
N-Ac-Sar-Gly-Val-D-Ile-Ser-Gln-Ile-Arg-Pro-OH,
N-Succinyl-Sar-Gly-Val-D-Ile-Thr-Nva-Ile-Arg-Pro-OH,
N-Succinyl-Sar-Gly-Val-D-Leu-Thr-Gln-Ile-Arg-Pro-OH
N-Ac-Sar-Gly-Asp-D-Leu-Thr-Nva-Ile-Arg-ProNHCH$_2$CH$_3$,
N-Ac-Sar-Gly-Ala-D-Leu-Thr-Nva-Ile-Arg-ProNHCH$_2$CH$_3$,
N-Ac-Sar-Gly-Cha-D-Leu-Thr-Nva-Ile-Arg-ProNHCH$_2$CH$_3$,
N-Ac-Sar-Gly-Met-D-Ile-Thr-Nva-Ile-Arg-ProNHCH$_2$CH$_3$,
N-Ac-Sar-Gly-Val-D-Ile-Thr-Hser-Ile-Arg-ProNHCH$_2$CH$_3$,
N-Ac-Cit-Gly-Val-D-Ile-Thr-Nva-Ile-Arg-ProNHCH$_2$CH$_3$,
N-Ac-Sar-Gly-Val-D-alloIle-His-Nva-Ile-Arg-ProNHCH$_2$CH$_3$,
N-Ac-Sar-Gly-Val-D-Ile-Thr-Nva-Ile-Arg-ProNH-n-Butyl,
N-Ac-Sar-Gly-Val-D-Ile-Thr-Nva-Ile-Arg-ProNH-iso-Butyl,
N-Ac-Sar-Gly-Val-D-Ile-Thr-Nva-Ile-Arg-ProNH-iso-Amyl,
N-Ac-Sar-Gly-Val-D-Ile-Thr-Nva-Ile-Arg-ProNH-n-hexyl,
N-Ac-Sar-Gly-Val-D-Ile-Thr-Nva-Ile-Arg-ProNH-(3,3-dimethyl)butyl,
N-Ac-Sar-Gly-Val-D-Ile-Thr-Nva-Ile-Arg-ProNH2-ethoxy)ethyl,
N-Ac-Sar-Gly-Val-D-Ile-Thr-Nva-Ile-Arg-ProNH-(2-isopropoxy)ethyl,
N-Ac-Sar-Gly-Val-D-Ile-Thr-Nva-Ile-Arg-ProNH-(3-methoxy)propyl,
N-Ac-Sar-Gly-Val-D-Ile-Thr-Nva-Ile-Arg-ProNH-(cyclopentyl)methyl, and
N-Ac-Sar-Gly-Val-D-Ile-Thr-Nva-Ile-Arg-ProNH-cyclohexyl.

Preferred compounds for the practice of the invention are:

N-Ac-Sar-Gly-Val-D-Ile-Thr-Nva-Ile-Arg-ProNHCH$_2$CH$_3$,
N-Ac-Sar-Gly-Val-D-Ile-Thr-Nva-Ile-Arg-ProNHCH$_2$CH$_2$ (1-pyrrolidine),
N-Ac-Sar-Gly-Val-D-Ile-Thr-Nva-Ile-Arg-ProNH(ethyl-1-(R)-cyclohexyl),
N-Ac-Sar-Gly-Val-D-Ile-Thr-Nva-Ile-Arg-ProNH$_2$,
N-Ac-Sar-Gly-Val-D-Ile-Thr-Nva-Ile-Arg-ProNHCH(CH$_3$)$_2$,
N-Ac-Sar-Gly-Val-D-alloIle-Thr-Nva-Ile-Arg-ProNHCH$_2$CH$_3$,
N-Ac-Sar-Gly-Val-D-Val-Thr-Nva-Ile-Arg-ProNHCH$_2$CH$_3$,
N-Ac-Sar-Gly-Val-D-Nle-Thr-Nva-Ile-Arg-ProNHCH$_2$CH$_3$,
N-Ac-Sar-Gly-Val-D-Phe-Thr-Nva-Ile-Arg-ProNHCH$_2$CH$_3$,
N-Ac-Sar-Gly-Val-D-Cha-Thr-Nva-Ile-Arg-ProNHCH$_2$CH$_3$,
N-Ac-Sar-Gly-Val-D-3,4-diClPhe-Thr-Nva-Ile-Arg-ProNHCH$_2$CH$_3$,
N-Ac-Sar-Gly-Val-D-3-ClPhe-Thr-Nva-Ile-Arg-ProNHCH$_2$CH$_3$,
N-Ac-Sar-Gly-Val-D-2-Thienylala-Thr-Nva-Ile-Arg-ProNHCH$_2$CH$_3$,
N-Ac-Sar-Gly-Val-D-3-CNPhe-Thr-Nva-Ile-Arg-ProNHCH$_2$CH$_3$,
N-Ac-Sar-Gly-Val-D-Ile-Thr-Cha-Ile-Arg-ProNHCH$_2$CH$_3$,
N[2-THFcarbonyl]-Sar-Gly-Val-D-Ile-Thr-Nva-Ile-Arg-ProNHCH$_2$CH$_3$,
N[6-N-acetyl(CH$_2$)$_5$C(O)]-Sar-Gly-Val-D-Ile-Thr-Nva-Ile-Arg-ProNHCH$_2$CH$_3$,
N-Hexanoyl-Sar-Gly-Val-D-Ile-Thr-Nva-Ile-Arg-ProNHCH$_2$CH$_3$,
N-[4-N-Acetylaminobutyryl]-Sar-Gly-Val-D-Ile-Thr-Nva-Ile-Arg-ProNHCH$_2$CH$_3$,
N—[CH$_3$C(O)NH—(CH$_2$)$_2$—O—(CH$_2$)$_2$—O—CH$_2$—C(O)]-Gly-Val-D-Ile-Thr-Nva-Ile-Arg-ProNHCH$_2$CH$_3$,
N-Ac-Pro-Gly-Val-D-Ile-Thr-Nva-Ile-Arg-ProNHCH$_2$CH$_3$,
N-Ac-NEtGly-Gly-Val-D-Ile-Thr-Nva-Ile-Arg-ProNHCH$_2$CH$_3$,
N-Ac-Sar-Gly-Val-D-Ile-Thr-Leu-Ile-Arg-ProNHCH$_2$CH$_3$,
N-Ac-Sar-Gly-Val-D-Ile-Thr-Ser-Ile-Arg-ProNHCH$_2$CH$_3$,
N-Ac-Sar-Gly-Val-D-Ile-Thr-Nva-Ile-Arg-Pro-D-AlaNH$_2$,
N-Ac-Sar-Gly-Val-D-Leu-Thr-Nva-Lys(Ac)-Arg-ProNHCH$_2$CH$_3$,
N-Ac-Sar-Gly-Val-D-Leu-Thr-Nva-Leu-Arg-ProNHCH$_2$CH$_3$,
N-Ac-Sar-Gly-Val-D-Leu-Thr-Nva-1Nal-Arg-ProNHCH$_2$CH$_3$,
N-Ac-Sar-Gly-Val-D-Leu-Thr-Nva-Allylgly-Arg-ProNHCH$_2$CH$_3$,
N-Ac-Sar-Gly-Val-D-Leu-Ala-Nva-Ile-Arg-ProNHCH$_2$CH$_3$,
N-Ac-Sar-Gly-Val-D-Leu-Trp-Nva-Ile-Arg-ProNHCH$_2$CH$_3$.
N-Ac-Sar-Gly-Val-D-Leu-Tyr-Nva-Ile-Arg-ProNHCH$_2$CH$_3$,
N-Ac-Sar-Gly-Val-D-Leu-Gly-Nva-Ile-Arg-ProNHCH$_2$CH$_3$,
N-Ac-Sar-Gly-Val-D-Leu-2Nal-Nva-Ile-Arg-ProNHCH$_2$CH$_3$,
N-Ac-Sar-Gly-Val-D-Leu-1Nal-Nva-Ile-Arg-ProNHCH$_2$CH$_3$,
N-Ac-Sar-Gly-Val-D-Leu-Octylgly-Nva-Ile-Arg-ProNHCH$_2$CH$_3$,
N-Ac-Sar-Gly-Val-D-Leu-Ser-Nva-Ile-Arg-ProNHCH$_2$CH$_3$,
N-Ac-Sar-Gly-Val-D-Leu-Allylgly-Nva-Ile-Arg-ProNHCH$_2$CH$_3$,
N-Ac-Sar-Gly-Val-D-Leu-D-Thr-Nva-Ile-Arg-ProNHCH$_2$CH$_3$,
N-Ac-Sar-Gly-Val-D-Ile-Thr-Tyr-Ile-Arg-ProNHCH$_2$CH$_3$,
N-Ac-Sar-Gly-Val-D-Ile-Thr-Glu-Ile-Arg-ProNHCH$_2$CH$_3$,
N-Ac-Sar-Gly-Val-D-Ile-Thr-Propargylgly-Ile-Arg-ProNHCH$_2$CH$_3$,
N-Ac-Sar-Gly-Val-D-alloIle-Thr-Gln-Ile-Arg-ProNHCH$_2$CH$_3$,
N-Ac-Bala-Sar-Gly-Val-D-Ile-Thr-Nva-Ile-Arg-ProNHCH$_2$CH$_3$,
N-Phenylacetyl-Sar-Gly-Val-D-Ile-Thr-Nva-Ile-Arg-ProNHCH$_2$CH$_3$,
N-Ac-Sar-Gly-Val-D-Ile-Thr-Nva-Ile-Arg-Pro-AzaglyNH$_2$,
N-Ac-Sar-Gly-Val-D-Ile-Thr-Nva-Ile-Arg-Pro-SerNH$_2$,
N-(6-Ac-Aca)-Sar-Gly-Val-D-Leu-Ser-Gln-Ile-Arg-ProNHCH$_2$(CH$_3$)$_2$,
N-(6-Ac-Aca)-Sar-Gly-Val-D-Leu-Ser-Nva-Ile-Arg-ProNHCH$_2$(CH$_3$)$_2$,
N-(4-Ac-Gaba)-Sar-Gly-Val-D-Leu-Ser-Gln-Ile-Arg-ProNHCH$_2$(CH$_3$)$_2$,
N-(4-Ac-Gaba)-Sar-Gly-Val-D-Leu-Ser-Nva-Ile-Arg-ProNHCH$_2$(CH$_3$)$_2$,
N-(2-Furoyl)-Sar-Gly-Val-D-Leu-Ser-Gln-Ile-Arg-ProNHCH$_2$(CH$_3$)$_2$,
N-(2-Furoyl)-Sar-Gly-Val-D-Leu-Ser-Nva-Ile-Arg-ProNHCH$_2$(CH$_3$)$_2$,
N-(Shikimyl)-Sar-Gly-Val-D-Leu-Ser-Gln-Ile-Arg-ProNHCH$_2$(CH$_3$)$_2$,
N-(Shikimyl)-Sar-Gly-Val-D-Leu-Ser-Nva-Ile-Arg-ProNHCH$_2$(CH$_3$)$_2$,
N-(Shikimyl)-Sar-Gly-Val-D-Leu-Ser-Gln-Ile-Arg-ProNHCH$_2$(CH$_3$)$_2$,
N-(Shikimyl)-Sar-Gly-Val-D-Leu-Ser-Nva-Ile-Arg-ProNHCH$_2$(CH$_3$)$_2$,
N-(2-Me-nicotinyl)-Sar-Gly-Val-D-Leu-Ser-Gln-Ile-Arg-ProNHCH$_2$(CH$_3$)$_2$,
N-(2-Me-nicotinyl)-Sar-Gly-Val-D-Leu-Ser-Nva-Ile-Arg-ProNHCH$_2$(CH$_3$)$_2$,
N-Ac-Sar-Gly-Val-D-Ile-Thr-Nva-Ile-Arg-Pro-OH,
N-Ac-Sar-Ala-Val-D-Ile-Thr-Nva-Ile-Arg-ProNHCH$_2$CH$_3$,
N-Ac-Sar-Gly-Val-D-Pen-Thr-Nva-Ile-Arg-ProNHCH$_2$CH$_3$,
N-Ac-Sar-Gly-Val-D-Phe(3,4,5-triF)-Thr-Nva-Ile-Arg-ProNHCH$_2$CH$_3$, and
N-Ac-Sar-Gly-Val-D-Phe(4-NH$_2$)-Thr-Nva-Ile-Arg-ProNHCH$_2$CH$_3$.

It is well known in the art that modifications and changes can be made in the structure of a polypeptide without substantially altering the biological function of that peptide. For example, certain amino acids can be substituted for other amino acids in a given polypeptide without any appreciable loss of function. In making such changes, substitutions of like amino acid residues can be made on the basis of relative similarity of side-chain substituents, for example, their size, charge, hydrophobicity, hydrophilicity, and the like.

In describing the invention, certain abbreviations are used for the sake of convenience throughout the specification, including the examples, to refer to reagents and compounds useful for preparing the compounds of the invention. When so used, the following abbreviations are meant to refer to the following: DMF for dimethylformamide; DMA for dimethylacetamide; DIEA for diisopropylethylamine; HATU for O-(7-aza-benzotriazol-1-yl)-N,N,N',N '-tetramethyluronium haxafluorophosphate; NMP for N-methylpyrrolidone; and TFA for trifluoroacetic acid.

Determination of Biological Activity

Pellet Preparation

Ten microliters of a mixture containing a final concentration of 1, 5, or 10 mM of the peptides of invention, 100 ng of bFGF (Collaborative Biomedical Products, Bedford, Mass.), and 6% Hydron (Sigma, St. Louis, Mo.) were pipetted into the tip of a sterile TeFlon rod. After drying for 1–2 hours, the pellets were stored at 4° C.

Pellet Implantation

A small (about 2 mm) radial incision at 1 mm from the center of the cornea was performed in anesthetized Sprague Dawley rats. With a curved iris spatula, an intrastromal pocket was made to a distance of 1 mm from the limbus-the circular blood vessels that surround the cornea. A single pellet was implanted. Antibiotic ointment (neosporin) was applied post surgery to the operated eye to prevent infection and to decrease inflammation.

Data Analysis

At day seven post-implantation, neovascularization was measured through a slitlamp biomicroscopy (Nikon NS-1), connected to an image analysis system (Leica Qwin). The response was calculated by colorimetrically detecting the area of new blood vessels, and calculating the new vessel surface area in $\mu m^2$. The compounds of the invention inhibit rat cornea neovascularization as shown in Table 2.

TABLE 2

Effect of the Compounds of the Invention on Rat Cornea Neovascularization

| Peptide | Number of Corneas/Dose | % Inhibition |
| --- | --- | --- |
| Example 1 | 6/10 µM | 92.6 |
| Example 1 | 5/5 µM | 74.8 |
| Example 1 | 4/6 µM | 71.5 |
| untreated | 5/— | — |

The compounds of the invention, including but not limited to those specified in the examples, possess antiangiogenic activity. As angiogenesis inhibitors, such compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e. chloromas, plasmacytomas and the plaques and tumors of mycosis fungoides and cutaneous T-cell lymphoma/ leukemia) as well as in the treatment of lymphomas (both Hodgkin's and non-Hodgkin s lymphomas). In addition, these compounds may be useful in the prevention of metastases from the tumors described above either when used alone or in combination with radiotherapy and/or other chemotherapeutic agents.

Further uses include the treatment and prophylaxis of autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemagiomnas, and capillary proliferation within atherosclerotic plaques; Osler-Webber Syndrome; myocardial angiogenesis; plaque neovascularization; telangiectasia; hemophiliac joints; angiofibroma; and wound granulation. Other uses include the treatment of diseases characterized by excessive or abnormal stimulation of endothelial cells, including but not limited to intestinal adhesions, Crohn's disease, atherosclerosis, scleroderma, and hypertrophic scars, i.e. keloids. Another use is as a birth control agent, by inhibiting ovulation and establishment of the placenta. The compounds of the invention are also useful in the treatment of diseases that have angiogenesis as a pathologic consequence such as cat scratch disease (*Rochele minalia quintosa*) and ulcers (*Helicobacter pylori*). The compounds of the invention are also useful to reduce bleeding by administration prior to sugery, especially for the treatment of resectable tumors.

The compounds of the invention may be used in combination with other compositions and procedures for the treatment of diseases. For example, a tumor may be treated conventionally with surgery, radiation or chemotherapy combined with a peptide of the present invention and then a peptide of the present invention may be subsequently administered to the patient to extend the dormancy of micrometastases and to stabilize and inhibit the growth of any residual primary tumor. Additionally, the compounds of the invention may be combined with pharmaceutically acceptable excipients, and optionally sustained-release matrices, such as biodegradable polymers, to form therapeutic compositions.

A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

When used in the above or other treatments, a therapeutically effective amount of one of the compounds of the present invention may be employed in pure form or, where such forms exist, in pharmaceutically acceptable salt form.

By a "therapeutically effective amount" of the compound of the invention is meant a sufficient amount of the compound to treat an angiogenic disease, (for example, to limit tumor growth or to slow or block tumor metastasis) at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific compound employed; and like factors well known in the medical arts. For example, it is well within the skill of the art to start doses of the compound at levels lower than those required to achieve the desired therapeutic effect and to gradually increase the dosage until the desired effect is achieved.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, phosphate, glutamate, bicarbonate,p-toluenesulfonate and undecanoate. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as acetic acid, maleic acid, succinic acid and citric acid. Other salts include salts with alkali metals or alkaline earth metals, such as sodium, potassium, calcium or magnesium or with organic basis. Preferred salts of the compounds of the invention include phosphate, tris and acetate.

Alternatively, a compound of the present invention may be administered as pharmaceutical compositions containing the compound of interest in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions may be administered parenterally, intracisternally, intravaginally, intraperitoneally, topically (as by powders, ointments, drops or transdermal patch), rectally, or bucally. The term "parenteral" as used herein refers to modes of administration which include intravenous, intramuscular, intraperitoneal, intaasternal, subcutaneous and intraarticular injection and infusion.

Pharmaceutical compositions for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Injectable depot forms are made by forming microencapsule matrices of the drug in biodegradable polymers such as polylactide-polyglycolide, poly(orthoesters), poly (anhydrides), and (poly)glycols, such as PEG. Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically-acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye. A compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the compounds of the invention may be injected directly into the vitreous and aqueous humour.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

While the compounds of the invention can be administered as the sole active pharmaceutical agent, they may also be used in combination with one or more agents which are conventionally administered to patients for treating angiogenic diseases. For example, the compounds of the invention are effective over the short term to make tumors more sensitive to traditional cytotoxic therapies such as chemicals and radiation. The compounds of the invention also enhance the effectiveness of existing cytotoxic adjuvant anticancer therapies. The compounds of the invention may also be combined with other antiangiogenic agents to enhance their effectiveness, or combined with other antiangiogenic agents and administered together with other cytoioxic agents. In particular, when used in the treatment of solid tumors, compounds of the invention may be administered with IL-12, retinoids, interferons, angiostatin, endostatin, thalidomide, thrombospondin-1, thrombospondin-2, captopryl, angioinhibins, TNP470, pentosan polysulfate, platelet factor 4, LM609, SU-5416, CM-101, Tecogalan, plasminogen-K-5, vasostatin, vitaxin, vasculostatin, squalamine, marimastat or other MMP inhibitors, anti-neoplastic agents such as alpha inteferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, cisplatin, taxol, etoposide/mechlorethamine, vincristine, prednisone and procarbazine), vincristine, vinblastine, and the like as well as with radiation.

Total daily dose of the compositions of the invention to be administered to a human or other mammal host in single or divided doses may be in amounts, for example, from 0.0001 to 300 mg/kg body weight daily and more usually 1 to 300 mg/kg body weight.

It will be understood that agents which can be combined with the compound of the present invention for the inhibition, treatment or prophylaxis of angiogenic diseases are not limited to those listed above, but include in principle any agents useful for the treatment or prophylaxis of angiogenic diseases.

The peptides of the invention may be used for the development of affinity columns for isolation of receptors relevant to the antiangiogenic activity of the peptide of the invention, e.g. TSP-1 receptor, in, for example, cultured endothelial cells. As is known in the art, isolation and purification of the receptor may be followed by amino acid sequencing to identify and isolate polynucleotides which encode the receptor. Recombinant expression of this receptor would allow greater amounts of receptor to be produced, e.g. to produce a sufficient quantity for use in high throughput screening assays to identify other angiogenesis inhibitors.

The peptides of the present invention may be chemically coupled to isotopes, enzymes, carrier proteins, cytotoxic agents, fluorescent molecules, chemiluminescent, bioluminescent and other compounds for a variety of applications. For example, a peptide may be labeled to facilitate testing of its ability to bind antisera or to detect cell types which possess a relevant receptor. The coupling technique is generally chosen on the basis of the functional groups available on the amino acids of the peptide including, but not limited to amino, sullhydral, carboxyl, amide, phenol, and imidazole. Various reagents used to effect such couplings include among others, glutaraldehyde, diazodized benzidine, carbodiimide, and p-benzoquinone.

The efficiency of the coupling reaction is determined using different techniques appropriate for the specific reaction. For example, radiolabeling of the peptide with $I^{125}$ may be accomplished using chloramine T and $NaI^{125}$ of high specific activity. The reaction is terminated with sodium metabisulfite and the mixture is desalted on disposable columns. The labeled peptide is eluted from the column and fractions are collected. Aliquots are removed from each fraction and radioactivity measured in a gamma counter. In this manner, a labeled peptide may be obtained which is free from unreacted $NaI^{125}$.

The peptides of the present invention can also be used as antigens to generate polyclonal or monoclonal antibodies. Such antibodies can be used in diagnostic methods and kits to detect or quantify the peptide of the invention, or peptides related thereto, in a body fluid or tissue. Results from these tests could be used to diagnose or determine the prognostic relevance of such peptides.

The use of the peptides of the present invention to generate monoclonal antibodies in animals such as the mouse, rabbit or sheep, follows techniques well known in the art. If desired, the antibodies can then be used to make anti-idiotype antibodies which in turn can be humanized as is known in the art to prevent immunological responses. The humanized antibodies can be used to inhibit angiogenesis or to make kits to detect the receptor as described herein.

For the production of polyclonal antisera in rabbits, sheep, goats or other animals the peptides of the invention are coupled, for example through lysine residues, to purified bovine serum albumin using glutaraldehyde. The efficiency of this reaction may be determined by measuring the incorporation of radiolabeled peptide. Unreacted glutaraldehyde and peptide may be separated by dialysis and the conjugate stored for subsequent use.

Serum samples from generation of polyclonal antisera or media samples from production of monoclonal antisera may be analyzed for determination of antibody titer and in particular, for the determination of high titer antisera Subsequently, the highest titer antisera may be tested to establish the following: a) optimal antiserum dilution for highest specific binding of the antigen and lowest non-specific binding, b) ability to bind increasing amounts of peptide in a standard displacement curve, c) potential cross-reactivity with immunologically-related peptides and proteins (including plasminogen, TSP-1, and TSP-1 of related species), and d) ability to detect the peptide of the invention in extracts of plasma, urine, tissues, and in cell culture media.

Titer may be established through several means known in the art, such as by dot blot and density analysis, and also by precipitation of radiolabeled peptide-antibody complexes using protein A, secondary antisera, cold ethanol or charcoal-dextran followed by activity measurement with a gamma counter. If desired, the highest titer antisera may be purified on affinity columns. For example, the peptides of the invention may be coupled to a commercially available resin and used to form an affinity column. Antiserum samples may then be passed through the column so that antibodies to the peptides of the invention bind (via the peptide) to the column. These bound antibodies are subsequently eluted, collected and evaluated for determination of titer and specificity.

Kits for measurement of the compounds of the invention are also contemplated as part of the present invention. Antisera that possess the highest titer and specificity and can detect the peptides of the invention in extracts of plasma, urine, tissues, and in cell culture media may be used to establish assay kits for rapid, reliable, sensitive, and specific measurement and localization of peptides of the invention. These assay kits may employ (but are not limited to) the following techniques: competitive and non-competitive assays, radioimmunoassay (RIA), bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit the range, sensitivity, precision, reliability, specificity and reproducibility of the assay are established by means well known to those skilled in the art.

The above described assay kit would provide instructions, antiserum, one or more peptides of the invention, and possibly radiolabeled peptides of the invention and/or reagents for precipitation of bound peptide/antibody complexes. Such a kit would be useful for the measurement of the peptide of the invention in biological fluids and tissue extracts of animals and humans with and without tumors, as is well known in the art.

Another kit may be used to visualize or localize the peptide of the invention in tissues and cells. Immunohistochemistry techniques and kits, for example, which employ such techniques are well known to those of ordinary skill in the art. Such a kit provides antisera to the peptide of the invention, and possibly blocking serum and secondary antiserum linked to a fluorescent molecule such as fluorescein isothiocyanate, or to some other reagent used to visualize the primary antiserum. Using this methodology, biopsied tumors may be examined for sites of peptide production or for sites of the peptide receptor. Alternatively, a kit may supply radiolabeled nucleic acids for use in in situ hybridization to probe for messenger RNA which encodes the compound of the invention.

Synthesis of the Peptides

The polypeptides of the present invention may be synthesized by any techniques that are known to those skilled in the art. For solid phase peptide synthesis, a summary of the many techniques may be found in J. M. Stewart and J. D. Young, Solid Phase Peptide Synthesis, W.H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Acacemic Press (New York), 1965.

Reagents, resins, amino acids, and amino acid derivatives are commercially available and can be purchased from Chem-Impex International, Inc. (Wood Dale, Ill., U.S.A.) or Calbiochem-Novabiochem Corp. (San Diego, Calif., U.S.A.) unless otherwise noted herein.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis.

In this particularly preferred method the alpha-amino function is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyl-oxycarbonyl, t-amyloxycarbonyl, isobornyloxycarbonyl, ($\alpha,\alpha$)-dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is preferred.

Particularly preferred side chain protecting groups are, for side chain amino groups as in lysine and arginine: 2,2,5,7,8-pentamethylchroman-6-sulfonyl (pmc), nitro, p-toluenesulfonyl, 4-methoxybenzenesulfonyl, Cbz, Boc, and adamantyloxycarbonyl; for tyrosine: benzyl, o-bromobenzyloxycarbonyl, 2,6-dichlorobenzyl, isopropyl, t-butyl (t-Bu), cyclohexyl, cyclopenyl and acetyl (Ac); for serine: 1-butyl, benzyl and tetrahydropyranyl; for histidine: trityl, benzyl, Cbz, p-toluenesulfonyl and 2,4-dinitrophenyl; for tryptophan: formyl and Boc.

In the solid phase peptide synthesis method, the C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. The preferred solid support for synthesis of C-terminal carboxy peptides is 4-hydroxymethylphenoxymethyl-copoly(styrene-1% divinylbenzene). The preferred solid support for C-terminal amide peptides is 4-(2',4'-dimethoxyphenyl-Fmoc-aminomethyl)phenoxyacetamidoethyl resin available from Applied Biosystems.

The C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCld), mediated coupling for from about 1 to about 24 hours at a temperature of between 10° and 50° C. in a solvent such as dichloromethane or DMF. When the solid support is 4-(2',4'-dimethoxyphenyl-Fmoc-aminomethyl)-phenoxyacetamidoethyl resin, the Fmoc group is cleaved with a secondary amine, preferably piperidine, prior to coupling with the C-terminal amino acid as described above. The preferred method for coupling to the deprotected 4(2,'4'-dimethoxyphenyl-Fmoc-aminomethylphenoxyacetamidoethyl resin is is O-benzotriazol-1-yl-N,N,N',N'-tetramethyluroniumhexafluorophosphate (HBTU, 1 equiv.) and 1-hydroxybenzotriazole (HOBT, 1 equiv.) in DMF.

The coupling of successive protected amino acids can be carried out in an automatic polypeptide synthesizer as is well known in the art. In a preferred embodiment, the α-amino function in the amino acids of the growing peptide chain are protected with Fmoc. The removal of the Fmoc protecting group from the N-terminal side of the growing peptide is accomplished by treatment with a secondary amine, preferably piperidine. Each protected amino acid is then introduced in about 3-fold molar excess and the coupling is preferably carried out in DMF. The coupling agent is normally O-benzotriazol-1-yl-N,N,N',N'-tetramethyluroniumhexafluorophosphate (HBTU, 1 equiv.) and 1-hydroxy-benzotriazole (HOBT, 1 equiv.).

At the end of the solid phase synthesis, the polypeptide is removed from the resin and deprotected, either in succession or in a single operation. Removal of the polypeptide and deprotection can be accomplished in a single operation by treating the resin-bound polypeptide with a cleavage reagent, for example thianisole, water, ethanedithiol and trifluoroacetic acid.

In cases wherein the C-terminus of the polypeptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage cocktail described above.

The fully deprotected peptide is purified by a sequence of chromatographic steps employing any or all of the following types: ion exchange on a weakly basic resin in the acetate form; hydrophobic adsorption chromatography on underivitized polystyrenedivinylbenzene (for example, AMBERLITE® XAD); silica gel adsorption chromatography; ion exchange chromatography on carboxymethylcellulose; partition chromatography, e.g. on SEPHADEX® G-25, LH-20 or countercurrent distribution; high performance liquid chromatography (HPLC), especially reverse-phase HPLC on octyl- or octadecylsilyl-silica bonded phase column packing.

The following examples will serve to further illustrate the preparation of the novel compounds of the invention.

Preparation of the Cleavage Reagent

The cleavage reagent (2 mL) is prepared by mixing, in the following order, thioanisole (100 μL), water (50 μL), ethanedithiol (50 μL) and trifluoroacetic acid (1.8 mL). The freshly-prepared mixture is cooled to −5° C. to −10° C. and used as described below.

Cleavage and Deprotection Procedure

A mixture of resin-bound polypeptide and cleavage reagent is stirred at 0° C. for 10–15 minutes and then at ambient temperature for a further 1.75 hours. The amount of time is increased by 0.5 hours for each additional arginine up to a total of three hours. The amount of cleavage reagent used is determined using the following formula:

| weight of resin (mg) | amount of cleavage reagent (μL) |
|---|---|
| 0–10 | 100 |
| 10–25 | 200 |
| 25–50 | 400 |
| 50–100 | 700 |
| 100–200 | 1200 |

The resin is then filtered off and rinsed with neat trifluoroacetic acid. The filtrate is then added in 0.5 mL portions to a centrifuge tube containing about 8 mL of cold diethyl ether. The suspension is then centrifuged and the supernatant is decanted off. The pellet is re-suspended in about 8 mL of ether, another 0.5 mL of the filtrate is added, and the process is repeated until all of the peptide is precipitated. The precipitated filtrate is then washed with ether, dried and lyophilized.

If the peptide does not precipitate upon addition to ether, the mixture is shaken with aqueous 30% acetic acid. The organic phase is then extracted twice with aqueous 30% acetic acid and the combined aqueous extracts are lyophilized.

EXAMPLE 1

N-Ac-Sar-Gly-Val-D-Ile-Thr-Nva-Ile-Arg-ProNHCH$_2$CH$_3$

In the peptide synthesis column position of a Perkin Elmer/Applied Biosynthesis SYNERGY® peptide synthesizer is placed an Pro(2-ClTrt) peptide synthesis column (25 μM amino acid; Nova Biochem). Amino acids are added sequentially according to the following synthetic cycle:

(1) Solvating the resin using DMF for about 5 minutes;

(2) Washing with DMF for about 5 minutes;

(3) Activating the incoming Fmoc protected amino acid (75 μM) using a 0.2 M solution of HBTU (75 μM) and HOBT (75 μM) in DMSO-NMP (N-methylpyrrolidone);

(4) Coupling using a solution in DMF of the activated Fmoc protected amino acid prepared in step 3 above for about 30 minutes;

(5) Washing with DMF for 5 minutes; and (6) For peptides capped with acetyl at the N-terminus, substituting acetic acid (87 μM) for an Fmoc protected amino acid and using 87 μM each of HBTU and HOBT.

(7) For peptides capped with ethylamide at the C-terminus, adding DMF to the resin followed by ByProp (1.1 equivalents) and ethylamine (20 equivalents) in THF.

The amino acids were coupled to the resin in the following order using the conditions indicated.

| # Amino Acid | Coupling |
|---|---|
| 1. Fmoc-Arg(Pmc) | 30 minutes |
| 2. Fmoc-Ile | 30 minutes |
| 3. Fmoc-Nva | 30 minutes |
| 4. Fmoc-Thr(t-Bu) | 30 minutes |
| 5. Fmoc-D-Ile | 30 minutes |
| 6. Fmoc-Val | 30 minutes |
| 7. Fmoc-Gly | 30 minutes |
| 8. Fmoc-Sar | 30 minutes |

Upon completion of the synthesis, the resin was washed with THF for about 5 minutes to remove DMF and shrink the resin. The resin was then gas dried with argon for about 10 minutes and nitrogen for a further 10 minutes to provide the resin-bound peptide (85 mg). Cleavage and deprotection are accomplished using the procedure described above (40 mg of dry resin-bound peptide, 700 µL of cleavage reagent, cleavage time 2.5 hours) to give the crude peptide (14 mg). Purification by HPLC using a 7 µm Symmetry Prep C18 column (7.8×300 mm) with solvent mixtures varying in a gradient from 5% to 100% acetonitrile-water over a period of 50 minutes followed by lyophilization provided the desired peptide.

The pure fractions were lyophilized to yield N-Ac-Sar-Gly-Val-D-Ile-Thr-Nva-Ile-Arg-ProNHCH$_2$CH$_3$ as the trifluoroacetate salt: R$_t$=26.5 min (10% to 40% acetonitrile in water containing 0.01% of TFA, over 30 min period); MS (ESI) m/e 994 (M+H)$^+$.

EXAMPLE 2

N-Ac-pyroGlu-Gly-Val-D-Ile-Thr-Nva-Ile-Arg-ProNHCH$_2$CH$_3$

| # Amino Acid | Coupling |
|---|---|
| 1. Fmoc-Arg(Pmc) | 30 minutes |
| 2. Fmoc-Ile | 30 minutes |
| 3. Fmoc-Nva | 30 minutes |
| 4. Fmoc-Thr(t-Bu) | 30 minutes |
| 5. Fmoc-D-Ile | 30 minutes |
| 6. Fmoc-Val | 30 minutes |
| 7. Fmoc-Gly | 30 minutes |
| 8. pyroGlu(Boc) | 30 minutes |

The desired peptide was prepared using the conditions described for Example 1. The amino acids were coupled to the resin in the following order using the conditions indicated.

The pure fractions were lyophilized to yield pyroGlu-Gly-Val-D-Ile-Thr-Nva-Ile-Arg-ProNHCH$_2$CH$_3$ as the trifluoroacetate salt: R$_t$=23.5 min (gradient of 10% to 40% acetonitrile in water containing 0.01% of TFA, over 30 min period); MS (ESI) m/e 994 (M+H)$^+$.

EXAMPLE 3

N-Ac-Sar-Gly-Val-D-Ile-Thr-Nva-Ile-Arg-ProNHCH$_3$

The procedure described in Example 1 was used but substituting methylamine (2.0 M solution in THF) for ethylamine. After cleavage of the peptide from the resin and removal of the protecting groups the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-ProNHCH$_3$ as the trifluoroacetate salt: R$_t$=3.224 min (gradient of 20% to 95% acetonitrile in water containing 0.01 M NH$_4$Ac over 10 min period); MS (ESI) m/e 930 (M+H)$^+$; Amino Acid Anal.: 1.09 Sar; 1.03 Gly; 0.98 Val; 0.98 Ile; 0.54 Thr; 1.72 Nva; 1.01 Arg; 1.08 Pro.

EXAMPLE 4

N-Ac-Sar-Gly-Val-D-Ile-Thr-Nva-Ile-Arg-ProNHCH(CH$_3$)$_2$

The procedure described in Example 1 was used but substituting isopropylamine for ethylamine. After cleavage of the peptide from the resin and removal of the protecting groups the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-ProNHIsopropyl as the trifluoroacetate salt: R$_t$=3.648 min (gradient of 20% to 95% acetonitrile in water containing 0.01 M NH$_4$Ac over 10 min period); MS (ESI) m/e 1008 (M+H)$^+$; Amino Acid Anal.: 1.10 Sar; 0.99 Gly; 0.96 Val; 1.88 Ile; 0.56 Thr; 1.67 Nva; 0.96 Arg; 1.09 Pro.

EXAMPLE 5

N-Ac-Sar-Gly-Val-D-Ile-Thr-Nva-Ile-Arg-ProNHethyl-(1-pyrrolidine)

Resin Preparation 4-(4-Formyl-3-methoxyphenoxy)butyryl AM resin (0.5 g, 0.54 mmol/g substitution) was placed in a solid phase synthesis reaction vessel containing (9:1) DMA/acetic acid (4 mL). The mixture was shaken for 5 min. The resin was drained and this process was repeated three times. To the swollen resin were added 10–15 grains of activated 4A molecular sieves and (9:1) DMA/acetic acid (4mL) and 10 molar equivalents of 1-(2-aminoethyl)pyrrolidine. The slurry was shaken for 1 h at rt and to it was added 10 molar equivalents of sodium triacetoxyborohydride. The slurry was shaken for 2 h at rt. The resin was drained and washed three times with DMA, three times with methanol, three times with dichloromethane, three times with diethyl ether and dried in vacuo at rt overnight. The dry resin was swollen in DMA (4 mL) and shaken for 5 min. This process was repeated twice.

Coupling of Fmoc-Pro

To the swollen resin in the reaction vessel were added sequentially the following chemicals; DMA (4 mL), one equivalent of DIEA, a DMA solution containing 3.0 equivalents of Fmoc-Pro, 3.0 equivalents of HATU, and 3.0 equivalents of DIEA. The slurry was shaken overnight. The resin was drained and washed three times with DMA, three times with methanol, three times with dichloromethane, three times with diethyl ether and dried in vacuo at rt overnight. A small portion of the resin was used to determine the Fmoc-Pro loading. The rest of the resin was shaken with DMA (4 mL) three times for 5 min and then for 1 h at rt with a solution of (8:1:1) DMA/pyridine/acetic anhydride (5 mL).

The resin was drained and washed three times with DMA, three times with methanol, three times with dichloromethane, and three times with diethyl ether. The resin was dried in vacuo at rt overnight and then used in the subsequent solid phase peptide synthesis.

Synthesis of Above Peptide

In the synthesis of the above peptide the amino acids, the coupling conditions and the synthetic protocol used were the identical to as those described in Example 1. Upon completion of the synthesis the peptide and the protecting groups were cleaved at rt using (95:5) TFA/anisole (3 mL) for 3 h. The resin was filtered and washed three times with methanol. The combined filtrates were concentrated in vacuo and to the residue was added diethylether. The solid precipitate was filtered. The crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-ProNHethyl(1-pyrrolidine) as the bis-trifluoroacetate salt: $R_t$=4.40 min (gradient of 20% to 95% acetonitrile in water containing 0.01 M $NH_4Ac$ over 10 min period); MS (ESI) m/e 1063 $(M+H)^+$; Amino Acid Anal.: 0.95 Sar; 1.0 Gly; 0.86 Val; 1.63 Ile; 0.56 Thr; 1.38 Nva; 0.88 Arg; 1.07 Pro.

EXAMPLE 6

N-Ac-Sar-Gly-Val-D-Ile-Thr-Nva-Ile-Arg-ProNHethyl(1-piperidine)

The procedure described in Example 5 was used but substituting 1-(2-amino-ethyl)piperidine for 1-(2-aminoethyl)pyrrolidine in the reductive alkylation step. After cleavage of the peptide from the resin and removal of the protecting groups the crude product was purified by C-18 column chromatography using a solvent mixture varying in a gradient of 100% to 50% acetonitrile-water containing 0.01% TFA. The pure fractions were lyophilized to yield N-Ac-Sar-Gly-Val-D-Ile-Thr-Nva-Ile-Arg-ProNHethyl-(1-piperidine) as the bis-trifluoroacetate salt: $R_t$=4.437 min (gradient of 20% to 95% acetonitrile in water containing 0.01 M $NH_4Ac$ over 10 min period); MS (ESI) m/e 1077 $(M+H)^+$; Amino Acid Anal.: 1.11 Sar; 1.04 Gly; 0.99 Val; 1.77 Ile; 0.61 Thr; 1.61 Nva; 0.97 Arg; 1.10 Pro.

EXAMPLE 7

N-Ac-Sar-Gly-Val-D-Ile-Thr-Nva-Ile-Arg-ProNHmethylcyclopropyl

The procedure described in Example 1 was used but substituting (aminoethyl)cyclopropane for 1-(2-aminoethyl)pyrrolidine. After cleavage of the peptide from the resin and removal of the protecting groups the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-ProNHmethylcyclopropyl as the trifluoroacetate salt: $R'$=3.815 min (gradient of 20% to 95% acetonitrile in water containing 0.01 M $NH_4Ac$ over 10 min period); MS (ESI) m/e 1020 $(M+H)^+$; Amino Acid Anal.: 1.01 Sar; 0.96 Gly; 0.96 Val; 1.66 Ile; 0.53 Thr; 1.65 Nva; 1.08 Arg; 1.09 Pro.

EXAMPLE 8

N-Ac-Sar-Gly-Val-D-Ile-Thr-Nva-Ile-Arg-ProNHethyl-1-(R)cyclohexyl

The procedure described in Example 5 was used but substituting (R)-1-cycloxylethylamine for 1-(2-aminoethylpyrrolidine). After cleavage of the peptide from the resin and removal of the protecting groups the crude product was purified by C-18 column chromatography using solvent mixture varying in a gradient of 10% to 50% acetonitrile-water containing 0.01% TFA. The pure factions were lyophilized to yield N-Ac-Sar-Gly-Val-D-Ile-Thr-Nva-Ile-Arg-ProNHethyl-1-(R)cyclohexyl as the trifluoroacetate salt: $R'$=5.196 min (gradient of 20% to 95% acetonitrile in water containing 0.01 M $NH_4Ac$ over 10 min period); MS (ESI) m/e 1076 $(M+H)^+$; Amino Acid Anal.: 1.19 Sar; 0.99 Gly; 0.62 Val; 1.47 Ile; 0.48 Thr; 1.57 Nva; 1.01 Arg; 0.83 Pro.

EXAMPLE 9

N-Ac-Sar-Gly-Val-D-Ile-Thr-Nva-Ile-Arg-ProNH(2-hydroxyethyl)

The procedure described in Example 5 was used but substituting O-TBDMS-ethanolamine for 1-(2-aminoethylpyrrolidine). After cleavage of the peptide from the resin and removal of the protecting groups the crude product was purified by C-18 column chromatography using solvent mixture varying in a gradient of 10% to 500% acetonitrile-water containing 0.01% TFA. The pure fractions were lyophilized to yield N-Ac-Sar-Gly-Val-D-Ile-Thr-Nva-Ile-Arg-ProNH(2-hydroxyethyl) as the trifluoroacetate salt: $R_t$=4.04 min (gradient of 20% to 95% acetonitrile in water containing 0.01 M $NH_4Ac$ over 10 min period); MS (ESI) m/e 1010 $(M+H)^+$; Amino Acid Anal.: 1.04 Sar; 1.01 Gly; 0.98 Val; 1.59 Ile; 0.44 Thr; 1.45 Nva; 0.99 Arg; 1.06 Pro.

EXAMPLE 10

N-Ac-Sar-Gly-Val-D-Ile-Thr-Nva-Ile-Arg-ProNH$_2$

The procedure described in Example 1 was used but substituting Fmoc-Pro-Sieber amide resin for H-Pro-2ClTrt resin. After cleavage of the peptide from the resin and removal of the protecting groups using (9:1) TFA/anisole (3 mL), the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-ProNH$_2$ as the trifluoroacetate salt: $R_t$=4.063 min (gradient of 20% to 95% acetonitrile in water containing 0.01 M $NH_4Ac$ over 10 min period); MS (ESI) m/e 966 $(M+H)^+$; Amino Acid Anal.: 0.87 Sar; 0.98 Gly; 0.94 Val; 1.73 Ile; 0.47 Thr; 1.35 Nva; 1.02 Arg; 1.05 Pro.

EXAMPLE 11

N-Ac-Sar-Gly-Val-D-Ile-Thr-Nva-Ile-Arg-ProNHCH$_2$CH$_2$OCH$_3$

The procedure described in Example 5 was used but substituting 2-methoxyethylamine for 1-(2-aminoethylpyrrolidine). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-ProNHCH$_2$CH$_2$—OCH$_3$ as the trifluoroacetate salt: $R_t$=3.40 min (gradient of 20% to 95% acetonitrile in water containing 0.01 M $NH_4Ac$ over 10 min period); MS (ESI) M/e 1024 $(M+H)^+$; Amino Acid Anal.: 1.02 Sar; 1.06 Gly; 0.97 Val; 1.54 Ile; 0.47 Thr; 1.81 Nva; 0.97 Arg; 1.25 Pro.

EXAMPLE 12

N-Ac-Sar-Gly-Val-D-Ile-Thr-Nva-Ile-Arg-ProNHCH$_2$CH$_2$-cyclohexyl

The procedure described in Example 5 was used but substituting cyclohexylethylamine for 1-(2-aminoethylpyrrolidine). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-ProNHCH$_2$CH$_2$-cyclohexyl as the trifluoroacetate salt: R$_t$=4.97 min (gradient of 20% to 95% acetonitrile in water containing 0.01 M NH$_4$Ac over 10 min period); MS (ESI) m/e 1076 (M+H)$^+$; Amino Acid Anal.: 0.87 Sar; 1.00 Gly; 0.88 Val; 1.34 Ile; 0.44 Thr; 1.61 Nva; 1.07 Arg; 1.05 Pro.

EXAMPLE 13

N-Ac-Sar-Gly-Val-D-Ile-Thr-Nva-Ile-Arg-ProNHCH$_2$CH$_2$CH$_3$

The procedure described in Example 1 was used but substituting propylamine for ethylamine. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-ProNHCH$_2$CH$_2$CH$_3$ as the trifluoroacetate salt: R$_t$=3.68 min (gradient of 20% to 95% acetonitrile in water containing 0.01 M NH$_4$Ac over 10 min period); MS (ESI) m/e 1008 (M+H)$^+$; Amino Acid Anal.: 0.94 Sar; 1.09 Gly; 0.96 Val; 1.58 Ile; 0.51 Thr; 1.78 Nva; 0.96 Arg; 1.23 Pro.

EXAMPLE 14

N-Ac-Sar-Gly-Val-D-alloIle-Thr-Nva-Ile-Arg-ProNHCH$_2$CH$_3$

The procedure described in Example 1 was used but substituting Fmoc-D-alloIle for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-alloIle-Thr-Nva-Ile-Arg-ProNHCH$_2$CH$_3$ as the trifluoroacetate salt: R$_t$=22.5 min (gradient of 10% to 30% acetonitrile in water containing 0.01% TFA over 30 min period); MS (ESI) m/e 994 (M+H)$^+$; Amino Acid Anal.: 0.95 Sar; 0.96 Gly; 0.97 Val; 0.99 Ile; 0.54 Thr; 1.66 Nva; 1.14 Arg; 1.08 Pro.

EXAMPLE 15

N-Ac-Sar-Gly-Val-D-Leu-Thr-Nva-Ile-Arg-ProNHCH$_2$CH$_3$

The procedure described in Example 1 was used but substituting Fmoc-D-Leu for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Ile-Arg-ProNHCH$_2$CH$_3$ as the trifluoroacetate salt: R$_t$=3.54 min (gradient of 10% to 30% acetonitrile in water containing 0.01% TFA over 30 min period); MS (ESI) M/e 994 (M+H)$^+$; Amino Acid Anal.: 1.00 Sar; 0.93 Gly; 0.96 Val; 1.02 Leu; 0.58Thr; 1.50 Nva; 0.99 Ile; 1.14 Arg; 1.08 Pro.

EXAMPLE 16

N-Ac-Sar-Gly-Val-Ile-Thr-Nva-Ile-Arg-ProNHCH$_2$CH$_3$

The procedure described in Example 1 was used but substituting Fmoc-Ile for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-Ile-Thr-Nva-Ile-Arg-ProNHCH$_2$CH$_3$ as the trifluoroacetate salt: R$_t$=3.28 min (gradient of 10% to 30% acetonitrile in water containing 0.01% TFA over 30 min period); MS (ESI) m/e 994 (M+H)$^+$; Amino Acid Anal.: 0.95 Sar; 0.94 Gly; 0.89 Val; 1.70 Ile; 0.52 Thr; 1.67 Nva; 0.99 Ile; 1.27 Arg; 1.06 Pro.

EXAMPLE 17

N-Ac-Sar-Gly-Val-Gly-Thr-Nva-Ile-Arg-ProNHCH$_2$CH$_3$

The procedure described in Example 1 was used but substituting Fmoc-Gly for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-Gly-Thr-Nva-Ile-Arg-ProNHCH$_2$CH$_3$ as the trifluoroacetate salt: R$_t$=2.47 min (gradient of 10% to 30% acetonitrile in water containing 0.01% TFA over 30 min period); MS (ESI) m/e 938 (M+H)$^+$; Amino Acid Anal.:1.10 Sar; 1.94 Gly; 1.03 Val; 0.98 1 Ile; 0.54 Thr; 1.61 Nva; 1.28 Arg; 1.05 Pro.

EXAMPLE 18

N-Ac-Sar-Gly-Val-D-Val-Thr-Nva-Ile-Arg-ProNHCH$_2$CH$_3$

The procedure described in Example 1 was used but substituting Fmoc-D-Val for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Val-Thr-Nva-Ile-Arg-ProNHCH$_2$CH$_3$ as the trifluoroacetate salt: R$_t$=3.13 min (gradient of 10% to 30% acetonitrile in water containing 0.01% TFA over 30 min period); MS (ESI) m/e 980 (M+H)$^+$; Amino Acid Anal.: 1.07 Sar; 1.0 Gly; 2.01 Val; 0.99 Ile; 0.62 Thr; 1.54 Nva; 1.49 Arg; 1. I 1 Pro.

EXAMPLE 19

N-Ac-Sar-Gly-Val-alloIle-Thr-Nva-Ile-Arg-ProNHCH$_2$CH$_3$

The procedure described in Example 1 was used but substituting Fmoc-alloIle for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-alloIle-Thr-Nva-Ile-Arg-ProNHCH$_2$CH$_3$ as the trifluoroacetate salt: R$_t$=4.174 min (gradient of 10% to 30% acetonitrile in water containing 0.01% TFA over 30 min period); MS (ESI) m/e 994 (M+H)$^+$; Amino Acid Anal.: 1.02 Sar; 0.99 Gly; 0.95 Val; 1.29 Ile; 0.45 Thr; 1.52 Nva; 1.54 Arg; 1.07 Pro.

EXAMPLE 20

N-Ac-Sar-Gly-Val-D-Ala-Thr-Nva-Ile-Arg-ProNHCH$_2$CH$_3$

The procedure described in Example 1 was used but substituting Fmoc-D-Ala for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ala-Thr-Nva-Ile-Arg-ProNHCH$_2$CH$_3$ as the trifluoroacetate salt: R$_t$=3.826 min (gradient of 10% to 30% acetonitrile in water containing 0.01% TFA over 30 min period); MS (APCI) m/e 952 (M)$^+$ and 908 (M-44)$^+$.

EXAMPLE 21

N-Ac-Sar-Gly-Val-D-Lys-Thr-Nva-Ile-Arg-ProNHCH$_2$CH$_3$

The procedure described in Example 1 was used but substituting Fmoc-Lys(Boc) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Lys-Thr-Nva-Ile-Arg-ProNHCH$_2$CH$_3$ as the trifluoroacetate salt: R$_t$=3.544 min (gradient of 10% to 30% acetonitrile in water containing 0.01% TFA over 30 min period); MS (APCI) m/e 1009 (M)$^+$ and 965 (M-44)$^+$.

EXAMPLE 22

N-Ac-Sar-Gly-Val-D-Met-Thr-Nva-Ile-Arg-ProNHCH$_2$CH$_3$

The procedure described in Example 1 was used but substituting Fmoc-D-Met for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Met-Thr-Nva-Ile-Arg-ProNHCH$_2$CH$_3$ as the trifluoroacetate salt: R$_t$=4.141 min (gradient of 10% to 30% acetonitrile in water containing 0.01% TFA over 30 min period); MS (APCI) m/e 1012 (M)$^+$.

EXAMPLE 23

N-Ac-Sar-Gly-Val-D-Nle-Thr-Nva-Ile-Arg-ProNHCH$_2$CH$_3$

The procedure described in Example 1 was used but substituting Fmoc-D-Nle for Fmoc-D-Ile. After cleavage of the peptide from the resin and removal of the protecting groups using (9;1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Nle-Thr-Nva-Ile-Arg-ProNHCH$_2$CH$_3$ as the trifluoroacetate salt: R$_t$=4.383 min (gradient of 10% to 30% acetonitrile in water containing 0.01% TFA over 30 min period); MS (APCI) m/e 994 (M)$^+$.

EXAMPLE 24

N-Ac-Sar-Gly-Val-D-Phe-Thr-Nva-Ile-Arg-ProNHCH$_2$CH$_3$

The procedure described in Example 1 was used but substituting Fmoc-D-Phe for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Phe-Thr-Nva-Ile-Arg-ProNHCH$_2$CH$_3$ as the trifluoroacetate salt: R$_t$=4.476 min (gradient of 10% to 30% acetonitrile in water containing 0.01% TFA over 30 min period); MS (APCI) m/e 1028 (M)$^+$.

EXAMPLE 25

N-Ac-Sar-Gly-Val-D-Trp-Thr-Nva-Ile-Arg-ProNHCH$_2$CH$_3$

The procedure described in Example 1 was used but substituting Fmoc-D-Trp(Boc) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Trp-Thr-Nva-Ile-Arg-ProNHCH$_2$CH$_3$ as the trifluoroacetate salt: R$_t$=4.430 min (gradient of 10% to 30% acetonitrile in water containing 0.01% TFA over 30 min period); MS (APCI) m/e 1024 (M)$^+$.

EXAMPLE 26

N-Ac-Sar-Gly-Val-D-Tyr-Thr-Nva-Ile-Arg-ProNHCH$_2$CH$_3$

The procedure described in Example 1 was used but substituting Fmoc-D-Tyr(2-ClTrt) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Tyr-Thr-Nva-Ile-Arg-ProNHCH$_2$CH$_3$ as the trifluoroacetate salt: R$_t$=3.964 min (gradient of 10% to 30% acetonitrile in water containing 0.01% TFA over 30 min period); MS (APCI) m/e 1045 (M)$^+$.

EXAMPLE 27

N-Ac-Sar-Gly-Val-D-4,4'-Biphenylala-Thr-Nva-Ile-Arg-ProNHCH$_2$CH$_3$

The procedure described in Example 1 was used but substituting Fmoc-D-4,4'-Biphenylala for Fmoc-D-Ile. After cleavage of the peptide from the resin and removal of raw the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-4,4'-Biphenylala-Thr-Nva-Ile-Arg-ProNHCH$_2$CH$_3$ as the trifluoroacetate salt: R$_t$=5.005 min (gradient of 10% to 30% acetonitrile in water containing 0.01% TFA over 30 min period); MS (APCI) m/e 1104 (M)$^+$.

EXAMPLE 28

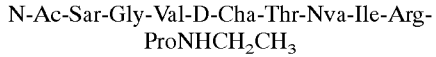

The procedure described in Example 1 was used but substituting Fmoc-D-Cha for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Cha-Thr-Nva-Ile-Arg-ProNHCH$_2$CH$_3$ as the trifluoroacetate salt: R$_t$=5.005 min (gradient of 10% to 30% acetonitrile in water containing 0.01% TFA over 30 min period); MS (APCI) m/e 1034 (M)$^+$.

EXAMPLE 29

N-Ac-Sar-Gly-Val-D-Chg-Thr-Nva-Ile-Arg-ProNHCH$_2$CH$_3$

The procedure described in Example 1 was used but substituting Fmoc-D-Chg for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Chg-Thr-Nva-Ile-Arg-ProNHCH$_2$CH$_3$ as the trifluoroacetate salt: R$_t$=4.377 min (gradient of 10% to 30% acetonitrile in water containing 0.01% TFA over 30 min period); MS (APCI) m/e 977 (M)$^+$.

EXAMPLE 30

The procedure described in Example 1 was used but substituting Fmoc-D-4-ClPhe for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-4-ClPhe-Thr-Nva-Ile-Arg-ProNHCH$_2$CH$_3$ as the trifluoroacetate salt: R$_t$=4.674 min (gradient of 10% to 30% acetonitrile in water containing 0.01% TFA over 30 min period); MS (APCI) m/e 1018 (M)$^+$.

EXAMPLE 31

The procedure described in Example 1 was used but substituting Fmoc-D-Hphe for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Hphe-Thr-Nva-Ile-Arg-ProNHCH$_2$CH$_3$ as the trifluoroacetate salt: R$_t$=4.597 min (gradient of 10% to 30% acetonitrile in water containing 0.01% TFA over 30 min period); MS (APCI) m/e 1042 (M)$^+$ and 998 (M-44)$^+$.

EXAMPLE 32

The procedure described in Example 1 was used but substituting Fmoc-Dehydroleu for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-Dehydroleu-Thr-Nva-Ile-Arg-ProNHCH$_2$CH$_3$ as the trifluoroacetate salt: R$_t$=4.1707 min (gradient of 10% to 30% acetonitrile in water containing 0.01% TFA over 30 min period); MS (APCI) m/e 992 (M)$^+$ and 949 (M-44)$^+$.

EXAMPLE 33

The procedure described in Example 1 was used but substituting Fmoc-D-3-CF$_3$Phe for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-3CF$_3$Phe-Thr-Nva-Ile-Arg-ProNHCH$_2$CH$_3$ as the trifluoroacetate salt: R$_t$=4.825 min (gradient of 10% to 30% acetonitrile in water containing 0.01% TFA over 30 min period); MS (APCI) m/e 1097 (M)$^+$ and 1053 (M44)$^+$.

EXAMPLE 34

The procedure described in Example 1 was used but substituting Fmoc-D-pentaFPhe for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-pentaFPhe-Thr-Nva-Ile-Arg-ProNHCH$_2$CH$_3$ as the trifluoroacetate salt: R$_t$=4.810 min (gradient of 10% to 30% acetonitrile in water containing 0.01% TFA over 30 min period); MS (APCI) m/e 1118 (M)$^+$ and 1075 (M-44)$^+$.

EXAMPLE 35

The procedure described in Example 1 was used but substituting Fmoc-D-3,4-diClPhe for Fmoc-D-Ile. After cleavage of the peptide from the resin and removal of the protecting groups using (9 1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-3,4-diClPhe-Thr-Nva-Ile-Arg-ProNHCH$_2$CH$_3$ as the trifluoroacetate salt: R$_t$=4.911 min (gradient of 10% to 30% acetonitrile in water containing 0.01% TFA over 30 min period); MS (APCI) m/e 1100 (M+3)$^+$.

EXAMPLE 36

N-Ac-Sar-Gly-Val-D-3-ClPhe-Thr-Nva-Ile-Arg-ProNHCH$_2$CH$_3$

The procedure described in Example 1 was used but substituting Fmoc-D-3-ClPhe for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-3-ClPhe-Thr-Nva-Ile-Arg-ProNHCH$_2$CH$_3$ as the trifluoroacetate salt: R$_t$=4.689 min (gradient of 10% to 30% acetonitrile in water containing 0.01% TFA over 30 min period); MS (APCI) m/e 1062 (M)$^+$.

EXAMPLE 37

N-Ac-Sar-Gly-Val-D-2-Thienylala-Thr-Nva-Ile-Arg-ProNHCH$_2$CH$_3$

The procedure described in Example 1 was used but substituting Fmoc-D-2-Thienylala for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-2-Thienylala-Thr-Nva-Ile-Arg-ProNHCH$_2$CH$_3$ as the trifluoroacetate salt: R$_t$=4.388 min (gradient of 10% to 30% acetonitrile in water containing 0.01% TFA over 30 min period); MS (APCI) m/e 1034 (M)$^+$.

EXAMPLE 38

N-Ac-Sar-Gly-Val-D-3CNPhe-Thr-Nva-Ile-Arg-ProNHCH$_2$CH$_3$

The procedure described in Example 1 was used but substituting Fmoc-D-3-CNPhe for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-3-CNPhe-Thr-Nva-Ile-Arg-ProNHCH$_2$CH$_3$ as the trifluoroacetate salt: R$_t$=4.361 min (gradient of 10% to 30% acetonitrile in water containing 0.01% TFA over 30 min period); MS (APCI) m/e 1009 (M)$^+$.

EXAMPLE 39

N-Ac-Sar-Gly-Val-D-3,3-Diphenylala-Thr-Nva-Ile-Arg-ProNHCH$_2$CH$_3$

The procedure described in Example 1 was used but substituting Fmoc-D-3,3'-Diphenylala for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-3,3'-Diphenylala-Thr-Nva-Ile-Arg-ProNHCH$_2$CH$_3$ as the trifluoroacetate salt: R$_t$=4.778 min (gradient of 10% to 30% acetonitrile in water containing 0.01% TFA over 30 min period); MS (APCI) m/e 1104 (M)$^+$.

EXAMPLE 40

N-Ac-Sar-Gly-Val-D-3-Benzothienylala-Thr-Nva-Ile-Arg-ProNHCH$_2$CH$_3$

The procedure described in Example 1 was used but substituting Fmoc-D-3-Benzothienylala for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-3-Benzothienylala-Thr-Nva-Ile-Arg-ProNHCH$_2$CH$_3$ as the trifluoroacetate salt: R$_t$=4.797 min (gradient of 10% to 30% acetonitrile in water containing 0.01% TFA over 30 min period); MS (APCI) m/e 1084 (M)$^+$.

EXAMPLE 41

N-Ac-Sar-Gly-Val-D-3,4-diF-Phe-Thr-Nva-Ile-Arg-ProNHCH$_2$CH$_3$

The procedure described in Example 1 was used but substituting Fmoc-D-3,4diF-Phe for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-3,4-diF-Phe-Thr-Nva-Ile-Arg-ProNHCH$_2$CH$_3$ as the trifluoroacetate salt: R$_t$=4.608 min (gradient of 10% to 30% acetonitrile in water containing 0.01% TFA over 30 min period); MS (APCI) m/e 1064 (M)$^+$.

EXAMPLE 42

N-Ac-Sar-Gly-Val-D-Ile-Thr-D-Nva-Ile-Arg-ProNHCH$_2$CH$_3$

The procedure described in Example 1 was used but substituting Fmoc-DNva for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-DNva-Ile-Arg-ProNHCH$_2$CH$_3$ as the trifluoroacetate salt: R$_t$=3.75 min (gradient of 10% to 30% acetonitrile in water containing 0.01% TFA over 30 min period); MS (ESI) m/e 994 (M+H)$^+$; Amino Acid Anal.: 1.08 Sar; 0.96 Gly; 0.95 Val; 1.74 Ile; 0.50 Thr; 1.69 Nva; 1.26 Arg; 1.09 Pro.

EXAMPLE 43

N-Ac-Sar-Gly-Val-D-Ile-Thr-Gln-Ile-Arg-ProNHCH$_2$CH$_3$

The procedure described in Example 1 was used but substituting Fmoc-Gln(Trt) for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Gln-Ile-Arg-ProNHCH$_2$CH$_3$ as the trifluoroacetate salt: R$_t$=3.047 min (gradient of 10% to 30% acetonitrile in water containing 0.01% TFA over 30 min period); MS (ESI) m/e 1023 (M+H)$^+$; Amino Acid Anal.: 1.15 Sar; 0.96 Gly; 0.63 Val; 1.7 Ile; 0.46 Thr; 0.65 Glu; 1.45 Arg; 1.04 Pro.

EXAMPLE 44

N-Ac-Sar-Gly-Val-D-Ile-Thr-Cha-Ile-Arg-ProNHCH$_2$CH$_3$

The procedure described in Example 1 was used but substituting Fmoc-Cha for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to $^{50}$% acetonitrile-water containing 0.01% TFA. The pure fractions were lyophilized to yield N-Ac-Sar-Gly-Val-D-Ile-Thr-Cha-Ile-Arg-ProNHCH$_2$CH$_3$ as the trifluoroacetate salt: R$_t$=4.503 min (gradient of 10% to 30% acetonitrile in water containing 0.01% TFA over 30 min period); MS (ES!) m/e 1048 (M+H)$^+$; Amino Acid Anal.: 1.18 Sar; 0.94 Gly; 0.59 Val; 1.65 Ile; 0.45 Thr; 0.37 Cha; 1.45 Arg; 1.06 Pro.

EXAMPLE 45

N-Ac-Sar-Gly-Val-D-Ile-Thr-Gly-Ile-Arg-ProNHCH$_2$CH$_3$

The procedure described in Example 1 was used but substituting Fmoc-Gly for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Gly-Ile-Arg-ProNHCH$_2$CH$_3$ as the trifluoroacetate salt: R$_t$=3.11 min (gradient of 10% to 30% acetonitrile in water containing 0.01% TFA over 30 min period); MS (ESI) m/e 952 (M+H)$^+$.

EXAMPLE 46

N-Ac-Sar-Gly-Val-D-Ile-Thr-Ala-Ile-Arg-ProNHCH$_2$CH$_3$

The procedure described in Example 1 was used but substituting Fmoc-Ala for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure factions were lyophilized to yield N-Ac-Sar-Gly-Val-D-Ile-Thr-Ala-Ile-Arg-ProNHCH$_2$CH$_3$ as the trifluoroacetate salt: R$_t$=3.16 min (gradient of 10% to 30% acetonitrile in water containing 0.01% TFA over 30 min period); MS (ESI) m/e 966 (M+H)$^+$.

EXAMPLE 47

N-Ac-Sar-Gly-Val-D-Ile-Thr-Val-Ile-Arg-ProNHCH$_2$CH$_3$

The procedure described in Example 1 was used but substituting Fmoc-Val for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Val-Ile-Arg-ProNHCH$_2$CH$_3$ as the trifluoroacetate salt: R$_t$=3.36 min (gradient of 10% to 30% acetonitrile in water containing 0.01% TFA over 30 min period); MS (ESI) m/e 994 (M+H)$^+$.

EXAMPLE 48

N-Ac-Sar-Gly-Val-D-Ile-Thr-Abu-Ile-Arg-ProNHCH$_2$CH$_3$

The procedure described in Example 1 was used but substituting Fmoc-Abu for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Abu-Ile-Arg-ProNHCH$_2$CH$_3$ as the trifluoroacetate salt: R$_t$=3.23 min. (gradient of 10% to 30% acetonitrile in water containing 0.01% TFA over 30 min period); MS (ESI) m/e 980 (M+H)$^+$.

EXAMPLE 49

N-Ac-Sar-Gly-Val-D-Ile-Thr-Allylgly-Ile-Arg-ProNHCH$_2$CH$_3$

The procedure described in Example 1 was used but substituting Fmoc-Allylgly for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Allylgly-Ile-Arg-ProNHCH$_2$CH$_3$ as the trifluoroacetate salt: R$_t$=3.40 min (gradient of 10% to 30% acetonitrile in water containing 0.01% TFA over 30 min period); MS (ESI) m/e 992 (M+H)$^+$.

EXAMPLE 50

N-Ac-Sar-Gly-Val-D-Ile-Thr-Octylgly-Ile-Arg-ProNHCH$_2$CH$_3$

The procedure described in Example 1 was used but substituting Fmoc-Octylgly for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Octylgly-Ile-Arg-ProNHCH$_2$CH$_3$ as the trifluoroacetate salt: R$_t$=5.30 min (gradient of 10% to 30% acetonitrile in water containing 0.01% TFA over 30 min period); MS (ESI) m/e 1064 (M+H)$^+$.

EXAMPLE 51

N-Ac-Sar-Gly-Val-D-Ile-Thr-Met-Ile-Arg-ProNHCH$_2$CH$_3$

The procedure described in Example 1 was used but substituting Fmoc-Met for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Met-Ile-Arg-ProNHCH$_2$CH$_3$ as the trifluoroacetate salt: R$_t$=3.48 min (gradient of 10% to 30% acetonitrile in water containing 0.01% TFA over 30 min period); MS (ESI) m/e 1027 (M+H)$^+$)$^+$.

EXAMPLE 52

N-Cyclohexylacetyl-Sar-Gly-Val-D-Ile-Thr-Nva-Ile-Arg-ProNHCH$_2$CH$_3$

The procedure described in Example 1 was used but substituting cyclohexylacetic acid for acetic acid. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Cyclohexylacetyl-Sar-Gly-Val-D-Ile-Thr-Nva-Ile-Arg-ProNHCH$_2$CH$_3$ as the trifluoroacetate salt: R$_t$=5.11 min (gradient of 10% to 30% acetonitrile in water containing 0.01% TFA over 30 min period); MS (ESI) m/e 1076 (M+H)$^+$)$^+$; Amino Acid Anal.: 1.15 Sar; 0.97 Gly; 0.95 Val; 1.79 Ile; 0.54 Thr; 1.66 Nva; 1.28 Arg; 1.08 Pro.

EXAMPLE 53

N-(2-Me-Nicotinyl)-Sar-Gly-Val-D-Ile-Thr-Nva-Ile-Arg-ProNHCH$_2$CH$_3$

The procedure described in Example 1 was used but substituting 2-Me-nicotinic acid for acetic acid. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-(2-Me-Nicotinyl)-Sar-Gly-Val-D-Ile-Thr-Nva-Ile-Arg-ProNHCH$_2$CH$_3$ as the trifluoroacetate salt: R$_t$=5.11 min (gradient of 10% to 30% acetonitrile in water containing 0.01% TFA over 30 min period); MS (ESI) m/e 1071 (M+H)$^+$; Amino Acid Anal.: 1.19 Sar; 1.01 Gly; 0.99 Val; 1.79 Ile; 0.57 Thr; 1.70 Nva; 1.59 Arg; 1.17 Pro.

EXAMPLE 54

N-Succinyl-Sar-Gly-Val-D-Ile-Thr-Nva-Ile-Arg-ProNHCH$_2$CH$_3$

The procedure described in Example 1 was used but acylating the peptide resin (after the Fmoc-Sar coupling and deprotection) with a (1:1) succinic anhydride/pyridine mixture (2 mL) overnight. After washing the resin and cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Succinyl-Sar-Gly-Val-D-Ile-Thr-Nva-Ile-Arg-ProNHCH$_2$CH$_3$ as the trifluoroacetate salt: R$_t$=2.72 min (gradient of 10% to 30% acetonitrile in water containing 0.01% TFA over 30 min period); MS (ESI) m/e 1052 (M+H)$^+$; Amino Acid Anal.: 1.16 Sar; 1.05 Gly; 0.95 Val; 1.85 Ile; 0.57 Thr; 1.70 Nva; 1.59 Arg; 1.17 Pro.

EXAMPLE 55

N-Nicotinyl-Sar-Gly-Val-D-Ile-Thr-Nva-Ile-Arg-ProNHCH$_2$CH$_3$

The procedure described in Example 1 was used but substituting nicotinic acid for acetic acid at the last coupling. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Nicotinyl-Sar-Gly-Val-D-Ile-Thr-Nva-Ile-Arg-ProNHCH$_2$CH$_3$ as the trifluoroacetate salt: R$_t$=3.6 min (gradient of 10% to 30% acetonitrile in water containing 0.01% TFA over 30 min period); MS (ESI) m/e 1057 (M+H)$^+$; Amino Acid Anal.: 1.03 Sar; 0.89 Gly; 0.81 Val; 1.48 Ile; 0.40 Thr; 1.46 Nva; 1.07 Arg; 1.04 Pro.

EXAMPLE 56

N-Propionyl-Sar-Gly-Val-D-Ile-Thr-Nva-Ile-Arg-ProNHCH$_2$CH$_3$

The procedure described in Example 1 was used but substituting propionic acid for acetic acid at the last coupling. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Propionyl-Sar-Gly-Val-D-Ile-Thr-Nva-Ile-Arg-ProNHCH$_2$CH$_3$ as the trifluoroacetate salt: R$_t$=3.7 min (gradient of 10% to 30% acetonitrile in water containing 0.01% TFA over 30 min period); MS (ES) m/e 1008 (M+H)$^+$; Amino Acid Anal.: 0.93 Sar; 0.97 Gly; 0.88 Val; 1.60 Ile; 0.44 Thr; 1.58 Nva; 1.17 Arg; 1.10 Pro.

EXAMPLE 57

N-MeOacetyl-Sar-Gly-Val-D-Ile-Thr-Nva-Ile-Arg-ProNHCH$_2$CH$_3$

The procedure described in Example 1 was used but substituting methoxyacetic acid for acetic acid at the last coupling. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-MeOacetyl-Sar-Gly-Val-D-Ile-Thr-Nva-Ile-Arg-ProNHCH$_2$CH$_3$ as the trifluoroacetate salt: R$_t$=3.45 min (gradient of 10% to 30% acetonitrile in water containing 0.01% TFA over 30 min period); MS (ESI) m/e 1024 (M+H)$^+$; Amino Acid Anal.: 1.12 Sar; 1.06 Gly; 0.94 Val; 1.62 Ile; 0.48 Thr; 1.91 Nva; 1.40 Arg; 1.27 Pro.

EXAMPLE 58

N-Shikimyl-Sar-Gly-Val-D-Ile-Thr-Nva-Ile-Arg-ProNHCH$_2$CH$_3$

The procedure described in Example 1 was used but substituting shikimic acid for acetic acid at the last coupling. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Shikimyl-Sar-Gly-Val-D-Ile-Thr-Nva-Ile-Arg-ProNHCH$_2$CH$_3$ as the trifluoroacetate salt. R$_t$=3.0 min (gradient of 10% to 30% acetonitrile in water containing 0.01% TFA over 30 min period); MS (ESI) m/e 1108 (M+H)$^+$; Amino Acid Anal.: 1.22 Sar; 1.06 Gly; 0.94 Val; 1.80 Ile; 0.55 Thr; 1.70 Nva; 1.28 Arg; 1.26 Pro.

EXAMPLE 59

N-(2-Furoyl)-Sar-Gly-Val-D-Ile-Thr-Nva-Ile-Arg-ProNHCH$_2$CH$_3$

The procedure described in Example 1 was used but substituting 2-furoic acid for acetic acid at the last coupling. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-(2-Furoyl)-Sar-Gly-Val-D-Ile-Thr-Nva-Ile-Arg-ProNHCH$_2$CH$_3$ as the trifluoroacetate salt: R$_t$=4.0 min (gradient of 10% to 30% acetonitrile in water containing 0.01% TFA over 30 min period); MS (ESI) m/e 1046 (M+H)$^+$; Amino Acid Anal.: 1.02 Sar; 1.00 Gly; 0.99 Val; 1.66 Ile; 0.45 Thr; 1.75 Nva; 1.45 Arg; 1.21 Pro.

EXAMPLE 60

N-Butyryl-Sar-Gly-Val-D-Ile-Thr-Nva-Ile-Arg-ProNHCH$_2$CH$_3$

The procedure described in Example 1 was used but substituting butyric acid for acetic acid at the last coupling. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Butyryl-Sar-Gly-Val-D-Ile-Thr-Nva-Ile-Arg-ProNHCH$_2$CH$_3$ as the trifluoroacetate salt: R$_t$=4.03 min (gradient of 10% to 30% acetonitrile in water containing 0.01% TFA over 30 min period); MS (ESI) m/e 1022 (M+H)$^+$; Amino Acid Anal.: 1.13 Sar; 0.99 Gly; 1.01 Val; 1.93 Ile; 0.67 Thr; 1.61 Nva; 1.45 Arg; 1.08 Pro.

EXAMPLE 61

N-(Tetrahydro-2-furoyl)-Sar-Gly-Val-D-Ile-Thr-Nva-Ile-Arg-ProNHCH$_2$CH$_3$

The procedure described in Example 1 was used but substituting tetrahydro-2-furoic acid for acetic acid at the last coupling. After cleavage of the peptide from the resin and removal of the protecting groups using (9:1) TFA/anisole (3 mL) the crude product was purified by C-18 column chromatography a solvent mixture varying in a gradient of 10% to 50% acetonitrile-water containing 0.01% TFA. The pure fractions were lyophilized to yield N-(tetrahydro-2furoyl)-Sar-Gly-Val-D-Ile-Thr-Nva-Ile-Arg-ProNHCH$_2$CH$_3$ as the trifluoroacetate salt: R$_t$=3.91 min (gradient of 10% to 30% acetonitrile in water containing 0.01% TFA over 30 min period); MS (ESI) m/e 1050 (M+H)$^+$; Amino Acid Anal.: 1.12 Sar; 0.97 Gly; 0.88 Val; 1.41 Ile; 0.42 Thr; 1.60 Nva; 1.43 Arg; 1.03 Pro.

EXAMPLE 62

N—[CH$_3$C(O)NH—(CH$_2$)$_2$—O—(CH$_2$)$_2$—O—CH$_2$—C(O)]-Sar-Gly-Val-D-Ile-Thr-Nva-Ile-Arg-ProNHCH$_2$CH$_3$

The procedure described in Example 1 was used but coupling with Fmoc-8-amino-3,6-dioxo-octanoic acid after the Fmoc-Sar coupling, after removal of the terminal Fmoc the peptide resin was coupled with acetic acid as described above. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N—[CH$_3$C(O)NH—(CH$_2$)$_2$—O—(CH$_2$)$_2$—O—CH$_2$—C(O)]-Sar-Gly-Val-D-Ile-Thr-Nva-Ile-Arg-ProNHCH$_2$CH$_3$ as the trifluoroacetate salt: R$_t$=3.32 min (gradient of 10% to 30% acetonitrile in water containing 0.01% TFA over 30min period); MS (ESI) m/e 1139(M+H)$^+$; Amino Acid Anal.: 1.04Sar; 1.01 Gly; 0.91 Val; 1.67 Ile; 0.53 Thr; 1.77 Nva; 1.39 Arg; 1.02 Pro.

EXAMPLE 63

N-[6-N'-Acetyl-(CH$_2$)$_5$C(O)]-Sar-Gly-Val-D-Ile-Thr-Nva-Ile-Arg-ProNHCH$_2$CH$_3$ The procedure described in Example 1 was used but coupling with Fmoc6-amino-hexanoic acid after the Fmoc-Sar coupling, after removal of the terminal Fmoc the peptide resin was coupled with acetic acid as described above. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-[6-N-Acetyl-(CH$_2$)$_5$C(O)]-Sar-Gly-Val-D-Ile-Thr-Nva-Ile-Arg-ProNHCH$_2$CH$_3$ as the trifluoroacetate salt: R$_t$=3.60 min (gradient of 10% to 30% acetonitrile in water containing 0.01% TFA over 30 min period); MS (ESI) m/e 1107 (M+H)$^+$; Amino Acid Anal.: 1.13 Sar; 0.96 Gly; 0.89 Val; 1.42 Ile; 0.43 Thr; 1.68 Nva; 1.44 Arg; 1.04 Pro.

EXAMPLE 64

N-Hexanoyl-Sar-Gly-Val-D-Ile-Thr-Nva-Ile-Arg-ProNHCH$_2$CH$_3$

The procedure described in Example 1 was used but substituting hexanoic acid for acetic acid. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Hexanoyl-Sar-Gly-Val-D-Ile-Thr-Nva-Ile-Arg-ProNHCH$_2$CH$_3$ as the trifluoroacetate salt: R$_t$=4.95 min (gradient of 10% to 30% acetonitrile in water containing 0.01% TFA over 30 min period); MS (ESI) m/e 1050 (M+H)$^+$; Amino Acid Anal.: 1.07 Sar; 0.93 Gly; 1.02 Val; 1.95 Ile; 0.56 Thr; 1.31 Nva; 1.52 Arg; 1.05 Pro.

EXAMPLE 65

N-[4-N'-Acetyl-butyryl]-Sar-Gly-Val-D-Ile-Thr-Nva-Ile-Arg-ProNHCH$_2$CH$_3$

The procedure described in Example 1 was used but coupling with Fmoc-4-amino-butyric acid after the Fmoc-Sar coupling, after removal of the terminal Fmoc the peptide resin was coupled with acetic acid as described above. After cleavage of the peptide from the resin and removal of the protecting groups using (9:1) TFA/anisole (3 mL) the crude product was purified by C-18 column chromatography a solvent mixture varying in a gradient of 10% to 50% acetonitrile-water containing 0.01% TFA. The pure fractions were lyophilized to yield N-[4N'Acetyl-butyryl]-Sar-Gly-Val-D-Ile-Thr-Nva-Ile-Arg-ProNHCH$_2$CH$_3$ as the trifluoroacetate salt: R$_t$=4.09 min (gradient of 10% to 30% acetonitrile in water containing 0.01% TFA over 30 min period); MS (ESI) m/e 1079 (M+H)$^+$; Amino Acid Anal.: 1.03 Gaba; 1.07 Sar; 0.93 Gly; 1.00 Val; 1.90 Ile; 0.54 Thr; 1.30 Nva; 1.54 Arg; 1.06 Pro.

EXAMPLE 66

H-Sar-Gly-Val-D-Ile-Thr-Nva-Ile-Arg-ProNHCH$_2$CH$_3$

The procedure described in Example 1 was used but omitting the acetic acid coupling at the end. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield H-Sar-Gly-Val-D-Ile-Thr-Nva-Ile-Arg-ProNHCH$_2$CH$_3$ as the bistrifluoroacetate salt: R$_t$=3.65 min (gradient of 10% to 30% acetonitrile in water containing 0.01% TFA over 30 min period); MS (ESI) m/e 952 (M+H)$^+$; Amino Acid Anal.: 1.00 Sar; 1.00 Gly; 0.99 Val; 1.67 Ile; 0.50 Thr; 1.76 Nva; 1.47 Arg; 1.22 Pro.

EXAMPLE 67

N-Ac-Sar-Gly-Asn-D-Ile-Thr-Nva-Ile-Arg-ProNHCH$_2$CH$_3$

The procedure described in Example 1 was used but substituting Fmoc-Asn(Trt) for Fmoc-Val. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Asn-D-Ile-Thr-Nva-Ile-Arg-ProNHCH$_2$CH$_3$ as the bistrifluoroacetate salt: R$_t$=2.45 min (gradient of 10% to 30% acetonitrile in water containing 0.01% TFA over 30 min period); MS (ESI) m/e 1009 (M+H)$^+$; Amino Acid Anal.: 1.05 Sar; 0.98 Gly; 0.96 Asp; 1.7 Ile; 0.48 Thr; 1.54 Nva; 1.32 Arg; 1.07 Pro.

EXAMPLE 68

N—[CH$_3$C(O)NH—(CH$_2$)$_2$—O—(CH$_2$)$_2$—O—CH$_2$—C(O)]-Gly-Val-D-Ile-Thr-Nva-Ile-Arg-ProNHCH$_2$CH$_3$

The procedure described in Example 1 was used but substituting Fmoc-8-amino-3,6-dioxo-octanoic acid for Fmoc-Sar. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N—[CH$_3$C(O)NH—(CH$_2$)$_2$—O—(CH$_2$)$_2$—O—CH$_2$—C(O)]-Gly-Val-D-Ile-Thr-Nva-Ile-Arg-ProNHCH$_2$CH$_3$ as the trifluoroacetate salt: R$_t$=4.12 min (gradient of 10% to 30% acetonitrile in water containing 0.01% TFA over 30 min period); MS (ESI) m/e 1068 (M+H)$^+$; Amino Acid Anal.: 0.93 Gly; 1.02 Val; 1.97 Ile; 0.57 Thr; 1.31 Nva; 1.54 Arg; 1.05 Pro.

EXAMPLE 69

N-Ac-Pro-Gly-Val-D-Ile-Thr-Nva-Ile-Arg-ProNHCH$_2$CH$_3$

The procedure described in Example 1 was used but substituting Fmoc-Pro for Fmoc-Sar. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Pro-Gly-Val-D-Ile-Thr-Nva-Ile-Arg-ProNHCH$_2$CH$_3$ as the trifluoroacetate salt: R$_t$=4.30 min (gradient of 10% to 30% acetonitrile in water containing 0.01% TFA over 30 min period); MS (ESI) m/e 1020 (M+H)$^+$; Amino Acid Anal.: 0.92 Gly; 0.99 Val; 1.80 Ile; 0.50 Thr; 1.32 Nva; 1.53 Arg; 2.09 Pro.

EXAMPLE 70

N-Ac-Gly-Gly-Val-D-Ile-Thr-Nva-Ile-Arg-ProNHCH$_2$CH$_3$

The procedure described in Example 1 was used but substituting Fmoc-Gly for Fmoc-Sar. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Gly-Gly-Val-D-Ile-Thr-Nva-Ile-Arg-ProNHCH$_2$CH$_3$ as the trifluoroacetate salt: R$_t$=4.08 min (gradient of 10% to 30% acetonitrile in water containing 0.01% TFA over 30 min period); MS (ESI) m/e 980 (M+H)$^+$; Amino Acid Anal.: 1.89 Gly; 1.02 Val; 1.91 Ile; 0.52 Thr; 1.35 Nva; 1.57 Arg; 1.09 Pro.

EXAMPLE 71

N-Ac-Ala-Gly-Val-D-Ile-Thr-Nva-Ile-Arg-ProNHCH$_2$CH$_3$

The procedure described in Example 1 was used but substituting Fmoc-Ala for Fmoc-Sar. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Ala-Gly-Val-D-Ile-Thr-Nva-Ile-Arg-ProNHCH$_2$CH$_3$ as the trifluoroacetate salt: R$_t$=4.00 min (gradient of 10% to 30% acetonitrile in water containing 0.01% TFA over 30 min period); MS (ESI) m/e 994 (M+H)$^+$; Amino Acid Anal.: 1.01 Ala; 0.93 Gly; 1.01 Val; 1.92 Ile; 0.56 Thr; 1.30 Nva; 1.51 Arg; 1.05 Pro.

EXAMPLE 72

N-Ac-NEtGly-Gly-Val-D-Ile-Thr-Nva-Ile-Arg-ProNHCH$_2$CH$_3$

The procedure described in Example 1 was used but substituting Fmoc-NEtGly for Fmoc-Sar. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-NEtGly-Gly-Val-D-Ile-Thr-Nva-Ile-Arg-ProNHCH$_2$CH$_3$ as the trifluoroacetate salt: R$_t$=4.24 min (gradient of 10% to 30% acetonitrile in water containing 0.01% TFA over 30 min period); MS (ESI) m/e 1008 (M+H)$^+$; Amino Acid Anal.: 0.95 Gly; 1.04 Val; 1.99 Ile; 0.59 Thr; 1.34 Nva; 1.50 Arg; 1.01 Pro.

EXAMPLE 73

N-Ac-Sar-Gly-Val-D-Ile-Thr-Leu-Ile-Arg-ProNHCH$_2$CH$_3$

The procedure described in Example 1 was used but subsituting Fmoc-Leu for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Leu-Ile-Arg-ProNHCH$_2$CH$_3$ as the trifluoroacetate salt: R$_t$=4.348 min (gradient of 10% to 30% acetonitrile in water containing 0.01% TFA over 30 min period); MS (ESI) m/e 1008 (M+H)$^+$; Amino Acid Anal.: 0.88 Sar; 0.99 Gly; 0.95 Val; 1.03 Ile; 0.55 Thr; 1.12 Leu; 1.53 Arg; 1.07 Pro.

EXAMPLE 74

N-Ac-Sar-Gly-Val-D-Ile-Thr-Ser-Ile-Arg-ProNHCH$_2$CH$_3$

The procedure described in Example 1 was used but substituting Fmoc-Ser(tBu) for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Ser-Ile-Arg-ProNHCH$_2$CH$_3$ as the trifluoroacetate salt: R$_t$=3.963 min (gradient of 10% to 30% acetonitrile in water containing 0.01% TFA over 30 min period); MS (ESI) m/e 982 (M+H)$^+$; Amino Acid Anal.: 0.91 Sar; 0.97 Gly; 1.00 Val; 1.03 Ile; 0.56 Thr; 0.23 Ser; 1.52 Arg; 1.08 Pro.

EXAMPLE 75

N-Ac-Sar-Gly-Val-D-Ile-Thr-Nva-Ile-Arg-Pro-D-AlaNH$_2$

The procedure described in Example 10 was used but substituting Fmoc-D-Ala-Sieber amide resin for Fmoc-Pro-Sieber amide resin. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-Pro-D-AlaNH$_2$ as the trifluoroacetate salt: R$_t$=4.117 min (gradient of 10% to 30% acetonitrile in water containing 0.01% TFA over 30 min period); MS (ESI) m/e 1037 (M+H)$^+$; Amino Acid Anal.: 0.85 Sar; 0.94 Gly; 0.92 Val; 1.83 Ile; 0.54 Thr; 1.18 Nva; 1.01 Arg; 1.04 Pro; 1.01 Ala.

EXAMPLE 76

N-Ac-Sar-Gly-Val-D-Ile-Thr-Nva-Ile-Arg-D-ProNHCH$_2$CH$_3$

The procedure described in Example 10 was used but substituting Fmoc-D-Pro-Sieber ethylamide resin for Fmoc-Pro-Sieber amide resin. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-D-Pro-NHCH$_2$CH$_3$ as the trifluoroacetate salt: R$_t$=4.20 min (gradient of 10% to 30% acetonitrile in water containing 0.01% TFA over 30 min period); MS (ESI) m/e 994 (M+H)$^+$.

EXAMPLE 77

N-Ac-Sar-Gly-Val-D-Ile-Thr-Nva-Ile-Arg-AbuNHCH$_2$CH$_3$

The procedure described in Example 10 was used but substituting Fmoc-Abu-Sieber ethylamide resin for Fmoc-Pro-Sieber amide resin. After cleavage of the peptide from the resin and removal of the protecting groups using (9:1) TFA/anisole (3 mL) the crude product was purified by C-18 column chromatography a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-AbuNHCH$_2$CH$_3$ as the trifluoroacetate salt: R$_t$=4.35 min (gradient of 10% to 30% acetonitrile in water containing 0.01% TFA over 30 min period); MS (ESI) m/e 982 (M+H)$^+$.

EXAMPLE 78

N-Ac-Sar-Gly-Val-D-Ile-Thr-Nva-Ile-Arg-PheNHCH$_2$CH$_3$

The procedure described in Example 10 was used but substituting Fmoc-Phe-Sieber ethylamide resin for Fmoc-Pro-Sieber amide resin. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-Phe-NHCH$_2$CH$_3$ as the trifluoroacetate salt: R$_t$=4.73 min (gradient of 10% to 30% acetonitrile in water containing 0.01% TFA over 30 min period); MS (ESI) m/e 1044 (M+H)$^+$.

EXAMPLE 79

N-Ac-Sar-Gly-Val-D-Ile-Thr-Nva-Ile-Arg-Tic-NHCH$_2$CH$_3$

The procedure described in Example 10 was used but substituting Fmoc-Tic-Sieber ethylamide resin for Fmoc-Pro-Sieber amide resin. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-Tic-NHCH$_2$CH$_3$ as the trifluoroacetate salt: R$_t$=4.68 min (gradient of 10% to 30% acetonitrile in water containing 0.01% TFA over 30 min period); MS (ESI) m/e 1056 (M+H)$^+$.

EXAMPLE 80

N-Ac-Sar-Gly-Val-D-Ile-Thr-Nva-Ile-Arg-Hyp-NHCH$_2$CH$_3$

The procedure described in Example 10 was used but substituting Fmoc-Hyp-Sieber ethylamide resin for Fmoc-Pro-Sieber amide resin. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-Hyp-NHCH$_2$CH$_3$ as the trifluoroacetate salt: R$_t$=3.95 min (gradient of 10% to 30% acetonitrile in water containing 0.01% TFA over 30 min period); MS (ESI) m/e 1010 (M+H)$^+$.

EXAMPLE 81

N-Ac-Sar-Gly-Val-D-Ile-Thr-Nva-Ile-Arg-Aib-NHCH$_2$CH$_3$

The procedure described in Example 10 was used but substituting Fmoc-Aib-Sieber ethylamide resin for Fmoc- Pro-Sieber amide resin. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-Aib-NHCH$_2$CH$_3$ as the trifluoroacetate salt: R$_t$=4.25 min (gradient of 10% to 30% acetonitrile in water containing 0.01% TFA over 30 min period); MS (ESI) m/e 982 (M+H)$^+$.

EXAMPLE 82

N-Ac-Sar-Gly-Val-D-Ile-Thr-Nva-Ile-Arg-D-Ala-NHCH$_2$CH$_3$

The procedure described in Example 10 was used but substituting Fmoc-D-Ala-Sieber ethylamide resin for Fmoc-Pro-Sieber amide resin. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-D-Ala-NHCH$_2$CH$_3$ as the trifluoroacetate salt: R$_t$=2.95 min (gradient of 10% to 30% acetonitrile in water containing 0.01% TFA over 30 m period); MS (ESI) m/e 968 (M+H)$^+$.

EXAMPLE 83

N-Ac-Sar-Gly-Val-D-Ile-Thr-Nva-Ile-Arg-Pip-NHCH$_2$CH$_3$

The procedure described in Example 10 was used but substituting Fmoc-Pip-Sieber ethylamide resin for Fmoc-Pro-Sieber amide resin. After cleavage of the peptide from the resin and removal of the protecting groups using (9.1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-Pip-NHCH$_2$CH$_3$ as the trifluoroacetate salt: R$_t$=3.30 min (gradient of 10% to 30% acetonitrile in water containing 0.01% TFA over 30 min period); MS (ESI) m/e 1008 (M+H)$^+$.

EXAMPLE 84

N-Ac-Sar-Gly-Val-D-Tyr(Et)-Thr-Nva-Ile-Arg-ProNHCH$_2$CH$_3$

The procedure described in Example 1 was used but substituting Fmoc-D-Tyr(Et) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Tyr(Et)-Thr-Nva-Ile-Arg-ProNHCH$_2$CH$_3$ as the trifluoroacetate salt: R$_t$=6.01 min (gradient of 10% to 30% acetonitrile in water containing 0.01% TFA over 30 min period); MS (APCI) m/e 1072 (M)$^+$.

EXAMPLE 85

N-Ac-Sar-Gly-Val-D-Cys(tBu)-Thr-Nva-Ile-Arg-ProNHCH$_2$CH$_3$

The procedure described in Example 1 was used but substituting Fmoc-D-Cys(tBu) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fictions were lyophilized to yield N-Ac-Sar-Gly-Val-D-Cys(tBu)-Thr-Nva-Ile-Arg-ProNHCH$_2$CH$_3$ as the trifluoroacetate salt: R$_t$=5.96 min (gradient of 10% to 30% acetonitrile in water containing 0.01% TFA over 30 min period); MS (APCI) m/e 1040 (M)$^+$.

EXAMPLE 86

N-Ac-Sar-Gly-Val-D-Cys(Acm)-Thr-Nva-Ile-Arg-ProNHCH$_2$CH$_3$

The procedure described in Example 1 was used but substituting Fmoc-D-Cys(Acm) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Cys(Acm)-Thr-Nva-Ile-Arg-ProNHCH$_2$CH$_3$ as the trifluoroacetate salt: R$_t$=5.12 min (gradient of 10% to 30% acetonitrile in water containing 0.01% TFA over 30 min period); MS (APCI) m/e 1044 (M)$^+$.

EXAMPLE 87

N-Ac-Sar-Gly-Val-D-Tyr(Bzl)-Thr-Nva-Ile-Arg-ProNHCH$_2$CH$_3$

The procedure described in Example 1 was used but substituting Fmoc-D-Tyr(Bzl) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Tyr(Bzl)Thr-Nva-Ile-Arg-ProNHCH$_2$CH$_3$ as the trifluoroacetate salt: R$_t$=6.74 min (gradient of 10% to 30% acetonitrile in water containing 0.01% TFA over 30 min period); MS (APCI) m/e 1135 (M+H)$^+$.

EXAMPLE 88

N-Ac-Sar-Gly-Val-D-Ser(Bzl)-Thr-Nva-Ile-Arg-ProNHCH$_2$CH$_3$

The procedure described in Example 1 was used but substituting Fmoc-D-Ser(Bzl) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ser(Bzl)-Thr-Nva-Ile-Arg-ProNHCH$_2$CH$_3$ as the trifluoroacetate salt: R$_t$=5.95 min (gradient of 10% to 30% acetonitrile in water containing 0.01% TFA over 30 min period); MS (APCI) m/e 1058 (M)$^+$.

EXAMPLE 89

N-Ac-Sar-Gly-Val-D-1Nal-Thr-Nva-Ile-ArgProNHCH$_2$CH$_3$

The procedure described in Example 1 was used but substituting Fmoc-D-1Nal for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-1Nal-Thr-Nva-Ile-Arg-ProNHCH$_2$CH$_3$ as the trifluoroacetate salt: R$_t$=6.30 min (gradient of 10% to 30% acetonitrile in water containing 0.01% TFA over 30 min period); MS (APCI) m/e 1081 (M+3)$^+$.

EXAMPLE 90

N-Ac-Sar-Gly-Val-D-tButylgly-Thr-Nva-Ile-Arg-ProNHCH$_2$CH$_3$

The procedure described in Example 1 was used but substituting Fmoc-D-tButylgly for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-tButylgly-Thr-Nva-Ile-Arg-ProNHCH$_2$CH$_3$ as the trifluoroacetate salt: R$_t$=5.46 min (gradient of 10% to 30% acetonitrile in water containing 0.01% TFA over 30 min period); MS (APCI) m/e 994 (M)$^+$.

EXAMPLE 91

N-Ac-Sar-Gly-Val-D-Orn-Thr-Nva-Ile-Arg-ProNHCH$_2$CH$_3$

The procedure described in Example 1 was used but substituting Fmoc-D-Orn(Boc) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Orn-Thr-Nva-Ile-Arg-ProNHCH$_2$CH$_3$ as the trifluoroacetate salt: R$_t$=1.69 min (gradient of 10% to 30% acetonitrile in water containing 0.01% TFA over 30 min period); MS (APCI) m/e 995 (M)$^+$.

EXAMPLE 92

N-Ac-Sar-Gly-Val-D-Thr(Bzl)-Thr-Nva-Ile-Arg-ProNHCH$_2$CH$_3$

The procedure described in Example 1 was used but substituting Fmoc-D-Thr(Bzl) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Thr(Bzl)-Thr-Nva-Ile-Arg-ProNHCH$_2$CH$_3$ as the trifluoroacetate salt: R$_t$=6.10 min (gradient of 10% to 30% acetonitrile in water containing 0.01% TFA over 30 min period); MS (APCI) m/e 1072 (M)$^+$.

EXAMPLE 93

N-Ac-Sar-Gly-Val-D-2Nal-Thr-Nva-Ile-Arg-ProNHCH$_2$CH$_3$

The procedure described in Example 1 was used but substituting Fmoc-D-2Nal for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-2Nal-Thr-Nva-Ile-Arg-ProNHCH$_2$CH$_3$ as the trifluoroacetate salt: R$_t$=6.33 min (gradient of 10% to 30% acetonitrile in water containing 0.01% TFA over 30 min period); MS (APCI) m/e 1078 (M)$^+$.

EXAMPLE 94

N-Ac-Sar-Gly-Val-D-Phe(4-Me)-Thr-Nva-Ile-Arg-ProNHCH$_2$CH$_3$

The procedure described in Example 1 was used but substituting Fmoc-D-Phe(4Me) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Phe(4-Me)-Thr-Nva-Ile-Arg-ProNHCH$_2$CH$_3$ as the trifluoroacetate salt: R$_t$=3.654 min (gradient of 10% to 30% acetonitrile in water containing 0.01% TFA over 30 min period); MS (ESI) m/e 1042 (M)$^+$.

EXAMPLE 95

N-Ac-Sar-Gly-Val-D-Phe(3,4-diMeO)-Thr-Nva-Ile-Arg-ProNHCH$_2$CH$_3$

The procedure described in Example 1 was used but substituting Fmoc-D-Phe(3,4-diMeO) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Phe(3,4-diMeO)-Thr-Nva-Ile-Arg-ProNHCH$_2$CH$_3$ as the trifluoroacetate salt: R$_t$=3.006 min (gradient of 10% to 30% acetonitrile in water containing 0.01% TFA over 30 min period); MS (ESI) m/e 1088 (M)$^+$.

EXAMPLE 96

N-Ac-Sar-Gly-Val-D-Phe(3,4,5-triF)-Thr-Nva-Ile-Arg-ProNHCH$_2$CH$_3$

The procedure described in Example 1 was used but substituting Fmoc-D-Phe(3,4,5-triF) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Phe(3,4,5-triF)-Thr-Nva-Ile-Arg-ProNHCH$_2$CH$_3$ as the trifluoroacetate salt: R$_t$=3.848 min (gradient of 10% to 30% acetonitrile in water containing 0.01% TFA over 30 min period); MS (ESI) m/e 1082 (M)$^+$.

EXAMPLE 97

N-Ac-Sar-Gly-Val-D-Phe(4NO$_2$)-Thr-Nva-Ile-Arg-ProNHCH$_2$CH$_3$

The procedure described in Example 1 was used but substituting Fmoc-D-Phe(4-NO$_2$) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Phe(4-NO$_2$)-Thr-Nva-Ile-Arg-ProNHCH$_2$CH$_3$ as the trifluoroacetate salt: R$_t$=3.483 min (gradient of 10% to 30% acetonitrile in water containing 0.01% TFA over 30 min period); MS (ESI) m/e 1073 (M)$^+$.

EXAMPLE 98

N-Ac-Sar-Gly-Val-D-Pen-Thr-Nva-Ile-Arg-ProNHCH$_2$CH$_3$

The procedure described in Example 1 was used but substituting Fmoc-D-Pen(Trt) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Pen-Thr-Nva-Ile-Arg-ProNHCH$_2$CH$_3$ as the trifluoroacetate salt: R$_t$=2.928 min (gradient of 10% to 30% acetonitrile in water containing 0.01% TFA over 30 min period); MS (ESI) m/e 1012 (M)$^+$.

EXAMPLE 99

N-Ac-Sar-Gly-Val-D-Pen(Acm)-Thr-Nva-Ile-Arg-ProNHCH$_2$CH$_3$

The procedure described in Example 1 was used but substituting Fmoc-D-Pen(Acm) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure factions were lyophilized to yield N-Ac-Sar-Gly-Val-D-Pen(Acm)-Thr-Nva-Ile-Arg-ProNHCH$_2$CH$_3$ as the trifluoroacetate salt: R$_t$=2.415 min (gradient of 10% to 30% acetonitrile in water containing 0.01% TFA over 30 min period); MS (ESI) m/e 1083 (M)$^+$.

EXAMPLE 100

N-Ac-Sar-Gly-Val-D-Pen(Bzl)-Thr-Nva-Ile-Arg-ProNHCH$_2$CH$_3$

The procedure described in Example 1 was used but substituting Fmoc-D-Pen(Bzl) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Pen(Bzl)-Thr-Nva-Ile-Arg-ProNHCH$_2$CH$_3$ as the trifluoroacetate salt: R$_t$=4.124 min (gradient of 10% to 30% acetonitrile in water containing 0.01% TFA over 30 min period); MS (ESI) m/e 1102 (M)$^+$.

EXAMPLE 101

N-Ac-Sar-Gly-Val-D-Abu-Thr-Nva-Ile-Arg-ProNHCH$_2$CH$_3$

The procedure described in Example 1 was used but substituting Fmoc-D-Abu for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Abu-Thr-Nva-Ile-Arg-ProNHCH$_2$CH$_3$ as the trifluoroacetate salt: R$_t$=2.533 min (gradient of 10% to 30% acetonitrile in water containing 0.01% TFA over 30 min period); MS (ESI) m/e 966 (M)$^+$.

EXAMPLE 102

N-Ac-Sar-Gly-Val-D-Phe(4-NH$_2$)-Thr-Nva-Ile-Arg-ProNHCH$_2$CH$_3$

The procedure described in Example 1 was used but substituting Fmoc-D-Phe(4-Boc-NH$_2$) for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Phe(4-NH$_2$)-Thr-Nva-Ile-Arg-ProNHCH$_2$CH$_3$ as the trifluoroacetate salt: R$_t$=2.545 min (gradient of 10% to 30% acetonitrile in water containing 0.01% TFA over 30 min period); MS (ESI) m/e 1043 (M)$^+$.

EXAMPLE 103

N-Ac-Sar-Gly-Val-D-Leu-Thr-Nva-Ala-Arg-ProNHCH$_2$CH$_3$

The procedure described in Example 15 was used but substituting Fmoc-Ala for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Ala-Arg-ProNHCH$_2$CH$_3$ as the trifluoroacetate salt: R$_t$=2.675 min (gradient of 10% to 30% acetonitrile in water containing 0.01% TFA over 30 min period); MS (ESI) m/e 952 (M)$^+$.

EXAMPLE 104

N-Ac-Sar-Gly-Val-D-Leu-Thr-Nva-Gln-Arg-ProNHCH$_2$CH$_3$

The procedure described in Example 15 was used but substituting Fmoc-Gln(Trt) for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Gln-Arg-ProNHCH$_2$CH$_3$ as the trifluoroacetate salt: R$_t$=2.46 min (gradient of 10% to 30% acetonitrile in water containing 0.01% TFA over 30 min period); MS (ESI) m/e 1009 (M)$^+$.

EXAMPLE 105

N-Ac-Sar-Gly-Val-D-Leu-Thr-Nva-Met-Arg-ProNHCH$_2$CH$_3$

The procedure described in Example 15 was used but substituting Fmoc-Met for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Met-Arg-ProNHCH$_2$CH$_3$ as the trifluoroacetate salt: R$_t$=3.219 min (gradient of 10% to 30% acetonitrile in water containing 0.01% TFA over 30 min period); MS (ESI) m/e 1012 (M)$^+$.

EXAMPLE 106

N-Ac-Sar-Gly-Val-D-Leu-Thr-Nva-Phe-Arg-ProNHCH$_2$CH$_3$

The procedure described in Example 15 was used but substituting Fmoc-Phe for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Phe-Arg-ProNHCH$_2$CH$_3$ as the trifluoroacetate salt: R$_t$=3.579 min (gradient of 10% to 30% acetonitrile in water containing 0.01% TFA over 30 min period); MS (ESI) m/e 1028 (M)$^+$.

EXAMPLE 107

N-Ac-Sar-Gly-Val-D-Leu-Thr-Nva-Pro-Arg-ProNHCH$_2$CH$_3$

The procedure described in Example 15 was used but substituting Fmoc-Pro for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Pro-Arg-ProNHCH$_2$CH$_3$ as the trifluoroacetate salt: R$_t$=2.704 min (gradient of 10% to 30% acetonitrile in water containing 0.01% TFA over 30 min period); MS (ESI) m/e 978 (M)$^+$.

EXAMPLE 108

N-Ac-Sar-Gly-Val-D-Leu-Thr-Nva-Ser-Arg-ProNHCH$_2$CH$_3$

The procedure described in Example 15 was used but substituting Fmoc-Ser(tBu) for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Ser-Arg-ProNHCH$_2$CH$_3$ as the trifluoroacetate salt: R$_t$=2.510 min (gradient of 10% to 30% acetonitrile in water containing 0.01% TFA over 30 min period); MS (ESI) m/e 968 (M)$^+$.

EXAMPLE 109

N-Ac-Sar-Gly-Val-D-Leu-Thr-Nva-Trp-Arg-ProNHCH$_2$CH$_3$

The procedure described in Example 15 was used but substituting Fmoc-Trp(Boc) for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Trp-Arg-ProNHCH$_2$CH$_3$ as the trifluoroacetate salt: R$_t$=3.625 min (gradient of 10% to 30% acetonitrile in water containing 0.01% TFA over 30 min period); MS (ESI) m/e 1067 (M)$^+$.

EXAMPLE 110

N-Ac-Sar-Gly-Val-D-Leu-Thr-Nva-Tyr-Arg-ProNHCH$_2$CH$_3$

The procedure described in Example 15 was used but substituting Fmoc-Tyr(tBu) for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Tyr-Arg-ProNHCH$_2$CH$_3$ as the trifluoroacetate salt: R$_t$=3.017 min (gradient of 10% to 30% acetonitrile in water containing 0.01% TFA over 30 min period); MS (ESI) m/e 1044 (M)$^+$.

EXAMPLE 111

N-Ac-Sar-Gly-Val-D-Leu-Thr-Nva-Nva-Arg-ProNHCH$_2$CH$_3$

The procedure described in Example 15 was used but substituting Fmoc-Nva for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Nva-Arg-ProNHCH$_2$CH$_3$ as the trifluoroacetate salt: R$_t$=3.139 min (gradient of 10% to 30% acetonitrile in water containing 0.01% TFA over 30 min period); MS (ESI) m/e 980 (M)$^+$.

EXAMPLE 112

N-Ac-Sar-Gly-Val-D-Leu-Thr-Nva-Asp-Arg-ProNHCH$_2$CH$_3$

The procedure described in Example 15 was used but substituting Fmoc-Asp(OtBu)OH for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Asp-Arg-ProNHCH$_2$CH$_3$ as the trifluoroacetate salt R$_t$=2.082 min (gradient of 10% to 30% acetonitrile in water containing 0.01% TFA over 30 min period); MS (ESI) m/e 996 (M)$^+$.

EXAMPLE 113

N-Ac-Sar-Gly-Val-D-Leu-Thr-Nva-Gly-Arg-ProNHCH$_2$CH$_3$

The procedure described in Example 15 was used but substituting Fmoc-Gly for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Gly-Arg-ProNHCH$_2$CH$_3$ as the trifluoroacetate salt: R$_t$=2.623 min (gradient of 10% to 30% acetonitrile in water containing 0.01% TFA over 30 min period); MS (ESI) m/e 938 (M)$^+$.

EXAMPLE 114

N-Ac-Sar-Gly-Val-D-Leu-Thr-Nva-Lys(Ac)-Arg-ProNHCH$_2$CH$_3$

The procedure described in Example 15 was used but substituting Fmoc-Lys(Ac) for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Lys(Ac>Arg-ProNHCH$_2$CH$_3$ as the trifluoroacetate salt: R$_t$=2.599 min (gradient of 10% to 30% acetonitrile in water containing 0.01% TFA over 30 min period); MS (ESI) m/e 1051 (M)$^+$.

EXAMPLE 115

N-Ac-Sar-Gly-Val-D-Leu-Thr-Nva-Leu-Arg-ProNHCH$_2$CH$_3$

The procedure described in Example 15 was used but substituting Fmoc-Leu for Fmoc-Ile. After cleavage of the peptide from the resin and removal of the protecting groups using (9:1) TFA/anisole (3 mL) the crude product was purified by C-1 8 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Leu-Arg-ProNHCH$_2$CH$_3$ as the trifluoroacetate salt: R$_t$=3.403 min (gradient of 10% to 30% acetonitrile in water containing 0.01% TFA over 30 min period); MS (ESI) m/e 994 (M)$^+$.

EXAMPLE 116

N-Ac-Sar-Gly-Val-D-Leu-Thr-Nva-2Nal-Arg-ProNHCH$_2$CH$_3$

The procedure described in Example 15 was used but substituting Fmoc-2Nal for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-2Nal-Arg-ProNHCH$_2$CH$_3$ as the trifluoroacetate salt: R$_t$=4.198 min (gradient of 10% to 30% acetonitrile in water containing 0.01% TFA over 30 min period); MS (ESI) m/e 1078 (M)$^+$.

EXAMPLE 117

N-Ac-Sar-Gly-Val-D-Leu-Thr-Nva-1Nal-Arg-ProNHCH$_2$CH$_3$

The procedure described in Example 15 was used but substituting Fmoc-1Nal for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-1Nal-Arg-ProNHCH$_2$CH$_3$ as the trifluoroacetate salt: R$_t$=4.217 min (gradient of 10% to 30% acetonitrile in water containing 0.0.1% TFA over 30 min period); MS (ESI) m/e 1078 (M)$^+$.

EXAMPLE 118

N-Ac-Sar-Gly-Val-D-Leu-Thr-Nva-Allylgly-Arg-ProNHCH$_2$CH$_3$

The procedure described in Example 15 was used but substituting Fmoc-Allylgly for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Allylgly-Arg-ProNHCH$_2$CH$_3$ as the trifluoroacetate salt: R$_t$=2.993 min (gradient of 10% to 30% acetonitrile in water containing 0.01% TFA over 30 min period); MS (ESI) m/e 978 (M)$^+$.

EXAMPLE 119

N-Ac-Sar-Gly-Val-D-Leu-Thr-Nva-Cit-Arg-ProNHCH$_2$CH$_3$

The procedure described in Example 15 was used but substituting Fmoc-Cit for Fmoc-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Nva-Cit-Arg-ProNHCH$_2$CH$_3$ as the trifluoroacetate salt: R$_t$=2.408 min (gradient of 10% to 30% acetonitrile in water containing 0.01% TFA over 30 min period); MS (ESI) m/e 1038 (M)$^+$.

EXAMPLE 120

N-Ac-Sar-Gly-Val-D-Leu-Ala-Nva-Ile-Arg-ProNHCH$_2$CH$_3$

The procedure described in Example 15 was used but substituting Fmoc-Ala for Fmoc-Thr(Bu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Ala-Nva-Ile-Arg-ProNHCH$_2$CH$_3$ as the trifluoroacetate salt: R$_t$=3.481 min (gradient of 10% to 30% acetonitrile in water containing 0.01% TFA over 30 min period); MS (ESI) m/e 964 (M)$^+$.

EXAMPLE 121

N-Ac-Sar-Gly-Val-D-Leu-Pro-Nva-Ile-Arg-ProNHCH$_2$CH$_3$

The procedure described in Example 15 was used but substituting Fmoc-Pro for Fmoc-Thr(tBu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Pro-Nva-Ile-Arg-ProNHCH$_2$CH$_3$ as the trifluoroacetate salt: R$_t$=3.621 min (gradient of 10% to 30% acetonitrile in water containing 0.01% TFA over 30 min period); MS (ESI) m/e 990 (M)$^+$.

EXAMPLE 122

N-Ac-Sar-Gly-Val-D-Leu-Trp-Nva-Ile-Arg-ProNHCH$_2$CH$_3$

The procedure described in Example 15 was used but substituting Fmoc-Trp(Boc) for Fmoc-Thr(tBu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Trp-Nva-Ile-Arg-ProNHCH$_2$CH$_3$ as the trifluoroacetate salt: R$_t$=4.378 min (gradient of 10% to 30% acetonitrile in water containing 0.01% TFA over 30 min period); MS (ESI) m/e 1079 (M)$^+$.

EXAMPLE 123

N-Ac-Sar-Gly-Val-D-Leu-Tyr-Nva-Ile-Arg-ProNHCH$_2$CH$_3$

The procedure described in Example 15 was used but substituting Fmoc-Tyr(tBu) for Fmoc-Thr(tBu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Tyr-Nva-Ile-Arg-ProNHCH$_2$CH$_3$ as the trifluoroacetate salt: R$_t$=3.606 min (gradient of 10% to 30% acetonitrile in water containing 0.01% TFA over 30 min period); MS (ESI) m/e 1056 (M)$^+$.

EXAMPLE 124

N-Ac-Sar-Gly-Val-D-Leu-Nva-Nva-Ile-Arg-ProNHCH$_2$CH$_3$

The procedure described in Example 15 was used but substituting Fmoc-Nva for Fmoc-Thr(tBu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Nva-Nva-Ile-Arg-ProNHCH$_2$CH$_3$ as the trifluoroacetate salt: R$_t$=3.870 min (gradient of 10% to 30% acetonitrile in water containing 0.01% TFA over 30 min period); MS (ESI) m/e 992 (M)$^+$.

EXAMPLE 125

N-Ac-Sar-Gly-Val-D-Leu-Gly-Nva-Ile-Arg-ProNHCH$_2$CH$_3$

The procedure described in Example 15 was used but substituting Fmoc-Gly for Fmoc-Thr(tBu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Gly-Nva-Ile-Arg-ProNHCH$_2$CH$_3$ as the trifluoroacetate salt: R$_t$=3.397 min (gradient of 10% to 30% acetonitrile in water containing 0.01% TFA over 30 min period); MS (ESI) m/e 950 (M)$^+$.

EXAMPLE 126

N-Ac-Sar-Gly-Val-D-Leu-Lys(Ac)-Nva-Ile-Arg-ProNHCH$_2$CH$_3$

The procedure described in Example 15 was used but substituting Fmoc-Lys(Ac) for Fmoc-Thr(Bu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Lys(Ac)-Nva-Ile-Arg-ProNHCH$_2$CH$_3$ as the trifluoroacetate salt: R$_t$=3.365 min (gradient of 10% to 30% acetonitrile in water containing 0.01% TFA over 30 min period); MS (ESI) m/e 1063 (M)$^+$.

EXAMPLE 127

N-Ac-Sar-Gly-Val-D-Leu-2Nal-Nva-Ile-Arg-ProNHCH$_2$CH$_3$

The procedure described in Example 15 was used but substituting Fmoc-2Nal for Fmoc-Thr(tBu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-2Nal-Nva-Ile-Arg-ProNHCH$_2$CH$_3$ as the trifluoroacetate salt: R$_t$=4.992 min (gradient of 10% to 30% acetonitrile in water containing 0.01% TFA over 30 min period); MS (ESI) m/e 1090 (M)$^+$.

EXAMPLE 128

N-Ac-Sar-Gly-Val-D-Leu-1Nal-Nva-Ile-Arg-ProNHCH$_2$CH$_3$

The procedure described in Example 15 was used but substituting Fmoc-1Nal for Fmoc-Thr(tBu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-1Nal-Nva-Ile-Arg-ProNHCH$_2$CH$_3$ as the trifluoroacetate salt: R$_t$=5.032 min (gradient of 10% to 30% acetonitrile in water containing 0.01% TFA over 30 min period); MS (ESI) m/e 1090 (M)$^+$.

EXAMPLE 129

N-Ac-Sar-Gly-Val-D-Leu-Octylgly-Nva-Ile-Arg-ProNHCH$_2$CH$_3$

The procedure described in Example 15 was used but substituting Fmoc-Octylgly for Fmoc-Thr(tBu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Octylgly-Nva-Ile-Arg-ProNHCH$_2$CH$_3$ as the trifluoroacetate salt: R$_t$=5.90 min (gradient of 10% to 30% acetonitrile in water containing 0.01% TFA over 30 min period); MS (ESI) m/e 1062 (M)$^+$.

EXAMPLE 130

N-Ac-Sar-Gly-Val-D-Leu-Gln-Nva-Ile-Arg-ProNHCH$_2$CH$_3$

The procedure described in Example 15 was used but substituting Fmoc-Gln(Trt) for Fmoc-Thr(tBu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Gln-Nva-Ile-Arg-ProNHCH$_2$CH$_3$ as the trifluoroacetate salt: R$_t$=3.323 min (gradient of 10% to 30% acetonitrile in water containing 0.01% TFA over 30 min period); MS (ESI) m/e 1021 (M)$^+$.

EXAMPLE 131

N-Ac-Sar-Gly-Val-D-Leu-Met-Nva-Ile-Arg-ProNHCH$_2$CH$_3$

The procedure described in Example 15 was used but substituting Fmoc-Met for Fmoc-Thr(tBu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TPA. The pure fractions were lyophilized to yield N-Ac-Sar-Gly-Val-D-Leu-Met-Nva-Ile-Arg-ProNHCH$_2$CH$_3$ as the trifluoroacetate salt: R$_t$=3.901 min (gradient of 10% to 30% acetonitrile in water containing 0.01% TFA over 30 min period); MS (ESI) m/e 1024 (M)$^+$.

EXAMPLE 132

N-Ac-Sar-Gly-Val-D-Leu-Ser-Nva-Ile-Arg-ProNHCH$_2$CH$_3$

The procedure described in Example 15 was used but substituting Fmoc-Ser(tBu) for Fmoc-Thr(tBu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Ser-Nva-Ile-Arg-ProNHCH$_2$CH$_3$ as the trifluoroacetate salt: R$_t$=3.414 min (gradient of 10% to 30% acetonitrile in water containing 0.01% TFA over 30 min period); MS (ESI) m/e 980 (M)$^+$.

EXAMPLE 133

N-Ac-Sar-Gly-Val-D-Leu-Allylgly-Nva-Ile-Arg-ProNHCH$_2$CH$_3$

The procedure described in Example 15 was used but substituting Fmoc-Allylgly for Fmoc-Thr(tBu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Allylgly-Nva-Ile-Arg-ProNHCH$_2$CH$_3$ as the trifluoroacetate salt: R$_t$=3.801 min (gradient of 10% to 30% acetonitrile in water containing 0.01% TFA over 30 min period); MS (ESI) m/e 990 (M)$^+$.

EXAMPLE 134

N-Ac-Sar-Gly-Val-D-Leu-Ile-Nva-Ile-Arg-ProNHCH$_2$CH$_3$

The procedure described in Example 15 was used but substituting Fmoc-Ile for Fmoc-Thr(tBu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Ile-Nva-Ile-Arg-ProNHCH$_2$CH$_3$ as the trifluoroacetate salt: R$_t$=4.028 min (gradient of 10% to 30% acetonitrile in water containing 0.01% TFA over 30 min period); MS (ESI) m/e 1006 (M)$^+$.

EXAMPLE 135

N-Ac-Sar-Gly-Val-D-Leu-D-Thr-Nva-Ile-Arg-ProNHCH$_2$CH$_3$

The procedure described in Example 15 was used but substituting Fmoc-D-Thr(tBu) for Fmoc-Thr(tBu). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-D-T-Nva-Ile-Arg-ProNHCH$_2$CH$_3$ as the trifluoroacetate salt: R$_t$=3.437 min (gradient of 10% to 30% acetonitrile in water containing 0.01% TFA over 30 min period); MS (ESI) m/e 994 (M)$^+$.

EXAMPLE 136

N-Ac-Sar-Gly-Val-D-Ile-Thr-Ile-Ile-Arg-ProNHCH$_2$CH$_3$

The procedure described in Example 1 was used but substituting Fmoc-Ile for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Ile-Ile-Arg-ProNHCH$_2$CH$_3$ as the trifluoroacetate salt: R$_t$=3.54 min (gradient of 10% to 30% acetonitrile in water containing 0.01% TFA over 30 min period); MS (ESI) m/e 1008 (M)$^+$; Amino Acid Anal.: 1.07 Sar; 0.94 Gly; 0.91 Val; 3.02 Ile; 0.47 Thr; 1.24 Arg; 1.04 Pro.

EXAMPLE 137

N-Ac-Sar-Gly-Val-D-Ile-Thr-Nle-Ile-Arg-ProNHCH$_2$CH$_3$

The procedure described in Example 1 was used but substituting Fmoc-Nle for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nle-Ile-Arg-ProNHCH$_2$CH$_3$ as the trifluoroacetate salt: R$_t$=3.80 min (gradient of 10% to 30% acetonitrile in water containing 0.01% TFA over 30 min period); MS (ESI) m/e 1006 (M)$^=$.

EXAMPLE 138

N-Ac-Sar-Gly-Val-D-Ile-Thr-Cit-Ile-Arg-ProNHCH$_2$CH$_3$

The procedure described in Example 1 was used but substituting Fmoc-Cit for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Cit-Ile-Arg-ProNHCH$_2$CH$_3$ as the trifluoroacetate salt: R$_t$=2.83 min (gradient of 10% to 30% acetonitrile in water containing 0.01% TFA over 30 min period); MS (ESI) m/e 1052 (M)$^+$; Acid Anal.: 1.05 Sar; 1.00 Gly; 1.00 Val; 2.13 Ile; 0.65 Thr; 1.11 Cit; 1.49 Arg; 1.10 Pro.

EXAMPLE 139

N-Ac-Sar-Gly-Val-D-Ile-Thr-Met(O$_2$)-Ile-Arg-ProNHCH$_2$CH$_3$

The procedure described in Example 1 was used but substituting Fmoc-Met(O$_2$) for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Met(O$_2$)-Ile-Arg-ProNHCH$_2$CH$_3$ as the trifluoroacetate salt: R$_t$=2.701 min (gradient of 10% to 30% acetonitrile in water containing 0.01% TFA over 30 min period); MS (ESI) m/e 1058 (M)$^+$; Acid Anal.: 1.36 Sar; 0.94 Gly; 0.62 Val; 2.06 Ile; 0.13 Thr; 0.66 Met(O2); 1.50 Arg; 0.68 Pro.

EXAMPLE 140

N-Ac-Sar-Gly-Val-D-Ile-Thr-Arg-Ile-Arg-ProNHCH$_2$CH$_3$

The procedure described in Example 1 was used but substituting Fmoc-Arg(Pmc) for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Arg-Ile-Arg-ProNHCH$_2$CH$_3$ as the trifluoroacetate salt: R$_t$=0.54 min (gradient of 10% to 30% acetonitrile in water containing 0.01% TFA over 30 min period); MS (ESI) m/e 1049 (M)$^+$; Acid Anal.: 0.92 Sar; 0.74 Gly; 0.86 Val; 2.00 Ile; 0.49 Thr; 2.67 Arg; 1.00 Pro.

EXAMPLE 141

N-Ac-Sar-Gly-Val-D-Ile-Thr-Tyr-Ile-Arg-ProNHCH$_2$CH$_3$

The procedure described in Example 1 was used but substituting Fmoc-Tyr(tBu) for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Tyr-Ile-Arg-ProNHCH$_2$CH$_3$ as the trifluoroacetate salt: R$_t$=3.048 min (gradient of 10% to 30% acetonitrile in water containing 0.01% TFA over 30 min period); MS (ESI) m/e 1058 (M)$^+$; Acid Anal.: 0.88 Sar; 0.99 Gly; 0.97 Val; 1.97 Ile; 0.52 Thr; 0.92 Tyr; 1.58Arg; 1.08 Pro.

EXAMPLE 142

N-Ac-Sar-Gly-Val-D-Ile-Thr-Glu-Ile-Arg-ProNHCH$_2$CH$_3$

The procedure described in Example 1 was used but substituting Fmoc-Glu(OtBu)-OH for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Glu-Ile-Arg-ProNHCH$_2$CH$_3$ as the trifluoroacetate salt: R$_t$=2.348 min (gradient of 10% to 30% acetonitrile in water containing 0.01% TFA over 30 min period); MS (ESI) m/e 1024 (M)$^+$; Acid Anal.: 1.05 Sar; 1.024 Gly; 0.94 Val; 2.67 Ile; 0.47 Thr; 0.94 Glu; 2.20 Arg; 1.09 Pro.

EXAMPLE 143

N-Ac-Sar-Gly-Val-D-Ile-Thr-Lys(Ac)-Ile-Arg-ProNHCH$_2$CH$_3$

The procedure described in Example 1 was used but substituting Fmoc-Lys(Ac) for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Lys(Ac)-Ile-Arg-ProNHCH$_2$CH$_3$ as the trifluoroacetate salt: R$_t$=2.744 min (gradient of 10% to 30% acetonitrile in water containing 0.01% TFA over 30 min period); MS (ESI) m/e 1065 (M)$^+$; Acid Anal.: 1.03 Sar; 0.99 Gly; 0.95 Val; 2.04 Ile; 0.66 Thr; 1.05 Lys; 1.41 Arg; 1.02 Pro.

EXAMPLE 144

N-Ac-Sar-Gly-Val-D-Ile-Thr-Propargylgly-Ile-Arg-ProNHCH2CH$_3$

The procedure described in Example 1 was used but substituting Fmoc-Propargylgly for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Propargylgly-Ile-Arg-ProNHCH$_2$CH$_3$ as the trifluoroacetate salt; R$_t$=3.003 min (gradient of 10% to 30% acetonitrile in water containing 0.01% TFA over 30 min period); MS (ESI) m/e 990 (M)$^+$; Acid Anal.: 1.05 Sar; 1.00 Gly; 0.93 Val; 2.10 Ile; 0.54 Thr; 1.71 Arg; 0.97 Pro.

EXAMPLE 145

N-Ac-Sar-Gly-Val-D-alloIle-Thr-Gln-Ile-Arg-ProNHCH$_2$CH$_3$

The procedure described in Example 1 was used but substituting Fmoc-D-alloIle for Fmoc-D-Ile and Fmoc-Gln (Trt) for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-alloIle-Thr-Gln-Ile-Arg-ProNHCH$_2$CH$_3$ as the trifluoroacetate salt: R$_t$=2.704 min (gradient of 10% to 30% acetonitrile in water containing 0.01% TFA over 30 min period); MS (ESI) m/e 1023 (M)$^+$; Acid Anal.: 0.93 Sar; 0.94 Gly; 0.94 Val; 2.10 Ile; 0.51 Thr; 0.87 Glu; 1.45 Arg; 1.03 Pro.

EXAMPLE 146

N-Ac-Sar-Gly-Val-D-Leu-Thr-Gln-Ile-Arg-ProNHCH$_2$CH$_3$

The procedure described in Example 15 was used but substituting Fmoc-Gln(Trt) for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Gln-Ile-Arg-ProNHCH$_2$CH$_3$ as the trifluoroacetate salt: R$_t$=2.685 min (gradient of 10% to 30% acetonitrile in water containing 0.01% TFA over 30 min period); MS (ESI) m/e 1023 (M)$^+$; Acid Anal.: 0.98 Sar; 0.74 Gly; 0.95 Val; 1.04 Ile; 0.49 Thr; 1.04 Leu; 0.94 Glu; 1.63 Arg; 0.97 Pro.

EXAMPLE 147

N-Ac-Bala-Sar-Gly-Val-D-Ile-Thr-Nva-Ile-Arg-ProNHCH$_2$CH$_3$

The procedure described in Example 65 was used but substituting Fmoc-beta-alanine for Fmoc-4-amino-butyric acid. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Bala-Sar-Gly-Val-D-Ile-Thr-Nva-Ile-Arg-ProNHCH$_2$CH$_3$ as the trifluoroacetate salt: R$_t$=2.92 min (gradient of 10% to 30% acetonitrile in water containing 0.01% TFA over 30 min period); MS (ESI) m/e 1065 (M)$^+$; Acid Anal.: 0.99 Sar; 0.99 Gly; 1.00 Val; 1.86Ile; 0.49 Thr; 1.07 Nva; 1.51 Arg; 1.02 Pro.

EXAMPLE 148

N-Phenylacetyl-Sar-Gly-Val-D-Ile-Thr-Nva-Ile-Arg-ProNHCH$_2$CH$_3$

The procedure described in Example 60 was used but substituting phenylacetic acid for butyric acid. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Phenylacetyl-Sar-Gly-Val-D-Ile-Thr-Nva-Ile-Arg-ProNHCH$_2$CH$_3$ as the trifluoroacetate salt: R$_t$=3.83 min (gradient of 10% to 30% acetonitrile in water containing 0.01% TFA over 30 min period); MS (ESI) m/e 1070 (M)$^+$; Acid Anal.: 1.04 Sar; 0.979 Gly; 1.01 Val; 1.90 Ile; 0.59 Thr; 1.09 Nva; 1.53 Arg; 1.03 Pro.

EXAMPLE 149

N-Ac-Sar-Gly-Val-D-Ile-Thr-Nva-Ile-Arg-Pro-Azagly-NH$_2$

To a solution of N-Ac-Sar-Gly-Val-D-Ile-Thr(tBu)-Nva-Ile-Arg(Pmc)-Pro-OH (0.1288 g) in DMF was added semi-carbazide hydrochloride (0.222 g) followed by DIEA (0.346 ml) and PyBrop (0.0513 g). The solution was stirred at rt for 36 hr. The solvent was removed in vacuo and the residue was treated with diethyl ether. The solid was filtered and then treated with (9:1) TFA/anisole (3 mL) at rt for 4 hr. The solvent was again removed in vacuo and the residue was treated with diethyl ether. The precipitate was filtered to give the crude product as a solid. This was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-Pro-Azagly-NH$_2$ as the trifluoroacetate salt: R$_t$=2.67 min (gradient of 10% to 30% acetonitrile in water containing 0.01% TFA over 30 min period); MS (ESI) m/e 1024 (M)$^+$; Acid Anal.: 0.99 Sar; 0.98 Gly; 1.00 Val; 2.13 Ile; 0.56 Thr; 1.09 Nva; 0.92 Arg; 1.02 Pro.

EXAMPLE 150

N-Ac-Sar-Gly-Val-D-Ile-Thr-Nva-Ile-Arg-Sar-NHCH$_2$CH$_3$

The procedure described in Example 76 was used but substituting Fmoc-Sar-Sieber ethylamide resin for Fmoc-D-Pro-Sieber ethylamide resin. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-Sar-NHCH$_2$CH$_3$ as the trifluoroacetate salt: R$_t$=2.93 min (gradient of 10% to 30% acetonitrile in water containing 0.01% TFA over 30 min period); MS (ESI) m/e 968 (M)$^+$; Acid Anal.: 1.96 Sar; 0.96 Gly; 0.98 Val; 2.07 Ile; 0.55 Thr; 1.05 Nva; 1.49 Arg.

EXAMPLE 151

N-Ac-Sar-Gly-Val-D-Ile-Thr-Nva-Ile-Arg-Pro-SerNH$_2$

The procedure described in Example 75 was used but substituting Fmoc-Ser(tBu)-Sieber amide resin for Fmoc-D-Ala-Sieber amide resin. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-Pro-SerNH$_2$ as the trifluoroacetate salt: R$_t$=2.65 min (gradient of 10% to 30% acetonitrile in water containing 0.01% TFA over 30 min period); MS (ESI) m/e 1053 (M)$^+$; Acid Anal.: 0.99 Sar; 0.95 Gly; 1.00 Val; 1.96 Ile; 0.57 Thr; 1.12 Nva; 1.03 Arg; 1.03 Pro; 0.27 Ser.

EXAMPLE 152

N-Succinyl-Sar-Gly-Val-D-Leu-Thr-Nva-Ile-Arg-ProNHCH$_2$CH$_3$

The procedure described in Example 54 was used but substituting Fmoc-D-Leu for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Succinyl-Sar-Gly-Val-D-Leu-Thr-Nva-Ile-Arg-ProNHCH$_2$CH$_3$ as the trifluoroacetate salt: R$_t$=2.85 min (gradient of 10% to 30% acetonitrile in water containing 0.01% TFA over 30 min period); MS (ESI) m/e 1052 (M)$^+$; Acid Anal.: 1.01 Sar; 0.93 Gly; 0.95Val; 1.16 Leu; 1.10 Ile; 0.51 Thr; 1.04 Nva; 1.67 Arg; 0.96 Pro.

EXAMPLE 153

N-Ac-Sar-Ala-Val-D-Ile-Thr-Nva-Ile-Arg-ProNHCH$_2$CH$_3$

The procedure described in Example 1 was used but substituting Fmoc-Ala for Fmoc-Gly. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Ala-Val-D-Ile-Thr-Nva-Ile-Arg-ProNHCH$_2$CH$_3$ as the trifluoroacetate salt: R$_t$=3.056 min (gradient of 10% to 30% acetonitrile in water containing 0.01% TFA over 30 min period); MS (ESI) m/e 1008 (M)$^+$; Acid Anal.: 1.32 Sar; 0.96 Ala; 0.94 Val; 2.10 Ile; 0.52 Thr; 0.98 Nva; 1.65 Arg; 1.01 Pro.

EXAMPLE 154

N-Ac-Sar-Leu-Val-D-Ile-Thr-Nva-Ile-Arg-ProNHCH$_2$CH$_3$

The procedure described in Example 1 was used but substituting Fmoc-Leu for Fmoc-Gly. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Leu-Val-D-Ile-Thr-Nva-Ile-Arg-ProNHCH$_2$CH$_3$ as the trifluoroacetate salt: R$_t$=3.628 min (gradient of 10% to 30% acetonitrile in water containing 0.01% TFA over 30 min period); MS (ESI) m/e 1050 (M)$^+$.

EXAMPLE 155

N-Ac-Sar-Ser-Val-D-Ile-Thr-Nva-Ile-Arg-ProNHCH$_2$CH$_3$

The procedure described in Example 1 was used but substituting Fmoc-Ser(tBu) for Fmoc-Gly. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Ser-Val-D-Ile-Thr-Nva-Ile-Arg-ProNHCH$_2$CH$_3$ as the trifluoroacetate salt: R$_t$=2.955 min (gradient of 10% to 30% acetonitrile in water containing 0.01% TFA over 30 min period); MS (ESI) m/e 1024 (M)$^+$.

EXAMPLE 156

N-Ac-Sar-Phe-Val-D-Ile-Thr-Nva-Ile-Arg-ProNHCH$_2$CH$_3$

The procedure described in Example 1 was used but substituting Fmoc-Phe for Fmoc-Gly. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Phe-Val-D-Ile-Thr-Nva-Ile-Arg-ProNHCH$_2$CH$_3$ as the trifluoroacetate salt: R$_t$=3.83 min (gradient of 10% to 30% acetonitrile in water containing 0.01% TFA over 30 min period); MS (ESI) m/e 1084 (M)$^+$.

EXAMPLE 157

N-Ac-Sar-Glu-Val-D-Ile-Thr-Nva-Ile-Arg-ProNHCH$_2$CH$_3$

The procedure described in Example 1 was used but substituting Fmoc-Glu(OtBu)-OH for Fmoc-Gly. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Glu-Val-D-Ile-Thr-Nva-Ile-Arg-ProNHCH$_2$CH$_3$ as the trifluoroacetate salt: R$_t$=3.08 min (gradient of 10% to 30% acetonitrile in water containing 0.01% TFA over 30 min period); MS (ESI) m/e 1065 (M)$^+$.

EXAMPLE 158

N-Ac-Sar-Pro-Val-D-Leu-Thr-Nva-Ile-Arg-ProNHCH$_2$CH$_3$

The procedure described in Example 1 was used but substituting Fmoc-Pro for Fmoc-Gly and Fmoc-D-Leu for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Pro-Val-D-Leu-Thr-Nva-Ile-Arg-ProNHCH$_2$CH$_3$ as the trifluoroacetate salt: R$_t$=3.343 min (gradient of 10% to 30% acetonitrile in water containing 0.01% TFA over 30 min period); MS (ESI) m/e 1034 (M)$^+$.

EXAMPLE 159

N-Ac-Sar-Asn-Val-D-Leu-Thr-Nva-Ile-Arg-ProNHCH$_2$CH$_3$

The procedure described in Example 1 was used but substituting Fmoc-Asn(Trt) for Fmoc-Gly and Fmoc-D-Leu for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Asn-Val-D-Leu-Thr-Nva-Ile-Arg-ProNHCH$_2$CH$_3$ as the trifluoroacetate salt: R$_t$=3.112 min (gradient of 10% to 30% acetonitrile in water containing 0.01% TFA over 30 min period); MS (ESI) m/e 1051 (M)$^+$.

EXAMPLE 160

N-Ac-Sar-Asp-Val-D-Leu-Thr-Nva-Ile-Arg-ProNHCH$_2$CH$_3$

The procedure described in Example 1 was used but substituting Fmoc-Asp(OtBu)OH for Fmoc-Gly and Fmoc-

81

D-Leu for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Asp-Val-D-Leu-Thr-Nva-Ile-Arg-ProNHCH$_2$CH$_3$ as the trifluoroacetate salt: R$_t$=2.9113 min (gradient of 10% to 30% acetonitrile in water containing 0.01% TFA over 30 min period); MS (ESI) m/e 1052 (M)$^+$.

EXAMPLE 161

N-Ac-Asn-Gly-Val-D-Leu-Thr-Nva-Ile-Arg-ProNHCH$_2$CH$_3$

The procedure described in Example 1 was used but substituting Fmoc-Asn(Trt) for Fmoc-Sar and Fmoc-D-Leu for Pmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Asn-Gly-Val-D-Leu-r-Nva-Ile-Arg-ProNHCH$_2$CH$_3$ as the trifluoroacetate salt: R$_t$=3.06 min (gradient of 10% to 30% acetonitrile in water containing 0.01% TFA over 30 min period); MS (ESI) m/e 1037 (M)$^+$.

EXAMPLE 162

N-Ac-Gln-Gly-Val-D-Leu-Thr-Nva-Ile-Arg-ProNHCH$_2$CH$_3$

The procedure described in Example 1 was used but substituting Fmoc-Gln(Trt) for Fmoc-Sar and Fmoc-D-Leu for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Gln-Gly-Val-D-Leu-Thr-Nva-Ile-Arg-ProNHCH$_2$CH$_3$ as the trifluoroacetate salt: R$_t$=3.10 min (gradient of 10% to 30% acetonitrile in water containing 0.01% TFA over 30 min period); MS (ESI) m/e 1051 (M)$^+$.

EXAMPLE 163

N-Ac-Ser-Gly-Val-D-Leu-Thr-Nva-Ile-Arg-ProNHCH$_2$CH$_3$

The procedure described in Example 1 was used but substituting Fmoc-Ser(tBu) for Fmoc-Sar and Fmoc-D-Leu for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Ser-Gly-Val-D-Leu-Thr-Nva-Ile-Arg-ProNHCH$_2$CH$_3$ as the trifluoroacetate salt: R$_t$=3.15 min (gradient of 10% to 30% acetonitrile in water containing 0.01% TFA over 30 min period); MS (ESI) m/e 1010 (M)$^+$.

EXAMPLE 164

N-Ac-Cit-Gly-Val-D-Ile-Thr-Nva-Ile-Arg-ProNHCH2CH$_3$

The procedure described in Example 1 was used but substituting Fmoc-Cit for Fmoc-Sar. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Cit-Gly-Val-D-Ile-Thr-Nva-Ile-Arg-ProNHCH$_2$CH$_3$ as the trifluoroacetate salt: R$_t$=2.97 min (gradient of 10% to 30% acetonitrile in water containing 0.01% TFA over 30 min period); MS (ESI) m/e 1080 (M)$^+$.

EXAMPLE 165

N-Ac-Glu-Gly-Val-D-Ile-Thr-Nva-Ile-Arg-ProNHCH$_2$CH3

The procedure described in Example 1 was used but substituting Fmoc-Glu(tBu)-OH for Fmoc-Sar. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Glu-Gly-Val-D-Ile-Thr-Nva-Ile-Arg-ProNHCH$_2$CH$_3$ as the trifluoroacetate salt: R$_t$=2.69 min (gradient of 10% to 30% acetonitrile in water containing 0.01% TFA over 30 min period); MS (ESI) m/e 1052 (M)$^+$.

EXAMPLE 166

N-Ac-Gaba-Gly-Val-D-Ile-Thr-Nva-Ile-Arg-ProNHCH$_2$CH3

The procedure described in Example 1 was used but substituting Fmoc-gamma-aminobutyric acid for Fmoc-Sar. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure factions were lyophilized to yield N-Ac-Gaba-Gly-Val-D-Ile-Thr-Nva-Ile-Arg-ProNHCH$_2$CH$_3$ as the trifluoroacetate salt: R$_t$=3.17 min (gradient of 10% to 30% acetonitrile in water containing 0.01% TFA over 30 min period); MS (ESI) m/e 1008 (M)$^+$.

EXAMPLE 167

N-Ac-Bala-Gly-Val-D-Ile-Thr-Nva-Ile-Arg-ProNHCH$_2$CH$_3$

The procedure described in Example 1 was used but substituting Fmoc-beta-alanine for Fmoc-Sar. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Bala-Gly-Val-D-Ile-Thr-Nva-Ile-Arg-ProNHCH$_2$CH$_3$ as the trifluoroacetate salt: R$_t$=3.14 min (gradient of 10% to 30% acetonitrile in water containing 0.01% TFA over 30 min period); MS (ESI) m/e 994 (M)$^+$.

EXAMPLE 168

N-Ac-Gln-Gly-Val-D-Ile-Thr-Nva-Ile-Arg-ProNHCH$_2$CH$_3$

The procedure described in Example 1 was used but substituting Fmoc-Gln(Trt) for Fmoc-Sar. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Gln-Gly-Val-D-Ile-Thr-Nva-Ile-Arg-ProNHCH$_2$CH$_3$ as the trifluoroacetate salt: R$_t$=3.00 min (gradient of 10% to 30% acetonitrile in water containing 0.01% TFA over 30 min period); MS (ESI) m/e 1051 (M)$^+$.

EXAMPLE 169

N-Ac-Sar-Gly-Gly-D-Ile-Thr-Nva-Ile-Arg-ProNHCH$_2$CH$_3$

The procedure described in Example 1 was used but substituting Fmoc-Gly for Fmoc-Val. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Gly-D-Ile-Thr-Nva-Ile-Arg-ProNHCH$_2$CH3 as the trifluoroacetate salt: R$_t$=2.46 min (gradient of 10% to 30% acetonitrile in water containing 0.01% TFA over 30 min period); MS (ESI) m/e 952 (M)$^+$.

EXAMPLE 170

N-Ac-Sar-Gly-Glu-D-Ile-Thr-Nva-Ile-Arg-ProNHCH$_2$CH$_3$

The procedure described in Example 1 was used but substituting Fmoc-Glu(OtBu) OH for Fmoc-Val. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Glu-D-Ile-Thr-Nva-Ile-Arg-ProNHCH$_2$CH$_3$ as the trifluoroacetate salt: R$_t$=1.74 min (gradient of 10% to 30% acetonitrile in water containing 0.01% TFA over 30 min period); MS (ESI) m/e 1024 (M)$^+$.

EXAMPLE 171

N-Ac-Sar-Gly-Val-D-Ile-Thr-Gln-Ile-Arg-ProNHCH(CH$_3$)$_2$

The procedure described in example 4 was used but substituting Fmoc-Gln(Trt) for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Gln-Ile-Arg-ProNHCH$_2$(CH$_3$)$_2$ as the trifluoroacetate salt: R$_t$=2.80 min (gradient of 10% to 30% acetonitrile in water containing 0.01% TFA over 30 min period); MS (ESI) m/e 1037 (M)$^+$; Acid Anal.: 0.98 Sar; 0.94 Gly; 0.97 Val; 2.23 Ile; 0.51 Thr; 0.90 Glu; 1.16 Arg; 1.03 Pro.

EXAMPLE 172

N-Ac-Sar-Gly-Val-D-Leu-Thr-Gln-Ile-Arg-ProNHCH(CH$_3$)$_2$

The procedure described in example 4 was used but substituting Fmoc-D-Leu for Fmoc-D-Ile and Fmoc-Gln (Trt) for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure factions were lyophilized to yield N-Ac-Sar-Gly-Val-D-Leu-Thr-Gln-Ile-Arg-ProNHCH (CH$_3$)$_2$ as the trifluoroacetate salt: R$_t$=2.90 min (gradient of 10% to 30% acetonitrile in water containing 0.01% TFA over 30 min period); MS (ESI) m/e 1037 (M)$^+$; Acid Anal.: 1.05 Sar; 0.97 Gly; 0.99 Val; 1.30 Leu 1.11 Ile; 0.52 Thr; 0.89Glu; 1.20 Arg; 1.04 Pro.

EXAMPLE 173

H-Sar-Gly-Val-D-Leu-Thr-Gln-Ile-Arg-ProNHCH(CH$_3$)$_2$

The procedure described in example 172 was used but omitting the last coupling with acetic acid. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield H-Sar-Gly-Val-D-Leu-Thr-Gln-Ile-Arg-ProNHCH(CH$_3$)$_2$ as the trifluoroacetate salt: R$_t$=2.55 min (gradient of 10% to 30% acetonitrile in water containing 0.01% TFA over 30 min period); MS (ESI) m/e 981 (M)$^+$; Acid Anal.: 1.02 Sar; 0.93 Gly; 1.02 Val; 1.05 Leu; 1.02 Ile; 0.55 Thr; 0.84 Gln; 1.31 Arg; 1.03 Pro.

EXAMPLE 174

N-Succinyl-Sar-Gly-Val-D-Ile-Thr-Gln-Ile-Arg-ProNHCH$_2$CH$_3$

The procedure described in Example 54 was used but substituting Fmoc-Gln(Trt) for Fmoc-Nva. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Succinyl-Sar-Gly-Val-D-Ile-Thr-Gln-Ile-Arg-ProNHCH$_2$CH$_3$ as the trifluoroacetate salt: R$_t$=2.02 min (gradient of 10% to 30% acetonitrile in water containing 0.01% TFA over 30 min period); MS (ESI) m/e 1081 (M)$^+$; Acid Anal.: 1.00 Sar; 0.94 Gly; 1.00 Val; 2.00 Ile; 0.52 Thr; 0.87 Gln; 1.37 Arg; 1.05 Pro.

EXAMPLE 175

N-Succinyl-Sar-Gly-Val-D-Leu-Thr-Gln-Ile-Arg-ProNHCH$_2$CH$_3$

The procedure described in Example 174 was used but substituting Fmoc-D-Leu for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Succinyl-Sar-Gly-Val-D-Leu-Thr-Gln-Ile-Arg-ProNHCH$_2$CH$_3$ as the trifluoroacetate salt: R$_t$=2.284 min (gradient of 10% to 30% acetonitrile in water containing 0.01% TFA over 30 min period); MS (ESI) m/e 1081 (M)$^{30}$.

EXAMPLE 176

N-Succinyl-Sar-Gly-Val-D-Leu-Thr-Gln-Ile-Arg-ProNHCH(CH$_3$)$_2$

The procedure described in example 4 was used but substituting Fmoc-D-Leu for Fmoc-D-Ile and Fmoc-Gln (Trt) for Fmoc-Nva. Following the coupling with Fmoc-Sar and protection the resin was treated with succinic anhydride/pyridine as described in example 54. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile/water containing 0.01% TFA. The pure fractions were lyophilized to yield N-Succinyl-Sar-Gly-Val-D-Ile-Thr-Gln-Ile-Arg-ProNHCH($CH_3$)$_2$ as the trifluoroacetate salt: $R_t$=2.56 min (gradient of 10% to 30% acetonitrile in water containing 0.01% TFA over 30 min period); MS (ESI) m/e 1095 (M)$^+$; Acid Anal.: 0.95 Sar; 0.94 Gly; 1.02 Val; 1.02 Leu; 1.05 Ile; 0.56 Thr; 0.86 Gln; 1.00 Arg; 1.07 Pro.

EXAMPLE 177

N-Ac-Sar-Gly-Val-D-Leu-Thr-Asp-Ile-Arg-ProNHCH$_2$CH$_3$

The procedure described in Example 146 was used but substituting Fmoc-Asp(OtBu)OH for Fmoc-Gln(Trt). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure factions were lyophilized to yield N-Ac-Sar-Gly-Val-D-Leu-Thr-Asp-Ile-Arg-ProNHCH$_2$CH$_3$ as the trifluoroacetate salt: $R_t$=2.53 min (gradient of 10% to 30% acetonitrile in water containing 0.01% TFA over 30 min period); MS (ESI) m/e 1010 (M)$^+$; Acid Anal.: 1.00 Sar; 0.95 Gly; 1.01 Val; 1.02 Leu; 1.00 Ile; 0.56 Thr; 0.99 Asp; 1.43 Arg; 1.03 Pro.

EXAMPLE 178

N-Ac-Sar-Gly-Val-D-Ile-Thr-Asp-Ile-Arg-ProNHCH$_2$CH$_3$

The procedure described in Example 142 was used but substituting Fmoc-Asp(OtBu)-OH for Fmoc-Glu(OtBu)OH. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Thr-Asp-Ile-Arg-ProNHCH$_2$CH$_3$ as the trifluoroacetate salt: $R_t$=2.455 min (gradient of 10% to 30% acetonitrile in water containing 0.01% TFA over 30 min period); MS (ESI) m/e 1010 (M)$^+$.

EXAMPLE 179

N-Ac-Sar-Gly-Val-D-Ile-Thr-Asn-Ile-Arg-ProNHCH$_2$CH$_3$

The procedure described in Example 43 was used but substituting Fmoc-Asn(Trt) for Fmoc-Gln(Trt). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Vat-D-Ile-Thr-Asn-Ile-Arg-ProNHCH$_2$CH$_3$ as the trifluoroacetate salt: $R_t$=2.68 min (gradient of 10% to 30% acetonitrile in water containing 0.01% TFA over 30 min period); MS (ESI) m/e 1009 (M)$^+$.

EXAMPLE 180

N-Ac-Sar-Gly-Val-D-Ile-Thr-Met(O)-Ile-Arg-ProNHCH$_2$CH$_3$

The procedure described in Example 139 was used but substituting Fmoc-Met(O) for Fmoc-Met(O$_2$). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Ile-Tr-Met(O)-Ile-Arg-ProNHCH$_2$CH$_3$ as the trifluoroacetate salt: $R_t$=2.713 min (gradient of 10% to 30% acetonitrile in water containing 0.01% TFA over 30 min period); MS (ESI) m/e 1042 (M)$^+$.

EXAMPLE 181

N-Ac-Sar-Gly-Val-D-Leu-Thr-Asn-Ile-Arg-ProNHCH$_2$CH$_3$

The procedure described in Example 146 was used but substituting Fmoc-Asn(Trt) for Fmoc-Gln(Trt). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Val-D-Leu-Thr-Asn-Ile-&g-ProNHCH$_2$CH$_3$ as the trifluoroacetate salt: $R_t$=2.752 min (gradient of 100% to 30% acetonitrile in water containing 0.01% TFA over 30 min period); MS (ESI) m/e 1009 (M)$^+$.

EXAMPLE 182

The procedure described in Example 1 is used but separately substituting in the syntheses Fmoc-D-Ile with the following amino acids: Fmoc-D-Thr(tBu), Fmoc-D-Ser(tBu), Fmoc-D-Hser(tBu), Fmoc-D-Gln(Trt), Fmoc-D-Asn(Trt), Fmoc-D-Cit, Fmoc-D-Hcit, Fmoc-D-Hle, Fmoc-D-Neopentylgly. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions arm lyophilized to yield the trifluoroacetate salt of the following peptides:

N-Ac-Sar-Gly-Val-D-Thr-Thr-Nva-Ile-Arg-ProNHCH$_2$CH$_3$,
N-Ac-Sar-Gly-Val-D-Ser-Thr-Nva-Ile-Arg-ProNHCH$_2$CH$_3$,
N-Ac-Sar-Gly-Val-D-Hser-Thr-Nva-Ile-Arg-ProNHCH$_2$CH$_3$,
N-Ac-Sar-Gly-Val-D-Gln-Thr-Nva-Ile-Arg-ProNHCH$_2$CH$_3$,
N-Ac-Sar-Gly-Val-D-Asn-Thr-Nva-Ile-Arg-ProNHCH$_2$CH$_3$,
N-Ac-Sar-Gly-Val-D-Cit-Thr-Nva-Ile-Arg-ProNHCH$_2$CH$_3$,
N-Ac-Sar-Gly-Val-D-Hcit-Thr-Nva-Ile-Arg-ProNHCH$_2$CH$_3$,
N-Ac-Sar-Gly-Val-D-Hle-Thr-Nva-Ile-Arg-ProNHCH$_2$CH$_3$, and
N-Ac-Sar-Gly-Val-D-Neopentylgly-Thr-Nva-Ile-Arg-ProNHCH$_2$CH$_3$.

EXAMPLE 183

N-Ac-Sar-Gly-Val-D-Ile-Thr-Phe(4CONH$_2$)-Ile-Arg-ProNHCH$_2$CH$_3$

The procedure described in Example 43 is used but substituting Fmoc-Phe[4-CONH(Trt)] for Fmoc-Gln(Trt). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Phe(4-CONH$_2$)Ile-Arg-ProNHCH$_2$CH$_3$.

EXAMPLE 184

N-Ac-Sar-Gly-Val-D-Ile-Thr-Nva-Ile-His-ProNHCH$_2$CH$_3$

The procedure described in Example 1 is used but substituting Fmoc-His(Boc) for Fmoc-Arg(Pmc). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-His-ProNHCH$_2$CH$_3$.

EXAMPLE 185

N-Ac-Sar-Gly-Val-D-Ile-Thr-Nva-Ile-Lys(Isp)-ProNHCH$_2$CH$_3$

The procedure described in Example 1 is used but substituting Fmoc-Lys(N-epsilon-Isp,N-epsilon-Boc) for Fmoc-Arg(Pmc). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-Lys(Isp)ProNHCH$_2$CH$_3$.

EXAMPLE 186

The procedure described in Example 185 is used but separately substituting in each synthesis Fmoc-Lys(N-epsilon-nicotinyl), Fmoc-Orn(N-delta-nicotinyl), Fmoc-Orn(N-delta-Isp,N-epsilon-Boc), Fmoc-Phe(4-N-Isp,4-N-Boc), Fmoc-Cha(4N-Isp,4-N-Boc) instead of Fmoc-Lys(N-epsilon.Isp,N-epsilon-Boc). After cleavage of the peptide from the resin and removal of the protecting groups using (9:1) TFA/anisole (3 mL) the crude products are purified by C-18 column chromatography using a solvent mixture varying in a gradient of 10% to 50% acetonitrile-water containing 0.01% TFA. The pure fractions are lyophilized to yield the following peptides:

N-Ac-Sar-Gly-Val-D-Ile-Thr-Nva-Ile-Lys(Nic)-ProNHCH$_2$CH$_3$,
N-Ac-Sar-Gly-Val-D-Ile-Thr-Nva-Ile-Orn(Nic)ProNHCH$_2$CH$_3$,
N-Ac-Sar-Gly-Val-D-Ile-Thr-Nva-Ile-Orn(Isp)-ProNHCH$_2$CH$_3$,
N-Ac-Sar-Gly-Val-D-Ile-Thr-Nva-Ile-Phe(4-NIsp)-ProNHCH$_2$CH$_3$, and
N-Ac-Sar-Gly-Val-D-Ile-Thr-Nva-Ile-Cha(4-NIsp)ProNHCH$_2$CH$_3$.

EXAMPLE 187

N-Ac-Sar-Gly-Val-D-Ile-Thr-Nva-Ile-Harg-ProNHCH$_2$CH$_3$

The procedure described in Example 1 is used but substituting Fmoc-Harg(Pmc) for Fmoc-Arg(Pmc). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-Harg-ProNHCH$_2$CH$_3$.

EXAMPLE 188

N-Ac-Sar-Gly-Val-D-Ile-Thr-Nva-Ile-Norarg-ProNHCH$_2$CH$_3$

The procedure described in Example 1 is used but substituting Fmoc-Norarg(N,N-bis-Boc) for Fmoc-Arg(Pmc). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-Norarg-ProNHCH$_2$CH$_3$.

EXAMPLE 189

N-Ac-Sar-Gly-Val-D-Ile-Thr-Nva-Ile-Cit-ProNHCH$_2$CH$_3$

The procedure described in Example 1 is used but substituting Fmoc-Cit for Fmoc-Arg(Pmc). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-Cit-ProNHCH$_2$CH$_3$.

EXAMPLE 190

N-Ac-Sar-Gly-Val-Ile-Thr-Nva-Ile-Lys-ProNHCH$_2$CH$_3$

The procedure described in Example 1 is used but substituting Fmoc-Lys(Boc) for Fmoc-Arg(Pmc). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-Lys-ProNHCH$_2$CH$_3$.

EXAMPLE 191

N-Ac-Sar-Gly-Val-D-Ile-Phe(4-CH$_2$OH)Nva-Ile-Arg-ProNHCH$_2$CH$_3$

The procedure described in Example 1 is used but substituting Fmoc-Phe[4-CH$_2$O(Trt)] for Fmoc-Thr(Trt). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Phe(4CH$_2$OH)-Nva-Ile-Arg-ProNHCH$_2$CH$_3$.

EXAMPLE 192

N-Ac-Sar-Gly-Val-D-Ile-Thr-Nva-Ile-Phe(4 guanidino)ProNHCH$_2$CH$_3$

The procedure described in Example 1 was used but substituting Fmoc-Phe(4-bis-Boc-guanidino) for Fmoc-Arg

EXAMPLE 193

N-Ac-Sar-Gly-Val-D-Ile-Thr-Nva-Ile-Aminopyrimidinylbutanoyl-ProNHCH$_2$CH$_3$.

The procedure described in Example 1 was used but substituting Fmoc-2-amino4-[(2-amino)pyrimidinyl]butanoic acid for Fmoc-Arg(Pmc). After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-Aminopyrimidinylbutanoyl-ProNHCH$_2$CH$_3$ as the trifluoroacetate salt: R$_t$=3.303 min (gradient of 10% to 30% acetonitrile in water containing 0.01% TFA over 30 min period); MS (ESI) m/e 1016 (M+H)$^+$.

EXAMPLE 194

N-Ac-Sar-Gly-Val-D-Ile-Thr-Nva-Ile-Phe(4-CH$_2$NHIsp)-ProNHCH$_2$CH$_3$

The procedure described in Example 1 is used but substituting Fmoc-Phe (4-CH$_2$NIsp-Boc) for Fmoc-Arg(Pmc). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-Phe(4-CH$_2$NHIsp)-ProNHCH$_2$CH$_3$ as the trifluoroacetate salt.

EXAMPLE 195

N-Ac-Sar-Gly-Val-D-Ile-Thr-Nva-Ile-Gly[4-Pip(N-amidino)]-ProNHCH$_2$CH$_3$

The procedure described in Example 1 is used but substituting Fmoc-Gly4-piperidinyl[N-amidino(BOC)$_2$] for Fmoc-Arg(Pmc). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-Gly (4Pip-amidino)-ProNHCH$_2$CH$_3$ as the trifluoroacetate salt.

EXAMPLE 196

N-Ac-Sar-Gly-Val-D-Ile-Thr-Nva-Ile-Ala[4-Pip(N-amidino)]-ProNHCH$_2$CH$_3$

The procedure described in Example 1 is used but substituting Fmoc-Ala-[4-piperidinyl-(N',N"-bis-Boc-amidino)] for Fmoc-Arg(Pmc). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-Ala[4-Pip(N-amidino)]-Pro-NHCH$_2$CH$_3$ as the trifluoroacetate salt.

EXAMPLE 197

N-Ac-Sar-Gly-Val-D-Ile-Thr-Nva-Ile-Ala(3-guanidino)ProNHCH$_2$CH$_3$

The procedure described in Example 1 is used but substituting Fmoc-Ala-[3bis-Boc)guanidino] for Fmoc-Arg(Pmc). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-Ala(3-guanidino)-ProNHCH$_2$CH$_3$ as the trifluoroacetate salt.

EXAMPLE 198

N-Ac-Sar-Gly-Val-D-Ile-Thr-Nva-Ile-Ala(3-pyrrolidinylamidino)-ProNHCH$_2$CH$_3$ The procedure described in Example 1 is used but substituting Fmoc-Ala[3-pyrroli-dinyl-(2-N,N'-bis-Boc-amidino)] for Fmoc-Arg(Pmc). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-Ala-(3-pyrrolidinyl-amidino)-ProNHCH$_2$CH$_3$ as the trifluoroacetate salt.

EXAMPLE 199

N-Ac-Sar-Gly-Val-D-Ile-Thr-Nva-Ile-Orn(2-imidazo)-ProNHCH$_2$CH$_3$

The procedure described in Example 1 is used but substituting Fmoc-Orn-[N-2-(1-Boc)imidazolinyl] for Fmoc-Arg(Pmc). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-Orn(2-imidazo)-ProNHCH$_2$CH$_3$ as the trifluoroacetate salt.

EXAMPLE 200

N-Succinyl-Sar-Gly-Val-D-alloIle-Thr-Nva-Ile-Arg-ProNHCH$_2$CH$_3$

The procedure described in Example 54 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Succinyl-Sar-Gly-Val-D-alloIle-Thr-Nva Ile-Arg-ProNHCH$_2$CH$_3$ as the trifluoroacetate salt.

---

(Pmc). After cleavage of the peptide from the resin and removal of the protecting groups using (9:1) TFA/anisole (3 mL) the crude product was purified by C-18 column chromatography using a solvent mixture varying in a gradient of 10% to S50% acetonitrile-water containing 0.01% TFA. The pure fractions are lyophilized to yield N-Ac-Sar-Gly-Val-D-Ile-Thr-Nva-Ile-Phe(4-guanidino)-ProNHCH$_2$CH$_3$ as the trifluoroacetate salt: R$_t$=3.423 min (gradient of 10% to 30% acetonitrile in water containing 0.01% TFA over 30 min period); MS (ESI) m/e 1042 (M+H)$^+$.

EXAMPLE 201

N-Succinyl-Sar-Gly-Val-D-Ile-Thr-Gln-Ile-Arg-ProNHCH$_2$CH$_3$

The procedure described in Example 54 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 500% acetonitrile-water containing 0.01% TFA. The pure fractions are lyophilized to yield N-Succinyl-Sar-Gly-Val-D-Ile-Thr-Gln-Ile-Arg-ProNHCH$_2$CH$_3$ as the trifluoroacetate salt.

EXAMPLE 202

N-Succinyl-Sar-Gly-Val-D-Ile-Thr-Gln-Ile-Arg-Pro-D-AlaNH$_2$

The procedure described in Example 75 is used but substituting Fmoc-Gln(Trt) for Fmoc-Nva and, after the coupling with Fmoc-Sar; acylating the peptide resin with succinic anhydride as described in Example 54. After cleavage of the peptide from the resin and removal of the protecting groups using (9:1) TFA/anisole (3 mL) the crude product is A purified by C-18 column chromatography using a solvent mixture varying in a gradient of 10% to 50% acetonitrile-water containing 0.01% TFA. The pure fractions are lyophilized to yield N-Succinyl-Sar-Gly-Val-D-Ile-Thr-Gln-Ile-Arg-Pro-D-AlaNH$_2$ as the trifluoroacetate salt.

EXAMPLE 203

N-Succinyl-Sar-Gly-Val-D-alloIle-Thr-Gln-Ile-Arg-ProNHCH$_2$CH$_3$

The procedure described in Example 201 is used but substituting Fmoc-D-alloIle for Fmoc-D-Ile. After cleavage of the peptide from the resin and removal of the protecting groups using (9:1) TFA/anisole (3 mid) the crude product is purified by C-18 column chromatography using a solvent mixture varying in a gradient of 10% to 50% acetonitrile-water containing 0.01% TFA. The pure fractions are lyophilized to yield N-Succinyl-Sar-Gly-Val-D-alloIle-Thr-Gln-Ile-Arg-ProNHCH$_2$CH$_3$ as the trifluoroacetate salt.

EXAMPLE 204

N-Succinyl-Sar-Gly-Val-D-alloIle-Thr-Gln-Ile-Arg-Pro-D-AlaNH$_2$

The procedure described in Example 202 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Succinyl-Sar-Gly-Val-D-alloIle-Thr-Gln-Ile-Arg-Pro-D-AlaNH$_2$ as the trifluoroacetate salt.

EXAMPLE 205

N-Succinyl-Sar-Gly-Val-D-alloIle-Thr-Gln-Ile-Arg-ProNHCH$_2$CH$_3$

The procedure described in example 175 is used but substituting Fmoc-D-alloIle for Fmoc-D-Leu. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Succinyl-Sar-Gly-Val-D-alloIle-Thr-Gln-Ile-Arg-ProNHCH$_2$CH$_3$ as the trifluoroacetate salt.

EXAMPLE 206

N-Succinyl-Sar-Gly-Val-D-Ile-Thr-Gln-Ile-Arg-ProNHCH$_2$CH$_3$

The procedure described in example 205 is used but substituting Fmoc-D-Ile for Fmoc-D-alloIle. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Succinyl-Sar-Gly-Val-D-Ile-Thr-Gln-Ile-Arg-ProNHCH$_2$CH$_3$ as the trifluoroacetate salt.

EXAMPLE 207

N-Ac-Sar-Gly-Val-D-alloIle-Thr-Nva-Ile-Arg-Pro-D-AlaNH$_2$

The procedure described in Example 75 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions arc lyophilized to yield N-Ac-Sar-Gly-Val-D-alloIle-Thr-Nva-Ile-Arg-Pro-D-Ala-NH$_2$ as the trifluoroacetate salt.

EXAMPLE 208

N-Ac-Sar-Gly-Val-D-alloIle-Thr-Nva-Ile-Arg-ProNHCH(CH$_3$)$_2$

The procedure described in example 4 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Thr-Gln-Ile-Arg-ProNHCH(CH$_3$)$_2$ as the trifluoroacetate salt.

EXAMPLE 209

N-Ac-Sar-Gly-Val-D-Ile-Thr-Gln-Ile-Arg-Pro-D-AlaNH$_2$

The procedure described in Example 75 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Gln-Ile-Arg-Pro-D-AlaNH$_2$ as the trifluoroacetate salt.

EXAMPLE 210

N-Ac-Sar-Gly-Val-D-Ile-Thr-Gln-Ile-Arg-ProNHCH(CH$_3$)$_2$

The procedure described in example 4 is used but substituting Fmoc-Gln(Trt) for Fmoc-Nva. After cleavage of the

EXAMPLE 211

N-Ac-Sar-Gly-Val-D-alloIle-Thr-Gln-Ile-Arg-Pro-D-AlaNH$_2$

The procedure described in Example 209 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Thr-Gln-Ile-Arg-Pro-D-AlaNH$_2$ as the trifluoroacetate salt.

EXAMPLE 212

N-Ac-Sar-Gly-Val-D-alloIle-Thr-Gln-Ile-Arg-ProNHCH(CH$_3$)$_2$

The procedure described in example 210 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Thr-Gln-Ile-Arg-ProNHCH(CH$_3$)$_2$ as the trifluoroacetate salt.

EXAMPLE 213

N-Ac-Sar-Gly-Val-D-Ile-Thr-Nva-Ile-Arg-Pro-SarNH$_2$

The procedure described in Example 75 is used but substituting Fmoc-Sar-Seiberamide-resin for Fmoc-D-Ala-Seiberamide-resin. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-Arg-Pro-SarNH$_2$ as the trifluoroacetate salt.

EXAMPLE 214

N-Ac-Sar-Gly-Val-D-alloIle-Thr-Nva-Ile-Arg-Pro-SarNH$_2$

The procedure described in Example 213 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Thr-Nva-Ile-Arg-Pro-SarNH$_2$ as the trifluoroacetate salt.

EXAMPLE 215

N-Ac-Sar-Gly-Val-D-Ile-Thr-Gln-Ile-Arg-Pro-SarNH$_2$

The procedure described in Example 213 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Gln-Ile-Arg-Pro-SarNH$_2$ as the trifluoroacetate salt.

EXAMPLE 216

N-Ac-Sar-Gly-Val-D-alloIle-Thr-Gln-Ile-Arg-Pro-SarNH$_2$

The procedure described in Example 215 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Thr-Gln-Ile-Arg-Pro-SarNH2 as the trifluoroacetate salt.

EXAMPLE 217

N-Ac-Sar-Gly-Val-D-alloIle-Thr-Ser-Ile-Arg-Pro-D-AlaNH$_2$

The procedure described in Example 207 is used but substituting Fmoc-Ser(tBu) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Thr-Ser-Ile-Arg-Pro-D-AlaNH$_2$ as the trifluoroacetate salt.

EXAMPLE 218

N-Ac-Sar-Gly-Val-D-alloIle-Thr-Ser-Ile-Arg-ProNHCH(CH$_3$)$_2$

The procedure described in example 208 is used but substituting Fmoc-Ser(tBu) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Thr-Ser-Ile-Arg-ProNHCH(CH$_3$)$_2$ as the trifluoroacetate salt.

EXAMPLE 219

N-Ac-Sar-Gly-Val-D-alloIle-Thr-Ser-Ile-Arg-ProNHCH$_2$CH$_3$

The procedure described in Example 15 is used but substituting Fmoc-Ser(tBu) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Thr-Ser-Ile-Arg-ProNHCH$_2$CH$_3$ as the trifluoroacetate salt.

EXAMPLE 220

N-Ac-Sar-Gly-Val-D-Ile-Thr-Orn(Ac)-Ile-Arg-ProNHCH$_2$CH$_3$

The procedure described in Example 1 is used but substituting Fmoc-Orn(Ac) for Fmoc-Nva. After cleavage of the (continued from previous column) peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Gln-Ile-Arg-ProNHCH(CH$_3$)$_2$ as the trifluoroacetate salt.

peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Orn(Ac)-Ile-Arg-ProNHCH$_2$CH$_3$ as the trifluoroacetate salt.

EXAMPLE 221

N-Ac-Sar-Gly-Val-D-Ile-Thr-Gln-Ile-Arg-Pro-AzaglyNH$_2$

The procedure described in Example 149 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Gln-Ile-Arg-Pro-AzaglyNH$_2$ as the trifluoroacetate salt.

EXAMPLE 222

N-Ac-Sar-Gly-Val-D-alloIle-Thr-Nva-Ile-Arg-Pro-AzaglyNH$_2$

The procedure described in Example 149 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Thr-Nva-Ile-Arg-Pro-AzaglyNH$_2$ as the trifluoroacetate salt.

EXAMPLE 223

N-Ac-Sar-Gly-Val-D-alloIle-Thr-Gln-Ile-Arg-Pro-AzaglyNH$_2$

The procedure described in Example 222 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Thr-Gln-Ile-Arg-Pro-AzaglyNH2 as the trifluoroacetate salt.

EXAMPLE 224

N-(2-THFcarbonyl)-Sar-Gly-Val-D-alloIle-Thr-Nva-Ile-Arg-ProNHCH$_2$CH$_3$

The procedure described in Example 61 is used but substituting tetrahydro2-furoic acid for acetic acid. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-(2-THFcarbonyl)-Sar-Gly-Val-D-alloIle-Thr-Nva-Ile-Arg-ProNHCH$_2$CH$_3$ as the trifluoroacetate salt.

EXAMPLE 225

N-(2-THFcarbonyl)-Sar-Gly-Val-D-Ile-Thr-Gln-Ile-Arg-ProNHCH$_2$CH$_3$

The procedure described in Example 61 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-(2-THFcarbonyl)-Sar-Gly-Val-D-Ile-Thr-Gln-Ile-Arg-ProNHCH$_2$CH$_3$ as the trifluoroacetate salt.

EXAMPLE 226

N-(2-THFcarbonyl)-Sar-Gly-Val-D-alloIle-Thr-Gln-Ile-Arg-ProNHCH$_2$CH$_3$

The procedure described in Example 225 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-(2-THFcarbonyl)-Sar-Gly-Val-D-alloIle-Thr-Gln-Ile-Arg-ProNHCH$_2$CH$_3$ as the trifluoroacetate salt.

EXAMPLE 227

N-(2-THFcarbonyl)-Sar-Gly-Val-D-Ile-Thr-Gln-Ile-Arg-Pro-D-AlaNH$_2$

The procedure described in Example 209 is used but substituting tetrahydro-2-furoic acid for acetic acid. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-(2-THFcarbonyl)-Sar-Gly-Val-D-Ile-Thr-Gln-Ile-Arg-Pro-D-AlaNH$_2$ as the trifluoroacetate salt.

EXAMPLE 228

N-(2-THFcarbonyl)-Sar-Gly-Val-D-alloIle-Thr-Gln-Ile-Arg-Pro-D-AlaNH$_2$

The procedure described in Example 227 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-(2-THFcarbonyl)-Sar-Gly-Val-D-alloIle-Thr-Gln-Ile-Arg-Pro-D-AlaNH$_2$ as the trifluoroacetate salt.

EXAMPLE 229

N-(2-THFcarbonyl)-Sar-Gly-Val-D-alloIle-Thr-Gln-Ile-Arg-ProNHCH(CH$_3$)$_2$

The procedure described in example 4 is used but substituting Fmoc-D-alloIle for Fmoc-D-Ile, Fmoc-Gln(Trt) for Fmoc-Nva and tetrahydro-2-furoic acid for acetic acid. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-(2-THFcarbonyl)-Sar-Gly-Val-D-alloIle-Thr-Gln-Ile-Arg-ProNHCH(CH$_3$)$_2$ as the trifluoroacetate salt.

EXAMPLE 230

The procedures described in examples 224, 225, 226, 227, 228, and 229 are used but substituting N-acetyl-6-aminocaproic acid (6-Ac-Aca) instead of tetrahydro-2furoic acid. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-(6-Ac-Aca)-Sar-Gly-Val-D-alloIle-Thr-Nva-Ile-Arg-ProNHCH$_2$CH$_3$,
N-(6-Ac-Aca)-Sar-Gly-Val-D-Ile-Thr-Gln-Ile-Arg-ProNHCH$_2$CH$_3$,
N-(6-Ac-Aca)-Sar-Gly-Val-D-alloIle-Thr-Gln-Ile-Arg-ProNHCH$_2$CH$_3$,
N-(6-Ac-Aca)-Sar-Gly-Val-D-Ile-Thr-Gln-Ile-Arg-Pro-D-AlaNH$_2$,
N-(6-Ac-Aca)-Sar-Gly-Val-D-alloIle-Thr-Gln-Ile-Arg-Pro-D-AlaNH$_2$, and
N-(6-Ac-Aca)-Sar-Gly-Val-D-alloIle-Thr-Gln-Ile-Arg-ProNHCH(CH$_3$)$_2$.

EXAMPLE 231

The procedures described in examples 224, 225, 226, 227, 228, and 229 are used but substituting N-acetyl-4-aminobutyric acid (4-Ac-Gaba) instead of tetrahydro-2-furoic acid. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-(4-Ac-Gaba)-Sar-Gly-Val-D-alloIle-Thr-Nva-Ile-Arg-ProNHCH$_2$CH$_3$,
N-(4-Ac-Gaba)-Sar-Gly-Val-D-Ile-Thr-Gln-Ile-Arg-ProNHCH$_2$CH$_3$,
N-(4-Ac-Gaba)-Sar-Gly-Val-D-alloIle-Thr-Gln-Ile-Arg-ProNHCH$_2$CH$_3$,
N-(4-Ac-Gaba)-Sar-Gly-Val-D-Ile-Thr-Gln-Ile-Arg-Pro-D-AlaNH$_2$,
N-(4-Ac-Gaba)-Sar-Gly-Val-D-alloIle-Thr-Gln-Ile-Arg-Pro-D-AlaNH$_2$, and
N-(4-Ac-Gaba)-Sar-Gly-Val-D-alloIle-Thr-Gln-Ile-Arg-ProNHCH(CH$_3$)$_2$.

EXAMPLE 232

The procedures described in examples 224, 225, 226, 227, 228, and 229 are used but substituting 2-furoic acid instead of tetrahydro-2-furoic acid. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-(42-Furoyl)-Sar-Gly-Val-D-alloIle-Thr-Nva-Ile-Arg-ProNHCH$_2$CH$_3$,
N-(2-Furoyl)-Sar-Gly-Val-D-Ile-Thr-Gln-Ile-Arg-ProNHCH$_2$CH$_3$,
N-(2-Furoyl)-Sar-Gly-Val-D-alloIle-Thr-Gln-Ile-Arg-ProNHCH$_2$CH$_3$,
N-(2-Furoyl)-Sar-Gly-Val-D-Ile-Thr-Gln-Ile-Arg-Pro-D-AlaNH$_2$,
N-(2-Furoyl)-Sar-Gly-Val-D-alloIle-Thr-Gln-Ile-Arg-Pro-D-AlaNH$_2$, and
N-(2-Furoyl)-Sar-Gly-Val-D-alloIle-Thr-Gln-Ile-Arg-ProNHCH(CH$_3$)$_2$.

EXAMPLE 233

The procedures described in examples 224, 225, 226, 227, 228, and 229 are used but substituting shikimic acid instead of tetrahydro-2-furoic acid. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-(4Shikimyl)-Sar-Gly-Val-D-alloIle-Thr-Nva-Ile-Arg-ProNHCH$_2$CH$_3$,
N-(Shikimyl)-Sar-Gly-Val-D-Ile-Thr-Gln-Ile-Arg-ProNHCH$_2$CH$_3$,
N-(Shikimyl)-Sar-Gly-Val-D-alloIle-Thr-Gln-Ile-Arg-ProNHCH$_2$CH$_3$,
N-(Shikimyl)-Sar-Gly-Val-D-Ile-Thr-Gln-Ile-Arg-Pro-D-AlaNH$_2$,
N-(Shikimyl)-Sar-Gly-Val-D-alloIle-Thr-Gln-Ile-Arg-Pro-D-AlaNH$_2$, and
N-(Shikimyl)-Sar-Gly-Val-D-alloIle-Thr-Gln-Ile-Arg-ProNHCH(CH$_3$)$_2$.

EXAMPLE 234

The procedures described in examples 224, 225, 226, 227, 228, and 229 are used but substituting 2-methyl-nicotinic acid instead of tetrahydro2-furoic acid. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides:

N-(2-Me-Nicotinyl)-Sar-Gly-Val-D-alloIle-Thr-Nva-Ile-Arg-ProNHCH$_2$CH$_3$,
N-(2-Me-Nicotinyl)-Sar-Gly-Val-D-Ile-Thr-Gln-Ile-Arg-ProNHCH$_2$CH$_3$,
N-(2-Me-Nicotinyl)-Sar-Gly-Val-D-alloIle-Thr-Gln-Ile-Arg-ProNHCH$_2$CH$_3$,
N-(2-Me-Nicotinyl)-Sar-Gly-Val-D-Ile-Thr-Gln-Ile-Arg-Pro-D-AlaNH$_2$,
N-(2-Me-Nicotinyl)-Sar-Gly-Val-D-alloIle-Thr-Gln-Ile-Arg-Pro-D-AlaNH$_2$, and
N-(2-Me-Nicotinyl)-Sar-Gly-Val-D-alloIle-Thr-Gln-Ile-Arg-ProNHCH(CH$_3$)$_2$.

EXAMPLE 235

N-Ac-Sar-Gly-Val-D-alloIle-Thr-Leu-Ile-Arg-Pro-D-AlaNH$_2$

The procedure described in Example 75 is used but substituting Fmoc-D-alloIle for Fmoc-D-Ile and Fmoc-Leu for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01%

TFA. The pure fractions are lyophilized to yield N-Ac-Sar-Gly-Val-D-alloIle-Thr-Leu-Ile-Arg-Pro-D-AlaNH$_2$ as the trifluoroacetate salt.

Example 236

N-Ac-Sar-Gly-Val-D-Ile-Thr-Leu-Ile-Arg-ProNHCH(CH$_3$)$_2$

The procedure described in example 4 is used but substituting Fmoc-Leu for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Leu-Ile-Arg-ProNHCH(CH$_3$)$_2$ as the trifluoroacetate salt.

EXAMPLE 237

N-Ac-Sar-Gly-Val-D-alloIle-Thr-Leu-Ile-Arg-ProNHCH$_2$CH$_3$

The procedure described in Example 73 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Thr-Leu-Ile-Arg-ProNHCH$_2$CH$_3$ as the trifluoroacetate salt.

EXAMPLE 238

N-Ac-Sar-Gly-Val-D-Ile-Thr-Leu-Ile-Arg-Pro-D-AlaNH$_2$

The procedure described in Example 75 is used but substituting Fmoc-Leu for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Leu-Ile-Arg-Pro-D-AlaNH$_2$ as the trifluoroacetate salt.

EXAMPLE 239

N-Succinyl-Sar-Gly-Val-D-Ile-Thr-Leu-Ile-Arg-Pro-D-AlaNH$_2$

The procedure described in Example 75 is used but substituting Fmoc-Leu for Fmoc-Nva and acylating with succinic anhydride after the coupling with Fmoc-Sar and deprotection as described in Example 54. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Succinyl-Sar-Gly-Val-D-Ile-Thr-Leu-Ile-Arg-Pro-D-AlaNH$_2$ as the trifluoroacetate salt.

EXAMPLE 240

N-Succinyl-Sar-Gly-Val-D-Ile-Thr-Leu-Ile-Arg-ProNHCH$_2$CH$_3$

The procedure described in Example 206 is used but substituting Fmoc-Leu for Fmoc-Gln(Trt) and acylating with succinic anhydride after the coupling with Fmoc-Sar and deprotection as described in Example 54. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Succinyl-Sar-Gly-Val-D-Ile-Thr-Leu-Ile-Arg-ProNHCH$_2$CH$_3$ as the trifluoroacetate salt.

EXAMPLE 241

The procedures described in Examples 201, 202 and 203 are used but substituting Fmoc-Leu instead of Fmoc-Gln (Trt). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides:

N-Succinyl-Sar-Gly-Val-D-Ile-Thr-Leu-Ile-Arg-ProNHCH$_2$CH$_3$,
N-Succinyl-Sar-Gly-Val-D-alloIle-Thr-Leu-Ile-Arg-ProNHCH$_2$CH$_3$, and
N-Succinyl-Sar-Gly-Val-D-alloIle-Thr-Leu-Ile-Arg-Pro-D-AlaNH$_2$.

EXAMPLE 242

N-Succinyl-Sar-Gly-Val-D-Ile-Thr-Leu-Ile-Arg-Pro-AzaglyNH$_2$

The procedure described in Example 149 is used but substituting Fmoc-Leu for Fmoc-Nva and acylating with succinic anhydride after the coupling with Fmoc-Sar and deprotection as described in Example 54. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Succinyl-Sar-Gly-Val-D-Ile-Thr-Leu-Ile-Arg-Pro-AzaglyNH$_2$ as the trifluoroacetate salt.

EXAMPLE 243

N-Ac-Sar-Gly-Val-D-alloIle-Thr-Nva-Ile-Arg-ProNHethyl-(1-pyrrolidine)

The procedure described in Example 5 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Thr-Nva-Ile-Arg-ProNHethyl-(1-pyrrolidine) as the trifluoroacetate salt.

EXAMPLE 244

N-Ac-Sar-Gly-Val-D-alloIle-Thr-Nva-Ile-Arg-ProNH(ethyl-1-cyclohexyl)

The procedure described in Example 8 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Thr-Nva-Ile-Arg-ProNH(ethyl-1-cyclohexyl) as the trifluoroacetate salt.

EXAMPLE 245

N-Ac-Sar-Gly-Val-D-Ile-Thr-Gln-Ile-Arg-ProNHethyl(1-pyrrolidine)

The procedure described in Example 5 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Gln-Ile-Arg-ProNHethyl-(1-pyrrolidine) as the trifluoroacetate salt.

EXAMPLE 246

N-Ac-Sar-Gly-Val-D-Ile-Thr-Gln-Ile-Arg-ProNH(ethyl-1-cyclohexyl)

The procedure described in Example 8 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Gln-Ile-Arg-ProNH(ethyl-1-cyclohexyl) as the trifluoroacetate salt.

EXAMPLE 247

N-Succinyl-Sar-Gly-Val-D-Ile-Thr-Gln-Ile-Arg-ProNH(ethyl-1-cyclohexyl)

The procedure described in Example 246 is used but acylating the peptide resin with succinic anhydride after the coupling with Fmoc-Sar and deprotection as described in Example 54. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Succinyl-Sar-Gly-Val-D-Ile-Thr-Gln-Ile-Arg-ProNH(ethyl-1-cyclohexyl) as the trifluoroacetate salt.

EXAMPLE 248

The procedures described in Examples 11 is used but substituting the appropriate protected amino acids as described in Examples 14, 43, 74, 73, 54, 174, and 132 respectively. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-Ac-Sar-Gly-Val-D-alloIle-Thr-Nva-Ile-Arg-ProNHCH$_2$CH$_2$OCH$_3$,
N-Ac-Sar-Gly-Val-D-Ile-Thr-Gln-Ile-Arg-ProNHCH$_2$CH$_2$OCH$_3$,
N-Ac-Sar-Gly-Val-D-Ile-Thr-Ser-Ile-Arg-ProNHCH$_2$CH$_2$OCH$_3$,
N-Ac-Sar-Gly-Val-D-Ile-Thr-Leu-Ile-Arg-ProNHCH$_2$CH$_2$OCH$_3$,
N-Succinyl-Sar-Gly-Val-D-Ile-Thr-Nva-Ile-Arg-ProNHCH$_2$CH$_2$OCH$_3$,
N-Succinyl-Sar-Gly-Val-D-Ile-Thr-Gln-Ile-Arg-ProNHCH$_2$CH$_2$OCH$_3$,
N-Succinyl-Sar-Gly-Val-D-alloIle-Thr-Gln-Ile-Arg-ProNHCH$_2$CH$_2$OCH$_3$,
N-Ac-Sar-Gly-Val-D-Ile-Ser-Nva-Ile-Arg-ProNHCH$_2$CH$_2$OCH$_3$, and
N-Ac-Sar-Gly-Val-D-Leu-Ser-Nva-Ile-Arg-ProNHCH$_2$CH$_2$OCH$_3$.

EXAMPLE 249

The procedures described in Examples 49 is used but substituting the appropriate protected amino acids as described in Examples 14,4, 75, 54 and 132 respectively. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA The pure fractions are lyophilized to yield the following peptides as trifluoroacetate salt:

N-Ac-Sar-Gly-Val-D-alloIle-Thr-Allygly-Ile-Arg-ProNHCH$_2$CH$_3$,
N-Ac-Sar-Gly-Val-D-Ile-Thr-Allygly-Ile-Arg-ProNHCH(CH$_3$)$_2$,
N-Ac-Sar-Gly-Val-D-Ile-Thr-Allygly-Ile-Arg-Pro-D-AlaNH$_2$,
N-Ac-Sar-Gly-Val-D-alloIle-Thr-Allygly-Ile-Arg-Pro-D-AlaNH$_2$,
N-Succinyl-Sar-Gly-Val-D-Ile-Thr-Allygly-Ile-Arg-Pro-D-AlaNH$_2$,
N-Ac-Sar-Gly-Val-D-Ile-Ser-Allygly-Ile-Arg-Pro-ProNHCH$_2$CH$_3$, and
N-Ac-Sar-Gly-Val-D-Leu-Ser-Allygly-Ile-Arg-Pro-ProNHCH$_2$CH$_3$.

EXAMPLE 250

N-Ac-Sar-Gly-Val-D-Ile-Thr-Nva-Ile-Arg-Pro-D-SerNH$_2$

The procedure described in Example 75 is used but substituting Fmoc-D-Ser(tBu)-Sieber amide resin for Fmoc-D-Ala-Sieber amide resin. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-Arg-Pro-D-SerNH$_2$ as the trifluoroacetate salt.

EXAMPLE 251

N-Ac-Sar-Gly-Val-D-Ile-Thr-Nva-Ile-Arg-ProNHOH

The procedure described in Example 149 is used but hydroxylamine hydrochloride for semicarbazide hydrochloride. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-Ile-Arg-ProNHOH as the trifluoroacetate salt.

EXAMPLE 252

N-Ac-Sar-Gly-Val-D-Ile-Ser-Nva-Ile-Arg-ProNHCH$_2$CH$_3$

The procedure described in Example 132 is used but substituting Fmoc-D-Ile for Fmoc-D-Leu After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Ser-Nva-Ile-Arg-ProNHCH$_2$CH$_3$ as the trifluoroacetate salt.

EXAMPLE 253

N-Ac-Sar-Gly-Val-D-alloIle-Ser-Nva-Ile-Arg-ProNHCH$_2$CH$_3$

The procedure described in Example 132 is used but substituting Fmoc-D-alloIle for Fmoc-D-Leu. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Ser-Nva-Ile-Arg-ProNHCH$_2$CH$_3$ as the trifluoroacetate salt.

EXAMPLE 254

N-Ac-Sar-Gly-Val-D-Leu-Hser-Nva-Ile-Arg-ProNHCH$_2$CH$_3$

The procedure described in Example 132 is used but substituting Fmoc-Hser(tBu) for Fmoc-Ser(tBu). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Leu-Hser-Nva-Ile-Arg-ProNHCH$_2$CH$_3$ as the trifluoroacetate salt.

EXAMPLE 255

N-Ac-Sar-Gly-Gln-D-Ile-Thr-Nva-Ile-Arg-ProNHCH$_2$CH$_3$

The procedure described in Example 1 was used but substituting Fmoc-Gln(Trt) for Fmoc-Val. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Gln-D-Ile-Thr-Nva-Ile-Arg-ProNHCH$_2$CH$_3$ as the trifluoroacetate salt: $R_t$=2.36 min (gradient of 10% to 30% acetonitrile in water containing 0.01% TFA over 30 min period); MS (ESI) m/e 1023 (M)$^+$.

EXAMPLE 256

N-Ac-Sar-Gly-Nva-D-Ile-Thr-Nva-Ile-Arg-ProNHCH$_2$CH$_3$

The procedure described in Example 1 was used but substituting Fmoc-Nva for Fmoc-Val. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Nva-D-Ile-Thr-Nva-Ile-Arg-ProNHCH$_2$CH$_3$ as the trifluoroacetate salt: $R_t$32 3.28 min (gradient of 10% to 30% acetonitrile in water containing 0.01% TFA over 30 min period); MS (ESI) m/e 994 (M)$^+$.

EXAMPLE 257

N-Ac-Sar-Gly-Ile-D-Ile-Thr-Nva-Ile-Arg-ProNHCH$_2$CH$_3$

The procedure described in Example 1 was used but substituting Fmoc-Ile for Fmoc-Val. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Ile-D-Ile-Thr-Nva-Ile-Arg-ProNHCH$_2$CH$_3$ as the trifluoroacetate salt: $R_t$=3.55 min (gradient of 10% to 30% acetonitrile in water containing 0.01% TFA over 30 min period); MS (ESI) m/e 1008 (M)$^+$.

EXAMPLE 258

N-Ac-Sar-Gly-Phe-D-Ile-Thr-Nva-Ile-Arg-ProNHCH$_2$CH$_3$

The procedure described in Example 1 was used but substituting Fmoc-Phe for Fmoc-Val. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Phe-D-Ile-Thr-Nva-Ile-Arg-ProNHCH$_2$CH$_3$ as the trifluoroacetate salt: $R_t$=3.77 min (gradient of 10% to 30% acetonitrile in water containing 0.01% TFA over 30 min period); MS (ESI) m/e 1042 (M)$^+$.

EXAMPLE 259

N-Ac-Sar-Gly-Leu-D-Ile-Thr-Nva-Ile-Arg-ProNHCH$_2$CH$_3$

The procedure described in Example 1 was used but substituting Fmoc-Leu for Fmoc-Val. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Leu-D-Ile-Thr-Nva-Ile-Arg-ProNHCH$_2$CH$_3$ as the trifluoroacetate salt: $R_t$=3.56 min (gradient of 10% to 30% acetonitrile in water containing 0.01% TFA over 30 min period); MS (ESI) m/e 1008 (M)$^+$.

EXAMPLE 260

N-Ac-Sar-Gly-Ser-D-Ile-Thr-Nva-Ile-Arg-ProNHCH$_2$CH$_3$

The procedure described in Example 1 was used but substituting Fmoc-Ser(tBu) for Fmoc-Val. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Sar-Gly-Ser-D-Ile-Thr-Nva-Ile-Arg-ProNHCH$_2$CH$_3$ as the trifluoroacetate salt: R$_t$=2.41 min (gradient of 10% to 30% acetonitrile in water containing 0.01% TFA over 30 min period); MS (ESI) m/e 982 (M)$^+$.

EXAMPLE 261

N-Ac-Thr-Gly-Val-D-Leu-Thr-Nva-Ile-Arg-ProNHCH$_2$CH$_3$

The procedure described in Example 1 was used but substituting Fmoc-Thr(tBu) for Fmoc-Sar and Fmoc-D-Leu for Fmoc-D-Ile. After cleavage of the peptide from the resin and removal of the protecting groups using (9:1) TFA/anisole (3 mL) the crude product was purified by C-18 column chromatography using a solvent mixture varying in a gradient of 10% to 50% acetonitrile-water containing 0.01% TFA. The pure fractions were lyophilized to yield N-Ac-Thr-Gly-Val-D-Leu-Thr-Nva-Ile-Arg-ProNHCH$_2$CH$_3$ as the trifluoroacetate salt: R$_t$=3.33 min (gradient of 10% to 30% acetonitrile in water containing 0.01% TFA over 30 min period); MS (ESI) m/e 1024 (M)$^+$.

EXAMPLE 262

The procedures described in Example 46 is used but substituting the appropriate protected amino acids as describes in Examples 75, 4, 54, and 132. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-Ac-Sar-Gly-Val-D-alloIle-Thr-Ala-Ile-Arg-ProNHCH$_2$CH$_3$,
N-Ac-Sar-Gly-Val-D-Ile-Thr-Ala-Ile-Arg-ProNHCH(CH$_3$)$_2$,
N-Ac-Sar-Gly-Val-D-Ile-Thr-Ala-Ile-Arg-Pro-D-AlaNH$_2$,
N-Ac-Sar-Gly-Val-D-alloIle-Thr-Ala-Ile-Arg-Pro-D-AlaNH$_2$,
N-Succinyl-Sar-Gly-Val-D-Ile-Thr-Ala-Ile-Arg-Pro-D-AlaNH$_2$,
N-Ac-Sar-Gly-Val-D-Ile-Ser-Ala-Ile-Arg-ProNHCH$_2$CH$_3$, and
N-Ac-Sar-Gly-Val-D-Leu-Ser-Ala-Ile-Arg-ProNHCH$_2$CH$_3$.

EXAMPLE 263

The procedures described in Example 262 is used but substituting Fmoc-Val for Fmoc-Ala. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-Ac-Sar-Gly-Val-D-alloIle-Thr-Val-Ile-Arg-ProNHCH$_2$CH$_3$,
N-Ac-Sar-Gly-Val-D-Ile-Thr-Val-Ile-Arg-ProNHCH(CH$_3$)$_2$,
N-Ac-Sar-Gly-Val-D-Ile-Thr-Val-Ile-Arg-Pro-D-AlaNH$_2$,
N-Ac-Sar-Gly-Val-D-alloIle-Thr-Val-Ile-Arg-Pro-D-AlaNH$_2$,
N-Succinyl-Sar-Gly-Val-D-Ile-Thr-Val-Ile-Arg-Pro-D-AlaNH$_2$,
N-Ac-Sar-Gly-Val-D-Ile-Ser-Val-Ile-Arg-ProNHCH$_2$CH$_3$, and
N-Ac-Sar-Gly-Val-D-Leu-Ser-Val-Ile-Arg-ProNHCH$_2$CH$_3$.

EXAMPLE 264

The procedures described in Example 263 is used but substituting Fmoc-DNva for Fmoc-Val. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-Ac-Sar-Gly-Val-D-alloIle-Thr-D-Nva-Ile-Arg-ProNHCH$_2$CH$_3$,
N-Ac-Sar-Gly-Val-D-Ile-Thr-D-Nva-Ile-Arg-ProNHCH(CH$_3$)$_2$,
N-Ac-Sar-Gly-Val-D-Ile-Thr-D-Nva-Ile-Arg-Pro-D-AlaNH$_2$,
N-Ac-Sar-Gly-Val-D-alloIle-Thr-D-Nva-Ile-Arg-Pro-D-AlaNH$_2$,
N-Succinyl-Sar-Gly-Val-D-Ile-Thr-D-Nva-Ile-Arg-Pro-D-AlaNH$_2$,
N-Ac-Sar-Gly-Val-D-Ile-Ser-D-Nva-Ile-Arg-Pro-ProNHCH$_2$CH$_3$, and
N-Ac-Sar-Gly-Val-D-Leu-Ser-D-Nva-Ile-Arg-Pro-ProNHCH$_2$CH$_3$.

EXAMPLE 265

N-Ac-Sar-Gly-Val-D-Ile-Ser-Gln-Ile-Arg-ProNHCH$_2$CH$_3$

The procedure described in Example 132 is used but substituting Fmoc-D-Ile for Fmoc-D-Leu and Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Ser-Gln-Ile-Arg-ProNHCH$_2$CH$_3$ as the trifluoroacetate salt.

EXAMPLE 266

N-Ac-Sar-Gly-Val-D-Leu-Ser-Gln-Ile-Arg-ProNHCH$_2$CH$_3$

The procedure described in Example 132 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Leu-Ser-Gln-Ile-Arg-ProNHCH$_2$CH$_3$ as the trifluoroacetate salt.

EXAMPLE 267

N-Ac-Sar-Gly-Val-D-Leu-Ser-Nva-Ile-Arg-Pro-D-AlaNH$_2$

The procedure described in Example 75 is used but substituting Fmoc-D-Leu for Fmoc-D-Ile and Fmoc-Ser (tBu) for Fmoc-Thr(tBu). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Leu-Ser-Nva-Ile-Arg-Pro-D-AlaNH$_2$ as the trifluoroacetate salt.

EXAMPLE 268

N-Ac-Sar-Gly-Val-D-Ile-Ser-Nva-Ile-Arg-Pro-D-AlaNH$_2$

The procedure described in Example 267 is used but substituting Fmoc-D-Ile for Fmoc-D-Leu and Fmoc-Ser(tBu) for Fmoc-Thr(tBu). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Ser-Nva-Ile-Arg-Pro D-AlaNH$_2$ as the trifluoroacetate salt.

EXAMPLE 269

N-Succinyl-Sar-Gly-Val-D-Leu-Ser-Nva-Ile-Arg-ProNHCH$_2$CH$_3$

The procedure described in Example 54 is used but substituting Fmoc-D-Leu for Fmoc-D-Ile and Fmoc-Ser(tBu) for Fmoc-Thr(tBu). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Succinyl-Sar-Gly-Val-D-Leu-Ser-Nva-Ile-Arg-ProNHCH$_2$CH$_3$ as the trifluoroacetate salt

EXAMPLE 270

N-Succinyl-Sar-Gly-Val-D-Ile-Ser-Nva-Ile-Arg-ProNHCH$_2$CH$_3$

The procedure described in Example 269 is used but substituting Fmoc-D-Ile for Fmoc-D-Leu. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Succinyl-Sar-Gly-Val-D-Ile-Ser-Nva-Ile-Arg-ProNHCH$_2$CH$_3$ as the trifluoroacetate salt.

EXAMPLE 271

N-Succinyl-Sar-Gly-Val-D-Leu-Ser-Gln-Ile-Arg-ProNHCH$_2$CH$_3$

The procedure described in Example 270 is used but substituting Fmoc-D-Leu for Fmoc-D-Ile and Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Succinyl-Sar-Gly-Val-D-Leu-Ser-Gln-Ile-Arg-ProNHCH$_2$CH$_3$ as the trifluoroacetate salt.

EXAMPLE 272

N-Succinyl-Sar-Gly-Val-D-Ile-Ser-Gln-Ile-Arg-ProNHCH$_2$CH$_3$

The procedure described in Example 270 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Succinyl-Sar-Gly-Val-D-Ile-Ser-Gln-Ile-Arg-ProNHCH$_2$CH$_3$ as the trifluoroacetate salt.

EXAMPLE 273

N-Ac-Sar-Gly-Val-D-Ile-Ser-Ser-Ile-Arg-ProNHCH$_2$CH$_3$

The procedure described in Example 265 is used but substituting Fmoc-Ser(tBu) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Ser-Ser-Ile-Arg-ProNHCH$_2$CH$_3$ as the trifluoroacetate salt.

EXAMPLE 274

N-Ac-Sar-Gly-Val-D-Leu-Ser-Ser-Ile-Arg-ProNHCH$_2$CH$_3$

The procedure described in Example 266 is used but substituting Fmoc-Ser(tBu) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Leu-Ser-Ser-Ile-Arg-ProNHCH$_2$CH$_3$ as the trifluoroacetate salt.

EXAMPLE 275

N-Ac-Sar-Gly-Val-D-Leu-Ser-Nva-Ile-Arg-ProNHCH$_2$CH$_2$CH$_3$

The procedure described in Example 13 is used but substituting Fmoc-D-Leu for Fmoc-D-Ile and Fmoc-Ser(tBu) for Fmoc-Thr(tBu). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Leu-Ser-Nva-Ile-Arg-ProNHCH$_2$CH$_2$CH$_3$ as the trifluoroacetate salt.

EXAMPLE 276

N-Ac-Sar-Gly-Val-D-Ile-Ser-Nva-Ile-Arg-ProNHCH$_2$CH$_2$CH$_3$

The procedure described in Example 13 is used but substituting Fmoc-Ser(tBu) for Fmoc-Thr(tBu). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Ser-Nva-Ile-Arg-ProNHCH$_2$CH$_2$CH$_3$ as the trifluoroacetate salt.

EXAMPLE 277

N-Ac-Sar-Gly-Val-D-Leu-Ser-Leu-Ile-Arg-ProNHCH$_2$CH$_3$

The procedure described in Example 132 is used but substituting Fmoc-Leu for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Leu-Ser-Leu-Ile-Arg-ProNHCH$_2$CH$_3$ as the trifluoroacetate salt.

EXAMPLE 278

N-Ac-Sar-Gly-Val-D-Ile-Ser-Leu-Ile-Arg-ProNHCH$_2$CH$_3$

The procedure described in Example 277 is used but substituting Fmoc-D-Ile for Fmoc-D-Leu. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Ser-Leu-Ile-Arg-ProNHCH$_2$CH$_3$ as the trifluoroacetate salt.

EXAMPLE 279

N-Ac-Sar-Gly-Val-D-alloIle-Ser-Nva-Ile-Arg-ProNHCH$_2$CH$_3$

The procedure described in Example 132 is used but substituting Fmoc-D-alloIle for Fmoc-D-Leu. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Ser-Nva-Ile-Arg-ProNHCH$_2$CH$_3$ as the trifluoroacetate salt.

EXAMPLE 280

N-Ac-Sar-Gly-Val-D-alloIle-Ser-Gln-Ile-Arg-ProNHCH$_2$CH$_3$

The procedure described in Example 265 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Ser-Gln-Ile-Arg-ProNHCH$_2$CH$_3$ as the trifluoroacetate salt.

EXAMPLE 281

N-Succinyl-Sar-Gly-Val-D-alloIle-Ser-Nva-Ile-Arg-ProNHCH$_2$CH$_3$

The procedure described in Example 270 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Succinyl-Sar-Gly-Val-D-alloIle-Ser-Nva-Ile-Arg-ProNHCH$_2$CH$_3$ as the trifluoroacetate.

EXAMPLE 282

N-Ac-Sar-Gly-Val-D-alloIle-Ser-Nva-Ile-Arg-ProNHCH$_2$CH$_2$CH$_3$

The procedure described in Example 276 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure factions are lyophilized to yield N-Ac-Sar-Gly-Val-D-alloIle-Ser-Nva-Ile-Arg-ProNHCH$_2$CH$_2$CH$_3$ as the trifluoroacetate.

EXAMPLE 283

N-Ac-Sar-Gly-Val-D-alloIle-Ser-Nva-Ile-Arg-Pro-D-AlaNH$_2$

The procedure described in Example 268 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to N-Ac-Sar-Gly-Val-D-alloIle-Ser-Nva-Ile-Arg-Pro-D-AlaNH$_2$ as the trifluoroacetate.

EXAMPLE 284

N-Ac-Sar-Gly-Val-D-alloIle-Ser-Leu-Ile-Arg-ProNHCH$_2$CH$_3$

The procedure described in Example 265 is used but substituting Fmoc-D-alloIle for Fmoc-D-Ile and Fmoc-Leu for Fmoc-Gln(Trt). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Ser-Leu-Ile-Arg-ProNHCH$_2$CH$_3$ as the trifluoroacetate.

EXAMPLE 285

N-Ac-Sar-Gly-Val-D-alloIle-Ser-Ser-Ile-Arg-ProNHCH$_2$CH$_3$

The procedure described in Example 276 is used but substituting Fmoc-D-alloIle for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloIle-Ser-Ser-Ile-Arg-ProNHCH$_2$CH$_3$ as the trifluoroacetate.

EXAMPLE 286

The procedure described in Example 125 is used but separately substituting Fmoc-D-Ile and Fmoc-D-alloIle, respectively, for Fmoc-D-Leu. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to the the following peptides as trifluoroacetate salt:

N-Ac-Sar-Gly-Val-D-Ile-Gly-Nva-Ile-Arg-ProNHCH$_2$CH$_3$ and
N-Ac-Sar-Gly-Val-D-alloIle-Gly-Nva-Ile-Arg-ProNHCH$_2$CH$_3$

EXAMPLE 287

The procedure described in Example 125 and 286 is used but separately substituting Fmoc-D-Ile and Fmoc-D-alloIle, respectively, for Fmoc-D-Leu and substituting Fmoc-Gln (Trt) for Fmoc-Nva . After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the trifluoroacetate salt of:

N-Ac-Sar-Gly-Val-D-Leu-Gly-Gln-Ile-Arg-ProNHCH$_2$CH$_3$,
N-Ac-Sar-Gly-Val-D-Ile-Gly-Gln-Ile-Arg-ProNHCH$_2$CH$_3$, and
N-Ac-Sar-Gly-Val-D-alloIle-Gly-Gln-Ile-Arg-ProNHCH$_2$CH$_3$.

EXAMPLE 288

The procedure described in Example 123 is used but separately substituting Fmoc-D-Ile and Fmoc-D-alloIle, respectively, for Fmoc-D-Leu. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the trifluoroacetate salt of:

N-Ac-Sar-Gly-Val-D-Ile-Tyr-Nva-Ile-Arg-ProNHCH$_2$CH$_3$ and N-Ac-Sar-Gly-Val-D-alloIle-Tyr-Nva-Ile-Arg-ProNHCH$_2$CH$_3$.

EXAMPLE 289

The procedure described in Example 123 and 288 is used but separately substituting Fmoc-D-Ile and Fmoc-D-alloIle, respectively, for Fmoc-D-Leu and substituting Fmoc-Gln (Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the trifluoroacetate salt of:

N-Ac-Sar-Gly-Val-D-Leu-Tyr-Gln-Ile-Arg-ProNHCH$_2$CH$_3$,
N-Ac-Sar-Gly-Val-D-Ile-Tyr-Gln-Ile-Arg-ProNHCH$_2$CH$_3$, and
N-Ac-Sar-Gly-Val-D-alloIle-Tyr-Gln-Ile-Arg-ProNHCH$_2$CH$_3$.

EXAMPLE 290

N-Ac-Sar-Gly-Val-D-Ser-Thr-Nva-Ile-Ar-ProNHCH$_2$CH$_3$

The procedure described in Example 1 is used but substituting Fmoc-D-Ser(tBu) for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ser-Thr-Nva-Ile-Arg-ProNHCH$_2$CH$_3$ as the trifluoroacetate.

EXAMPLE 291

N-Ac-Sar-Gly-Val-D-Thr-Thr-Nva-Ile-Arg-ProNHCH$_2$CH$_3$

The procedure described in Example 1 is used but substituting Fmoc-D-Thr(tBu) for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Thr-Thr-Nva-Ile-Arg-ProNHCH$_2$CH$_3$ as the trifluoroacetate.

EXAMPLE 292

N-Ac-Sar-Gly-Val-D-Gln-Thr-Nva-Ile-Arg-ProNHCH$_2$CH$_3$

The procedure described in Example 1 is used but substituting Fmoc-D-Gln(Trt) for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Gln-Thr-Nva-Ile-Arg-ProNHCH$_2$CH$_3$ as the trifluoroacetate.

EXAMPLE 293

N-Ac-Sar-Gly-Val-D-Asn-Thr-Nva-Ile-Arg-ProNHCH$_2$CH$_3$

The procedure described in Example 1 is used but substituting Fmoc-D-Asn(Trt) for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Asn-Thr-Nva-Ile-Arg-ProNHCH$_2$CH$_3$ as the trifluoroacetate.

EXAMPLE 294

N-Ac-Sar-Gly-Val-D-Arg-Thr-Nva-Ile-Arg-ProNHCH$_2$CH$_3$

The procedure described in Example 1 is used but substituting Fmoc-D-Arg(Pmc) for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Arg-Thr-Nva-Ile-Arg-ProNHCH$_2$CH$_3$ as the trifluoroacetate.

EXAMPLE 295

N-Ac-Sar-Gly-Val-D-3-Pal-Thr-Nva-Ile-Arg-ProNHCH$_2$CH$_3$

The procedure described in Example 1 is used but substituting Fmoc-D-3-Pal for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-3-Pal-Thr-Nva-Ile-Arg-ProNHCH$_2$CH$_3$ as the trifluoroacetate.

EXAMPLE 296

N-Ac-Sar-Gly-Val-D-Glu-Thr-Nva-Ile-Arg-ProNHCH$_2$CH$_3$

The procedure described in Example 1 is used but substituting Fmoc-D-Glu(OtBu)-OH for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Glu-Thr-Nva-Ile-Arg-ProNHCH$_2$CH$_3$ as the trifluoroacetate.

EXAMPLE 297

N-Ac-Sar-Gly-Val-D-Asp-Thr-Nva-Ile-Arg-ProNHCH$_2$CH$_3$

The procedure described in Example 1 is used but substituting Fmoc-D-Asp(OtBu)-OH for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Asp-Thr-Nva-Ile-Arg-ProNHCH$_2$CH$_3$ as the trifluoroacetate.

EXAMPLE 298

N-Ac-Sar-Gly-Val-D-His-Thr-Nva-Ile-Arg-ProNHCH$_2$CH$_3$

The procedure described in Example 1 is used but substituting Fmoc-D-His(Boc)-OH for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-His-Thr-Nva-Ile-Arg-ProNHCH$_2$CH$_3$ as the trifluoroacetate.

EXAMPLE 299

N-Ac-Sar-Gly-Val-D-Hser-Thr-Nva-Ile-Arg-ProNHCH$_2$CH$_3$

The procedure described in Example 1 is used but substituting Fmoc-D-Hser(tBu) for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Hser-Thr-Nva-Ile-Arg-ProNHCH$_2$CH$_3$ as the trifluoroacetate.

EXAMPLE 300

N-Ac-Sar-Gly-Val-D-alloThr-Thr-Nva-Ile-Arg-ProNHCH$_2$CH$_3$

The procedure described in Example 1 is used but substituting Fmoc-D-alloThr(tBu) for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloThr-Thr-Nva-Ile-Arg-ProNHCH$_2$CH$_3$ as the trifluoroacetate.

EXAMPLE 301

N-Ac-Sar-Gly-Val-D-Ile-Thr-Nva-D-Ile-Arg-ProNHCH$_2$CH$_3$

The procedure described in Example 1 is used but substituting Fmoc-D-Ile for Fmoc-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Nva-D-Ile-Arg-ProNHCH$_2$CH$_3$ as the trifluoroacetate.

EXAMPLE 302

N-Ac-Sar-Gly-Val-D-Ser-Thr-Gln-Ile-Arg-ProNHCH$_2$CH$_3$

The procedure described in Example 290 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ser-Thr-Gln-Ile-Arg-ProNHCH$_2$CH$_3$ as the trifluoroacetate.

EXAMPLE 303

N-Ac-Sar-Gly-Val-D-Thr-Thr-Gln-Ile-Arg-ProNHCH$_2$CH$_3$

The procedure described in Example 291 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Thr-Thr-Gln-Ile-Arg-ProNHCH$_2$CH$_3$ as the trifluoroacetate.

EXAMPLE 304

N-Ac-Sar-Gly-Val-D-alloThr-Thr-Gln-Ile-Arg-ProNHCH$_2$CH$_3$

The procedure described in Example 300 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloThr-Thr-Gln-Ile-Arg-ProNHCH$_2$CH$_3$ as the trifluoroacetate.

EXAMPLE 305

N-Ac-Sar-Gly-Val-D-Ser-Ser-Nva-Ile-Arg-ProNHCH$_2$CH$_3$

The procedure described in Example 290 is used but substituting Fmoc-Ser(tBu) for Fmoc-Thr(tBu). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to N-Ac-Sar-Gly-Val-D-Ser-Ser-Nva-Ile-Arg-ProNHCH$_2$CH$_3$ as the trifluoroacetate.

EXAMPLE 306

N-Ac-Sar-Gly-Val-D-Thr-Ser-Nva-Ile-Arg-ProNHCH$_2$CH$_3$

The procedure described in Example 291 is used but substituting Fmoc-Ser(tBu) for Fmoc-Thr(tBu). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Thr-Ser-Nva-Ile-Arg-ProNHCH$_2$CH$_3$ as the trifluoroacetate.

EXAMPLE 307

N-Ac-Sar-Gly-Val-D-alloThr-Ser-Nva-Ile-Arg-ProNHCH$_2$CH$_3$

The procedure described in Example 300 is used but substituting Fmoc-Ser(tBu) for Fmoc-Thr(tBu). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloThr-Ser-Nva-Ile-Arg-ProNHCH$_2$CH$_3$ as the trifluoroacetate.

EXAMPLE 308

N-Ac-Sar-Gly-Val-D-alloThr-Ser-Gln-Ile-Arg-ProNHCH$_2$CH$_3$

The procedure described in Example 304 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-alloThr-Ser-Gln-Ile-Arg-ProNHCH$_2$CH$_3$ as the trifluoroacetate.

EXAMPLE 309

N-Ac-Sar-Gly-Val-D-Thr-Ser-Gln-Ile-Arg-ProNHCH$_2$CH$_3$

The procedure described in Example 303 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Thr-Ser-Gln-Ile-Arg-ProNHCH$_2$CH$_3$ as the trifluoroacetate.

EXAMPLE 310

The procedure described in Examples 132 and 266 is used but substituting N-acetyl-6-aminocaproic acid (6-Ac-Aca) for acetic acid. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N(6-Ac-Aca)-Sar-Gly-Val-D-Leu-Ser-Gln-Ile-Arg-ProNHCH CH$_3$, and N-(6Ac-Aca)-Sar-Gly-Val-D-Leu-Ser-Nva-Ile-Arg-ProNHCH2CH$_3$

EXAMPLE 311

The procedure described in Examples 310 is used but substituting N-acetyl-4-aminobutyric acid (4-Ac-Gaba) instead of N-acetyl-6-aminocaproic acid. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure factions are lyophilized to yield the following peptides as trifluoroacetate salt:

N-(4-Ac-Gaba)-Sar-Gly-Val-D-Leu-Ser-Gln-Ile-Arg-ProNHCH$_2$CH$_3$, and

N-(4-Ac-Gaba)-Sar-Gly-Val-D-Leu-Ser-Nva-Ile-Arg-ProNHCH$_2$CH$_3$.

EXAMPLE 312

The procedure described in Examples 311 is used but substituting 2-furoic acid instead of N-acetyl-4-aminobutyric acid. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-(2-Furoyl)-Sar-Gly-Val-D-Leu-Ser-Gln-Ile-ArgProNHCH$_2$CH$_3$, and

N-(2-Furoyl)-Sar-Gly-Val-D-Leu-Ser-Nva-Ile-Arg-ProNHCH$_2$CH$_3$.

EXAMPLE 313

The procedure described in Examples 312 is used but substituting shikimic acid instead of 2-furoic acid. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

EXAMPLE 315

The procedure described in Examples 311 is used but substituting 2-methyl-nicotinic acid instead of 2-furoic acid. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-(2-Me-nicotinyl)-Sar-Gly-Val-D-Leu-Ser-Nva-Ile-Arg-ProNHCH$_2$CH$_3$, and
N-(2-Me-nicotinyl)-Sar-Gly-Val-D-Leu-Ser-Nva-Ile-Arg-ProNHCH$_2$CH$_3$,

EXAMPLE 316

N-Ac-Sar-Gly-Val-D-Leu-Ser-Nva-Ile-Arg-ProNHethyl-1-(R)-cyclohexyl

The procedure described in Example 8 is used but substituting Fmoc-D-Leu for Fmoc-D-Ile and Fmoc-Ser(tBu) for Fmoc-Thr(tBu). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Leu-Ser-Nva-Ile-Arg-ProNHethyl-1-(R)-cyclohexyl as the trifluoroacetate.

EXAMPLE 317

N-Ac-Sar-Gly-Val-D-Ile-Thr-Ser-Ile-Arg-ProNHethyl-1-(R)cyclohexyl

The procedure described in Example 8 is used but substituting Fmoc-Ser(tBu) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Ser-Ile-Arg-ProNHethyl-1-(R)-cyclohexyl as the trifluoroacetate.

EXAMPLE 318

N-Ac-Sar-Gly-Val-D-Ile-Thr-Leu-Ile-Arg-ProNHethyl-1-(R)-cyclohexyl

The procedure described in Example 8 is used but substituting Fmoc-Leu for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Ile-Thr-Leu-Ile-Arg-ProNHethyl-1-(R)-cyclohexyl as the trifluoroacetate.

EXAMPLE 319

N-Ac-Sar-Gly-Val-D-Leu-Thr-Nva-Ile-Arg-ProNHethyl-1-(R)-cyclohexyl

The procedure described in Example 8 is used but substituting Fmoc-D-Leu for Fmoc-D-Ile. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Leu-Thr-Nva-Ile-Arg-ProNHethyl-1-(R)cyclohexyl as the trifluoroacetate.

EXAMPLE 320

N-Ac-Sar-Gly-Val-D-Leu-Ser-Ser-Ile-Arg-ProNHethyl-1-(R)-cyclohexyl

The procedure described in Example 316 is used but substituting Fmoc-Ser(tBu) for Fmoc-Nva. After cleavage of the peptide from the resin and removal of the protecting groups using (9:1) TFA/anisole (3 mL) the crude product is purified by C-18 column chromatography using a solvent mixture varying in a gradient of 100% to 50% acetonitrile-water containing 0.01% TFA1 The pure fractions are lyophilized to yield N-Ac-Sar-Gly-Val-D-Leu-Ser-Ser-Ile-Arg-ProNHethyl-1-(R)cyclohexyl as the trifluoroacetate.

EXAMPLE 321

N-Ac-Sar-Gly-Val-D-Leu-Ser-Gln-Ile-Arg-ProNHethyl-1-(R)-cyclohexyl

The procedure described in Example 316 is used but substituting Fmoc-Gln(Trt) for Fmoc-Nva. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-Ac-Sar-Gly-Val-D-Leu-Ser-Gln-Ile-Arg-ProNHethyl-1-(R)-cyclohexyl as the trifluoroacetate.

EXAMPLE 322

N-Ac-Sar-Gly-Val-D-Ile-Thr-Nva-Ile-Arg-ProNHethyl-1-(S)cyclohexyl

The procedure described in Example 8 is used but substituting (S)-1-cycloxylethylamine for (R)-1-cycloxylethylamine. After cleavage of the peptide from the resin and removal of the protecting groups the crude product was purified by C-18 column chromatography using solvent mixture varying in a gradient of 10% to 50% acetonitrile-water containing 0.01% TFA. The pure fractions were lyophilized to yield N-Ac-Sar-Gly-Val-D-Ile-Thr-Nva-Ile-Arg-ProNHethyl-1-(S)-cyclohexyl as the trifluoroacetate salt.

EXAMPLE 323

The procedures described in Example 98 is used but substituting the appropriate protected amino acids as describes in Examples 132, 43, 54, and 75. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-Ac-Sar-Gly-Val-D-Pen-Ser-Nva-Ile-Arg-ProNHCH$_2$CH$_3$,
N-Ac-Sar-Gly-Val-D-Pen-Gly-Nva-Ile-Arg-ProNHCH$_2$CH$_3$.
N-Ac-Sar-Gly-Val-D-Pen-Thr-Gln-Ile-Arg-ProNHCH$_2$CH$_3$,
N-Ac-Sar-Gly-Val-D-Pen-Ser-Nva-Ile-Arg-ProNHCH(CH$_3$)$_2$,
N-Succinyl-Sar-Gly-Val-D-Pen-Ser-Nva-Ile-Arg-ProNHCH$_2$CH$_3$,
N-Ac-Sar-Gly-Val-D-Pen-Ser-Nva-Ile-Arg-Pro-D-AlaNH$_2$,
N-Ac-Sar-Gly-Val-D-Pen-Ser-Gln-Ile-Arg-ProNHCH$_2$CH$_3$,
N-Ac-Sar-Gly-Val-D-Pen-Gly-Gln-Ile-Arg-ProNHCH$_2$CH$_3$,
N-Ac-Sar-Gly-Val-D-Pen-Ser-Ser-Ile-Arg-ProNHCH$_2$CH$_3$,
N-Ac-Sar-Gly-Val-D-Pen-Thr-Ser-Ile-Arg-ProNHCH$_2$CH$_3$,
N-Ac-Sar-Gly-Val-D-Pen-Thr-Leu-Ile-Arg-ProNHCH$_2$CH$_3$, N-Ac-Sar-Gly-Val-D-Pen-Ser-Leu-Ile-Arg-ProNHCH₂CH₃,
N-Succinyl-Sar-Gly-Val-D-Pen-Ser-Ser-Ile-Arg-ProNHCH₂CH₃,
N-Succinyl-Sat-Gly-Val-D-Pen-Ser-Leu-Ile-Arg-ProNHCH₂CH₃, and
N-Succinyl-Sar-Gly-Val-D-Pen-Thr-Gln-Ile-Arg-ProNHCH(CH₃)2.

EXAMPLE 324

N-Ac-Sar-Gly-Val-D-Cys-Thr-Nva-Ile-Arg-ProNHCH₂CH₃

The procedure described in Example 98 is used but substituting Fmoc-D-Cys(Trt) for Fmoc-D-Pen(Trt). After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield N-N-Ac-Sar-Gly-Val-D-Cys-Thr-Nva-Ile-Arg-ProNHCH₂CH₃ as the trifluoroacetate.

EXAMPLE 325

The procedures described in Example 324 is used but substituting the appropriate protected amino acids as describes in Examples 132, 43, 54, and 75. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-Ac-Sar-Gly-Val-D-Cys-Ser-Nva-Ile-Arg-ProNHCH₂CH₃,
N-Ac-Sar-Gly-Val-D-Cys-Gly-Nva-Ile-Arg-ProNHCH₂CH₃,
N-Ac-Sar-Gly-Val-D-Cys-Thr-Gln-Ile-Arg-ProNHCH₂CH₃,
N-Ac-Sar-Gly-Val-D-Cys-Ser-Nva-Ile-Arg-ProNHCH(CH₃)₂,
N-Succinyl-Sar-Gly-Val-Pen-Ser-Nva-Ile-Arg-ProNHCH₂CH₃,
N-Ac-Sar-Gly-Val-D-Cys-Ser-Nva-Ile-Arg-Pro-D-AlaNH₂,
N-Ac-Sar-Gly-Val-D-Cys-Ser-Gln-Ile-Arg-ProNHCH₂CH₃,
N-Ac-Sar-Gly-Val-D-Cys-Gly-Gln-Ile-Arg-ProNHCH₂CH₃,
N-Ac-Sar-Gly-Val-D-Cys-Ser-Ser-Ile-Arg-ProNHCH₂CH₃,
N-Ac-Sar-Gly-Val-D-Cys-Thr-Ser-Ile-Arg-ProNHCH₂CH₃,
N-Ac-Sar-Gly-Val-D-Cys-Thr-Leu-Ile-Arg-ProNHCH₂CH₃,
N-Ac-Sar-Gly-Val-D-Cys-Ser-Leu-Ile-Arg-ProNHCH₂CH₃,
N-Succinyl-Sar-Gly-Val-D-Cys-Ser-Ser-Ile-Arg-ProNHCH₂CH₃, and
N-Succinyl-Sar-Gly-Val-D-Cys-Ser-Leu-Ile-Arg-ProNHCH₂CH₃.

EXAMPLE 326

N-Ac-Sar-Gly-Pen-D-Ile-Thr-Nva-Ile-Arg-ProNHCH₂CH₃

The procedure described in Example 1 is used but substituting Fmoc-Pen(Trt) for Fmoc-Val. After cleavage of the peptide from the resin and removal of the protecting groups the crude product was purified by C-18 column chromatography using solvent mixture varying in a gradient of 10% to 50% acetonitrile-water containing 0.01% TFA. The pure fractions were lyophilized to yield N-Ac-Sar-Gly-Pen-D-Ile-Thr-Nva-Ile-Arg-ProNHCH₂CH₃ as the trifluoroacetate salt.

EXAMPLE 327

N-Ac-Sar-Gly-Cys-D-Ile-Thr-Nva-Ile-Arg-ProNHCH₂CH₃

The procedure described in Example 1 is used but substituting Fmoc-Cys(Trt) for Fmoc-Val. After cleavage of the peptide from the resin and removal of the protecting groups the crude product was purified by C-18 column chromatography using solvent mixture varying in a gradient of 10% to 50% acetonitrile-water containing 0.01% TFA. The pure fractions were lyophilized to yield N-Ac-Sar-Gly-Cys-D-Ile-Thr-Nva-Ile-Arg-ProNHCH₂CH₃ as the trifluoroacetate salt.

EXAMPLE 328

The procedures described in Example 326 is used but substituting the appropriate protected amino acids as describes in Examples 14, 15, 132, 43, 54, and 75. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-Ac-Sar-Gly-Pen-D-alloIle-Thr-Nva-Ile-Arg-ProNHCH₂CH₃,
N-Ac-Sar-Gly-Pen-D-Leu-Thr-Nva-Ile-Arg-ProNHCH₂CH₃,
N-Ac-Sar-Gly-Pen-D-Ile-Thr-Gln-Ile-Arg-ProNHCH₂CH₃,
N-Ac-Sar-Gly-Pen-D-Ile-Ser-Nva-Ile-Arg-ProNHCH₂CH₃,
N-Ac-Sar-Gly-Pen-D-Ile-Thr-Nva-Ile-Arg-ProNHCH(CH₃)₂,
N-Ac-Sar-Gly-Pen-D-Ile-Thr-Nva-Ile-Arg-Pro-D-AlaNH₂,
N-Succinyl-Gly-Pen-D-Ile-Thr-Nva-Ile-Arg-ProNHCH₂CH₃,
N-Succinyl-Sar-Gly-Pen-D-Ile-Thr-Gln-Ile-Arg-ProNHCH₂CH₃, and
N-Succinyl-Sar-Gly-Pen-D-Ile-Thr-Gln-Ile-Arg-ProNHCH(CH₃)₂.

EXAMPLE 329

N-Ac-Sar-Gly-Val-D-Leu-Pen-Nva-Ile-Arg-ProNHCH₂CH₃

The procedure described in Example 120 is used but substituting Fmoc-Pen(Trt) for Fmoc-Ala. After cleavage of the peptide from the resin and removal of the protecting groups the crude product was purified by C-18 column chromatography using solvent mixture varying in a gradient of 10% to 50% acetonitrile-water containing 0.01% TFA. The pure fractions were lyophilized to yield N-Ac-Sar-Gly-Val-D-Leu-Pen-Nva-Ile-Arg-ProNHCH₂CH₃ as the trifluoroacetate salt.

EXAMPLE 330

The procedures described in Example 329 is used but substituting the appropriate protected amino acids as describes in Examples 14, 15, 132, 43, 54, and 75. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-Ac-Sar-Gly-Val-D-Ile-Pen-Nva-Ile-Arg-ProNHCH$_2$CH$_3$,
N-Ac-Sar-Gly-Val-D-alloIle-Pen-Nva-Ile-Arg-ProNHCH$_2$CH$_3$,
N-Ac-Sar-Gly-Val-D-Ile-Pen-Gln-Ile-Arg-ProNHCH$_2$CH$_3$,
N-Ac-Sar-Gly-Val-D-Ile-Pen-Ser-Ile-Arg-ProNHCH$_2$CH$_3$,
N-Ac-Sar-Gly-Val-D-Ile-Pen-Leu-Ile-Arg-ProNHCH$_2$CH$_3$,
N-Ac-Sar-Gly-Val-D-Ile-Pen-Nva-Ile-Arg-ProNHCH(CH$_3$)$_2$,
N-Ac-Sar-Gly-Val-D-Ile-Pen-Nva-Ile-Arg-Pro-D-AlaNH$_2$,
N-Succinyl-Sar-Gly-Val-D-Ile-Pen-Nva-Ile-Arg-ProNHCH$_2$CH$_3$,
N-Succinyl-Sar-Gly-Val-D-Ile-Pen-Gln-Ile-Arg-ProNHCH$_2$CH$_3$, and
N-Succinyl-Sar-Gly-Val-D-Ile-Pen-Gln-Ile-Arg-ProNHCH(CH$_3$)2.

EXAMPLE 331

N-Ac-Sar-Gly-Val-D-Ile-Thr-Pen-Ile-Arg-ProNHCH$_2$CH$_2$OCH$_3$

The procedure described in Example 11 is used but substituting Fmoc-Pen(Trt) for Fmoc-Nva. After cleavage of the peptide from the resin and removal of the protecting groups the crude product was purified by C-18 column chromatography using solvent mixture varying in a gradient of 10% to 50% acetonitrile water containing 0.01% TFA. The pure fractions were lyophilized to yield N-Ac-Sar-Gly-Val-D-Ile-Thr-Pen-Ile-Arg-ProNHCH$_2$CH$_2$OCH$_3$ as the trifluoroacetate salt.

EXAMPLE 332

The procedures described in Example 331 is used but substituting the appropriate protected amino acids as describes in Examples 14, 15, 132, 43, 54, and 75. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-Ac-Sar-Gly-Val-D-alloIle-Thr-Pen-Ile-Arg-ProNHCH$_2$CH$_3$,
N-Ac-Sar-Gly-Val-D-Leu-Thr-Pen-Ile-Arg-ProNHCH$_2$CH$_3$,
N-Ac-Sar-Gly-Val-D-Ile-Thr-Pen-Ile-Arg-Pro-D-AlaNH$_2$,
N-Succinyl-Sar-Gly-Val-D-Ile-Thr-Pen-Ile-Arg-ProNHCH$_2$CH$_3$,
N-Ac-Sar-Gly-Val-D-Ile-Thr-Pen-Ile-Arg-ProNHCH(CH$_3$)$_2$,
N-Ac-Sar-Gly-Val-D-Leu-Ser-Pen-Ile-Arg-ProNHCH$_2$CH$_3$,
N-Ac-Sar-Gly-Val-D-Leu-Gly-Pen-Ile-Arg-ProNHCH$_2$CH$_3$, and
N-Succinyl-Sar-Gly-Val-D-Leu-Ser-Pen-Ile-Arg-ProNHCH$_2$CH$_3$.

EXAMPLE 333

N-Ac-Sar-Gly-Val-D-Phe(3,4,5-triF)-Thr-Gln-Ile-Arg-ProNHCH$_2$CH$_3$

The procedure described in Example 96 is used but substituting Fmoc-Gln(Trt) for Fmoc-Nva. After cleavage of the peptide from the resin and removal of the protecting groups the crude product was purified by C-18 column chromatography using solvent mixture varying in a gradient of 10% to 50% acetonitrile-water containing 0.01% TFA. The pure fractions were lyophilized to yield N-Ac-Sar-Gly-Val-D)-Phe(3,4,5-triF)-Thr-Gln-Ile-Arg-ProNHCH$_2$CH$_3$ as the trifluoroacetate salt.

EXAMPLE 334

The procedures described in Example 333 is used but substituting the appropriate protected amino acids as describes in Examples 132, 43, 54, and 75. After cleavage of the peptide from the resin and removal of the protecting groups using (9:1) TFA/anisole (3 mL) the crude product is purified by C-18 column chromatography using a solvent mixture varying in a gradient of 10% to 5% acetonitrile-water containing 0.01% TFA. The pure fractions are lyophilized to yield the following peptides as trifluoroacetate salt:

N-Ac-Sar-Gly-Val-D-Phe(3,4,5-triF)-Ser-Nva-Ile-Arg-ProNHCH$_2$CH$_3$,
N-Ac-Sar-Gly-Val-D-Phe(3,4,5-triF)-Gly-Nva-Ile-Arg-ProNHCH$_2$CH$_3$,
N-Ac-Sar-Gly-Val-D-Phe(3,4,5-triF)-Ser-Leu-Ile-Arg-ProNHCH$_2$CH$_3$,
N-Ac-Sar-Gly-Val-D-Phe(3,4,5-triF)-Ser-Nva-Ile-Arg-Pro-D-AlaNH$_2$,
N-Succinyl-Sar-Gly-Val-D-Phe(3,4,5-triF)-Thr-Gln-Ile-Arg-ProNHCH$_2$CH$_3$,
N-Succinyl-Sar-Gly-Val-D-Phe(3,4,5-triF)-Ser-Gln-Ile-Arg-ProNHCH$_2$CH$_3$,
N-Succinyl-Sar-Gly-Val-D-Phe(3,4,5-triF)-Thr-Gln-Ile-Arg-ProNHCH(CH$_3$)$_2$,
N-Ac-Sar-Gly-Val-D-Phe(3,4,5-triF)-Ser-Gln-Ile-Arg-ProNHCH$_2$CH$_3$, and
N-Ac-Sar-Gly-Val-D-Phe(3,4,5-triF)-Ser-Ser-Ile-Arg-ProNHCH$_2$CH$_3$.

EXAMPLE 335

N-Ac-Sar-Ala-Val-D-alloIle-Thr-Nva-Ile-Arg-ProNHCH$_2$CH$_3$

The procedure described in Example 153 is used but substituting Fmoc-D-alloIle for Fmoc-D-Ile. After cleavage of the peptide from the resin and removal of the protecting groups the crude product was purified by C-18 column chromatography using solvent mixture varying in a gradient of 10% to 50% acetonitrile-water containing 0.01% TFA. The pure fractions were lyophilized to yield N-Ac-Sar-Ala-Val-D-alloIle-Thr-Nva-Ile-Arg-ProNHCH$_2$CH$_3$ as the trifluoroacetate salt.

EXAMPLE 336

The procedures described in Example 335 is used but substituting the appropriate protected amino acids as described in Examples 132, 43, 54, and 75. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-Ac-Sar-Ala-Val-D-Leu-Thr-Nva-Ile-Arg-ProNHCH$_2$CH$_3$,

N-Ac-Sar-Ala-Val-D-Ile-Thr-Gln-Ile-Arg-ProNHCH$_2$CH$_3$,
N-Ac-Sar-Ala-Val-D-Leu-Ser-Nva-Ile-Arg-ProNHCH$_2$CH$_3$,
N-Ac-Sar-Ala-Val-D-Leu-Ser-Gln-Ile-Arg-ProNHCH$_2$CH$_3$,
N-Succinyl-Sar-Ala-Val-D-Ile-Thr-Nva-Ile-Arg-ProNHCH$_2$CH$_3$,
N-Succinyl-Sar-Ala-Val-D-Ile-Thr-Gln-Nva-Ile-Arg-ProNHCH$_2$CH$_3$,
N-Succinyl-Sar-Ala-Val-D-Ile-Thr-Gln-Nva-Ile-Arg-ProNHCH(CH$_3$)$_2$, and
N-Succinyl-Sar-Ala-Val-D-Ile-Thr-Gln-Nva-Ile-Arg-Pro-D-AlaNH$_2$.

EXAMPLE 337

The procedure described in Example 231 used but substituting N-acetyl-beta-alanine (3-Ac-Bala) for N-acetyl-4-aminobutyric acid. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-(3-Ac-Bala)-Sar-Gly-Val-D-alloIle-Thr-Nva-Ile-Arg-ProNHCH$_2$CH$_3$,
N-(3-Ac-Bala)-Sar-Gly-Val-D-Ile-Thr-Gln-Ile-Arg-ProNHCH$_2$CH$_3$,
N-(3-Ac-Bala)-Sar-Gly-Val-D-alloIle-Thr-Gln-Ile-Arg-ProNHCH$_2$CH$_3$,
N-(3-Ac-Bala)-Sar-Gly-Val-D-Ile-Thr-Gln-Ile-Arg-Pro-D-AlaNH$_2$,
N-(3-Ac-Bala)-Sar-Gly-Val-D-alloIle-Thr-Gln-Ile-Arg-Pro-D-AlaNH$_2$,
N-(3-Ac-Bala)-Sar-Gly-Val-D-alloIle-Thr-Gln-Ile-Arg-ProNHCH(CH$_3$)$_2$,
N-(3-Ac-Bala)-Sar-Gly-Val-D-Leu-Ser-Nva-Ile-Arg-ProNHCH$_2$CH$_3$,
N-(3-Ac-Bala)-Sar-Gly-Val-D-Leu-Thr-Nva-Ile-Arg-ProNHCH$_2$CH$_3$,
N-(3-Ac-Bala)-Sar-Gly-Val-D-Pen-Thr-Nva-Ile-Arg-ProNHCH$_2$CH$_3$,
N-(3-Ac-Bala)-Sar-Gly-Val-D-Ile-Ser-Nva-Ile-Arg-ProNHCH$_2$CH$_3$,
N-(3-Ac-Bala)-Sar-Ala-Val-D-alloIle-Ser-Nva-Ile-Arg-ProNHCH$_2$CH$_3$,
N-(3-Ac-Bala)-Sar-Ala-Val-D-Ile-Ser-Nva-Ile-Arg-ProNHCH$_2$CH$_3$,
N-(3-Ac-Bala)-Sar-Ala-Val-D-Leu-Ser-Nva-Ile-Arg-ProNHCH$_2$CH$_3$, and
N-(3-Ac-Bala)-Sar-Ala-Val-D-Leu-Ser-Gln-Ile-Arg-ProNHCH$_2$CH$_3$.

EXAMPLE 338

N-Ac-Sar-Gly-Val-D-Ile-Thr-Nva-Ile-Arg-Pro-OH

The procedure described in Example 1 is used but substituting omitting the coupling with ethylamine. After cleavage of the peptide from the resin and removal of the protecting groups the crude product was purified by C-18 column chromatography using solvent mixture varying in a gradient of 10% to $^{50}$% acetonitrile-water containing 0.01% TFA. The pure fractions were lyophilized to yield N-Ac-Sar-Gly-Val-D-Ile-Thr-Nva-Ile-Arg-Pro-OH as the trifluoroacetate salt.

EXAMPLE 339

The procedures described in Example 338 is used but substituting the appropriate protected amino acids as described in Examples 14, 15, 132, 43, 54, and 75. After cleavage of the peptide from the resin and removal of the protecting groups using (9:1) TFA/anisole (3 mL) the crude product is purified by C-18 column chromatography using a solvent mixture varying in a gradient of 10% to 50% acetonitrile-water containing 0.01% TFA. The pure fractions are lyophilized to yield the following peptides as trifluoroacetate salt:

N-Ac-Sar-Gly-Val-D-alloIle-Thr-Nva-Ile-Arg-Pro-OH,
N-Ac-Sar-Gly-Val-D-Leu-Thr-Nva-Ile-Arg-Pro-OH,
N-Ac-Sar-Gly-Val-D-Pen-Thr-Nva-Ile-Arg-Pro-OH,
N-Ac-Sar-Gly-Val-D-Phe(3,4,5-triF)-Thr-Nva-Ile-Arg-Pro-OH,
N-Ac-Sar-Gly-Val-D-Ile-Thr-Gln-Ile-Arg-Pro-OH,
N-Ac-Sar-Gly-Val-D-Leu-Ser-Nva-Ile-Arg-Pro-OH,
N-Ac-Sar-Ala-Val-D-Ile-Thr-Nva-Ile-Arg-Pro-OH,
N-Ac-Sar-Gly-Val-D-Ile-Ser-Gln-Ile-Arg-Pro-OH,
N-Succinyl-Sar-Gly-Val-D-Ile-Thr-Nva-Ile-Arg-Pro-OH, and
N-Succinyl-Sar-Gly-Val-D-Leu-Thr-Gln-Ile-Arg-Pro-OH.

EXAMPLE 340

N-Ac-Sar-Gly-Asp-D-Leu-Thr-Nva-Ile-Arg-ProNHCH$_2$CH$_3$

In an Applied Biosystems 433A peptide synthesizer, 0.1 mM of Fmoc-Pro-Sieber ethylamide resin was placed in the reaction vessel and cartridges of 1 mM amino acids were sequentially loaded. The Fastmoc 0.1 with previous peak monitoring protocol was used. The following is the synthetic cycle:

1. Solvating resin with N-methylpyrrolidone (NMP) for about 5 minutes;
2. Washing with NMP for about 5 minutes;
3. Removing the Fmoc group using 50% piperidine solution in NMP for 5 minutes, washing and repeating the process 3 to 4 times;
4. Activating the Fmoc-amino acid using 1 mM of 0.5 M solution of 2-(1H-benzotriazole-1-yl)-1,1,3,3-tetramethyluronium hexafluorophosphate (HBTU) in DMF;
5. Adding the activated Fmoc-amino acid to the reaction vessel followed by 1 mM of 2 M diisopropylamine in NMP solution;
6. Coupling of the Fmoc-amino acid for 20 minutes;
7. Washing and removal of Fmoc-group using 50% piperidine in NMP.

The following protected amino acids were sequentially coupled to the resin using above protocol in Table 2, below:

TABLE 2

| Amino acid | Coupling time |
| --- | --- |
| 1. Fmoc-Arg(Pmc) | 20 minutes |
| 2. Fmoc-Ile | 20 minutes |
| 3. Fmoc-Nva | 20 minutes |
| 4. Fmoc-Thr(t-Bu) | 20 minutes |
| 5. Fmoc-D-Leu | 20 minutes |
| 6. Fmoc-Asp(OtBu) | 20 minutes |
| 7. Fmoc-Gly | 20 minutes |
| 8. Fmoc-Sar | 20 minutes |
| 9. acetic acid | 20 minutes |

Upon completion of the synthesis the resin-bound peptide was washed with methanol three times and dried in vacuo, then treated with a (95:5) TFA/water solution (3mL) at room temperature overnight. The resin was filtered and washed 3 times with methanol. The filtrates and the washes were combined and concentrated in vacuo. The residue was treated with ether and the precipitate was filtered to give the crude peptide as amorphous powder. This was purified by preparative HPLC using C-18 column with a mixture of solvents varying in a gradient from 5% to 100% acetonitrile/water containing 0.1% TFA over a period of 50 min. The pure fractions were lyophilized to yield N-Ac-Sar-Gly-As-D-Leu-Thr-Nva-Ile-Arg-ProNHCH$_2$CH$_3$ as trifluoroacetate salt; R$_t$=2.23 min (using C-18 column and solvents mixture varying in a gradient from 20% to 95% acetonitrile/water containing 10 mM ammonium acetate over a period of 10 min); MS (ESI) m/e 1010 (M$^+$).

EXAMPLE 341

N-Ac-Sar-Gly-Ala-D-Leu-Thr-Nva-Ile-Arg-ProNHCH$_2$CH$_3$

The procedure described in example 340 was used but substituting Fmoc-Ala for Fmoc-Asp(OtBu). After cleavage of the peptide from the resin and removal of the protecting groups the product was precipitated with ether. The crude compound was purified by preparative HPLC to give N-Ac-Sar-Gly-Ala-D-Leu-Thr-Nva-Ile-Arg-ProNHCH$_2$CH$_3$ as trifluoroacetate salt; R$_t$=2.828 min (using C-18 column and solvents mixture varying in a gradient from 20% to 95% acetonitrile/water containing 10 mM ammonium acetate over a period of 10 min); MS (ESI) m/e 966 (M$^+$).

EXAMPLE 342

N-Ac-Sar-Gly-Cha-D-Leu-Thr-Nva-Ile-Arg-ProNHCH$_2$CH$_3$

The procedure described in example 340 was used but substituting Fmoc-Cha for Fmoc-Asp(OtBu). After cleavage of the peptide from the resin and removal of the protecting groups the product was precipitated with ether. The crude compound was purified by preparative HPLC to give N-Ac-Sar-Gly-Cha-D-Leu-Thr-Nva-Ile-Arg-ProNHCH$_2$CH$_3$ as trifluoroacetate salt; R$_t$=4.48 min (using C-18 column and solvents mixture varying in a gradient from 20% to 95% acetonitrile/water containing 10 mM ammonium acetate over a period of 10 min); MS (ESI) m/e 1048 (M$^+$).

EXAMPLE 343

N-Ac-Sar-Gly-Met-D-Ile-Thr-Nva-Ile-Arg-ProNHCH$_2$CH$_3$

The procedure described in example 340 was used but substituting Fmoc-Met for Fmoc-Asp(OtBu) and Fmoc-D-Ile for Fmoc-D-Leu. After cleavage of the peptide from the resin and removal of the protecting groups the product was precipitated with ether. The crude compound was purified by preparative HPLC to give N-Ac-Sar-Gly-Met-D-Ile-Thr-Nva-Ile-Arg-ProNHCH$_2$CH$_3$ as trifluoroacetate salt; R$_t$=3.25 min (using C-18 column and solvents mixture varying in a gradient from 20% to 95% acetonitrile/water containing 10 mM ammonium acetate over a period of 10 min); MS (ESI) m/e 1026 (M+H); Amino Acid Anal.: 1.09 Sar; 0.97 Gly; 0.94 Met; 2.08 Ile; 0.47 Thr; 1.00 Nva; 1.34 Arg; 1.01 Pro.

EXAMPLE 344

N-Ac-Cit-Gly-Val-D-Ile-Thr-Nva-Ile-Arg-ProNHCH$_2$CH$_3$

The procedure described in example 340 was used but substituting Fmoc-Cit for Fmoc-Sar, Fmoc-Val for Fmoc-Asp(OtBu) and Fmoc-D-Ile for Fmoc-D-Leu. After cleavage of the peptide from the resin and removal of the protecting groups the product was precipitated with ether. The crude compound was purified by preparative HPLC to N-Ac-Cit-Gly-Val-D-Ile-Thr-Nva-Ile-Arg-ProNHCH$_2$CH$_3$ as trifluoroacetate salt; R$_t$=2.97 min (using C-18 column and solvents mixture varying in a gradient from 20% to 95% acetonitrile/water containing 10 mM ammonium acetate over a period of 10 min); MS (ESI) m/e 1080 (M+H); Amino Acid Anal.: 0.98 Cit; 0.93 Gly; 0.98 Val; 2.05 Ile; 0.51 Thr; 0.99 Nva; 1.37 Arg; 1.01 Pro.

EXAMPLE 345

N-Ac-Sar-Gly-Val-D-Ile-Thr-Hser-Ile-Arg-ProNHCH$_2$CH$_3$

The procedure described in example 340 was used but substituting Fmoc-Hser(t-Bu) for Fmoc-Nva, Fmoc-Val for Fmoc-Asp(OtBu), and Fmoc-D-Ile for Fmoc-D-Leu. After cleavage of the peptide from the resin and removal of the protecting groups the product was precipitated with ether. The crude compound was purified by preparative HPLC to give N-Ac-Sar-Gly-Val-D-Ile-Thr-Hser-Ile-Arg-ProNHCH$_2$CH$_3$ as trifluoroacetate salt; R$_t$=2.782 min (using C-18 column and solvents mixture varying in a gradient from 10% to 40% acetonitrile/water containing 0.1% TFA over a period of 33 min); MS (ESI) m/e 996 (M+H); Amino Acid Anal.: 1.00 Sar; 0.95 Gly; 1.01 Val; 1.99 Ile; 0.60 Thr; 1.07 Arg; 1.04 Pro.

EXAMPLE 346

N-Ac-Sar-Gly-Val-D-alloIle-His-Nva-Ile-Arg-ProNHCH$_2$CH$_3$

The procedure described in example 340 was used but substituting Fmoc-Val for Fmoc-Asp(OtBu), Fmoc-D-alloIle for Fmoc-D-Leu, and Fmoc-His(Boc) for Fmoc-Thr(t-Bu). After cleavage of the peptide from the resin and removal of the protecting groups the product was precipitated with ether. The crude compound was purified by preparative HPLC to give N-Ac-Sar-Gly-Val-D-alloIle-His-Nva-Ile-Arg-ProNHCH$_2$CH$_3$ as a trifluoroacetate salt; R$_t$=3.12 min (using C-18 column and solvents mixture varying in a gradient from 10% to 40% acetonitrile/water containing 0.1% TFA over a period of 33 min); MS (ESI) m/e 1030 (M$^+$).

EXAMPLE 347

N-Ac-Sar-Gly-Val-D-Ile-Thr-Nva-Ile-Arg-ProNH-n-Butyl

Resin Preparation 4-(4-Formyl-3-methoxyphenoxy)butyryl AM resin (0.5 g, 0.54 mmol/g substitution) was placed in a solid phase synthesis reaction vessel containing (9:1) DMA/acetic acid (4 mL). The mixture was shaken for 5 min. The resin was drained and this process was repeated three times. To the swollen resin were added 10–15 grains of activated 4A molecular sieves and (9:1) DMA/acetic acid (4mL) and 10 molar equivalents of n-butylamine. The slurry was shaken for 1 h at rt and to it was added 10 molar equivalents of sodium triacetoxyborohydride. The slurry was shaken for 2 h at rt. The resin was drained and washed three times with DMA, three times with methanol, three times with dichloromethane, three times with diethyl ether and dried in vacuo at rt overnight. The dry resin was swollen in DMA (4 mL) and shaken for 5 min. This process was repeated twice.

Coupling of Fmoc-Pro

To the swollen resin in the reaction vessel were added sequentially the following chemicals: DMA (4 mL), one equivalent of DIEA, a DMA solution containing 3.0 equivalents of Fmoc-Pro, 3.0 equivalents of HATU, and 3.0 equivalents of DIEA. The slurry was shaken overnight. The resin was drained and washed three times with DMA, three times with methanol, three times with dichloromethane, three times with diethyl ether and dried in vacuo at rt overnight. A small portion of the resin was used to determine the Fmoc-Pro loading. The rest of the resin was shaken with DMA (4 mL) three times for 5 min and then for 1 h at rt with a solution of (8:1:1) DMA/pyridine/acetic anhydride (5 mL). The resin was drained and washed three times with DMA, three times with methanol, three times with dichloromethane, and three times with diethyl ether. The resin was dried in vacuo at rt overnight and then used in the subsequent solid phase peptide synthesis.

Synthesis of Peptide

In the synthesis of the above peptide, the amino acids, the coupling conditions and the synthetic protocol used were identical to those described in Example 340. Upon completion of the synthesis the peptide and the protecting groups were cleaved at rt using (95:5) TFA/water (3 mL) for 3h. The resin was filtered and washed three times with methanol. The combined filtrates were concentrated in vacuo and to the residue was added diethylether. The solid precipitate was filtered. The crude product was purified by C-18 column chromatography using a solvent mixture varying in a gradient of 10% to 50% acetonitrile-water containing 0.1% TFA. The pure fractions were lyophilized to yield NAcSar-Gly-Val-D-Ile-Thr-Nva-Ile-Arg-ProNH-n-Butyl as the trifluoroacetate salt: $R_t$=3.792 min (gradient of 20% to 95% acetonitrile in water containing 0.01 M $NH_4Ac$ over 10 min period); MS (ESI) m/e 1022 (M$^+$).

EXAMPLE 348

N-Ac-Sar-Gly-Val-D-Ile-Thr-Nva-Ile-Arg-ProNH-iso-Butyl

The procedure described in example 347 was used but substituting isobutylamine for n-butylamine. After cleavage of the peptide from the resin and precipitation with ether the crude product was obtained. This was purified by C-18 column chromatography using a solvent mixture varying in a gradient of 10% to 50% acetonitrile-water containing 0.1% TFA. The pure fractions were lyophilized to NAcSar-Gly-Val-D-Ile-Thr-Nva-Ile-Arg-ProNH-iso-Butyl as the trifluoroacetate salt: $R_t$=3.731 min (gradient of 20% to 95% acetonitrile in water containing 0.01 M $NH_4Ac$ over 10 min period); MS (ESI) m/e 1022 (M$^+$).

EXAMPLE 349

N-Ac-Sar-Gly-Val-D-Ile-Thr-Nva-Ile-Arg-ProNH-iso-Amyl

The procedure described in example 347 was used but substituting isoamylamine for n-butylamine. After cleavage of the peptide from the resin and precipitation with ether the crude product was obtained. This was purified by C-18 column chromatography using a solvent mixture varying in a gradient of 10% to 50% acetonitrile-water containing 0.1% TFA. The pure fractions were lyophilized to NAcSar-Gly-Val-D-Ile-Thr-Nva-Ile-Arg-ProNH-iso-Amyl as the trifluoroacetate salt: $R_t$=4.086 min (gradient of 20% to 95% acetonitrile in water containing 0.01 M $NH_4Ac$ over 10 min period); MS (ESI) m/e 1036 (M$^+$).

EXAMPLE 350

N-Ac-Sar-Gly-Val-D-Ile-Thr-Nva-Ile-Arg-ProNH-n-hexyl

The procedure described in example 347 was used but substituting in n-hexylamine for n-butylamine. After cleavage of the peptide from the resin and precipitation with ether the crude product was obtained. This was purified by C-18 column chromatography using a solvent mixture varying in a gradient of 10% to 50% acetonitrile-water containing 0.1% TFA. The pure fractions were lyophilized to NAcSar-Gly-Val-Ile-Thr-Nva-Ile-Arg-ProNH-n-Hexyl as the trifluoroacetate salt: $R_t$=4.527 min (gradient of 20% to 95% acetonitrile in water containing 0.01 M $NH_4Ac$ over 10 min period); MS (ESI) m/e 1050 (M$^{30}$).

EXAMPLE 351

N-Ac-Sar-Gly-Val-D-Ile-Thr-Nva-Ile-Arg-ProNH(3,3-dimethyl)butyl

The procedure described in example 347 was used but substituting (3,3-dimethyl)butylamine for n-butylamine. After cleavage of the peptide from the resin and precipitation with ether the crude product was obtained. This was purified by C-18 column chromatography using a solvent mixture varying in a gradient of 10% to 50% acetonitrile-water containing 0.1% TFA. The pure fractions were lyophilized to NAcSar-Gly-Val-D-Ile-Thr-Nva-Ile-Arg-ProNH-(3,3-dimethyl)butyl as the trifluoroacetate salt: $R_t$=4.366 min (gradient of 20% to 95% acetonitrile in water containing 0.01 M $NH_4Ac$ over 10 min period); MS (ESI) m/e 1050 (M$^+$).

EXAMPLE 352

N-Ac-Sar-Gly-Val-D-Ile-Thr-Nva-Ile-Arg-ProNH-(2-ethoxy)ethyl

The procedure described in example 347 was used but substituting (2-ethoxy)ethylamine for n-butylamine. After cleavage of the peptide from the resin and precipitation with ether the crude product was obtained. This was purified by C-18 column chromatography using a solvent mixture varying in a gradient of 10% to 50% acetonitrile-water containing 0.1% TFA. The pure fractions were lyophilized to NAcSar-Gly-Val-D-Ile-Thr-Nva-Ile-Arg-ProNH-(2-ethoxy)ethyl as the trifluoroacetate salt: $R_t$=3.356 min (gradient of 20% to 95% acetonitrile in water containing 0.01 M $NH_4Ac$ over 10 min period); MS (ESI) m/e 1038 (M$^+$).

EXAMPLE 353

N-Ac-Sar-Gly-Val-D-Ile-T-Nva-Ile-Arg-ProNH-(2-isopropoxy)ethyl

The procedure described in example 347 was used but substituting (2-isopropoxy)ethylamine for n-butylamine. After cleavage of the peptide from the resin and precipitation with ether the crude product was obtained. This was purified by C-18 column chromatography using a solvent mixture varying in a gradient of 10% to 50% acetonitrile-water containing 0.1% TFA. The pure fractions were lyophilized to NAcSar-Gly-Val-D-Ile-Thr-Nva-Ile-Arg-ProNH-(2-isopropoxy)ethyl as the trifluoroacetate salt: $R_t$=3.57 min (gradient of 20% to 95% acetonitrile in water containing 0.01 M NH$_4$Ac over 10 min period); MS (ESI) m/e 1052 (M$^+$).

EXAMPLE 354

N-Ac-Sar-Gly-Val-D-Ile-Thr-Nva-Ile-Arg-ProNH-(3-methoxy)propyl

The procedure described in example 347 was used but substituting (3-methoxy)propylamine for n-butylamine. After cleavage of the peptide from the resin and precipitation with ether the crude product was obtained. This was purified by C-18 column chromatography using a solvent mixture varying in a gradient of 10% to 50% acetonitrile-water containing 0.1% TFA. The pure fractions were lyophilized to NAcSar-Gly-Val-D-Ile-Thr-Nva-Ile-Arg-ProNH-(3-methoxy)propyl as the trifluoroacetate salt: $R_t$=3.26 min (gradient of 20% to 95% acetonitrile in water containing 0.01 M NH$_4$Ac over 10 min period); MS (ESI) m/e 1038 (M$^+$).

EXAMPLE 355

N-Ac-Sar-Gly-Val-D-Ile-Thr-Nva-Ile-Arg-ProNH-(cyclopentyl)methyl

The procedure described in example 347 was used but substituting (cyclopentyl)methylamine for n-butylamine. After cleavage of the peptide from the resin and precipitation with ether the crude product was obtained. This was purified by C-18 column chromatography using a solvent mixture varying in a gradient of 10% to 50% acetonitrile-water containing 0.1% TFA. The pure fractions were lyophilized to NAc-Sar-Gly-Val-D-Ile-Thr-Nva-Ile-Arg-ProNH-(cyclopentyl)methyl as the trifluoroacetate salt-$R_t$=4.148 min (gradient of 20% to 95% acetonitrile in water containing 0.01 M NH$_4$Ac over 10 min period); MS (ESI) m/e 1048 (M$^+$).

EXAMPLE 356

N-Ac-Sar-Gly-Val-D-Ile-Thr-Nva-Ile-Arg-ProNH-cyclohexyl

The procedure described in example 347 was used but substituting cyclohexylamine for n-butylamine. After cleavage of the peptide from the resin and precipitation with ether the crude product was obtained. This was purified by C-18 column chromatography using a solvent mixture varying in a gradient of 10% to 50% acetonitrile-water containing 0.1% TFA. The pure fractions were lyophilized to NAcSar-Gly-Val-D-Ile-Thr-Nva-Ile-Arg- ProNH-cyclohexyl as the trifluoroacetate salt: $R_t$=4.070 min (gradient of 20% to 95% acetonitrile in water containing 0.01 M NH$_4$Ac over 10 min period); MS (ESI) m/e 1048 (M$^+$).

In Vitro Assay for Angiogenic Activity

The human microvascular endothelial (HMVEC) migration assay was run according to the procedure of S. S. Tolsma, O. V. Volpert, D. J. Good, W. F. Frazier, P. J. Polverini and N. Bouck, J. Cell Biol. 122, 497–511 (1993).

The HMVEC migration assay was carried out using Human Microvascular Endothelial Cells-Dermal (single donor) and Human Microvascular Endothelial Cells, (neonatal). The BCE or HMVEC cells were starved overnight in DME containing 0.1% bovine serum albumin (BSA). Cells were then harvested with trypsin and resuspended in DME with 0.1% BSA at a concentration of 1.5×10$^6$ cells per ml. Cells were added to the bottom of a 48 well modified Boyden chamber (Nucleopore Corporation, Cabin John, MD). The chamber was assembled and inverted, and cells were allowed to attach for 2 hours at 37° C. to polycarbonate chemotaxis membranes (5 μm pore size) that had been soaked in 0.1% gelatin overnight and dried. The chamber was then reinverted, and test substances (total volume of 50 μl), including activators, 15 ng/ml bFGF/VEGF, were added to the wells of the upper chamber. The apparatus was incubated for 4 hours at 37° C. Membranes were recovered, fixed and stained (Diff Quick, Fisher Scientific) and the number of cells that had migrated to the upper chamber per 3 high power fields counted. Background migration to DME +0.1 BSA was subtracted and the data reported as the number of cells migrated per 10 high power fields (400X) or, when results from multiple experiments were combined, as the percent inhibition of migration compared to a positive control.

The compounds described in Examples 1 to 339 inhibited human endothelial cell migration in the above assay from about 30% to about 95% inhibition when tested at concentrations of 10 nM or 20 nM, as reported below in Table 3.

TABLE 3

| | In Vitro Angiogenic Activity | |
|---|---|---|
| Ex. # | % Inhib. @ 20 nM | % Inhib. @ 10 nM |
| 1 | 87.3 | 76.9 |
| 3 | 56.0 | — |
| 4 | 71.3 | — |
| 5 | — | 87.2 |
| 8 | — | 88.2 |
| 11 | 70.4 | — |
| 12 | 55.8 | — |
| 18 | — | 51.4 |
| 28 | — | 47.0 |
| 42 | 60.2 | — |
| 43 | — | 94.1 |
| 46 | 77.5 | — |
| 47 | 69.7 | — |
| 49 | 83.4 | — |
| 50 | 71.6 | — |
| 51 | 67.0 | — |
| 52 | 46.5 | — |
| 53 | 76.7 | — |
| 54 | 81.3 | — |
| 55 | 59.2 | — |
| 56 | 49.9 | — |
| 57 | 56.6 | — |
| 58 | 68.8 | — |
| 59 | 82.3 | — |
| 60 | 75.3 | — |
| 61 | — | 83.7 |
| 63 | — | 82.4 |
| 66 | 76.1 | — |

What is claimed is:

1. A compound of the formula:

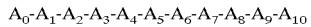

or a pharmaceutically acceptable salt, ester, solvate or prodrug thereof, wherein:

$A_0$ is an acyl group selected from:
(1) R—(CH$_2$)$_n$—C(O)—; wherein n is an integer from 0 to 8 and R is selected from hydroxyl; methyl; N-acetylamino; methoxyl; carboxyl; cyclohexyl optionally containing one or two double bonds and optionally substituted with one to three hydroxyl groups; and a 5- or 6-membered aromatic or non-aromatic ring optionally containing one or two heteroatoms selected from nitrogen, oxygen, and sulfur, wherein the ring is optionally substituted with a moiety selected from alkyl, alkoxy, and halogen; and
(2) R$^1$—CH$_2$CH$_2$—(OCH$_2$CH$_2$O)$_p$—CH$_2$—C(O)—; wherein R$^1$ is selected from hydrogen, alkyl, and N-acetylamino, and p is an integer from 1 to 8;

$A_1$ is an amino acyl residue selected from:
(1) alanyl,
(2) asparaginyl,
(3) citrullyl,
(4) glutaminyl,
(5) glutamyl,
(6) N-ethylglycyl,
(7) methionyl,
(8) N-methylalanyl,
(9) prolyl,
(10) pyro-glutamyl,
(11) sarcosyl,
(12) seryl,
(13) threonyl,
(14) —HN—(CH$_2$)$_q$—C(O)—, wherein q is 1 to 8, and
(15) —HN—CH$_2$CH$_2$—(OCH$_2$CH$_2$O)$_r$—CH$_2$—C(O)—, wherein r is 1 to 8;

$A_2$ is an amino acyl residue selected from:
(1) alanyl,
(2) asparaginyl,
(3) aspartyl, (4) glutaminyl,
(5) glutamyl,
(6) leucyl,
(7) methionyl,
(8) phenylalanyl,
(9) prolyl,
(10) seryl,
(11) —HN—(CH$_2$)$_q$—C(O)—, wherein q is 1 to 8,
(12) —HN—CH$_2$CH$_2$—(OCH$_2$CH$_2$O)$_r$—CH$_2$—C(O)—, wherein r is 1 to 8 and
(13) glycyl;

A$_3$ is an amino acyl residue selected from:
(1) alanyl,
(2) asparaginyl,
(3) citrullyl,
(4) cyclohexylalanyl,
(5) cyclohexylglycyl,
(6) glutaminyl,
(7) glutamyl,
(8) glycyl,
(9) isoleucyl,
(10) leucyl,
(11) methionyl,
(12) norvalyl,
(13) phenylalanyl,
(14) seryl,
(15) t-butylglycyl,
(16) threonyl,
(17) valyl,
(18) penicillaminyl, and
(19) cystyl;

A$_4$ is an amino acyl residue selected from:
(1) L- or D-allo-isoleucyl,
(2) glycyl,
(3) L- or D-isoleucyl,
(4) L- or D-prolyl,
(5) L- or D-dehydroleucyl,
(6) D-alanyl,
(7) D-3-(naphth-1-yl)alanyl,
(8) D-3-(naphth-2-yl)alanyl,
(9) D-(3-pyridyl)-alanyl,
(10) D-2-aminobutyryl,
(11) D-allo-threonyl,
(12) D-allylglycyl,
(13) D-asparaginyl,
(14) D-aspartyl,
(15) D-3-(3-benzothienyl)alanyl
(16) D-3-(4,4'-biphenyl)alanyl,
(17) D-3-(3-chlorophenyl)alanyl,
(18) D-3-(4-chlorophenyl)alanyl,
(19) D-3-(3-trifluoromethylphenyl)alanyl,
(20) D-3-(3-cyanophenyl)alanyl,
(21) D-3-(3,4-difluorophenyl)alanyl,
(22) D-citrullyl,
(23) D-cyclohexylalanyl,
(24) D-cyclohexylglycyl,
(25) D-cystyl,
(26) D-cystyl(S-t-butyl),
(27) D-glutaminyl,
(28) D-glutamyl,
(29) D-histidyl,
(30) D-homoisoleucyl,
(31) D-homophenylalanyl,
(32) D-homoseryl,
(33) D-leucyl,
(34) D-lysyl(N-epsilon-nicotinyl),
(35) D-lysyl,
(36) D-methionyl,
(37) D-neopentylglycyl,
(38) D-norleucyl,
(39) D-norvalyl,
(40) D-ornithyl,
(41) D-penicillaminyl,
(42) D-penicillaminyl(acetamidomethyl),
(43) D-penicillaminyl(S-benzyl),
(44) D-phenylalanyl,
(45) D-3-(4-aminophenyl)alanyl,
(46) D-3-(4-methylphenyl)alanyl,
(47) D-3-(4-nitrophenyl)alanyl,
(48) D-3-(3,4dimethoxyphenyl)alanyl,
(49) D-3-(3,4,5-trifluorophenyl)alanyl,
(50) D-seryl,
(51) D-seryl(O-benzyl),
(52) D-t-butylglycyl,
(53) D-thienylalanyl,
(54) D-threonyl,
(55) D-threonyl(O-benzyl),
(56) D-tryptyl,
(57) D-tyrosyl(O-benzyl),
(58) D-tyrosyl(O-ethyl),
(59) D-tyrosyl, and
(60) D-valyl;

A$_5$ is a glycyl residue or an amino acyl residue of L or D configuration selected from:
(1) alanyl,
(2) (3-pyridyl)alanyl,
(3) 3-(naphth-1-yl)alanyl,
(4) 3-(naphth-2-yl)alanyl,
(5) allo-threonyl,
(6) allylglycyl,
(7) glutaminyl,
(8) histidyl,
(9) homoseryl,
(10) isoleucyl,
(11) lysyl(N-epsilon-acetyl),
(12) methionyl,
(13) norvalyl,
(14) octylglycyl,
(15) ornmithyl,
(16) 3-(4-hydroxymethylphenyl)alanyl,
(17) prolyl,
(18) seryl,
(19) threonyl
(20) tryptyl,
(21) tyrosyl,
(22) D-allo-threonyl,
(23) D-homoseryl,
(24) D-seryl,
(25) D-threonyl
(26) penicillaminyl, and
(27) cystyl;

A$_6$ is a glycyl residue or an amino acyl residue of L or D configuration selected from:
(1) alanyl,
(2) 3-(naphth-1-yl)alanyl,
(3) 3-(naphth-2-yl)alanyl,
(4) 3-pyridyl)alanyl,
(5) 2-aminobutyryl,
(6) allylglycyl,
(7) arginyl,
(8) asparaginyl,
(9) aspartyl,
(10) citrullyl,
(11) 3-(cyclohexyl)alanyl,

(12) glutaminyl
(13) glutamyl,
(14) histidyl,
(15) homoalanyl,
(16) homoleucyl,
(17) homoseryl,
(18) isoleucyl,
(19) leucyl,
(20) lysyl(N-epsilon-acetyl),
(21) lysyl(N-epsilon-isopropyl),
(22) methionyl(sulfone),
(23) methionyl(sulfoxide),
(24) methionyl,
(25) norleucyl,
(26) norvalyl,
(27) octylglycyl,
(28) phenylalanyl,
(29) 3-(4-carboxyamidephenyl)alanyl,
(30) propargylglycyl,
(31) seryl,
(32) threonyl,
(33) tryptyl,
(34) tyrosyl,
(35) valyl,
(36) D-3-(naphth-1-yl)alanyl,
(37) D-3-(naphth-2-yl)alanyl,
(38) D-glutaminyl,
(39) D-homoseryl,
(40) D-leucyl,
(41) D-norvalyl,
(42) D-seryl),
(43) penicillaminyl, and
(44) cystyl;

$A_7$ is a glycyl residue or an amino acyl residue of L or D configuration selected from:
(1) alanyl,
(2) allylglycyl,
(3) aspartyl,
(4) citrullyl,
(5) cyclohexylglycyl,
(6) glutamyl,
(9) homoseryl,
(10) isoleucyl,
(11) allo-isoleucyl,
(12) leucyl,
(13) lysyl(N-epsilon-acetyl),
(14) methionyl,
(15) 3-(naphth-1-yl)alanyl,
(16) 3-(naphth-2-yl)alanyl,
(17) norvalyl,
(18) phenylalanyl,
(19) prolyl,
(20) seryl
(21) t-butylglycyl,
(22) tryptyl,
(23) tyrosyl,
(24) valyl,
(25) D-allo-isoleucyl,
(26) D-isoleucyl,
(27) penicillaminyl, and
(28) cystyl;

$A_8$ is an amino acyl residue selected from:
(1) 2-amino-4-[(2-amino)pyrimidinyl]butanoyl,
(2) alanyl(3-guanidino),
(3) alanyl(3-pyrrolidinylamidino),
(4) alanyl[4-piperidinyl(N-amidino)],
(5) arginyl,
(6) arginyl($N^G N^{G'}$diethyl),
(7) citrully,
(8) 3-(cyclohexyl)alanyl(4-N'-isopropyl),
(8) glycyl[4-piperidinyl(N-amidino)],
(10) histidyl,
(11) homoarginyl,
(12) lysyl,
(13) lysyl(N-epsilon-isopropyl),
(14) lysyl(N-epsilon-nicotinyl),
(15) norarginyl,
(16) ornithyl(N-delta-isopropyl),
(17) ornithyl(N-delta-nicotinyl),
(18) ornithyl[N-delta-(2-imidazolinyl)],
(19) [(4-amino(N-isopropyl)methyl)phenyl]alanyl,
(20) 3-(4-guanidinophenyl)alanyl, and
(21) 3-(4-amino-N-isopropylphenyl)alanyl;

$A_9$ is an amino acyl residue of L or D configuration selected from:
(1) 2-amino-butyryl,
(2) 2-amino-isobutyryl,
(3) homoprolyl,
(4) 4-hydroxyprolyl,
(5) isoleucyl,
(6) leucyl,
(7) phenylalanyl,
(8) prolyl,
(9) seryl,
(10) t-butylglycyl,
(11) 1,2,3,4-tetrahydroisoquinoline-3-carbonyl,
(12) threonyl,
(13) valyl,
(14) D-alanyl, and
(15) D-prolyl; and $A_{10}$ is selected from:
(1) hydroxyl,
(2) azaglycylamide,
(3) D-alanylamide,
(4) D-alanylethylamide,
(5) glycylamide,
(6) glycylethylamide,
(7) sarcosylamide,
(8) serylamide,
(9) D-serylamide,
(10) a group represented by the formula

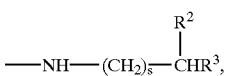

and
(11) a group represented by the formula —NH—$R^4$;
wherein:
s is an integer selected from 0 to 8,
$R^2$ is selected from hydrogen, alkyl, and a 5- to 6-membered cycloalkyl ring;
$R^3$ is selected from hydrogen, hydroxy, alkyl, phenyl, alkoxy, and a 5- to 6-membered ring optionally containing from one to two heteroatoms selected from oxygen, nitrogen, and sulfur, provided that s is not zero when $R^3$ is hydroxy or alkoxy; and
$R^4$ is selected from hydrogen, hydroxy, and a 5- to 6-membered cycloalkyl ring.

2. A compound according to claim 1, wherein $A_1$ is sarcosyl, $A_2$ is glycyl, $A_3$ is valyl, $A_7$ is isoleucyl, $A_8$ is arginyl, $A_9$ is prolyl, and $A_0$, $A_4$, $A_5$, $A_6$, and $A_{10}$ are as defined in claim 1.

3. A compound according to claim 2, wherein $A_4$ is an amino acyl residue having a D configuration selected from:
(1) D-alanyl,
(2) D-3-(naphth-1-yl)alanyl,
(3) D-3-(naphth-2-yl)alanyl,
(4) D-(3-pyridyl)-alanyl,
(5) D-2-aminobutyryl,
(6) D-allo-isoleucyl,
(7) D-allo-threonyl,
(8) D-allylglycyl,
(9) D-asparaginyl,
(10) D-aspartyl,
(11) D-chlorophenylalanyl,
(12) D-3-(3-trifluoromethylphenyl)alanyl,
(13) D-3-(3-cyanophenyl)alanyl,
(14) D-3-(3,4-difluorophenyl)alanyl,
(15) D-cyclohexylalanyl,
(16) D-cyclohexylglycyl,
(17) D-cystyl,
(18) D-glutaminyl,
(19) D-glutamyl,
(20) D-histidyl,
(21) D-homoisoleucyl,
(22) D-homophenylalanyl,
(23) D-homoseryl,
(24) D-isoleucyl,
(25) D-leucyl,
(26) D-lysyl(N-epsilon-nicotinyl),
(27) D-methionyl,
(28) D-neopentylglycyl,
(29) D-norleucyl,
(30) D-norvalyl,
(31) D-penicillaminyl,
(32) D-penicillaminyl(acetamidomethyl),
(33) D-penicillaminyl(S-benzyl),
(34) D-phenylalanyl,
(35) D-3-(4-aminophenyl)alanyl,
(36) D-3-(4-methylphenyl)alanyl,
(37) D-3-(4-nitrophenyl)alanyl,
(38) D-3-(3,4-dimethoxyphenyl)alanyl,
(39) D-3-(3,4,5-trifluorophenyl)alanyl,
(40) D-prolyl,
(41) D-seryl,
(42) D-seryl(O-benzyl),
(43) D-t-butylglycyl,
(44) D-thienylalanyl,
(45) D-threonyl,
(46) D-threonyl(O-benzyl),
(47) D-tyrosyl(O-ethyl),
(48) D-tyrosyl, and
(49) D-valyl.
4. A compound according to claim 3, wherein $A_4$ is an amino acyl residue having a D configuration selected from:
(1) D-allo-isoleucyl,
(2) D-allylglycyl,
(3) D-3-(3-cyanophenyl)alanyl,
(4) D-cystyl,
(5) D-isoleucyl,
(6) D-leucyl,
(7) D-penicillaminyl,
(8) D-phenylalanyl,
(9) D-3-(3,4,5-trifluorophenyl)alanyl, and
(10) D-3-(4-aminophenyl)alanyl.
5. A compound according to claim 2, wherein $A_5$ is selected from:
(1) glycyl,
(2) octylglycyl,
(3) penicillaminyl,
(4) seryl,
(5) threonyl, and
(6) tyrosyl.
6. A compound according to claim 2, wherein $A_6$ is selected from:
(1) glutaminyl,
(2) leucyl,
(3) norvalyl, and
(4) seryl.
7. A compound according to claim 3 wherein $A_0$ is selected from:
(1) acetyl,
(2) butyryl,
(3) caproyl,
(4) (4-N-acetylamino)butyryl,
(5) N-acetyl-beta-alanyl,
(6) (6-N-acetylamino)caproyl,
(7) chloronicotinyl,
(8) cyclohexylacetyl,
(9) furoyl,
(10) 2-methoxyacetyl,
(11) methylnicotinyl,
(12) nicotinyl,
(13) (8-N-acetylamino)-3,6-dioxo-octanoyl,
(14) phenylacetyl,
(15) propionyl,
(16) shikimyl,
(17) succinyl, and
(18) tetrahydrofuroyl.
8. A compound according to claim 3, wherein $A_{10}$ is selected from:
(1) D-alanylamide,
(2) azaglycylamide,
(3) serylamide,
(4) ethylamide,
(5) hydroxylamide,
(6) isopropylamide,
(7) propylamide,
(8) 2-(cyclohexyl)ethylamide,
(9) 2-(1-pyrrolidine)ethylamide,
(10) 1-(cyclohexyl)ethylamide,
(11) 2-(methoxy)ethylamide,
(12) 2-(hydroxy)ethylamide,
(13) 2-(2-pyridine)ethylamide,
(14) (2-pyridine)methylamide,
(15) 2-(3-pyridine)ethylamide,
(16) 2-(2-(1-methyl)pyrrolidine)ethylamide,

(17) 2-(N-morpholine)ethylamide, and
(18) cyclopropylmethylamide.

9. A compound according to claim 1, wherein
$A_4$ is an amino acyl residue having a D configuration selected from:
(1) D-allo-isoleucyl,
(2) D-allylglycyl,
(3) D-3-(3-cyanophenyl)alanyl,
(4) D-cystyl,
(5) D-isoleucyl,
(6) D-leucyl,
(7) D-penicillaminyl,
(8) D-phenylalanyl,
(9) D-3-(3,4,5-trifluorophenyl)alanyl, and
(10) D-3-(4-aminophenyl)alanyl;

$A_5$ is an amino acyl residue selected from:
(1) octylglycyl,
(2) glycyl,
(3) penicillaminyl,
(4) seryl,
(5) threonyl, and
(6) tyrosyl; and $A_6$ is an amino acyl residue selected from:
(1) glutaminyl,
(2) leucyl,
(3) norvalyl, and
(4) seryl.

10. A compound according to claim 9 wherein $A_0$ is selected from:
(1) acetyl,
(2) butyryl,
(3) caproyl,
(4) (4-N-acetylamino)butyryl,
(5) N-acetyl-beta-alanyl,
(6) (6-N-acetylamino)caproyl,
(7) chloronicotinyl,
(8) cyclohexylacetyl,
(9) furoyl,
(10) 2-methoxyacetyl,
(11) methylnicotinyl,
(12) nicotinyl,
(13) (8-N-acetylamino)-3,6-dioxo-octanoyl,
(14) phenylacetyl,
(15) propionyl,
(16) shikimyl,
(17) succinyl, and
(18) tetrahydrofuroyl.

11. A compound according to claim 9, wherein $A_{10}$ is selected from:
(1) D-alanylamide,
(2) azaglycylamide,
(3) serylamide,
(4) ethylamide,
(5) hydroxylamide,
(6) isopropylamide,
(7) propylamide,
(8) 2-(cyclohexyl)ethylamide,
(9) 2-(1-pyrrolidine)ethylamide,
(10) 1-(cyclohexyl)ethylamide,
(11) 2-(methoxy)ethylamide,
(12) 2-(hydroxy)ethylamide,
(13) 2-(2-pyridine)ethylamide,
(14) (2-pyridine)methylamide,
(15) 2-(3-pyridine)ethylamide,
(16) 2-(2-(1-methyl)pyrrolidine)ethylamide,
(17) 2-(N-morpholine)ethylamide, and
(18) cyclopropylmethylamide.

12. A compound, or a pharmaceutically acceptable salt, ester, solvate or prodrug thereof, selected from
(1) N-Ac-Sar-Gly-Val-D-Ile-Thr-Nva-Ile-Arg-ProNHCH$_2$CH$_3$,
(2)
(3) N-Ac-Sar-Gly-Val-D-Ile-Thr-Nva-Ile-Arg-ProNHCH$_3$,
(4) N-Ac-Sar-Gly-Val-D-Ile-Thr-Nva-Ile-Arg-ProNHCH(CH$_3$)$_2$,
(5) N-Ac-Sar-Gly-Val-D-Ile-Thr-Nva-Ile-Arg-ProNHCH$_2$CH$_2$-(1-pyrrolidine),
(6) N-Ac-Sar-Gly-Val-D-Ile-Thr-Nva-Ile-Arg-ProNHethyl(1-piperidine),
(7) N-Ac-Sar-Gly-Val-D-Ile-Thr-Nva-Ile-Arg-ProNHmethylcyclopropyl,
(8) N-Ac-Sar-Gly-Val-D-Ile-Thr-Nva-Ile-Arg-ProNH(ethyl-1-(R)-cyclohexyl),
(9) N-Ac-Sar-Gly-Val-D-Ile-Thr-Nva-Ile-Arg-ProNH$_2$,
(10) N-Ac-Sar-Gly-Val-D-Ile-Thr-Nva-Ile-Arg-ProNHCH$_2$CH$_2$OCH$_3$,
(11) N-Ac-Sar-Gly-Val-D-Ile-Thr-Nva-Ile-Arg-ProNHCH$_2$CH$_2$cyclohexyl,
(12) N-Ac-Sar-Gly-Val-D-Ile-Thr-Nva-Ile-Arg-ProNHCH$_2$CH$_3$,
(13) N-Ac-Sar-Gly-Val-D-alloIle-Thr-Nva-Ile-Arg-ProNHCH$_2$CH$_3$,
(14) N-Ac-Sar-Gly-Val-D-Leu-Thr-Nva-Ile-Arg-ProNHCH$_2$CH$_3$,
(15) N-Ac-Sar-Gly-Val-Ile-Thr-Nva-Ile-Arg-ProNHCH$_2$CH$_3$,
(16) N-Ac-Sar-Gly-Val-Gly-Thr-Nva-Ile-Arg-ProNHCH$_2$CH$_3$,
(17) N-Ac-Sar-Gly-Val-D-Val-Thr-Nva-Ile-Arg-ProNHCH$_2$CH$_3$,
(18) N-Ac-Sar-Gly-Val-D-Ala-Thr-Nva-Ile-Arg-ProNHCH$_2$CH$_3$,
(19) N-Ac-Sar-Gly-Val-D-Met-Thr-Nva-Ile-Arg-ProNHCH$_2$CH$_3$,
(20) N-Ac-Sar-Gly-Val-D-Nle-Thr-Nva-Ile-Arg-ProNHCH$_2$CH$_3$,
(21) N-Ac-Sar-Gly-Val-D-Phe-Thr-Nva-Ile-Arg-ProNHCH$_2$CH$_3$,
(22) N-Ac-Sar-Gly-Val-D-Tyr-Thr-Nva-Ile-Arg-ProNHCH$_2$CH$_3$,
(23) N-Ac-Sar-Gly-Val-D-4,4'-Biphenylala-Thr-Nva-Ile-Arg-ProNHCH$_2$CH$_3$,
(24) N-Ac-Sar-Gly-Val-D-Cha-Thr-Nva-Ile-Arg-ProNHCH$_2$CH$_3$,
(25) N-Ac-Sar-Gly-Val-D-Chg-Thr-Nva-Ile-Arg-ProNHCH$_2$CH$_3$,
(26) N-Ac-Sar-Gly-Val-D-4-ClPhe-Thr-Nva-Ile-Arg-ProNHCH$_2$CH$_3$,
(27) N-Ac-Sar-Gly-Val-D-Hphe-Thr-Nva-Ile-Arg-ProNHCH$_2$CH$_3$,
(28) N-Ac-Sar-Gly-Val-Dehydroleu-Thr-Nva-Ile-Arg-ProNHCH$_2$CH$_3$,

(29) N-Ac-Sar-Gly-Val-D-3-CF₃Phe-Thr-Nva-Ile-Arg-ProNHCH₂CH₃,
(30) N-Ac-Sar-Gly-Val-D-pentaFPhe-Thr-Nva-Ile-Arg-ProNHCH₂CH₃,
(31) N-Ac-Sar-Gly-Val-D-3,4-diClPhe-Thr-Nva-Ile-Arg-ProNHCH₂CH₃,
(32) N-Ac-Sar-Gly-Val-D-3-ClPhe-Thr-Nva-Ile-Arg-ProNHCH₂CH₃,
(33) N-Ac-Sar-Gly-Val-D-2-Thienylala-Thr-Nva-Ile-Arg-ProNHCH₂CH₃,
(34) N-Ac-Sar-Gly-Val-D-3-CNPhe-Thr-Nva-Ile-Arg-ProNHCH₂CH₃,
(35) N-Ac-Sar-Gly-Val-D-Ile-Thr-DNva-Ile-Arg-ProNHCH₂CH₃,
(36) N-Ac-Sar-Gly-Val-D-Ile-Thr-Gln-Ile-Arg-ProNHCH₂CH₃,
(37) N-Ac-Sar-Gly-Val-D-Ile-Thr-Cha-Ile-Arg-ProNHCH₂CH₃,
(38) N-Ac-Sar-Gly-Val-D-Ile-Thr-Gly-Ile-Arg-ProNHCH₂CH₃,
(39) N-Ac-Sar-Gly-Val-D-Ile-Thr-Ala-Ile-Arg-ProNHCH₂CH₃,
(40) N-Ac-Sar-Gly-Val-D-Ile-Thr-Val-Ile-Arg-ProNHCH₂CH₃,
(41) N-Ac-Sar-Gly-Val-D-Ile-Thr-Abu-Ile-Arg-ProNHCH₂CH₃,
(42) N-Ac-Sar-Gly-Val-D-Ile-Thr-Allylgly-Ile-Arg-ProNHCH₂CH₃,
(43) N-Ac-Sar-Gly-Val-D-Ile-Thr-Octylgly-Ile-Arg-ProNHCH₂CH₃,
(44) N-Ac-Sar-Gly-Val-D-Ile-Thr-Met-Ile-Arg-ProNHCH₂CH₃,
(45) N-Cyclohexylacetyl-Sar-Gly-Val-D-Ile-Thr-Nva-Ile-Arg-ProNHCH₂CH₃,
(46) N-(2-Me-Nicotinyl)-Sar-Gly-Val-D-Ile-Thr-Nva-Ile-Arg-ProNHCH₂CH₃,
(47) N-Succinyl-Sar-Gly-Val-D-Ile-Thr-Nva-Ile-Arg-ProNHCH₂CH₃,
(48) N-Nicotinyl-Sar-Gly-Val-D-Ile-Thr-Nva-Ile-Arg-ProNHCH₂CH₃,
(49) N-Propionyl-Sar-Gly-Val-D-Ile-Thr-Nva-Ile-Arg-ProNHCH₂CH₃,
(50) N-(MeO)acetyl-Sar-Gly-Val-D-Ile-Thr-Nva-Ile-Arg-ProNHCH₂CH₃,
(51) N-(Shikimyl)-Sar-Gly-Val-D-Ile-Thr-Nva-Ile-Arg-ProNHCH₂CH₃,
(52) N-(2-Furoyl)-Sar-Gly-Val-D-Ile-Thr-Nva-Ile-Arg-ProNHCH₂CH₃,
(53) N-Butyryl-Sar-Gly-Val-D-Ile-Thr-Nva-Ile-Arg-ProNHCH₂CH₃,
(54) N-[2-THFcarbonyl]-Sar-Gly-Val-D-Ile-Thr-Nva-Ile-Arg-ProNHCH₂CH₃,
(55) N-[CH₃C(O)NH—(CH₂)₂—O—(CH₂)₂—O—CH₂—C(O)]-Sar-Gly-Val-D-Ile-Thr-Nva-Ile-Arg-ProNHCH₂CH₃,
(56) N-[6-N-acetyl-(CH₂)₅C(O)]-Sar-Gly-Val-D-Ile-Thr-Nva-Ile-Arg-ProNHCH₂CH₃,
(57) N-Hexanoyl-Sar-Gly-Val-D-Ile-Thr-Nva-Ile-Arg-ProNHCH₂CH₃,
(58) N-[4-N-Acetylaminobutyryl]-Sar-Gly-Val-D-Ile-Thr-Nva-Ile-Arg-ProNHCH₂CH₃,
(59)
(60) N-Ac-Sar-Gly-Asn-D-Ile-Thr-Nva-Ile-Arg-ProNHCH₂CH₃,
(61) N—[CH₃C(O)NH—(CH₂)₂—O—(CH₂)₂—O—CH₂—C(O)]-Gly-Val-D-Ile-Thr-Nva-Ile-Arg-ProNHCH₂CH₃,
(62) N-Ac-Pro-Gly-Val-D-Ile-Thr-Nva-Ile-Arg-ProNHCH₂CH₃,
(63) N-Ac-Gly-Gly-Val-D-Ile-Thr-Nva-Ile-Arg-ProNHCH₂CH₃,
(64) N-Ac-Ala-Gly-Val-D-Ile-Thr-Nva-Ile-Arg-ProNHCH₂CH₃,
(65) N-Ac-NEtGly-Gly-Val-D-Ile-Thr-Nva-Ile-Arg-ProNHCH₂CH₃,
(66) N-Ac-Sar-Gly-Val-D-Ile-Thr-Leu-Ile-Arg-ProNHCH₂CH₃,
(67) N-Ac-Sar-Gly-Val-D-Ile-Thr-Ser-Ile-Arg-ProNHCH₂CH₃,
(68) N-Ac-Sar-Gly-Val-D-Ile-Thr-Nva-Ile-Arg-Pro-D-AlaNH₂,
(69) N-Ac-Sar-Gly-Val-D-Ile-Thr-Nva-Ile-Arg-D-ProNHCH₂CH₃,
(70) N-Ac-Sar-Gly-Val-D-Ile-Thr-Nva-Ile-Arg-AbuNHCH₂CH₃,
(71) N-Ac-Sar-Gly-Val-D-Ile-Thr-Nva-Ile-Arg-Phe-NHCH₂CH₃,
(72) N-Ac-Sar-Gly-Val-D-Ile-Thr-Nva-Ile-Arg-Tic-NHCH₂CH₃,
(73) N-Ac-Sar-Gly-Val-D-Ile-Thr-Nva-Ile-Arg-Hyp-NHCH₂CH₃,
(74) N-Ac-Sar-Gly-Val-D-Ile-Thr-Nva-Ile-Arg-Aib-NHCH₂CH₃,
(75) N-Ac-Sar-Gly-Val-D-Ile-Thr-Nva-Ile-Arg-D-Ala-NHCH₂CH₃,
(76) N-Ac-Sar-Gly-Val-D-Ile-Thr-Nva-Ile-Arg-Pip-NHCH₂CH₃,
(77) N-Ac-Sar-Gly-Val-D-Tyr(Et)-Thr-Nva-Ile-Arg-ProNHCH₂CH₃,
(78) N-Ac-Sar-Gly-Val-D-Cys(tBu)-Thr-Nva-Ile-Arg-ProNHCH₂CH₃,
(79) N-Ac-Sar-Gly-Val-D-Cys(Acm)-Thr-Nva-Ile-Arg-ProNHCH₂CH₃,
(80) N-Ac-Sar-Gly-Val-D-Tyr(Bzl)-Thr-Nva-Ile-Arg-ProNHCH₂CH₃,
(81) N-Ac-Sar-Gly-Val-D-Ser(Bzl)-Thr-Nva-Ile-Arg-ProNHCH₂CH₃,
(82) N-Ac-Sar-Gly-Val-D-1Nal-Thr-Nva-Ile-Arg-ProNHCH₂CH₃,
(83) N-Ac-Sar-Gly-Val-D-tButylgly-Thr-Nva-Ile-Arg-ProNHCH₂CH₃,
(84) N-Ac-Sar-Gly-Val-D-Orn-Thr-Nva-Ile-Arg-ProNHCH₂CH₃,
(85) N-Ac-Sar-Gly-Val-D-Thr(Bzl)-Thr-Nva-Ile-Arg-ProNHCH₂CH₃,
(86) N-Ac-Sar-Gly-Val-D-2Nal-Thr-Nva-Ile-Arg-ProNHCH₂CH₃,
(87) N-Ac-Sar-Gly-Val-D-Phe(4-Me)-Thr-Nva-Ile-Arg-ProNHCH₂CH₃,
(88) N-Ac-Sar-Gly-Val-D-Phe(3,4diMeO)-Thr-Nva-Ile-Arg-ProNHCH₂CH₃,
(89) N-Ac-Sar-Gly-Val-D-Phe(3,4,5-triF)-Thr-Nva-Ile-Arg-ProNHCH₂CH₃,
(90) N-Ac-Sar-Gly-Val-D-Phe(4-NO₂)-Thr-Nva-Ile-Arg-ProNHCH₂CH₃,

(91) N-Ac-Sar-Gly-Val-D-Pen-Thr-Nva-Ile-Arg-ProNHCH$_2$CH$_3$,
(92) N-Ac-Sar-Gly-Val-D-Pen(Acm)-Thr-Nva-Ile-Arg-ProNHCH$_2$CH$_3$,
(93) N-Ac-Sar-Gly-Val-D-Abu-Thr-Nva-Ile-Arg-ProNHCH$_2$CH$_3$,
(94) N-Ac-Sar-Gly-Val-D-Phe(4-NH$_2$)-Thr-Nva-Ile-Arg-ProNHCH$_2$CH$_3$,
(95) N-Ac-Sar-Gly-Val-D-Leu-Thr-Nva-Ala-Arg-ProNHCH$_2$CH$_3$,
(96) N-Ac-Sar-Gly-Val-D-Leu-Thr-Nva-Met-Arg-ProNHCH$_2$CH$_3$,
(97) N-Ac-Sar-Gly-Val-D-Leu-Thr-Nva-Phe-Arg-ProNHCH$_2$CH$_3$,
(98) N-Ac-Sar-Gly-Val-D-Leu-Thr-Nva-Tyr-Arg-ProNHCH$_2$CH$_3$,
(99) N-Ac-Sar-Gly-Val-D-Leu-Thr-Nva-Nva-Arg-ProNHCH$_2$CH$_3$,
(100) N-Ac-Sar-Gly-Val-D-Leu-Thr-Nva-Asp-Arg-ProNHCH$_2$CH$_3$,
(101) N-Ac-Sar-Gly-Val-D-Leu-Thr-Nva-Gly-Arg-ProNHCH$_2$CH$_3$,
(102) N-Ac-Sar-Gly-Val-D-Leu-Thr-Nva-Lys(Ac)-Arg-ProNHCH$_2$CH$_3$,
(103) N-Ac-Sar-Gly-Val-D-Leu-Thr-Nva-Leu-Arg-ProNHCH$_2$CH$_3$,
(104) N-Ac-Sar-Gly-Val-D-Leu-Thr-Nva-2Nal-Arg-ProNHCH$_2$CH$_3$,
(105) N-Ac-Sar-Gly-Val-D-Leu-Thr-Nva-1Nal-Arg-ProNHCH$_2$CH$_3$,
(106) N-Ac-Sar-Gly-Val-D-Leu-Thr-Nva-Allylgly-Arg-ProNHCH$_2$CH$_3$,
(107) N-Ac-Sar-Gly-Val-D-Leu-Thr-Nva-Cit-Arg-ProNHCH$_2$CH$_3$,
(108) N-Ac-Sar-Gly-Val-D-Leu-Ala-Nva-Ile-Arg-ProNHCH$_2$CH$_3$,
(109) N-Ac-Sar-Gly-Val-D-Leu-Pro-Nva-Ile-Arg-ProNHCH$_2$CH$_3$,
(110) N-Ac-Sar-Gly-Val-D-Leu-Trp-Nva-Ile-Arg-ProNHCH$_2$CH$_3$,
(111) N-Ac-Sar-Gly-Val-D-Leu-Tyr-Nva-Ile-Arg-ProNHCH$_2$CH$_3$,
(112) N-Ac-Sar-Gly-Val-D-Leu-Nva-Nva-Ile-Arg-ProNHCH$_2$CH$_3$,
(113) N-Ac-Sar-Gly-Val-D-Leu-Gly-Nva-Ile-Arg-ProNHCH$_2$CH$_3$,
(114) N-Ac-Sar-Gly-Val-D-Leu-Lys(Ac)-Nva-Ile-Arg-ProNHCH$_2$CH$_3$,
(115) N-Ac-Sar-Gly-Val-D-Leu-2Nal-Nva-Ile-Arg-ProNHCH$_2$CH$_3$,
(116) N-Ac-Sar-Gly-Val-D-Leu-1Nal-Nva-Ile-Arg-ProNHCH$_2$CH$_3$,
(117) N-Ac-Sar-Gly-Val-D-Leu-Octylgly-Nva-Ile-Arg-ProNHCH$_2$CH$_3$,
(118) N-Ac-Sar-Gly-Val-D-Leu-Gln-Nva-Ile-Arg-ProNHCH$_2$CH$_3$,
(119) N-Ac-Sar-Gly-Val-D-Leu-Met-Nva-Ile-Arg-ProNHCH$_2$CH$_3$,
(120) N-Ac-Sar-Gly-Val-D-Leu-Ser-Nva-Ile-Arg-ProNHCH$_2$CH$_3$,
(121) N-Ac-Sar-Gly-Val-D-Leu-Allylgly-Nva-Ile-Arg-ProNHCH$_2$CH$_3$,
(122) N-Ac-Sar-Gly-Val-D-Leu-Ile-Nva-Ile-Arg-ProNHCH$_2$CH$_3$,
(123) N-Ac-Sar-Gly-Val-D-Leu-D-Thr-Nva-Ile-Arg-ProNHCH$_2$CH$_3$,
(124) N-Ac-Sar-Gly-Val-D-Ile-Thr-Ile-Ile-Arg-ProNHCH$_2$CH$_3$,
(125) N-Ac-Sar-Gly-Val-D-Ile-Thr-Nle-Ile-Arg-ProNHCH$_2$CH$_3$,
(126) N-Ac-Sar-Gly-Val-D-Ile-Thr-Cit-Ile-Arg-ProNHCH$_2$CH$_3$,
(127) N-Ac-Sar-Gly-Val-D-Ile-Thr-Met(O$_2$)-Ile-Arg-ProNHCH$_2$CH$_3$,
(128) N-Ac-Sar-Gly-Val-D-Ile-Thr-Arg-Ile-Arg-ProNHCH$_2$CH$_3$,
(129) N-Ac-Sar-Gly-Val-D-Ile-Thr-Tyr-Ile-Arg-ProNHCH$_2$CH$_3$,
(130) N-Ac-Sar-Gly-Val-D-Ile-Thr-Glu-Ile-Arg-ProNHCH$_2$CH$_3$,
(131) N-Ac-Sar-Gly-Val-D-Ile-Thr-Lys(Ac)-Ile-Arg-ProNHCH$_2$CH$_3$,
(132) N-Ac-Sar-Gly-Val-D-Ile-Thr-Propargylgly-Ile-Arg-ProNHCH$_2$CH$_3$,
(133) N-Ac-Sar-Gly-Val-D-alloIle-Thr-Gln-Ile-Arg-ProNHCH$_2$CH$_3$,
(134) N-Ac-Sar-Gly-Val-D-Leu-Thr-Gln-Ile-Arg-ProNHCH$_2$CH$_3$,
(135) N-Ac-Bala-Sar-Gly-Val-D-Ile-Thr-Nva-Ile-Arg-ProNHCH$_2$CH$_3$,
(136) N-Phenylacetyl-Sar-Gly-Val-D-Ile-Thr-Nva-Ile-Arg-ProNHCH$_2$CH$_3$,
(137) N-Ac-Sar-Gly-Val-D-Ile-Thr-Nva-Ile-Arg-Pro-AzaglyNH$_2$,
(138) N-Ac-Sar-Gly-Val-D-Ile-Thr-Nva-Ile-Arg-Sar-NHCH$_2$CH$_3$,
(139) N-Ac-Sar-Gly-Val-D-Ile-Thr-Nva-Ile-Arg-Pro-SerNH$_2$,
(140) N-Succinyl-Sar-Gly-Val-D-Leu-Thr-Nva-Ile-Arg-ProNHCH$_2$CH$_3$,
(141) N-Ac-Sar-Ala-Val-D-Ile-Thr-Nva-Ile-Arg-ProNHCH$_2$CH$_3$,
(142) N-Ac-Sar-Leu-Val-D-Ile-Thr-Nva-Ile-Arg-ProNHCH$_2$CH$_3$,
(143) N-Ac-Sar-Phe-Val-D-Ile-Thr-Nva-Ile-Arg-ProNHCH$_2$CH$_3$,
(144) N-Ac-Sar-Glu-Val-D-Ile-Thr-Nva-Ile-Arg-ProNHCH$_2$CH$_3$,
(145) N-Ac-Sar-Pro-Val-D-Leu-Thr-Nva-Ile-Arg-ProNHCH$_2$CH$_3$,
(146) N-Ac-Sar-Asn-Val-D-Leu-Thr-Nva-Ile-Arg-ProNHCH$_2$CH$_3$,
(147) N-Ac-Sar-Asp-Val-D-Leu-Thr-Nva-Ile-Arg-ProNHCH$_2$CH$_3$,
(148) N-Ac-Asn-Gly-Val-D-Leu-Thr-Nva-Ile-Arg-ProNHCH$_2$CH$_3$,
(149) N-Ac-Gln-Gly-Val-D-Leu-Thr-Nva-Ile-Arg-ProNHCH$_2$CH$_3$,
(150) N-Ac-Ser-Gly-Val-D-Leu-Thr-Nva-Ile-Arg-ProNHCH$_2$CH$_3$,
(151) N-Ac-Cit-Gly-Val-D-Ile-Thr-Nva-Ile-Arg-ProNHCH$_2$CH$_3$,
(152) N-Ac-Glu-Gly-Val-D-Ile-Thr-Nva-Ile-Arg-ProNHCH$_2$CH$_3$, (153) N-Ac-Gaba-Gly-Val-D-Ile-Thr-Nva-Ile-Arg-ProNHCH$_2$CH$_3$,
(154) N-Ac-Bala-Gly-Val-D-Ile-Thr-Nva-Ile-Arg-ProNHCH$_2$CH$_3$,
(155) N-Ac-Gln-Gly-Val-D-Ile-Thr-Nva-Ile-Arg-ProNHCH$_2$CH$_3$,
(156) N-Ac-Sar-Gly-Gly-D-Ile-Thr-Nva-Ile-Arg-ProNHCH$_2$CH$_3$,
(157) N-Ac-Sar-Gly-Glu-D-Ile-Thr-Nva-Ile-Arg-ProNHCH$_2$CH$_3$,
(158) N-Ac-Sar-Gly-Val-D-Ile-Thr-Gln-Ile-Arg-ProNHCH(CH$_3$)$_2$,
(159) N-Succinyl-Sar-Gly-Val-D-Ile-Thr-Gln-Ile-Arg-ProNHCH$_2$CH$_3$,
(160) N-Succinyl-Sar-Gly-Val-D-Leu-Thr-Gln-Ile-Arg-ProNHCH$_2$CH$_3$,
(161) N-Succinyl-Sar-Gly-Val-D-Leu-Thr-Gln-Ile-Arg-ProNHCH(CH$_3$)$_2$,
(162) N-Ac-Sar-Gly-Val-D-Leu-Thr-Asp-Ile-Arg-ProNHCH$_2$CH$_3$,
(163) N-Ac-Sar-Gly-Val-D-Ile-Thr-Asp-Ile-Arg-ProNHCH$_2$CH$_3$,
(164) N-Ac-Sar-Gly-Val-D-Ile-Thr-Asn-Ile-Arg-ProNHCH$_2$CH$_3$,
(165) N-Ac-Sar-Gly-Val-D-Ile-Thr-Met(O)-Ile-Arg-ProNHCH$_2$CH$_3$,
(166) N-Ac-Sar-Gly-Val-D-Leu-Thr-Asn-Ile-Arg-ProNHCH$_2$CH$_3$,
(167) N-Ac-Sar-Gly-Val-D-Thr-Thr-Nva-Ile-Arg-ProNHCH$_2$CH$_3$,
(168) N-Ac-Sar-Gly-Val-D-Ser-Thr-Nva-Ile-Arg-ProNHCH$_2$CH$_3$,
(169) N-Ac-Sar-Gly-Val-D-Hser-Thr-Nva-Ile-Arg-ProNHCH$_2$CH$_3$,
(170) N-Ac-Sar-Gly-Val-D-Gln-Thr-Nva-Ile-Arg-ProNHCH$_2$CH$_3$,
(171) N-Ac-Sar-Gly-Val-D-Asn-Thr-Nva-Ile-Arg-ProNHCH$_2$CH$_3$,
(172) N-Ac-Sar-Gly-Val-D-Cit-Thr-Nva-Ile-Arg-ProNHCH$_2$CH$_3$,
(173) N-Ac-Sar-Gly-Val-D-Hcit-Thr-Nva-Ile-Arg-ProNHCH$_2$CH$_3$,
(174) N-Ac-Sar-Gly-Val-D-Hle-Thr-Nva-Ile-Arg-ProNHCH$_2$CH$_3$,
(175) N-Ac-Sar-Gly-Val-D-Neopentylgly-Thr-Nva-Ile-Arg-ProNHCH$_2$CH$_3$,
(176) N-Ac-Sar-Gly-Val-D-Ile-Thr-Phe(4-CONH$_2$)-Ile-Arg-ProNHCH$_2$CH$_3$,
(177) N-Ac-Sar-Gly-Val-D-Ile-Thr-Nva-Ile-His-ProNHCH$_2$CH$_3$,
(178) N-Ac-Sar-Gly-Val-D-Ile-Thr-Nva-Ile-Lys(Isp)-ProNHCH$_2$CH$_3$,
(179) N-Ac-Sar-Gly-Val-D-Ile-Thr-Nva-Ile-Lys(Nic)-ProNHCH$_2$CH$_3$,
(180) N-Ac-Sar-Gly-Val-D-Ile-Thr-Nva-Ile-Orn(Nic)-ProNHCH$_2$CH$_3$,
(181) N-Ac-Sar-Gly-Val-D-Ile-Thr-Nva-Ile-Orn(Isp)-ProNHCH$_2$CH$_3$,
(182) N-Ac-Sar-Gly-Val-D-Ile-Thr-Nva-Ile-Phe(4-NIsp)-ProNHCH$_2$CH$_3$,
(183) N-Ac-Sar-Gly-Val-D-Ile-Thr-Nva-Ile-Cha(4-NIsp)-ProNHCH$_2$CH$_3$,
(184) N-Ac-Sar-Gly-Val-D-Ile-Thr-Nva-Ile-Harg-ProNHCH$_2$CH$_3$,
(185) N-Ac-Sar-Gly-Val-D-Ile-Thr-Nva-Ile-Norarg-ProNHCH$_2$CH$_3$,
(186) N-Ac-Sar-Gly-Val-D-Ile-Thr-Nva-Ile-Cit-ProNHCH$_2$CH$_3$,
(187) N-Ac-Sar-Gly-Val-D-Ile-Thr-Nva-Ile-Lys-ProNHCH$_2$CH$_3$,
(188) N-Ac-Sar-Gly-Val-D-Ile-Phe(4-CH$_2$OH)-Nva-Ile-Arg-ProNHCH$_2$CH$_3$,
(189) N-Ac-Sar-Gly-Val-D-Ile-Thr-Nva-Ile-Phe(4guanidino)-ProNHCH$_2$CH$_3$,
(190) N-Ac-Sar-Gly-Val-D-Ile-Thr-Nva-Ile-Aminopyrimidinylbutanoyl-Pro-NHCH$_2$CH$_3$,
(191) N-Ac-Sar-Gly-Val-D-Ile-Thr-Nva-Ile-Phe(4-CH$_2$NHIsp)-ProNHCH$_2$CH$_3$,
(192) N-Ac-Sar-Gly-Val-D-Ile-Thr-Nva-Ile-Gly[4-Pip(N-amidino)]-Pro-NHCH$_2$CH$_3$,
(193) N-Ac-Sar-Gly-Val-D-Ile-Thr-Nva-Ile-Ala[4-Pip(N-amidino)]-Pro-NHCH$_2$CH$_3$,
(194) N-Ac-Sar-Gly-Val-D-Ile-Thr-Nva-Ile-Ala(3-guanidino)-ProNHCH$_2$CH$_3$,
(195) N-Ac-Sar-Gly-Val-D-Ile-Thr-Nva-Ile-Ala(3-pyrrolidinylamidino)-Pro-NHCH$_2$CH$_3$,
(196) N-Ac-Sar-Gly-Val-D-Ile-Thr-Nva-Ile-Orn(2-imidazo)-ProNHCH$_2$CH$_3$,
(197) N-Succinyl-Sar-Gly-Val-D-alloIle-Thr-Nva-Ile-Arg-ProNHCH$_2$CH$_3$,
(198) N-Succinyl-Sar-Gly-Val-D-Ile-Thr-Gln-Ile-Arg-ProNHCH$_2$CH$_3$,
(199) N-Succinyl-Sar-Gly-Val-D-Ile-Thr-Gln-Ile-Arg-Pro-D-AlaNH$_2$,
(200) N-Succinyl-Sar-Gly-Val-D-alloIle-Thr-Gln-Ile-Arg-ProNHCH$_2$CH$_3$,
(201) N-Succinyl-Sar-Gly-Val-D-alloIle-Thr-Gln-Ile-Arg-Pro-D-AlaNH$_2$,
(202) N-Succinyl-Sar-Gly-Val-D-alloIle-Thr-Gln-Ile-Arg-ProNHCH$_2$CH$_3$,
(203) N-Succinyl-Sar-Gly-Val-D-Ile-Thr-Gln-Ile-Arg-ProNHCH$_2$CH$_3$,
(204) N-Ac-Sar-Gly-Val-D-alloIle-Thr-Nva-Ile-Arg-Pro-D-AlaNH$_2$,
(205) N-Ac-Sar-Gly-Val-D-alloIle-Thr-Nva-Ile-Arg-ProNHCH(CH$_3$)$_2$,
(206) N-Ac-Sar-Gly-Val-D-Ile-Thr-Gln-Ile-Arg-Pro-D-AlaNH$_2$,
(207) N-Ac-Sar-Gly-Val-D-Ile-Thr-Gln-Ile-Arg-ProNHCH(CH$_3$)$_2$,
(208) N-Ac-Sar-Gly-Val-D-alloIle-Thr-Gln-Ile-Arg-Pro-D-AlaNH$_2$,
(209) N-Ac-Sar-Gly-Val-D-alloIle-Thr-Gln-Ile-Arg-ProNHCH(CH$_3$)$_2$,
(210) N-Ac-Sar-Gly-Val-D-Ile-Thr-Nva-Ile-Arg-Pro-SarNH$_2$,
(211) N-Ac-Sar-Gly-Val-D-alloIle-Thr-Nva-Ile-Arg-Pro-SarNH$_2$,
(212) N-Ac-Sar-Gly-Val-D-Ile-Thr-Gln-Ile-Arg-Pro-SarNH$_2$,
(213) N-Ac-Sar-Gly-Val-D-alloIle-Thr-Gln-Ile-Arg-Pro-SarNH$_2$,
(214) N-Ac-Sar-Gly-Val-D-alloIle-Thr-Ser-Ile-Arg-Pro-D-AlaNH$_2$, (215) N-Ac-Sar-Gly-Val-D-alloIle-Thr-Ser-Ile-Arg-ProNHCH(CH$_3$)$_2$, (216) N-Ac-Sar-Gly-Val-D-alloIle-Thr-Ser-Ile-Arg-ProNHCH$_2$CH$_3$, (217) N-Ac-Sar-Gly-Val-D-Ile-Thr-Orn(Ac)-Ile-Arg-ProNHCH$_2$CH$_3$, (218) N-Ac-Sar-Gly-Val-D-Ile-Thr-Gln-Ile-Arg-Pro-AzaglyNH$_2$, (219) N-Ac-Sar-Gly-Val-D-alloIle-Thr-Nva-Ile-Arg-Pro-AzaglyNH$_2$, (220) N-Ac-Sar-Gly-Val-D-alloIle-Thr-Gln-Ile-Arg-Pro-AzaglyNH$_2$, (221) N-(2-THFcarbonyl)-Sar-Gly-Val-D-alloIle-Thr-Nva-Ile-Arg-Pro-NHCH$_2$CH$_3$, (222) N-(2-THFcarbonyl)-Sar-Gly-Val-D-Ile-Thr-Gln-Ile-Arg-ProNHCH$_2$CH$_3$, (223) N-(2-THFcarbonyl)-Sar-Gly-Val-D-alloIle-Thr-Gln-Ile-Arg-Pro-NHCH$_2$CH$_3$, (224) N-(2-THFcarbonyl)-Sar-Gly-Val-D-Ile-Thr-Gln-Ile-Arg-Pro-D-AlaNH$_2$, (225) N-(2-THFcarbonyl)-Sar-Gly-Val-D-alloIle-Thr-Gln-Ile-Arg-Pro-D-AlaNH$_2$, (226) N-(2-THFcarbonyl)-Sar-Gly-Val-D-alloIle-Thr-Gln-Ile-Arg-Pro-NHCH$_2$(CH$_3$)$_2$, (227) N-(6-Ac-Aca)-Sar-Gly-Val-D-alloIle-Thr-Nva-Ile-Arg-ProNHCH$_2$CH$_3$, (228) N-(6-Ac-Aca)-Sar-Gly-Val-D-Ile-Thr-Gln-Ile-Arg-ProNHCH$_2$CH$_3$, (229) N-(6-Ac-Aca)-Sar-Gly-Val-D-alloIle-Thr-Gln-Ile-Arg-ProNHCH$_2$CH$_3$, (230) N-(6-Ac-Aca)-Sar-Gly-Val-D-Ile-Thr-Gln-Ile-Arg-Pro-D-AlaNH$_2$, (231) N-(6-Ac-Aca)-Sar-Gly-Val-D-alloIle-Thr-Gln-Ile-Arg-Pro-D-AlaNH$_2$, (232) N-(6-Ac-Aca)-Sar-Gly-Val-D-alloIle-Thr-Gln-Ile-Arg-ProNHCH(CH$_3$)$_2$, (233) N-(4-Ac-Gaba)-Sar-Gly-Val-D-alloIle-Thr-Nva-Ile-Arg-ProNHCH$_2$CH$_3$, (234) N-(4-Ac-Gaba)-Sar-Gly-Val-D-Ile-Thr-Gln-Ile-Arg-ProNHCH$_2$CH$_3$, (235) N-(4-Ac-Gaba)-Sar-Gly-Val-alloIle-Thr-Gln-Ile-Arg-ProNHCH$_2$CH$_3$, (236) N-(4-Ac-Gaba)-Sar-Gly-Val-D-Ile-Thr-Gln-Ile-Arg-Pro-D-AlaNH$_2$, (237) N-(4-Ac-Gaba)-Sar-Gly-Val-D-alloIle-Thr-Gln-Ile-Arg-Pro-D-AlaNH$_2$, (238) N-(4-Ac-Gaba)-Sar-Gly-Val-D-alloIle-Thr-Gln-Ile-Arg-Pro-NHCH(CH$_3$)$_2$, (239) N-(2-Furoyl)-Sar-Gly-Val-D-alloIle-Thr-Nva-Ile-Arg-ProNHCH$_2$CH$_3$, (240) N-(2-Furoyl)-Sar-Gly-Val-D-Ile-Thr-Gln-Ile-Arg-ProNHCH$_2$CH$_3$, (241) N-(2-Furoyl)-Sar-Gly-Val-D-alloIle-Thr-Gln-Ile-Arg-ProNHCH$_2$CH$_3$, (242) N-(2-Furoyl)-Sar-Gly-Val-D-Ile-Thr-Gln-Ile-Arg-Pro-D-AlaNH$_2$, (243) N-(2-Furoyl)-Sar-Gly-Val-alloIle-Thr-Gln-Ile-Arg-Pro-D-AlaNH$_2$, (244) N-(2-Furoyl)-Sar-Gly-Val-D-alloIle-Thr-Gln-Ile-Arg-ProNHCH(CH$_3$)$_2$, (245) N-(Shikimyl)-Sar-Gly-Val-D-alloIle-Thr-Nva-Ile-Arg-ProNHCH$_2$CH$_3$, (246) N-(Shikimyl)-Sar-Gly-Val-D-Ile-Thr-Gln-Ile-Arg-ProNHCH$_2$CH$_3$, (247) N-(Shikimyl)-Sar-Gly-Val-D-alloIle-Thr-Gln-Ile-Arg-ProNHCH$_2$CH$_3$, (248) N-(Shikimyl)-Sar-Gly-Val-D-Ile-Thr-Gln-Ile-Arg-Pro-D-AlaNH$_2$, (249) N-(Shikimyl)-Sar-Gly-Val-D-alloIle-Thr-Gln-Ile-Arg-Pro-D-AlaNH$_2$, (250) N-(Shikimyl)-Sar-Gly-Val-D-alloIle-Thr-Gln-Ile-Arg-ProNHCH(CH$_3$)$_2$, (251) N-(2-Me-Nicotinyl)-Sar-Gly-Val-D-alloIle-Thr-Nva-Ile-Arg-Pro-NHCH$_2$CH$_3$, (252) N-(2-Me-Nicotinyl)-Sar-Gly-Val-D-Ile-Thr-Gln-Ile-Arg-ProNHCH$_2$CH$_3$, (253) N-(2-Me-Nicotinyl)-Sar-Gly-Val-D-alloIle-Thr-Gln-Ile-Arg-Pro-NHCH$_2$CH$_3$, (254) N-(2-Me-Nicotinyl)-Sar-Gly-Val-D-Ile-Thr-Gln-Ile-Arg-Pro-D-AlaNH$_2$, (255) N-(2-Me-Nicotinyl)-Sar-Gly-Val-D-alloIle-Thr-Gln-Ile-Arg-Pro-D-AlaNH$_2$, (256) N-(2-Me-Nicotinyl)-Sar-Gly-Val-D-alloIle-Thr-Gln-Ile-Arg-Pro-NHCH(CH$_3$)$_2$, (257) N-Ac-Sar-Gly-Val-D-alloIle-Thr-Leu-Ile-Arg-Pro-D-AlaNH$_2$, (258) N-Ac-Sar-Gly-Val-D-Ile-Thr-Leu-Ile-Arg-ProNHCH(CH$_3$)$_2$, (259) N-Ac-Sar-Gly-Val-D-alloIle-Thr-Leu-Ile-Arg-ProNHCH$_2$CH$_3$, (260) N-Ac-Sar-Gly-Val-D-Ile-Thr-Leu-Ile-Arg-Pro-D-AlaNH$_2$, (261) N-Succinyl-Sar-Gly-Val-D-Ile-Thr-Leu-Ile-Arg-Pro-D-AlaNH$_2$, (262) N-Succinyl-Sar-Gly-Val-D-Ile-Thr-Leu-Ile-Arg-ProNHCH$_2$CH$_3$, (263) N-Succinyl-Sar-Gly-Val-D-Ile-Thr-Leu-Ile-Arg-ProNHCH$_2$CH$_3$, (264) N-Succinyl-Sar-Gly-Val-D-alloIle-Thr-Leu-Ile-Arg-ProNHCH$_2$CH$_3$, (265) N-Succinyl-Sar-Gly-Val-D-alloIle-Thr-Leu-Ile-Arg-Pro-D-AlaNH$_2$, (266) N-Succinyl-Sar-Gly-Val-D-Ile-Thr-Leu-Ile-Arg-Pro-AzaglyNH$_2$, (267) N-Ac-Sar-Gly-Val-D-alloIle-Thr-Nva-Ile-Arg-ProNHethyl-(1-pyrrolidine), (268) N-Ac-Sar-Gly-Val-D-alloIle-Thr-Nva-Ile-Arg-ProNH(ethyl-1-cyclohexyl), (269) N-Ac-Sar-Gly-Val-D-Ile-Thr-Gln-Ile-Arg-ProNHethyl-(1-pyrrolidine), (270) N-Ac-Sar-Gly-Val-D-Ile-Thr-Gln-Ile-Arg-ProNH(ethyl-1-cyclohexyl), (271) N-Succinyl-Sar-Gly-Val-D-Ile-Thr-Gln-Ile-Arg-ProNH(ethyl-1-cyclohexyl), (272) N-Ac-Sar-Gly-Val-D-alloIle-Thr-Nva-Ile-Arg-ProNHCH$_2$CH$_2$OCH$_3$, (273) N-Ac-Sar-Gly-Val-D-Ile-Thr-Gln-Ile-Arg-ProNHCH$_2$CH$_2$OCH$_3$, (274) N-Ac-Sar-Gly-Val-D-Ile-Thr-Ser-Ile-Arg-ProNHCH$_2$CH$_2$OCH$_3$, (275) N-Ac-Sar-Gly-Val-D-Ile-Thr-Leu-Ile-Arg-ProNHCH$_2$CH$_2$OCH$_3$, (276) N-Succinyl-Sar-Gly-Val-D-Ile-Thr-Nva-Ile-Arg-ProNHCH$_2$CH$_2$OCH$_3$, (277) N-Succinyl-Sar-Gly-Val-D-Ile-Thr-Gln-Ile-Arg-ProNHCH$_2$CH$_2$OCH$_3$, (278) N-Succinyl-Sar-Gly-Val-D-alloIle-Thr-Gln-Ile-Arg-ProNHCH$_2$CH$_2$OCH$_3$, (279) N-Ac-Sar-Gly-Val-D-Ile-Ser-Nva-Ile-Arg-ProNHCH$_2$CH$_2$OCH$_3$, (280) N-Ac-Sar-Gly-Val-D-Leu-Ser-Nva-Ile-Arg-ProNHCH$_2$CH$_2$OCH$_3$, (281) N-Ac-Sar-Gly-Val-D-alloIle-Thr-Allygly-Ile-Arg-ProNHCH$_2$CH$_3$, (282) N-Ac-Sar-Gly-Val-D-Ile-Thr-Allygly-Ile-Arg-ProNHCH(CH$_3$)$_2$, (283) N-Ac-Sar-Gly-Val-D-Ile-Thr-Allygly-Ile-Arg-Pro-D-AlaNH$_2$, (284) N-Ac-Sar-Gly-Val-D-alloIle-Thr-Allygly-Ile-Arg-Pro-D-AlaNH$_2$, (285) N-Succinyl-Sar-Gly-Val-D-Ile-Thr-Allygly-Ile-Arg-Pro-D-AlaNH$_2$, (286) N-Ac-Sar-Gly-Val-D-Ile-Ser-Allygly-Ile-Arg-Pro-ProNHCH$_2$CH$_3$, (287) N-Ac-Sar-Gly-Val-D-Leu-Ser-Allygly-Ile-Arg-Pro-ProNHCH$_2$CH$_3$, (288) N-Ac-Sar-Gly-Val-D-Ile-Thr-Nva-Ile-Arg-Pro-SarNH$_2$, (289) N-Ac-Sar-Gly-Val-D-Ile-Thr-Nva-Ile-Arg-ProNHOH, (290) N-Ac-Sar-Gly-Val-D-Ile-Ser-Nva-Ile-Arg-ProNHCH$_2$CH$_3$, (291) N-Ac-Sar-Gly-Val-D-alloIle-Ser-Nva-Ile-Arg-ProNHCH$_2$CH$_3$.

(292) N-Ac-Sar-Gly-Val-D-Leu-Hser-Nva-Ile-Arg-ProNHCH$_2$CH$_3$, (293) N-Ac-Sar-Gly-Gln-D-Ile-Thr-Nva-Ile-Arg-ProNHCH$_2$CH$_3$, (294) N-Ac-Sar-Gly-Nva-D-Ile-Thr-Nva-Ile-Arg-ProNHCH$_2$CH$_3$, (295) N-Ac-Sar-Gly-Ile-D-Ile-Thr-Nva-Ile-Arg-ProNHCH$_2$CH$_3$, (296) N-Ac-Sar-Gly-Phe-D-Ile-Thr-Nva-Ile-Arg-ProNHCH$_2$CH$_3$, (297) N-Ac-Sar-Gly-Leu-D-Ile-Thr-Nva-Ile-Arg-ProNHCH$_2$CH$_3$, (298) N-Ac-Sar-Gly-Ser-D-Ile-Thr-Nva-Ile-Arg-ProNHCH$_2$CH$_3$, (299) N-Ac-Thr-Gly-Val-D-Leu-Thr-Nva-Ile-Arg-ProNHCH$_2$CH$_3$, (300) N-Ac-Sar-Gly-Val-D-alloIle-Thr-Ala-Ile-Arg-ProNHCH$_2$CH$_3$, (301) N-Ac-Sar-Gly-Val-D-Ile-Thr-Ala-Ile-Arg-ProNHCH(CH$_3$)$_2$, (302) N-Ac-Sar-Gly-Val-D-Ile-Thr-Ala-Ile-Arg-Pro-D-AlaNH$_2$, (303) N-Ac-Sar-Gly-Val-D-alloIle-Thr-Ala-Ile-Arg-Pro-D-AlaNH$_2$, (304) N-Succinyl-Sar-Gly-Val-D-Ile-Thr-Ala-Ile-Arg-Pro-D-AlaNH$_2$, (305) N-Ac-Sar-Gly-Val-D-Ile-Ser-Ala-Ile-Arg-ProNHCH$_2$CH$_3$, (306) N-Ac-Sar-Gly-Val-D-Leu-Ser-Ala-Ile-Arg-ProNHCH$_2$CH$_3$, (307) N-Ac-Sar-Gly-Val-D-alloIle-Thr-Val-Ile-Arg-ProNHCH$_2$CH$_3$, (308) N-Ac-Sar-Gly-Val-D-Ile-Thr-Val-Ile-Arg-ProNHCH(CH$_3$)$_2$, (309) N-Ac-Sar-Gly-Val-D-Ile-Thr-Val-Ile-Arg-Pro-D-AlaNH$_2$, (310) N-Ac-Sar-Gly-Val-D-alloIle-Thr-Val-Ile-Arg-Pro-D-AlaNH$_2$, (311) N-Succinyl-Sar-Gly-Val-D-Ile-Thr-Val-Ile-Arg-Pro-D-AlaNH$_2$, (312) N-Ac-Sar-Gly-Val-D-Ile-Ser-Val-Ile-Arg-ProNHCH$_2$CH$_3$, (313) N-Ac-Sar-Gly-Val-D-Leu-Ser-Val-Ile-Arg-ProNHCH$_2$CH$_3$, (314) N-Ac-Sar-Gly-Val-D-alloIle-Thr-D-Nva-Ile-Arg-ProNHCH$_2$CH$_3$, (315) N-Ac-Sar-Gly-Val-D-Ile-Thr-D-Nva-Ile-Arg-ProNHCH(CH$_3$)$_2$, (316) N-Ac-Sar-Gly-Val-D-Ile-Thr-D-Nva-Ile-Arg-Pro-D-AlaNH$_2$, (317) N-Ac-Sar-Gly-Val-D-alloIle-Thr-D-Nva-Ile-Arg-Pro-D-AlaNH$_2$, (318) N-Succinyl-Sar-Gly-Val-D-Ile-Thr-D-Nva-Ile-Arg-Pro-D-AlaNH$_2$, (319) N-Ac-Sar-Gly-Val-D-Ile-Ser-D-Nva-Ile-Arg-ProNHCH$_2$CH$_3$, (320) N-Ac-Sar-Gly-Val-D-Leu-Ser-D-Nva-Ile-Arg-ProNHCH$_2$CH$_3$, (321) N-Ac-Sar-Gly-Val-D-Ile-Ser-Gln-Ile-Arg-ProNHCH$_2$CH$_3$, (322) N-Ac-Sar-Gly-Val-D-Leu-Ser-Gln-Ile-Arg-ProNHCH$_2$CH$_3$, (323) N-Ac-Sar-Gly-Val-D-Leu-Ser-Nva-Ile-Arg-Pro-D-AlaNH$_2$, (324) N-Ac-Sar-Gly-Val-D-Ile-Ser-Nva-Ile-Arg-Pro-D-AlaNH$_2$, (325) N-Succinyl-Sar-Gly-Val-D-Leu-Ser-Nva-Ile-Arg-ProNHCH$_2$CH$_3$, (326) N-Succinyl-Sar-Gly-Val-D-Ile-Ser-Nva-Ile-Arg-ProNHCH$_2$CH$_3$, (327) N-Succinyl-Sar-Gly-Val-D-Leu-Ser-Gln-Ile-Arg-ProNHCH$_2$CH$_3$, (328) N-Succinyl-Sar-Gly-Val-D-Ile-Ser-Gln-Ile-Arg-ProNHCH$_2$CH$_3$, (329) N-Ac-Sar-Gly-Val-D-Ile-Ser-Ser-Ile-Arg-ProNHCH$_2$CH$_3$, (330) N-Ac-Sar-Gly-Val-D-Leu-Ser-Ser-Ile-Arg-ProNHCH$_2$CH$_3$, (331) N-Ac-Sar-Gly-Val-D-Leu-Ser-Nva-Ile-Arg-ProNHCH$_2$, CH$_2$CH$_3$, (332) N-Ac-Sar-Gly-Val-D-Ile-Ser-Nva-Ile-Arg-ProNHCH$_2$CH$_2$CH$_3$, (333) N-Ac-Sar-Gly-Val-D-Leu-Ser-Leu-Ile-Arg-ProNHCH$_2$CH$_3$, (334) N-Ac-Sar-Gly-Val-D-Ile-Ser-Leu-Ile-Arg-ProNHCH$_2$CH$_3$, (335) N-Ac-Sar-Gly-Val-D-alloIle-Ser-Nva-Ile-Arg-ProNHCH$_2$CH$_3$, (336) N-Ac-Sar-Gly-Val-D-alloIle-Ser-Gln-Ile-Arg-ProNHCH$_2$CH$_3$, (337) N-Succinyl-Sar-Gly-Val-D-alloIle-Ser-Nva-Ile-Arg-ProNHCH$_2$CH$_3$, (338) N-Ac-Sar-Gly-Val-D-alloIle-Ser-Nva-Ile-Arg-ProNHCH$_2$CH$_2$CH$_3$, (339) N-Ac-Sar-Gly-Val-D-alloIle-Ser-Nva-Ile-Arg-Pro-D-AlaNH₂,
(340) N-Ac-Sar-Gly-Val-D-alloIle-Ser-Leu-Ile-Arg-ProNHCH₂CH₃,
(341) N-Ac-Sar-Gly-Val-D-alloIle-Ser-Ser-Ile-Arg-ProNHCH₂CH₃,
(342) N-Ac-Sar-Gly-Val-D-Ile-Gly-Nva-Ile-Arg-ProNHCH₂CH₃,
(343) N-Ac-Sar-Gly-Val-D-alloIle-Gly-Nva-Ile-Arg-ProNHCH₂CH₃,
(344) N-Ac-Sar-Gly-Val-D-Leu-Gly-Gln-Ile-Arg-ProNHCH₂CH₃,
(345) N-Ac-Sar-Gly-Val-D-Ile-Gly-Gln-Ile-Arg-ProNHCH₂CH₃,
(346) N-Ac-Sar-Gly-Val-D-alloIle-Gly-Gln-Ile-Arg-ProNHCH₂CH₃,
(347) N-Ac-Sar-Gly-Val-D-Ile-Tyr-Nva-Ile-Arg-ProNHCH₂CH₃,
(348) N-Ac-Sar-Gly-Val-D-alloIle-Tyr-Nva-Ile-Arg-ProNHCH₂CH₃,
(349) N-Ac-Sar-Gly-Val-D-Leu-Tyr-Gln-Ile-Arg-ProNHCH₂CH₃,
(350) N-Ac-Sar-Gly-Val-D-Ile-Tyr-Gln-Ile-Arg-ProNHCH₂CH₃,
(351) N-Ac-Sar-Gly-Val-D-alloIle-Tyr-Gln-Ile-Arg-ProNHCH₂CH₃,
(352) N-Ac-Sar-Gly-Val-D-Ser-Thr-Nva-Ile-Arg-ProNHCH₂CH₃,
(353) N-Ac-Sar-Gly-Val-D-Thr-Thr-Nva-Ile-Arg-ProNHCH₂CH₃,
(354) N-Ac-Sar-Gly-Val-D-Gln-Thr-Nva-Ile-Arg-ProNHCH₂CH₃,
(355) N-Ac-Sar-Gly-Val-D-Asn-Thr-Nva-Ile-Arg-ProNHCH₂CH₃,
(356) N-Ac-Sar-Gly-Val-D-Arg-Thr-Nva-Ile-Arg-ProNHCH₂CH₃,
(357) N-Ac-Sar-Gly-Val-D-3-Pal-Thr-Nva-Ile-Arg-ProNHCH₂CH₃,
(358) N-Ac-Sar-Gly-Val-D-Glu-Thr-Nva-Ile-Arg-ProNHCH₂CH₃,
(359) N-Ac-Sar-Gly-Val-D-Asp-Thr-Nva-Ile-Arg-ProNHCH₂CH₃,
(360) N-Ac-Sar-Gly-Val-D-His-Thr-Nva-Ile-Arg-ProNHCH₂CH₃,
(361) N-Ac-Sar-Gly-Val-D-Hser-Thr-Nva-Ile-Arg-ProNHCH₂CH₃,
(362) N-Ac-Sar-Gly-Val-D-alloThr-Thr-Nva-Ile-Arg-ProNHCH₂CH₃,
(363) N-Ac-Sar-Gly-Val-D-Ile-Thr-Nva-D-Ile-Arg-ProNHCH₂CH₃,
(364) N-Ac-Sar-Gly-Val-D-Ser-Thr-Gln-Ile-Arg-ProNHCH₂CH₃,
(365) N-Ac-Sar-Gly-Val-D-Thr-Thr-Gln-Ile-Arg-ProNHCH₂CH₃,
(366) N-Ac-Sar-Gly-Val-D-alloThr-Thr-Gln-Ile-Arg-ProNHCH₂CH₃,
(367) N-Ac-Sar-Gly-Val-D-Ser-Ser-Nva-Ile-Arg-ProNHCH₂CH₃,
(368) N-Ac-Sar-Gly-Val-D-Thr-Ser-Nva-Ile-Arg-ProNHCH₂CH₃,
(369) N-Ac-Sar-Gly-Val-D-alloThr-Ser-Nva-Ile-Arg-ProNHCH₂CH₃,
(370) N-Ac-Sar-Gly-Val-D-alloThr-Ser-Gln-Ile-Arg-ProNHCH₂CH₃,
(371) N-Ac-Sar-Gly-Val-D-Thr-Ser-Gln-Ile-Arg-ProNHCH₂CH₃,
(372) N-(6-Ac-Aca)-Sar-Gly-Val-D-Leu-Ser-Gln-Ile-Arg-Pro NHCH₂CH₃,
(373) N-(6-Ac-Aca)-Sar-Gly-Val-D-Leu-Ser-Nva-Ile-Arg-Pro NHCH₂CH₃,
(374) N-(4-Ac-Gaba)-Sar-Gly-Val-D-Leu-Ser-Gln-Ile-Arg-Pro NHCH₂CH₃,
(375) N-(4-Ac-Gaba)-Sar-Gly-Val-D-Leu-Ser-Nva-Ile-Arg-Pro NHCH₂CH₃,
(376) N-(2-Furoyl)-Sar-Gly-Val-D-Leu-Ser-Gln-Ile-Arg-Pro NHCH₂CH₃,
(377) N-(2-Furoyl)-Sar-Gly-Val-D-Leu-Ser-Nva-Ile-Arg-Pro NHCH₂CH₃,
(378) N-(Shikimyl)-Sar-Gly-Val-D-Leu-Ser-Gln-Ile-Arg-Pro NHCH₂CH₃,
(379) N-(Shikimyl)-Sar-Gly-Val-D-Leu-Ser-Nva-Ile-Arg-Pro NHCH₂CH₃,
(380)
(381)
(382) N-(2-Me-nicotinyl)-Sar-Gly-Val-D-Leu-Ser-Gln-Ile-Arg-Pro CH₂CH₃,
(383) N-(2-Me-nicotinyl)-Sar-Gly-Val-D-Leu-Ser-Nva-Ile-Arg-Pro NHCH₂CH₃,
(384) N-Ac-Sar-Gly-Val-D-Leu-Ser-Nva-Ile-Arg-ProNHethyl-1-(R)-cyclohexyl,
(385) N-Ac-Sar-Gly-Val-D-Leu-Ser-Gln-Ile-Arg-ProNHethyl-1-(R)cyclohexyl,
(386) N-Ac-Sar-Gly-Val-D-Ile-Thr-Ser-Ile-Arg-ProNHethyl-1-(R)-cyclohexyl,
(387) N-Ac-Sar-Gly-Val-D-Leu-Thr-Nva-Ile-Arg-ProNHethyl-1-(R)-cyclohexyl,
(388) N-Ac-Sar-Gly-Val-D-Leu-Ser-Ser-Ile-Arg-ProNHethyl-1-(R)-cyclohexyl,
(389) N-Ac-Sar-Gly-Val-D-Ile-Thr-Nva-Ile-Arg-ProNHethyl-1-(S)-cyclohexyl,
(390) N-Ac-Sar-Gly-Val-D-Pen-Ser-Nva-Ile-Arg-ProNHCH₂CH₃,
(391) N-Ac-Sar-Gly-Val-D-Pen-Gly-Nva-Ile-Arg-ProNHCH₂CH₃,
(392) N-Ac-Sar-Gly-Val-D-Pen-Thr-Gln-Ile-Arg-ProNHCH₂CH₃,
(393) N-Ac-Sar-Gly-Val-D-Pen-Ser-Nva-Ile-Arg-ProNHCH(CH₃)₂,
(394) N-Succinyl-Sar-Gly-Val-D-Pen-Ser-Nva-Ile-Arg-ProNHCH₂CH₃,
(395) N-Ac-Sar-Gly-Val-D-Pen-Ser-Nva-Ile-Arg-Pro-D-AlaNH₂,
(396) N-Ac-Sar-Gly-Val-D-Pen-Ser-Gln-Ile-Arg-ProNHCH₂CH₃,
(397) N-Ac-Sar-Gly-Val-D-Pen-Gly-Gln-Ile-Arg-ProNHCH₂CH₃,
(398) N-Ac-Sar-Gly-Val-D-Pen-Ser-Ser-Ile-Arg-ProNHCH₂CH₃,
(399) N-Ac-Sar-Gly-Val-D-Pen-Thr-Ser-Ile-Arg-ProNHCH₂CH₃,
(400) N-Ac-Sar-Gly-Val-D-Pen-Thr-Leu-Ile-Arg-ProNHCH₂CH₃,
(401) N-Ac-Sar-Gly-Val-D-Pen-Ser-Leu-Ile-Arg-ProNHCH₂CH₃, (402) N-Succinyl-Sar-Gly-Val-D-Pen-Ser-Ser-Ile-Arg-ProNHCH$_2$CH$_3$,
(403) N-Succinyl-Sar-Gly-Val-D-Pen-Ser-Leu-Ile-Arg-ProNHCH$_2$CH$_3$,
(404) N-Succinyl-Sar-Gly-Val-D-Pen-Thr-Gln-Ile-Arg-ProNHCH(CH$_3$)$_2$,
(405) N-Ac-Sar-Gly-Val-D-Cys-Thr-Nva-Ile-Arg-ProNHCH$_2$CH$_3$,
(406) N-Ac-Sar-Gly-Val-D-Cys-Ser-Nva-Ile-Arg-ProNHCH$_2$CH$_3$,
(407) N-Ac-Sar-Gly-Val-D-Cys-Gly-Nva-Ile-Arg-ProNHCH$_2$CH$_3$,
(408) N-Ac-Sar-Gly-Val-D-Cys-Thr-Gln-Ile-Arg-ProNHCH$_2$CH$_3$,
(409) N-Ac-Sar-Gly-Val-D-Cys-Ser-Nva-Ile-Arg-ProNHCH(CH$_3$)$_2$,
(410) N-Succinyl-Sar-Gly-Val-D-Cys-Ser-Nva-Ile-Arg-ProNHCH$_2$CH$_3$,
(411) N-Ac-Sar-Gly-Val-D-Cys-Ser-Nva-Ile-Arg-Pro-D-AlaNH$_2$,
(412) N-Ac-Sar-Gly-Val-D-Cys-Ser-Gln-Ile-Arg-ProNHCH$_2$CH$_3$,
(413) N-Ac-Sar-Gly-Val-D-Cys-Gly-Gln-Ile-Arg-ProNHCH$_2$CH$_3$,
(414) N-Ac-Sar-Gly-Val-D-Cys-Ser-Ser-Ile-Arg-ProNHCH$_2$CH$_3$,
(415) N-Ac-Sar-Gly-Val-D-Cys-Thr-Ser-Ile-Arg-ProNHCH$_2$CH$_3$,
(416) N-Ac-Sar-Gly-Val-D-Cys-Thr-Leu-Ile-Arg-ProNHCH$_2$CH$_3$,
(417) N-Ac-Sar-Gly-Val-D-Cys-Ser-Leu-Ile-Arg-ProNHCH$_2$CH$_3$,
(418) N-Succinyl-Sar-Gly-Val-D-Cys-Ser-Ser-Ile-Arg-ProNHCH$_2$CH$_3$,
(419) N-Succinyl-Sar-Gly-Val-D-Cys-Ser-Leu-Ile-Arg-ProNHCH$_2$CH$_3$,
(420) N-Ac-Sar-Gly-Pen-DIle-Thr-Nva-Ile-Arg-ProNHCH$_2$CH$_3$,
(421) N-Ac-Sar-Gly-Cys-DIle-Thr-Nva-Ile-Arg-ProNHCH$_2$CH$_3$,
(422) N-Ac-Sar-Gly-Pen-D-alloIle-Thr-Nva-Ile-Arg-ProNHCH$_2$CH$_3$,
(423) N-Ac-Sar-Gly-Pen-D-Leu-Thr-Nva-Ile-Arg-ProNHCH$_2$CH$_3$,
(424) N-Ac-Sar-Gly-Pen-D-Ile-Thr-Gln-Ile-Arg-ProNHCH$_2$CH$_3$,
(425) N-Ac-Sar-Gly-Pen-D-Ile-Ser-Nva-Ile-Arg-ProNHCH$_2$CH$_3$,
(426) N-Ac-Sar-Gly-Pen-D-Ile-Thr-Nva-Ile-Arg-ProNHCH(CH$_3$)$_2$,
(427) N-Ac-Sar-Gly-Pen-D-Ile-Thr-Nva-Ile-Arg-Pro-D-AlaNH$_2$,
(428) N-Succinyl-Gly-Pen-D-Ile-Thr-Nva-Ile-Arg-ProNHCH$_2$CH$_3$,
(429) N-Succinyl-Sar-Gly-Pen-D-Ile-Thr-Gln-Ile-Arg-ProNHCH$_2$CH$_3$,
(430) N-Succinyl-Sar-Gly-Pen-D-Ile-Thr-Gln-Ile-Arg-ProNHCH(CH$_3$)$_2$,
(431) N-Ac-Sar-Gly-Val-D-Leu-Pen-Nva-Ile-Arg-ProNHCH$_2$CH$_3$,
(432) N-Ac-Sar-Gly-Val-D-Ile-Pen-Nva-Ile-Arg-ProNHCH$_2$CH$_3$,
(433) N-Ac-Sar-Gly-Val-D-alloIle-Pen-Nva-Ile-Arg-ProNHCH$_2$CH$_3$,
(434) N-Ac-Sar-Gly-Val-D-Ile-Pen-Gln-Ile-Arg-ProNHCH$_2$CH$_3$,
(435) N-Ac-Sar-Gly-Val-D-Ile-Pen-Ser-Ile-Arg-ProNHCH$_2$CH$_3$,
(436) N-Ac-Sar-Gly-Val-D-Ile-Pen-Leu-Ile-Arg-ProNHCH$_2$CH$_3$,
(437) N-Ac-Sar-Gly-Val-D-Ile-Pen-Nva-Ile-Arg-ProNHCH(CH$_3$)$_2$,
(438) N-Ac-Sar-Gly-Val-D-Ile-Pen-Nva-Ile-Arg-Pro-D-AlaNH$_2$,
(439) N-Succinyl-Sar-Gly-Val-D-Ile-Pen-Nva-Ile-Arg-ProNHCH$_2$CH$_3$,
(440) N-Succinyl-Sar-Gly-Val-D-Ile-Pen-Gln-Ile-Arg-ProNHCH$_2$CH$_3$,
(441) N-Succinyl-Sar-Gly-Val-D-Ile-Pen-Gln-Ile-Arg-ProNHCH(CH$_3$)$_2$,
(442) N-Ac-Sar-Gly-Val-D-Ile-Thr-Pen-Ile-Arg-ProNHCH$_2$CH$_2$OCH3,
(443) N-Ac-Sar-Gly-Val-D-alloIle-Thr-Pen-Ile-Arg-ProNHCH$_2$CH$_3$,
(444) N-Ac-Sar-Gly-Val-D-Leu-Thr-Pen-Ile-Arg-ProNHCH$_2$CH$_3$,
(445) N-Ac-Sar-Gly-Val-D-Ile-Thr-Pen-Ile-Arg-Pro-D-AlaNH$_2$,
(446) N-Succinyl-Sar-Gly-Val-D-Ile-Thr-Pen-Ile-Arg-ProNHCH$_2$CH$_3$,
(447) N-Ac-Sar-Gly-Val-D-Ile-Thr-Pen-Ile-Arg-ProNHCH(CH$_3$)$_2$,
(448) N-Ac-Sar-Gly-Val-D-Leu-Ser-Pen-Ile-Arg-ProNHCH$_2$CH$_3$,
(449) N-Ac-Sar-Gly-Val-D-Leu-Gly-Pen-Ile-Arg-ProNHCH$_2$CH$_3$,
(450) N-Succinyl-Sar-Gly-Val-D-Leu-Ser-Pen-Ile-Arg-ProNHCH$_2$CH$_3$,
(451) N-Ac-Sar-Gly-Val-D-Phe(3,4,5-triF)-Thr-Gln-Ile-Arg-ProNHCH$_2$CH$_3$,
(452) N-Ac-Sar-Gly-Val-D-Phe(3,4,5-triF)-Ser-Nva-Ile-Arg-ProNHCH$_2$CH$_3$,
(453) N-Ac-Sar-Gly-Val-D-Phe(3,4,5-triF)-Gly-Nva-Ile-Arg-ProNHCH$_2$CH$_3$,
(454) N-Ac-Sar-Gly-Val-D-Phe(3,4,5-triF)-Ser-Leu-Ile-Arg-ProNHCH$_2$CH$_3$,
(455) N-Ac-Sar-Gly-Val-D-Phe(3,4,5-triF)-Ser-Nva-Ile-Arg-Pro-D-AlaNH$_2$,
(456) N-Succinyl-Sar-Gly-Val-D-Phe(3,4,5-triF)-Thr-Gln-Ile-Arg-ProNHCH$_2$CH$_3$,
(457) N-Succinyl-Sar-Gly-Val-D-Phe(3,4,5-triF)-Ser-Gln-Ile-Arg-ProNHCH$_2$CH$_3$,
(458) N-Succinyl-Sar-Gly-Val-D-Phe(3,4,5-triF)-Thr-Gln-Ile-Arg-ProNHCH($_3$)$_2$,
(459) N-Ac-Sar-Gly-Val-D-Phe(3,4,5-triF)-Ser-Gln-Ile-Arg-ProNHCH$_2$CH$_3$,
(460) N-Ac-Sar-Gly-Val-D-Phe(3,4,5-triF)-Ser-Ser-Ile-Arg-ProNHCH$_2$CH$_3$,
(461) N-Ac-Sar-Ala-Val-D-alloIle-Thr-Nva-Ile-Arg-ProNHCH$_2$CH$_3$,
(462) N-Ac-Sar-Ala-Val-D-Leu-Thr-Nva-Ile-Arg-ProNHCH$_2$CH$_3$,
(463) N-Ac-Sar-Ala-Val-D-Ile-Thr-Gln-Ile-Arg-ProNHCH$_2$CH$_3$, (464) N-Ac-Sar-Ala-Val-D-Leu-Ser-Nva-Ile-Arg-ProNHCH₂CH₃,
(465) N-Ac-Sar-Ala-Val-D-Leu-Ser-Gln-Ile-Arg-ProNHCH₂CH₃,
(466) N-Succinyl-Sar-Ala-Val-D-Ile-Thr-Nva-Ile-Arg-ProNHCH₂CH₃,
(467) N-Succinyl-Sar-Ala-Val-D-Ile-Thr-Gln-Nva-Ile-Arg-ProNHCH₂CH₃,
(468) N-Succinyl-Sar-Ala-Val-D-Ile-Thr-Gln-Nva-Ile-Arg-ProNHCH(CH₃)₂,
(469) N-Succinyl-Sar-Ala-Val-D-Ile-Thr-Gln-Nva-Ile-Arg-Pro-D-AlaNH₂,
(470) N-(3-Ac-Bala)-Sar-Gly-Val-D-alloIle-Thr-Nva-Ile-Arg-ProNHCH₂CH₃,
(471) N-(3-Ac-Bala)-Sar-Gly-Val-D-Ile-Thr-Gln-Ile-Arg-ProNHCH₂CH₃,
(472) N-(3-Ac-Bala)-Sar-Gly-Val-D-alloIle-Thr-Gln-Ile-Arg-ProNHCH₂CH₃,
(473) N-(3-Ac-Bala)-Sar-Gly-Val-D-Ile-Thr-Gln-Ile-Arg-Pro-DAlaNH₂,
(474) N-(3-Ac-Bala)-Sar-Gly-Val-D-alloIle-Thr-Gln-Ile-Arg-Pro-DAlaNH₂,
(475) N-(3-Ac-Bala)-Sar-Gly-Val-D-alloIle-Thr-Gln-Ile-Arg-ProNHCH(CH₃)₂,
(476) N-(3-Ac-Bala)-Sar-Gly-Val-D-Leu-Ser-Nva-Ile-Arg-ProNHCH₂CH₃,
(477) N-(3-Ac-Bala)-Sar-Gly-Val-D-Leu-Thr-Nva-Ile-Arg-ProNHCH₂CH₃,
(478) N-(3-Ac-Bala)-Sar-Gly-Val-D-Pen-Thr-Nva-Ile-Arg-ProNHCH₂CH₃,
(479) N-(3-Ac-Bala)-Sar-Gly-Val-D-Ile-Ser-Nva-Ile-Arg-ProNHCH₂CH₃,
(480) N-(3-Ac-Bala)-Sar-Ala-Val-D-alloIle-Ser-Nva-Ile-Arg-ProNHCH₂CH₃,
(481) N-(3-Ac-Bala)-Sar-Ala-Val-D-Ile-Ser-Nva-Ile-Arg-ProNHCH₂CH₃,
(482) N-(3-Ac-Bala)-Sar-Ala-Val-D-Leu-Ser-Nva-Ile-Arg-ProNHCH₂CH₃,
(483) N-(3-Ac-Bala)-Sar-Ala-Val-D-Leu-Ser-Gln-Ile-Arg-ProNHCH₂CH₃,
(484) N-Ac-Sar-Gly-Val-D-Ile-Thr-Nva-Ile-Arg-Pro-OH,
(485) N-Ac-Sar-Gly-Val-D-alloIle-Thr-Nva-Ile-Arg-Pro-OH,
(486) N-Ac-Sar-Gly-Val-D-Leu-Thr-Nva-Ile-Arg-Pro-OH,
(487) N-Ac-Sar-Gly-Val-D-Pen-Thr-Nva-Ile-Arg-Pro-OH,
(488) N-Ac-Sar-Gly-Val-D-Phe(3,4,5-triF)-Thr-Nva-Ile-Arg-Pro-OH,
(489) N-Ac-Sar-Gly-Val-D-Ile-Thr-Gln-Ile-Arg-Pro-OH,
(490) N-Ac-Sar-Gly-Val-D-Leu-Ser-Nva-Ile-Arg-Pro-OH,
(491) N-Ac-Sar-Ala-Val-D-Ile-Thr-Nva-Ile-Arg-Pro-OH,
(492) N-Ac-Sar-Gly-Val-D-Ile-Ser-Gln-Ile-Arg-Pro-OH,
(493) N-Succinyl-Sar-Gly-Val-D-Ile-Thr-Nva-Ile-Arg-Pro-OH,
(494) N-Succinyl-Sar-Gly-Val-D-Leu-Thr-Gln-Ile-Arg-Pro-OH,
(495) N-Ac-Sar-Gly-Asp-D-Leu-Thr-Nva-Ile-Arg-ProNHCH₂CH₃,
(496) N-Ac-Sar-Gly-Ala-D-Leu-Thr-Nva-Ile-Arg-ProNHCH₂CH₃,
(497) N-Ac-Sar-Gly-Cha-D-Leu-Thr-Nva-Ile-Arg-ProNHCH₂CH₃,
(498) N-Ac-Sar-Gly-Met-D-Ile-Thr-Nva-Ile-Arg-ProNHCH₂CH₃,
(499) N-Ac-Cit-Gly-Val-D-Ile-Thr-Nva-Ile-Arg-ProNHCH₂CH₃,
(500) N-Ac-Sar-Gly-Val-D-Ile-Thr-Hser-Ile-Arg-ProNHCH₂CH₃,
(501) N-Ac-Sar-Gly-Val-D-alloIle-His-Nva-Ile-Arg-ProNHCH₂CH₃,
(502) N-Ac-Sar-Gly-Val-D-Ile-Thr-Nva-Ile-Arg-ProNH-n-Butyl,
(503) N-Ac-Sar-Gly-Val-D-Ile-Thr-Nva-Ile-Arg-ProNH-iso-Butyl,
(504) N-Ac-Sar-Gly-Val-D-Ile-Thr-Nva-Ile-Arg-ProNH-iso-Amyl,
(505) N-Ac-Sar-Gly-Val-D-Ile-Thr-Nva-Ile-Arg-ProNH-n-hexyl,
(506) N-Ac-Sar-Gly-Val-D-Ile-Thr-Nva-Ile-Arg-ProNH-(3,3-dimethyl)butyl,
(507) N-Ac-Sar-Gly-Val-D-Ile-Thr-Nva-Ile-Arg-ProNH-(2-ethoxy)ethyl,
(508) N-Ac-Sar-Gly-Val-D-Ile-Thr-Nva-Ile-Arg-ProNH-(2-isopropoxy)ethyl,
(509) N-Ac-Sar-Gly-Val-D-Ile-Thr-Nva-Ile-Arg-ProNH-(3-methoxy)propyl,
(510) N-Ac-Sar-Gly-Val-D-Ile-Thr-Nva-Ile-Arg-ProNH-(cyclopentyl)methyl,
(511) N-Ac-Sar-Gly-Val-D-Ile-Thr-Nva-Ile-Arg-ProNH-cyclohexyl,
(512) N-Ac-Sar-Gly-Val-allo-Ile-Thr-Nva-Ile-Arg-ProNHCH₂CH₃,
(513) N-Ac-Sar-Gly-Val-D-Lys-Thr-Nva-Ile-Arg-ProNHCH₂CH₃,
(514) N-Ac-Sar-Gly-Val-D-Trp-Thr-Nva-Ile-Arg-ProNHCH₂CH₃,
(515) N-Ac-Sar-Gly-Val-D-3,3-Dipheylala-Thr-Nva-Ile-Arg-ProNHCH₂CH₃,
(516) N-Ac-Sar-Gly-Val-D-3-Benzothienylala-Thr-Nva-Ile-Arg-ProNHCH₂CH₃,
(517) N-Ac-Sar-Gly-Val-D-3,4diF-Phe-Thr-Nva-Ile-Arg-ProNHCH₂CH₃,
(518) N-Ac-Sar-Gly-Val-D-Pen(Bzl)-Thr-Nva-Ile-Arg-ProNHCH₂CH₃,
(519) N-Ac-Sar-Gly-Val-D-Leu-Thr-Gln-Ile-Arg-ProNHCH(CH₃)₂,
(520)
(521) N-Ac-Sar-Gly-Val-D-Leu-Thr-Nva-Gln-Arg-ProNHCH₂CH₃,
(522) N-Ac-Sar-Gly-Val-D-Leu-Thr-Nva-Pro-Arg-ProNHCH₂CH₃,
(523) N-Ac-Sar-Gly-Val-D-Leu-Thr-Nva-Ser-Arg-ProNHCH₂CH₃,
(524) N-Ac-Sar-Gly-Val-D-Leu-Thr-Nva-Trp-Arg-ProNHCH₂CH₃,
(525) N-Ac-Sar-Gly-Val-D-Ile-Thr-Nva-Ile-Arg-ProNHCH₂CH₂OH,
(526) N-Ac-Sar-Ser-Val-D-Ile-Thr-Nva-Ile-Arg-ProNHCH₂CH₃, and
(527) N-Ac-Sar-Gly-Val-D-Ile-Thr-Leu-Ile-Arg-ProNHethyl-1-cyclohexyl.

13. A compound according to claim 12, selected from:
(1) N-Ac-Sar-Gly-Val-D-Ile-Thr-Nva-Ile-Arg-ProNHCH₂CH₃,
(2) N-Ac-Sar-Gly-Val-D-Ile-Thr-Nva-Ile-Arg-ProNHCH₂CH₂-(1-pyrrolidine),
(3) N-Ac-Sar-Gly-Val-D-Ile-Thr-Nva-Ile-Arg-ProNH(ethyl-1-(R)-cyclohexyl),
(4) N-Ac-Sar-Gly-Val-D-Ile-Thr-Nva-Ile-Arg-ProNH₂,
(5) N-Ac-Sar-Gly-Val-D-Ile-Thr-Nva-Ile-Arg-ProNHCH₂CH₂CH₃,
(6) N-Ac-Sar-Gly-Val-D-alloIle-Thr-Nva-Ile-Arg-ProNHCH₂CH₃,
(7) N-Ac-Sar-Gly-Val-D-Val-Thr-Nva-Ile-Arg-ProNHCH₂CH₃,
(8) N-Ac-Sar-Gly-Val-D-Nle-Thr-Nva-Ile-Arg-ProNHCH₂CH₃,
(9) N-Ac-Sar-Gly-Val-D-Phe-Thr-Nva-Ile-Arg-ProNHCH₂CH₃,
(10) N-Ac-Sar-Gly-Val-D-Cha-Thr-Nva-Ile-Arg-ProNHCH₂CH₃,
(11) N-Ac-Sar-Gly-Val-D-3,4-diClPhe-Thr-Nva-Ile-Arg-ProNHCH₂CH₃,
(12) N-Ac-Sar-Gly-Val-D-3-ClPhe-Thr-Nva-Ile-Arg-ProNHCH₂CH₃,
(13) N-Ac-Sar-Gly-Val-D-2-Thienylala-Thr-Nva-Ile-Arg-ProNHCH₂CH₃,
(14) N-Ac-Sar-Gly-Val-D-3-CNPhe-Thr-Nva-Ile-Arg-ProNHCH₂CH₃,
(15) N-Ac-Sar-Gly-Val-D-Ile-Thr-Cha-Ile-Arg-ProNHCH₂CH₃,
(16) N[2-THF-C(O)]-Sar-Gly-Val-D-Ile-Thr-Nva-Ile-Arg-ProNHCH₂CH₃,
(17) N[6-N-acetyl-(CH₂)₅C(O)]-Sar-Gly-Val-D-Ile-Thr-Nva-Ile-Arg-ProNHCH₂CH₃,
(18) N-Hexanoyl-Sar-Gly-Val-D-Ile-Thr-Nva-Ile-Arg-ProNHCH₂CH₃,
(19) N-[4-N-Acetylaminobutyryl]-Sar-Gly-Val-D-Ile-Thr-Nva-Ile-Arg-ProNHCH₂CH₃,
(20) N—[CH₃C(O)NH—(CH₂)₂—O—(CH₂)₂—O—CH₂—C(O)]-Gly-Val-D-Ile-Thr-Nva-Ile-Arg-ProNHCH₂CH₃,
(21) N-Ac-Pro-Gly-Val-D-Ile-Thr-Nva-Ile-Arg-ProNHCH₂CH₃,
(22) N-Ac-NEtGly-Gly-Val-D-Ile-Thr-Nva-Ile-Arg-ProNHCH₂CH₃,
(23) N-Ac-Sar-Gly-Val-D-Ile-Thr-Leu-Ile-Arg-ProNHCH₂CH₃,
(24) N-Ac-Sar-Gly-Val-D-Ile-Thr-Ser-Ile-Arg-ProNHCH₂CH₃,
(25) N-Ac-Sar-Gly-Val-D-Ile-Thr-Nva-Ile-Arg-Pro-D-AlaNH₂,
(26) N-Ac-Sar-Gly-Val-D-Leu-Thr-Nva-Lys(Ac)-Arg-ProNHCH₂CH₃,
(27) N-Ac-Sar-Gly-Val-D-Leu-Thr-Nva-Leu-Arg-ProNHCH₂CH₃,
(28) N-Ac-Sar-Gly-Val-D-Leu-Thr-Nva-1Nal-Arg-ProNHCH₂CH₃,
(29) N-Ac-Sar-Gly-Val-D-Leu-Thr-Nva-Allylgly-Arg-ProNHCH₂CH₃,
(30) N-Ac-Sar-Gly-Val-D-Leu-Ala-Nva-Ile-Arg-ProNHCH₂CH₃,
(31) N-Ac-Sar-Gly-Val-D-Leu-Trp-Nva-Ile-Arg-ProNHCH₂CH₃,
(32) N-Ac-Sar-Gly-Val-D-Leu-Tyr-Nva-Ile-Arg-ProNHCH₂CH₃,
(33) N-Ac-Sar-Gly-Val-D-Leu-Gly-Nva-Ile-Arg-ProNHCH₂CH₃,
(34) N-Ac-Sar-Gly-Val-D-Leu-2Nal-Nva-Ile-Arg-ProNHCH₂CH₃,
(35) N-Ac-Sar-Gly-Val-D-Leu-1Nal-Nva-Ile-Arg-ProNHCH₂CH₃,
(36) N-Ac-Sar-Gly-Val-D-Leu-Octylgly-Nva-Ile-Arg-ProNHCH₂CH₃,
(37) N-Ac-Sar-Gly-Val-D-Leu-Ser-Nva-Ile-Arg-ProNHCH₂CH₃,
(38) N-Ac-Sar-Gly-Val-D-Leu-Allylgly-Nva-Ile-Arg-ProNHCH₂CH₃,
(39) N-Ac-Sar-Gly-Val-D-Leu-D-Thr-Nva-Ile-Arg-ProNHCH₂CH₃,
(40) N-Ac-Sar-Gly-Val-D-Ile-Thr-Tyr-Ile-Arg-ProNHCH₂CH₃,
(41) N-Ac-Sar-Gly-Val-D-Ile-Thr-Glu-Ile-Arg-ProNHCH₂CH₃,
(42) N-Ac-Sar-Gly-Val-D-Ile-Thr-Propargylgly-Ile-Arg-ProNHCH₂CH₃,
(43) N-Ac-Sar-Gly-Val-D-alloIle-Thr-Gln-Ile-Arg-ProNHCH₂CH₃,
(44) N-Ac-Bala-Sar-Gly-Val-D-Ile-Thr-Nva-Ile-Arg-ProNHCH₂CH₃,
(45) N-Phenylacetyl-Sar-Gly-Val-D-Ile-Thr-Nva-Ile-Arg-ProNHCH₂CH₃,
(46) N-Ac-Sar-Gly-Val-D-Ile-Thr-Nva-Ile-Arg-Pro-AzaglyNH₂,
(47) N-Ac-Sar-Gly-Val-D-Ile-Thr-Nva-Ile-Arg-Pro-SerNH₂,
(48) N-(6-Ac-Aca)-Sar-Gly-Val-D-Leu-Ser-Gln-Ile-Arg-ProNHCH₂CH₃,
(49) N-(6-Ac-Aca)-Sar-Gly-Val-D-Leu-Ser-Nva-Ile-Arg-ProNHCH₂CH₃,
(50) N-(4-Ac-Gaba)-Sar-Gly-Val-D-Leu-Ser-Gln-Ile-Arg-ProNHCH₂CH₃,
(51) N-(4-Ac-Gaba)-Sar-Gly-Val-D-Leu-Ser-Nva-Ile-Arg-ProNHCH₂CH₃,
(52) N-(2-Furoyl)-Sar-Gly-Val-D-Leu-Ser-Gln-Ile-Arg-ProNHCH₂CH₃,
(53) N-(2-Furoyl)-Sar-Gly-Val-D-Leu-Ser-Nva-Ile-Arg-ProNHCH₂CH₃,
(54) N-(Shikimyl)-Sar-Gly-Val-D-Leu-Ser-Gln-Ile-Arg-ProNHCH₂CH₃,
(55) N-(Shikimyl)-Sar-Gly-Val-D-Leu-Ser-Nva-Ile-Arg-ProNHCH₂CH₃,
(56)
(57)
(58) N-(2-Me-nicotinyl)-Sar-Gly-Val-D-Leu-Ser-Gln-Ile-Arg-ProNHCH₂CH₃,
(59) N-(2-Me-nicotinyl)-Sar-Gly-Val-D-Leu-Ser-Nva-Ile-Arg-ProNHCH₂CH₃,
(60) N-Ac-Sar-Gly-Val-D-Ile-Thr-Nva-Ile-Arg-Pro-OH,
(61) N-Ac-Sar-Ala-Val-D-Ile-Thr-Nva-Ile-Arg-ProNHCH₂CH₃,
(62) N-Ac-Sar-Gly-Val-D-Pen-Thr-Nva-Ile-Arg-ProNHCH₂CH₃,

(63) N-Ac-Sar-Gly-Val-D-Phe(3,4,5-triF)-Thr-Nva-Ile-Arg-ProNHCH$_2$CH$_3$, and

(64) N-Ac-Sar-Gly-Val-D-Phe(4-NH$_2$)-Thr-Nva-Ile-Arg-ProNHCH$_2$CH$_3$.

14. A compound, or a pharmaceutically acceptable salt, ester, solvate, or prodrug thereof, selected from the group consisting of N-Ac-Sar-Gly-Val-D-Ile-Thr-Nva-Ile-Arg-ProNHCH$_2$CH$_3$, N-Ac-Sar-Gly-Val-D-alloIle-Thr-Nva-Ile-Arg-ProNHCH$_2$CH$_3$, N-Ac-Sar-Gly-Val-D-Ile-Thr-Gln-Ile-Arg-ProNHCH$_2$CH$_3$, and N-Ac-Sar-Gly-Val-D-alloIle-Ser-Ser-Ile-Arg-ProNHCH$_2$CH$_3$.

15. The compound, or pharmaceutically acceptable salt, ester, solvate, or prodrug thereof which is N-Ac-Sar-Gly-Val-D-Ile-Thr-Nva-Ile-Arg-ProNHCH$_2$CH$_3$.

16. The compound, or pharmaceutically acceptable salt, ester, solvate, or prodrug thereof, which is N-Ac-Sar-Gly-Val-D-alloIle-Thr-Ile-Arg-ProNHCH$_2$CH$_3$.

17. The compound, or pharmaceutically acceptable salt, ester, solvate, or prodrug thereof, which is N-Ac-Sar-Gly-Val-D-Ile-Thr-Gln-Ile-Arg-ProNHCH$_2$CH$_3$.

18. The compound, or pharmaceutically acceptable salt, ester, solvate, or prodrug thereof, which is N-Ac-Sar-Gly-Val-D-alloIle-Ser-Ser-Ile-Arg-ProNHCH$_2$CH$_3$.

19. A composition comprising a compound, or a pharmaceutically acceptable salt, ester, solvate, or prodrug thereof, selected from the group consisting of N-Ac-Sar-Gly-Val-D-Ile-Thr-Nva-Ile-Arg-ProNHCH$_2$CH$_3$, N-Ac-Sar-Gly-Val-D-alloIle-Thr-Nva-Ile-Arg-ProNHCH$_2$CH$_3$, N-Ac-Sar-Gly-Val-D-Ile-Thr-Gln-Ile-Arg-ProNHCH$_2$CH$_3$, and N-Ac-Sar-Gly-Val-D-alloIle-Ser-Ser-Ile-Arg-ProNHCH$_2$CH$_3$, and a pharmaceutically acceptable carrier.

20. A composition comprising N-Ac-Sar-Gly-Val-D-Ile-Thr-Nva-Ile-Arg-ProNHCH$_2$CH$_3$, or a pharmaceutically acceptable salt, ester, solvate, or prodrug thereof, and a pharmaceutically acceptable carrier.

21. A composition comprising N-Ac-Sar-Gly-Val-D-alloIle-Thr-Nva-Ile-Arg-ProNHCH$_2$CH$_3$, or a pharmaceutically acceptable salt, ester, solvate, or prodrug thereof, and a pharmaceutically acceptable carrier.

22. A composition comprising N-Ac-Sar-Gly-Val-D-Ile-Thr-Gln-Ile-Arg-ProNHCH$_2$CH$_3$, or a pharmaceutically acceptable salt, ester, solvate, or prodrug thereof, and a pharmaceutically acceptable carrier.

23. A composition comprising N-Ac-Sar-Gly-Val-D-alloIle-Ser-Ser-Ile-Arg-ProNHCH$_2$CH$_3$, or a pharmaceutically acceptable salt, ester, solvate, or prodrug thereof, and a pharmaceutically acceptable carrier.

24. A composition comprising a compound, or a pharmaceutically acceptable salt, ester, solvate, or prodrug thereof selected from the group consisting of N-Ac-Sar-Gly-Val-D-Ile-Thr-Nva-Ile-Arg-ProNHCH$_2$CH$_3$, N-Ac-Sar-Gly-Val-D-alloIle-Thr-Nva-Ile-Arg-ProNHCH$_2$CH$_3$, N-Ac-Sar-Gly-Val-D-Ile-Thr-Gln-Ile-Arg-ProNHCH$_2$CH$_3$, and N-Ac-Sar-Gly-Val-D-alloIle-Ser-Ser-Ile-Arg-ProNHCH$_2$CH$_3$, and a pharmaceutically acceptable carrier.

25. A composition comprising N-Ac-Sar-Gly-Val-D-Ile-Thr-Nva-Ile-Arg-ProNHCH$_2$CH$_3$, or a pharmaceutically acceptable salt, ester, solvate, or prodrug thereof, and a pharmaceutically acceptable carrier.

26. A composition comprising N-Ac-Sar-Gly-Val-D-alloIle-Thr-Nva-Ile-Arg-ProNHCH$_2$CH$_3$, or a pharmaceutically acceptable salt, ester, solvate, or prodrug thereof, and a pharmaceutically acceptable carrier.

27. A composition comprising N-Ac-Sar-Gly-Val-D-Ile-Thr-Gln-Ile-Arg-ProNHCH$_2$CH$_3$, or a pharmaceutically acceptable salt, ester, solvate, or prodrug thereof, and a pharmaceutically acceptable carrier.

28. A composition comprising N-Ac-Sar-Gly-Val-D-alloIle-Ser-Ser-Ile-Arg-ProNHCH$_2$CH$_3$, or a pharmaceutically acceptable salt, ester, solvate, or prodrug thereof, and a pharmaceutically acceptable carrier.

29. A composition comprising a pharmaceutically acceptable carrier in combination with a compound according to claim 1 in an amount effective to inhibit angiogenesis.

30. A composition comprising a pharmaceutically acceptable carrier in combination with a compound according to claim 12 in an amount effective to inhibit angiogenesis.

31. A composition comprising a pharmaceutically acceptable carrier in combination with a compound selected from the group consisting of N-Ac-Sar-Gly-Val-D-Ile-Thr-Nva-Ile-Arg-ProNHCH$_2$CH$_3$, N-Ac-Sar-Gly-Val-D-alloIle-Thr-Nva-Ile-Arg-ProNHCH$_2$CH$_3$, N-Ac-Sar-Gly-Val-D-Ile-Thr-Gln-Ile-Arg-ProNHCH$_2$CH$_3$, and N-Ac-Sar-Gly-Val-D-alloIle-Ser-Ser-Ile-Arg-ProNHCH$_2$CH$_3$, in an amount effective to inhibit angiogenesis.

32. A composition according to claim 31 wherein the compound is N-Ac-Sar-Gly-Val-D-Ile-Thr-Nva-Ile-Arg-ProNHCH$_2$CH$_3$.

33. A composition according to claim 31 wherein the compound is N-Ac-Sar-Gly-Val-D-alloIle-Thr-Nva-Ile-Arg-ProNHCH$_2$CH$_3$.

34. A composition according to claim 31 wherein the compound is N-Ac-Sar-Gly-Val-D-Ile-Thr-Gln-Ile-Arg-ProNHCH$_2$CH$_3$.

35. A composition according to claim 31 wherein the compound is N-Ac-Sar-Gly-Val-D-alloIle-Ser-Ser-Ile-Arg-ProNHCH$_2$CH$_3$.

36. A composition comprising a pharmaceutically acceptable carrier in combination with a compound according to claim 1 in an amount effective to inhibit proliferation of tumor cells.

37. A composition comprising a pharmaceutically acceptable carrier in combination with a compound according to claim 12 in an amount effective to inhibit proliferation of tumor cells.

38. A composition comprising a pharmaceutically acceptable carrier in combination with a compound selected from the group consisting of N-Ac-Sar-Gly-Val-D-Ile-Thr-Nva-Ile-Arg-ProNHCH$_2$CH$_3$, N-Ac-Sar-Gly-Val-D-alloIle-Thr-Nva-Ile-Arg-ProNHCH$_2$CH$_3$, N-Ac-Sar-Gly-Val-D-Ile-Thr-Gln-Ile-Arg-ProNHCH$_2$CH$_3$, and N-Ac-Sar-Gly-Val-D-alloIle-Ser-Ser-Ile-Arg-ProNHCH$_2$CH$_3$, in an amount effective to inhibit proliferation of tumor cells.

39. A composition according to claim 38 wherein the compound is N-Ac-Sar-Gly-Val-D-Ile-Thr-Nva-Ile-Arg-ProNHCH$_2$CH$_3$.

40. A composition according to claim 38 wherein the compound is N-Ac-Sar-Gly-Val-D-alloIle-Thr-Nva-Ile-Arg-ProNHCH$_2$CH$_3$.

41. A composition according to claim 38 wherein the compound is N-Ac-Sar-Gly-Val-D-Ile-Thr-Gln-Ile-Arg-ProNHCH$_2$CH$_3$.

42. A composition according to claim 38 wherein the compound is N-Ac-Sar-Gly-Val-D-alloIle-Ser-Ser-Ile-Arg-ProNHCH$_2$CH$_3$.

* * * * *

UNITED STATES PATENT AND TRADEMARK OFFICE
CERTIFICATE OF CORRECTION

PATENT NO. : 6,716,963 B1
DATED : April 6, 2004
INVENTOR(S) : Jack Henkin et al.

It is certified that error appears in the above-identified patent and that said Letters Patent is hereby corrected as shown below:

Column 135,
Line 65, "CH2-OCH2" should read -- CH2-(OCH2 --.

Column 150,
Line 13, "(4guanidino)" should read -- (4-guanidino) --.

Column 151,
Line 26, delete "NHCH2" and insert -- NHCH --.

Column 154,
Line 52, "ProNHCH2," should read -- Pro NHCH2 --.

Column 156,
Line 26, "CH2CH3," should read -- NHCH2CH3 --.
Lines 33 and 40, "D-Ile" should read -- DIle --.

Column 158,
Line 67, "(" should read -- (CH3)2, --.

Column 160,
Line 10, "DalloIle" should read -- D-alloIle --.
Line 45, "3,4diF" should read -- 3,4-diF --.

Column 163,
Line 18, "thereof" should read -- thereof, --.

Signed and Sealed this

Tenth Day of January, 2006

JON W. DUDAS
*Director of the United States Patent and Trademark Office*

SEQUENCE LISTING

<160> NUMBER OF SEQ ID NOS: 6

<210> SEQ ID NO 1
<211> LENGTH: 10
<212> TYPE: PRT
<213> ORGANISM: Artificial Sequence
<220> FEATURE:
<223> OTHER INFORMATION: Antiangiogenetic Peptide
<221> NAME/KEY: VARIANT
<222> LOCATION: (1)...(1)
<223> OTHER INFORMATION: Xaa = Ala, Asn, Cit, Gln, Glu, NEtGly, Met,
      N-methylalanyl, Pro, pyro-Glu, Sar, Ser, or Thr at
      position 1
<221> NAME/KEY: VARIANT
<222> LOCATION: (2)...(2)
<223> OTHER INFORMATION: Xaa = Ala, Asn, Asp, Gln, Glu, Leu, Met, Phe,
      Pro, or Ser at position 2
<221> NAME/KEY: VARIANT
<222> LOCATION: (3)...(3)
<223> OTHER INFORMATION: Xaa = Ala, Asn, Cit, Cha, Chg, Gln, Glu, Gly,
      Ile, Leu, Met, Nva, Phe, Ser, tButylgly, Thr, Val, Pen,
      or Cys at position 3
<221> NAME/KEY: VARIANT
<222> LOCATION: (4)...(4)
<223> OTHER INFORMATION: Xaa = alloIle, Gly, Ile, Pro, or dehydroleu at
      position 4
<221> NAME/KEY: VARIANT
<222> LOCATION: (5)...(5)
<223> OTHER INFORMATION: Xaa = Ala, 3-Pal, 1-Nal, 2-Nal, allo-threonyl,
      allylgly, Gln, Gly, His, Hser, Ile, Lys(Ac), Met,
      Nva, Octylgly, Orn, Phe(4-CH2OH), Pro, Ser, Thr,
      Trp, Tyr, Pen, or Cys at position 5
<221> NAME/KEY: VARIANT
<222> LOCATION: (6)...(6)
<223> OTHER INFORMATION: Xaa = Ala, 1-Nal, 2-Nal, 3-Pal, Abu, allylgly,
      Arg, Asn, Asp, Cit, Cha, Gln, Glu, Gly, His,
      Homoala, Hle, Hser, Ile, Leu, Lys(Ac), Lys(Isp),
      at position 6
<221> NAME/KEY: VARIANT
<222> LOCATION: (6)...(6)
<223> OTHER INFORMATION: 6 Cont'd:
      Xaa = Met(O2), Met(O), Met, Nor, Nva, Octygly,
      Phe, Phe(4-CONH2), Propargylgly, Ser, Thr, Trp,
      Tyr, Val, Pen, or Cys at position 6
<221> NAME/KEY: VARIANT
<222> LOCATION: (7)...(7)
<223> OTHER INFORMATION: Xaa = Ala, Allylgly, Asn, Cit, Chg, Gln, Gly,
      Hser, Ile, alloIle, Leu, Lys(Ac), Met, 1-Nal,
      2-Nal, Nva, Phe, Pro, Ser, tButylgly, Trp, Tyr,
      Val, Pen, or Cys at position 7
<221> NAME/KEY: VARIANT
<222> LOCATION: (8)...(8)
<223> OTHER INFORMATION: Xaa = Aminopyprimidinobutanoyl,
      Ala(3-guanidino), Ala(3-pyrrolidinylamidino),
      Ala[4-Pip(N-amidino)], Arg, arginyl(NGNG'diethyl), Cit,
      Cha(4-NIsp), Gly[4-pip(N-amido)], at position 8
<221> NAME/KEY: VARIANT
<222> LOCATION: (8)...(8)
<223> OTHER INFORMATION: 8 Cont'd:
      Xaa = His, Harg, Lys, Lys(Ile), Lys(Nic), Norarg,
      Orn(Isp), Orn(Nic), Orn(2-imidazo),
      Phe(4-CH2NHIsp), Phe(4-guanidino), or Phe(4-NIsp)
      at position 8
<221> NAME/KEY: VARIANT
<222> LOCATION: (9)...(9)
<223> OTHER INFORMATION: Xaa = Abu, Aib, homoprolyl, hydroxyprolyl, Ile,
      Leu, Phe, Pro, Ser, tButylgly, Tic, Thr, or Val at
      position 9
<221> NAME/KEY: VARIANT
<222> LOCATION: (10)...(10)
<223> OTHER INFORMATION: Xaa = azaglycylamide, glycylamide,
      glycylethylamide, sarcosylamide, serylamide at
      position 10

<400> SEQUENCE: 1

```
Xaa Xaa Xaa Xaa Xaa Xaa Xaa Xaa Xaa Xaa
 1               5                   10

<210> SEQ ID NO 2
<211> LENGTH: 9
<212> TYPE: PRT
<213> ORGANISM: Artificial Sequence
<220> FEATURE:
<223> OTHER INFORMATION: Antiangiogenetic peptide
<221> NAME/KEY: VARIANT
<222> LOCATION: (1)...(1)
<223> OTHER INFORMATION: Xaa = sarcosyl at position 1
<221> NAME/KEY: VARIANT
<222> LOCATION: (6)...(6)
<223> OTHER INFORMATION: Xaa = norvaline at position 6

<400> SEQUENCE: 2

Xaa Gly Val Ile Thr Xaa Ile Arg Pro
 1               5

<210> SEQ ID NO 3
<211> LENGTH: 9
<212> TYPE: PRT
<213> ORGANISM: Artificial Sequence
<220> FEATURE:
<223> OTHER INFORMATION: Antiangiogenetic peptide
<221> NAME/KEY: VARIANT
<222> LOCATION: (1)...(1)
<223> OTHER INFORMATION: Xaa = sarcosyl at position 1
<221> NAME/KEY: VARIANT
<222> LOCATION: (6)...(6)
<223> OTHER INFORMATION: Xaa = norvaline at position 6

<400> SEQUENCE: 3

Xaa Gly Val Gly Thr Xaa Ile Arg Pro
 1               5

<210> SEQ ID NO 4
<211> LENGTH: 9
<212> TYPE: PRT
<213> ORGANISM: Artificial Sequence
<220> FEATURE:
<223> OTHER INFORMATION: Antiangiogenetic peptide
<221> NAME/KEY: VARIANT
<222> LOCATION: (1)...(1)
<223> OTHER INFORMATION: Xaa = sarcosyl at position 1
<221> NAME/KEY: VARIANT
<222> LOCATION: (4)...(4)
<223> OTHER INFORMATION: Xaa = allo-isoleucyl at position 4
<221> NAME/KEY: VARIANT
<222> LOCATION: (6)...(6)
<223> OTHER INFORMATION: Xaa = norvaline at position 6

<400> SEQUENCE: 4

Xaa Gly Val Xaa Thr Xaa Ile Arg Pro
 1               5

<210> SEQ ID NO 5
<211> LENGTH: 9
<212> TYPE: PRT
<213> ORGANISM: Artificial Sequence
<220> FEATURE:
<223> OTHER INFORMATION: Antiangiogenetic peptide
<221> NAME/KEY: VARIANT
<222> LOCATION: (1)...(1)
<223> OTHER INFORMATION: Xaa = sarcosyl at position 1
<221> NAME/KEY: VARIANT
<222> LOCATION: (4)...(4)
<223> OTHER INFORMATION: Xaa = dehydroleucyl at position 4
<221> NAME/KEY: VARIANT
<222> LOCATION: (6)...(6)
<223> OTHER INFORMATION: Xaa = norvaline at position 6
```

```
<400> SEQUENCE: 5

Xaa Gly Val Xaa Thr Xaa Ile Arg Pro
 1               5

<210> SEQ ID NO 6
<211> LENGTH: 11
<212> TYPE: PRT
<213> ORGANISM: Artificial Sequence
<220> FEATURE:
<223> OTHER INFORMATION: Antiangiogenetic Peptide
<221> NAME/KEY: VARIANT
<222> LOCATION: (1)...(1)
<223> OTHER INFORMATION: Xaa = R-(CH2)n-C(O)- where R is N-acetylamino
      at position 1
<221> NAME/KEY: VARIANT
<222> LOCATION: (2)...(2)
<223> OTHER INFORMATION: Xaa = Sar at position 2
<221> NAME/KEY: VARIANT
<222> LOCATION: (5)...(5)
<223> OTHER INFORMATION: Xaa = AlloIle, dehydroleu, Gly, Ile or Pro at
      position 5
<221> NAME/KEY: VARIANT
<222> LOCATION: (6)...(6)
<223> OTHER INFORMATION: Xaa = Ala, 3-Pal, 1-Nal, 2-Nal, allo-threonyl,
      allylgly, Gln, Gly, His, Hser, Ile, Lys(Ac), Met,
      Nva, Octylgly, Orn, Phe(3-CH2OH), Pro, Ser, Thr,
      Trp, Tyr, Pen or Cys at position 6
<221> NAME/KEY: VARIANT
<222> LOCATION: (7)...(7)
<223> OTHER INFORMATION: Xaa = Ala, 1-Nal, 2-Nal, 3-Pal, Abu, allylgly,
      Arg, Asn, Asp, Cit, Cha, Gln, Glu, Gly, His,
      Homoala, Hle, Hser, Ile, Leu, Lys(Ac), Lys(Isp),
      at position 7
<221> NAME/KEY: VARIANT
<222> LOCATION: (7)...(7)
<223> OTHER INFORMATION: 7 Con'td:
      Xaa = Met(O2), Met(O), Met, Nor, Nva, Octygly,
      Phe, Phe(4-CONH2), Proparglygly, Ser, Thr, Trp,
      Tyr, Val, Pen, or Cys at position 7
<221> NAME/KEY: VARIANT
<222> LOCATION: (11)...(11)
<223> OTHER INFORMATION: Xaa = Azaglycylamide, glycylamide,
      glycylethylamide, sarcosylamide, serylamide at
      position 11

<400> SEQUENCE: 6

Xaa Xaa Gly Val Xaa Xaa Xaa Ile Arg Pro Xaa
 1               5                   10
```